(12) United States Patent
Strong et al.

(10) Patent No.: US 10,377,543 B1
(45) Date of Patent: Aug. 13, 2019

(54) DETERMINING USE AND VALIDITY OF VEHICLES THROUGH ACOUSTIC EMISSIONS

(71) Applicant: Kali Care, Inc., Mountain View, CA (US)

(72) Inventors: John Francis Strong, Saratoga, CA (US); Abhijit Kalamkar, Sunnyvale, CA (US); Sina Fateh, Sunnyvale, CA (US)

(73) Assignee: KALI CARE, INC., Mountain View, CA (US)

( * ) Notice: Subject to any disclaimer, the term of this patent is extended or adjusted under 35 U.S.C. 154(b) by 0 days.

(21) Appl. No.: 16/192,450

(22) Filed: Nov. 15, 2018

Related U.S. Application Data

(63) Continuation-in-part of application No. 15/885,681, filed on Jan. 31, 2018.

(51) Int. Cl.
  *B65D 55/02* (2006.01)
  *G10K 1/00* (2006.01)
  *B65D 41/04* (2006.01)

(52) U.S. Cl.
  CPC ....... *B65D 55/028* (2013.01); *B65D 41/0471* (2013.01); *G10K 1/00* (2013.01);
  (Continued)

(58) Field of Classification Search
  CPC .............. B65D 41/0471; B65D 55/028; B65D 2251/023; B65D 2543/00851;
  (Continued)

(56) References Cited

U.S. PATENT DOCUMENTS 3,230,661 A * 1/1966 Gleason ................... A63H 5/00
                                                       116/67 R
5,130,696 A * 7/1992 Liebman .................. G08B 3/10
                                                       340/384.71
(Continued)

FOREIGN PATENT DOCUMENTS

WO    WO-2013120149 A1 * 8/2013 ........... B65D 55/028

OTHER PUBLICATIONS

International Search Report and Written Opinion dated Apr. 12, 2019 for International Patent Application No. PCT/US2019/013291, 13 pages.
(Continued)

*Primary Examiner* — Steven Lim
*Assistant Examiner* — Mancil Littlejohn, Jr.
(74) *Attorney, Agent, or Firm* — Perkins Coie LLP

(57) ABSTRACT

Arrangements are provided for "smart" functionality with "dumb" containers, such as for determining medication adherence, tracking product use, and validating product authenticity. An acoustic emitter is engaged with a container or other vehicle. Opening the container causes the acoustic emitter to produce an acoustic emission, without requiring power, processing capacity, or sensors. A cell phone or other station receives and registers acoustic emissions, such as by logging opening of the container, verifying authenticity of the acoustic emission, communicating with an oversight system, or similar. Data as may be encoded in an acoustic emission may include vehicle detection data (e.g., logging a container being opened), vehicle information (e.g., lot number, contents name), vehicle validation (e.g., valid or counterfeit numerical code), and audible user recognition (e.g., brand jingles, warning sounds).

1 Claim, 60 Drawing Sheets

(52) U.S. Cl.
CPC ............... *B65D 2251/023* (2013.01); *B65D 2543/00842* (2013.01); *B65D 2543/00851* (2013.01)

(58) Field of Classification Search
CPC .. B65D 2543/00842; G10K 1/00; G10K 1/32; G10K 1/10; G10K 1/072; G10K 1/067
USPC ........ 340/572.8; 604/66, 290, 295, 298, 300
See application file for complete search history.

(56) References Cited

U.S. PATENT DOCUMENTS

| | | | | |
|---|---|---|---|---|
| 5,803,287 | A * | 9/1998 | Kusz | B65D 41/0471 215/330 |
| 6,299,006 | B1 * | 10/2001 | Samonek | B65D 23/00 116/112 |
| 9,283,150 | B2 * | 3/2016 | Bujalski | A61J 7/0076 |
| 9,918,905 | B1 * | 3/2018 | Howard | A61J 1/03 |
| 10,138,036 | B1 * | 11/2018 | Schwimer | B65D 51/248 |
| 2002/0000908 | A1 | 1/2002 | Burg et al. | |
| 2004/0155780 | A1 | 8/2004 | Rapchak | |
| 2006/0186075 | A1 * | 8/2006 | Rainey | A45D 40/0068 215/202 |
| 2008/0110850 | A1 * | 5/2008 | Tilton | B65D 41/0471 215/330 |
| 2014/0088524 | A1 * | 3/2014 | Marx | A61F 9/0026 604/298 |
| 2014/0228783 | A1 | 8/2014 | Kraft | |
| 2014/0257206 | A1 | 9/2014 | Fateh | |
| 2015/0359667 | A1 | 12/2015 | Brue | |
| 2016/0106375 | A1 | 4/2016 | Leydon | |

OTHER PUBLICATIONS

Harrison, Chris, et al., "Acoustic Barcodes: Passive, Durable and Inexpensive Notched Identification Tags", Oct. 7-10, 2012, 4 pgs., Human-Computer Interaction Institute and Heinz College Center for the Future of Work Carnegie Mellon University, Pittsburgh PA, Cambridge, MA, Copyright 2012 ACM 978-1-4503-1580.

Savage, Valkyrie, et al., "Lamello: Passive Acoustic Sensing for Tangible Input Components", Apr. 18-23, 2015, 4 pgs., Adobe Research, UC Berkeley EECS, ACM 978-1-4503-4315, May 15, 2004; http://dx.doi.org/10.1145/2702123.2702207.

* cited by examiner

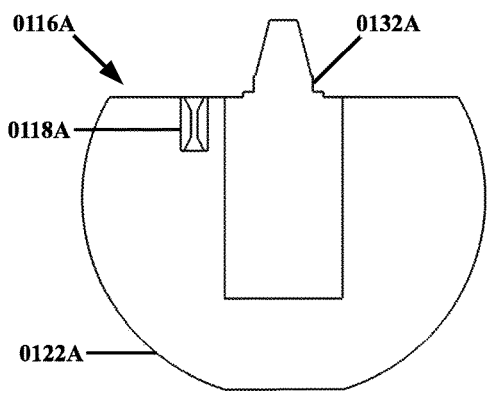
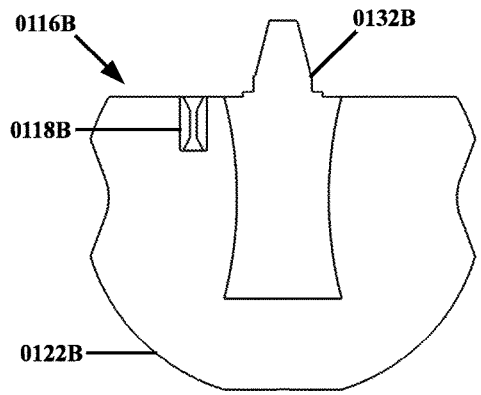
FIG. 1A
FIG. 1B
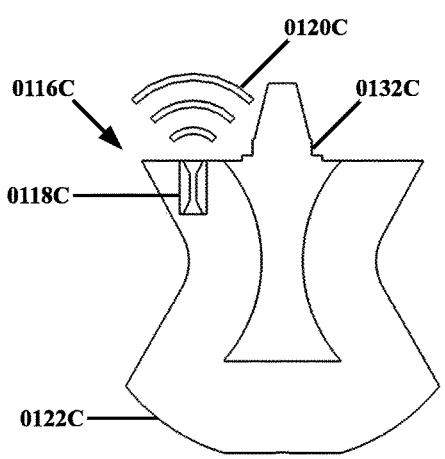
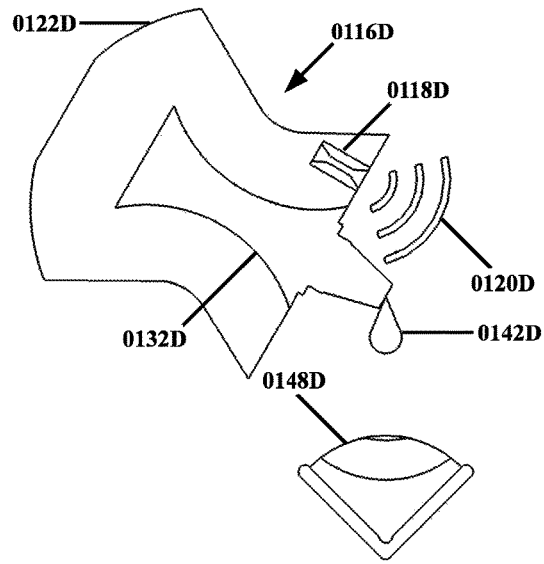
FIG. 1C
FIG. 1D

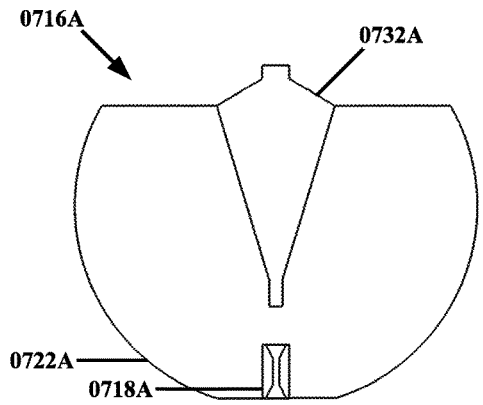
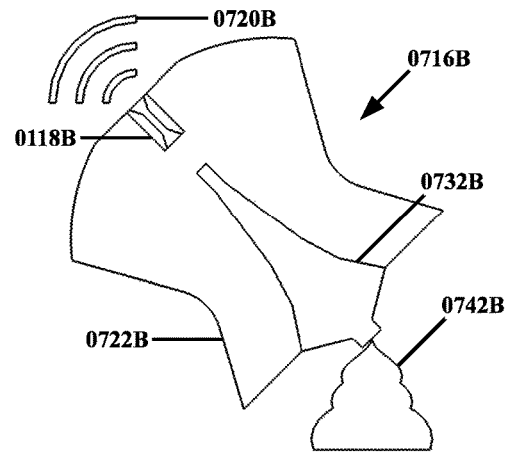
FIG. 7A
FIG. 7B
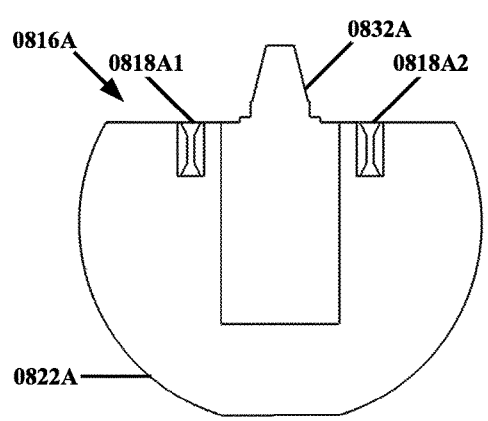
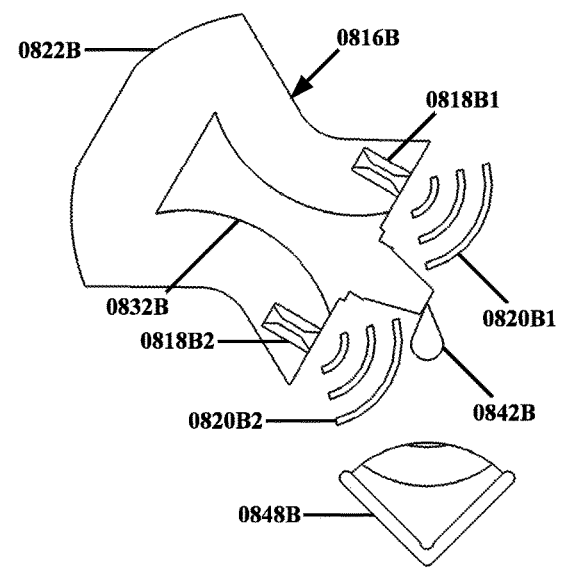
FIG. 8A
FIG. 8B

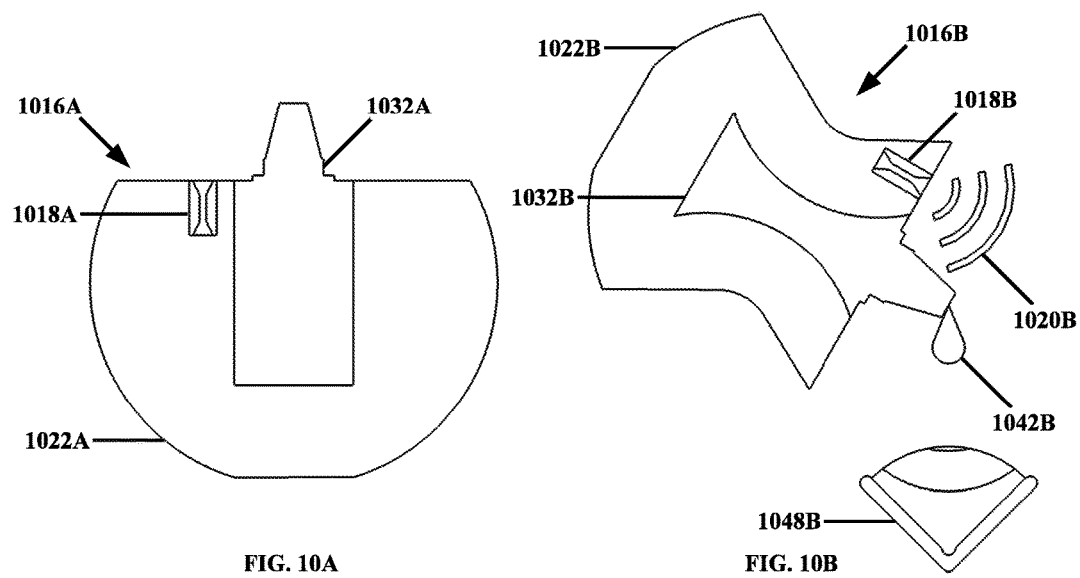
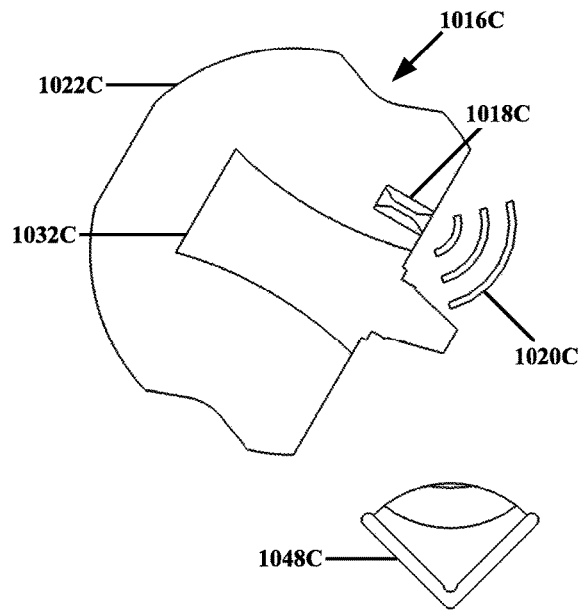
FIG. 10A  FIG. 10B
FIG. 10C

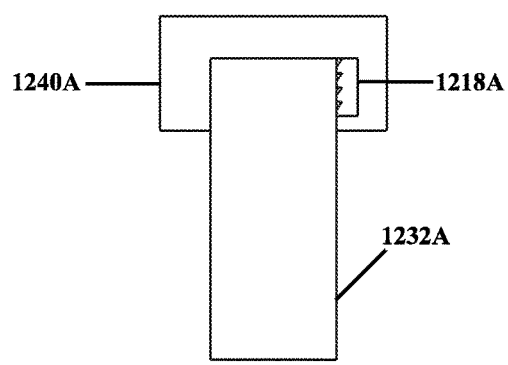
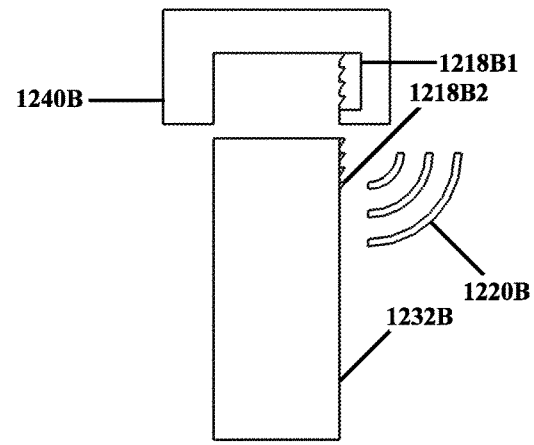
FIG. 12A
FIG. 12B
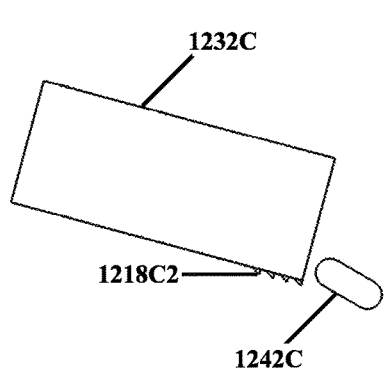
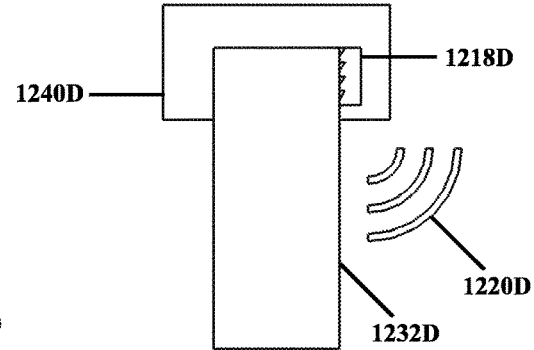
FIG. 12C
FIG. 12D

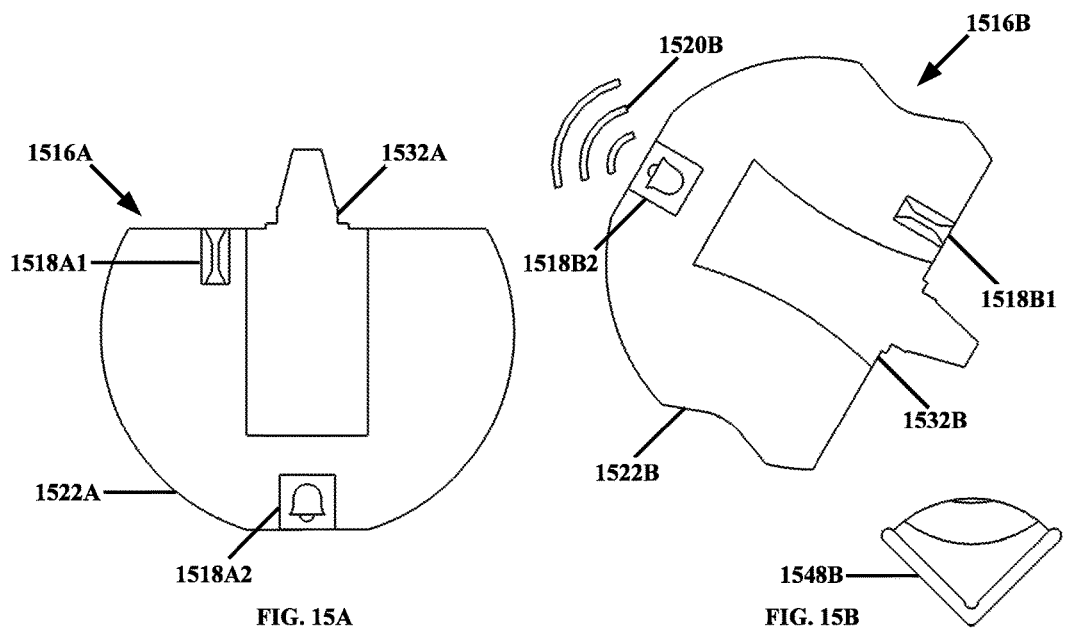
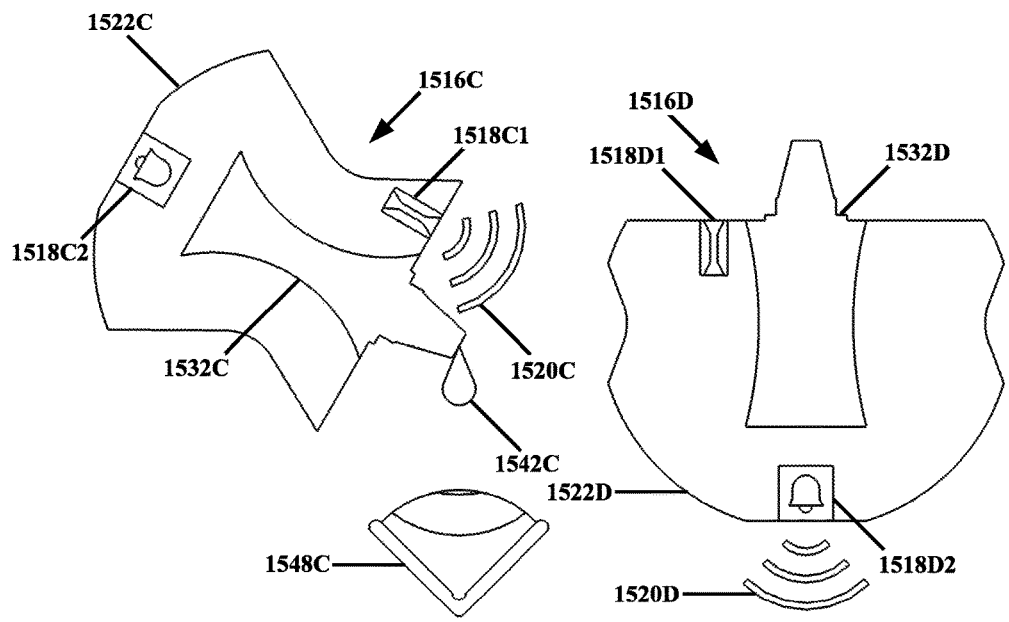

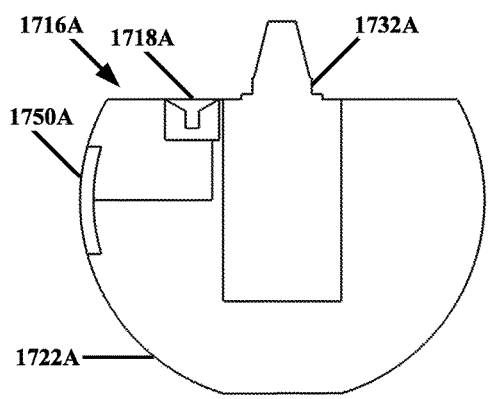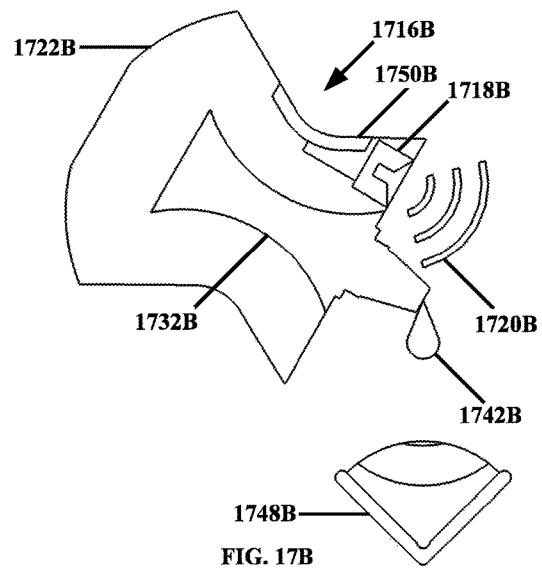
FIG. 17A  FIG. 17B
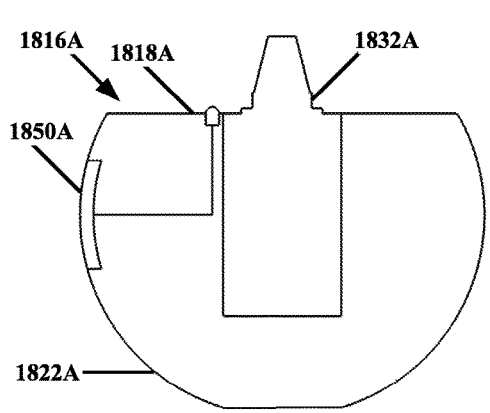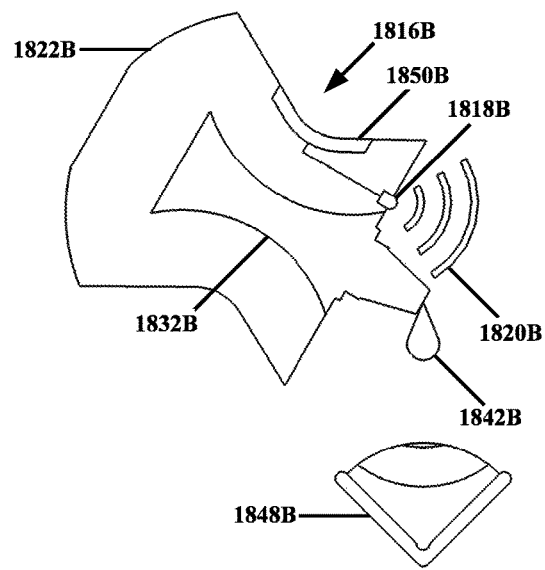
FIG. 18A  FIG. 18B

DETERMINING USE AND VALIDITY OF VEHICLES THROUGH ACOUSTIC EMISSIONS

CROSS-REFERENCE TO RELATED APPLICATIONS

This application is a continuation-in-part of U.S. application Ser. No. 15/885,681 filed Jan. 31, 2018, which is incorporated herein by reference for all purposes.

FIELD OF THE INVENTION

Various embodiments concern determining, facilitating, and/or communicating vehicle detection, vehicle information, vehicle validity, and vehicle user recognition. More particularly, various embodiments relate to producing a purposed acoustic emission from a vehicle such as a container, receiving that acoustic emission, and registering an event associated with that vehicle such as opening the container. Various embodiments refer to carrying out such functions via arrangements as may not require "smart" functionality in/on the vehicle or acoustic emitter. Various embodiments also refer to carrying out such functions via arrangements as may be material/mechanical in nature.

BACKGROUND

Point-of-action data associated with events such as opening a container (whether of medication, soda, some other product, etc.) may be useful in various capacities. Merely detecting such an event may be of interest. For example, determining when a medication container is opened may facilitate tracking of medication use (e.g., using the opening of a container of eyedrops to infer that the eyedrops have been administered) so as to support adherence to a prescribed medication treatment regimen, provide data for clinical studies, etc. Communicating information at time-of-action, such as the lot number of a produce, name, contents, etc. may facilitate use tracking and/or other functions. Providing validation data, e.g., a "code" as may identify genuine items may facilitate the verification that medication or other products are not counterfeit (for example, if a numerical code for a genuine article produces a predicted result when transformed by a complex and/or confidential mathematical algorithm, then it may be inferred that the code was assigned by an authorized manufacturer, e.g., someone with access to the algorithm). Facilitating user recognition, such as providing some positive confirmation of a user that the correct container is being opened, etc., also may be of interest.

At least in principle, certain forms of point-of-action data may be obtained or carried out through self-reporting; however, self-reporting may present certain concerns. For example, the accuracy and/or reliability of the data may be in question. Considering detecting the use of medication as an example, if patients may not reliably remember to take their medication or do so on time, can patients be relied upon to reliably remember to accurately report their use of medication? Even the degree of accuracy, reliability, etc. may be unknown. As another example, while validation may be attempted by user inspection, given a sufficiently sophisticated counterfeit an individual may be unable to reliably determine visually whether a given container of medication is genuine or not. (Such concerns may apply similarly to validation by inspection for other products including but not limited to bottled water, foods, cosmetics, software, audio and/or video recordings, etc.)

Also at least in principle, certain point-of-action data may be actively reported by an autonomous system, e.g., by incorporating electronic sensors, processors, communication systems into a container. However this too may present challenges. Such components typically require electrical power, and may be inoperable without power. Electronics may be susceptible to damage from various ambient conditions, e.g., if wet, dropped, sat upon (for example if kept in a pocket), exposed to extreme temperatures (for example if left in a car on a hot day or kept in an outer coat pocket in cold weather), etc. Cost, complexity, potential contamination, weight, etc. also may be of concern.

BRIEF SUMMARY OF THE INVENTION

This disclosure contemplates a variety of systems, apparatus, methods, and paradigms for targeted and/or interactive approaches for determining the use of medication, identification of products, validation of products, and similar through emitting and interpreting acoustic emissions.

In one embodiment an apparatus is provided, including a container adapted to contain and dispense a product, the container having an aperture adapted to pass the product therethrough, a container thread disposed around the aperture, and a shoulder disposed around the aperture and the container thread. The apparatus includes a cap adapted to removably engage the container so as to restrict passing the product through the aperture, the cap including an inner wall, a cap thread on the inner wall adapted to engage the container thread so as to enable the cap to be removably engaged with the container through rotating the cap relative to the container, and an outer wall spaced apart from the inner wall so as to define a channel between the inner and outer walls. The apparatus also includes an acoustic emitter, the acoustic emitter including an anvil disposed on the shoulder of the container and integral with the container, pedestals engaged with the cap between the inner and outer walls and integral with the closure, and strikers disposed on the pedestals and integral therewith, each striker having a striker length.

The anvil and strikers are disposed such that rotating the cap engages the strikers sequentially with the anvil so as to produce an acoustic emission with a sequence of components from the strikers, without requiring any of a power source, a data processor, and a sensor. An acoustic emission pitch from each of the strikers corresponds to a striker length thereof, such that the acoustic emissions exhibit a sequential nonuniformity of the acoustic emission pitches. The striker lengths of the strikers are configured to encode data into the acoustic emission in the sequential nonuniformity of the acoustic emission pitches.

In another embodiment an apparatus is provided, including a container adapted to contain and dispense a product, a closure adapted to removably engage the container so as to restrict passing the product therefrom, and at least one acoustic emitter engaged with the container and/or the closure. Disengaging the closure from the container actuates the acoustic emitter so as to produce an acoustic emission. The acoustic emitter exhibits a physical structure so as to produce a sequential nonuniformity of the acoustic emission, and the physical structure of the acoustic emitter is configured so as to encode data into the acoustic phrase in the sequential nonuniformity of the acoustic emission.

The acoustic emitter may include a first portion engaged with a first of the container and the closure and a second portion engaged with a second of the container and the closure. The first portion may include multiple strikers, and the second portion may an anvil. The first portion may include a striker, and the second portion may include multiple anvils.

The container may be adapted to contain therein and dispense therefrom oral medication pills, oral liquid medication, eyedrop liquid medication, oral supplement pills, oral liquid supplement, eyedrop liquid supplement, beverages, foods, cosmetics, household chemicals, and/or industrial products. The closure may include a screw cap, a flip cap, a pull cap, and/or a sealing strip. The closure may include a sealing strip, and the acoustic emitter may include frangible filaments engaged with the sealing strip and adapted to emit the acoustic emissions via breakage of the filaments as the sealing strip is separated to open the container, and/or an adhesive beads having an adhesive bond with the sealing strip and the container, and adapted to emit the acoustic emissions via disengaging the adhesive bond from the sealing strip and/or the container.

The physical structure of the acoustic emitter may be invariant for disengagings of the closure from the container, such that the acoustic emission is invariant for disengagings. At least a portion of the physical structure of the acoustic emitter may be varied in response to a first disengaging of the closure from the container, such that the acoustic emission is variant for the first disengaging compared to successive disengagings. The acoustic emitter may include strikers and an anvil, and at least one of the strikers may be frangible so as to break in producing the acoustic emissions in a first disengaging of the closure from the container and no longer produce the acoustic emissions for subsequent disengagings.

The container, the closure, and the acoustic emitter may be configured such that a dispensing path for the product does not contact the acoustic emitter. The acoustic emitter may be engaged with the container and/or the closure via integral continuity therewith. The acoustic emitter may be engaged with the container and/or the closure but not integrally continuous therewith.

Engaging the closure with the container may actuate the acoustic emitter so as to produce a second acoustic emission. No electrical source, data processor, and/or sensor may be required to produce the acoustic emission.

The physical structure of the acoustic emitter may be configured so as to encode characteristic access recognition data for the product within the acoustic emission. The physical structure of the acoustic emitter may be configured so as to encode product information data for the product within the acoustic emission. The product information data may include a name of the product, a manufacturer name of the product, an ID number for the product, a description of the product, directions for the product, information regarding the product, a manufacture date of the product, a manufacture location for the product, a use-by date for the product, a prescription date for the product, a prescriber name for the product, a dispensing pharmacy identity for the product, a lot number of the product, and/or a serial number for the product. The physical structure of the acoustic emitter may be configured so as to encode product validation data for the product adapted to facilitate distinction between authentic and counterfeit product within the acoustic emission. The physical structure of the acoustic emitter may be configured so as to encode audible user-recognizable style data for the product within the acoustic emission. The audible user-recognizable style data may include an ad jingle, an audible brand identifier, an audible warning, and/or an audible owner identifier.

In another embodiment a method is provided, including establishing a container adapted to contain a product therein and dispense the product therefrom, establishing a cap adapted to removably engage the container so as to restrict passing the product therefrom, and engaging an acoustic emitter with the container and/or the closure such that disengaging the closure from the container actuates the acoustic emitter so as to produce an acoustic emission including a sequence of acoustic emissions. The method includes configuring a physical structure of the acoustic emitter so as to produce a sequential nonuniformity of the acoustic emissions therefrom, and configuring the physical structure of the acoustic emitter so as to encode data in the sequential nonuniformity of the acoustic emissions.

Engaging the acoustic emitter with the container and/or the closure may include fabricating the acoustic emitter integrally therewith. Engaging the acoustic emitter with the container and/or the closure may include molding the acoustic emitter integrally therewith, at least in part from a polymer. Engaging the acoustic emitter with the container and/or the closure may include fabricating the acoustic emitter separately therefrom and disposing the acoustic emitter thereon.

Engaging the acoustic emitter with the container and/or the closure may include fabricating the acoustic emitter separately therefrom and disposing the acoustic emitter thereon subsequent to the product being disposed in the container and the closure being engaged with the container.

In another embodiment an apparatus is provided, including means for controllably containing a product and dispensing the product, means for emitting acoustic emissions engaged with the means for controllably containing the product such that configuring the means for controllably containing the product to dispense the product actuates the means for emitting acoustic emissions so as to produce an acoustic emission exhibiting sequential nonuniformity, and means for encoding data in the sequential nonuniformity of the acoustic emission via a physical structure of the means for emitting acoustic emissions.

In another embodiment an apparatus is provided, including a vehicle and an acoustic emitter engaged with the vehicle and adapted to produce a purposed acoustic emission in response to and actuated by a vehicle event. The acoustic emitter exhibits a physical structure so as to produce a sequential nonuniformity in the acoustic emission. The physical structure of the acoustic emitter is configured so as to encode data into the acoustic phrase in the sequential nonuniformity of the acoustic emission.

The vehicle may include a container, and the vehicle event may include opening the container. The encoded data may include vehicle detection data adapted to facilitate detection of the vehicle event from the acoustic emission. The encoded data may include vehicle information data regarding the vehicle. The encoded data may include validation data adapted to facilitate distinguishing a genuine validation status of the vehicle from a counterfeit validation status of the vehicle. The encoded data may include recognition data adapted to facilitate user audible recognition of the acoustic emission.

In another embodiment a method is provided, including engaging an acoustic emitter with the vehicle such that a vehicle event actuates the acoustic emitter to produce an acoustic emission, configuring a structure of the acoustic emitter so as to produce a sequential nonuniformity in the acoustic emission, and configuring the structure of the acoustic emitter so as to encode data in the sequential nonuniformity of the acoustic emission.

In another embodiment an apparatus is provided, including a vehicle, an acoustic emitter engaged with the vehicle and adapted to produce a purposed acoustic emission in response to and actuated by a vehicle event, and a station adapted to receive the acoustic emission. The acoustic emitter exhibits a physical structure so as to produce a sequential nonuniformity in the acoustic emission. The physical structure of the acoustic emitter is configured so as to encode data into the acoustic phrase in the sequential nonuniformity of the acoustic emissions. The station is adapted to register the vehicle event in response to receiving the acoustic emission.

The vehicle may include a container; and the vehicle event may include opening the container. The encoded data may include vehicle detection data adapted to facilitate detection of the vehicle event from the acoustic emission, the station may be adapted to recognize the vehicle detection data, and registering the vehicle event may include registering the detection data. The encoded data may include vehicle information data regarding the vehicle, the station may be adapted to recognize the vehicle information data, and registering the vehicle event may include registering the vehicle information data.

The encoded data may include validation data adapted to facilitate distinguishing a genuine validation status of the vehicle from a counterfeit validation status of the vehicle, the station may be adapted to determine the validation status of the vehicle from the acoustic emission, and registering the vehicle event may include registering the validation status. The encoded data may include recognition data adapted to facilitate user audible recognition of the acoustic emission.

In another embodiment a method is provided, including engaging an acoustic emitter with the vehicle such that a vehicle event actuates the acoustic emitter to produce an acoustic emission, configuring a structure of the acoustic emitter so as to produce a sequential nonuniformity in the acoustic emission, and configuring the structure of the acoustic emitter so as to encode data in the sequential nonuniformity of the acoustic emissions. The method includes receiving the acoustic emission in a station and registering the vehicle event via the station in response to receiving the acoustic emission.

In another embodiment an apparatus is provided, including a vehicle, an acoustic emitter engaged with the vehicle and adapted to produce a purposed acoustic emission in response to and actuated by a vehicle event, and a station adapted to receive the acoustic emission. The apparatus includes an oversight system in communication with the station. The acoustic emitter exhibits a physical structure so as to produce a sequential nonuniformity in the acoustic emission, and the physical structure of the acoustic emitter is configured so as to encode data into the acoustic phrase in the sequential nonuniformity of the acoustic emissions. The station is adapted to register the vehicle event in response to receiving the acoustic emission, registering the vehicle event including communicating the vehicle event to the oversight system, and the oversight system is adapted to aggregate a plurality of the vehicle events from a plurality of the stations, and to execute an intervention in response thereto.

The encoded data may include vehicle detection data adapted to facilitate detection of the vehicle event from the acoustic emission, the station may be adapted to recognize the vehicle detection data, registering the vehicle event may include registering the detection data, and the intervention may include a response to the detection data. The encoded data may include vehicle information data regarding the vehicle, the station may be adapted to recognize the vehicle information data, registering the vehicle event may include registering the vehicle information data, and the intervention may include a response to the vehicle information data. The encoded data may include validation data adapted to facilitate distinguishing a genuine validation status of the vehicle from a counterfeit validation status of the vehicle, the station may be adapted to determine the validation status of the vehicle from the acoustic emission, registering the vehicle event may include registering the validation status, and the intervention may include a response to the validation data. The encoded data may include recognition data adapted to facilitate user audible recognition of the acoustic emission.

In another embodiment a method is provided, including engaging an acoustic emitter with the vehicle such that a vehicle event actuates the acoustic emitter to produce an acoustic emission, configuring a structure of the acoustic emitter so as to produce a sequential nonuniformity in the acoustic emission, and configuring the structure of the acoustic emitter so as to encode data in the sequential nonuniformity of the acoustic emissions. The method includes receiving the acoustic emission in a station and registering the vehicle event via the station in response to receiving the acoustic emission, wherein registering the vehicle event includes communicating the vehicle event to an oversight system. The method includes aggregating a plurality of the vehicle events from a plurality of the stations in the oversight system, and executing an intervention in response to the aggregated vehicle events via the oversight system.

BRIEF DESCRIPTION OF THE SEVERAL VIEWS OF THE DRAWINGS

Various objects, features, and characteristics will become more apparent to those skilled in the art from a study of the following Detailed Description in conjunction with the appended claims and drawings, all of which form a part of this specification. While the accompanying drawings include illustrations of various embodiments, the drawings are not intended to limit the claimed subject matter.

FIG. 1A through FIG. 1D depict an example remote and an example container adapted to dispense eye drops, in cross-section view.

FIG. 7A and FIG. 7B depict an example remote and an example container adapted to ointment, in cross-section view.

FIG. 8A and FIG. 8B depict an example remote with two parallel emitters and an example container, in cross-section view.

FIG. 10A through FIG. 10C depict an example remote with an emitter operating in two functions and an example container, in cross-section view.

FIG. 12A through FIG. 12D depict an example emitter integrated with an example container, in cross-section view.

FIG. 15A through FIG. 15D depict an example remote adapted to indicate motion thereof and dispensing of medication from an example container, in cross-section view.

FIG. 17A and FIG. 17B depict an example remote with an electrical acoustic emitter and an example container, in cross-section view.

FIG. 18A and FIG. 18B depict an example remote with an electrical optical emitter and an example container, in cross-section view.

Figure 2A:
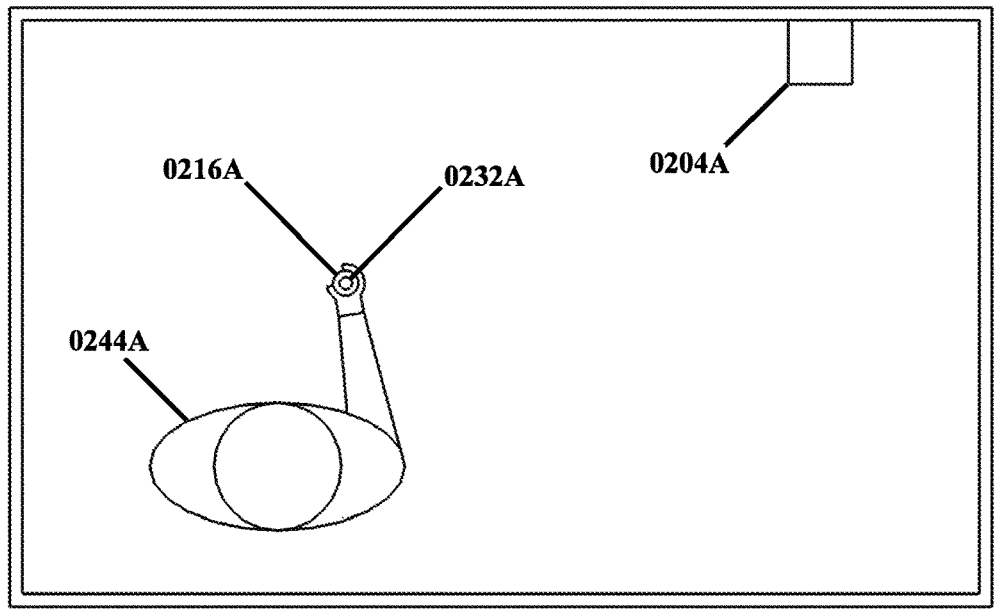
FIG. 2A and FIG. 2B depict an example station and an example remote as may be utilized by an individual, in top-down view.

The figures depict various embodiments described throughout the Detailed Description for the purposes of illustration only. While specific embodiments have been shown by way of example in the drawings and are described in detail below, the technology is amenable to various modifications and alternative forms. The intention is not to limit the technology to the particular embodiments described. Accordingly, the claimed subject matter is intended to cover all modifications, equivalents, and alternatives falling within the scope of the technology as defined by the appended claims.

DETAILED DESCRIPTION OF THE INVENTION

Various embodiments are described herein that relate to determining the use of a medication through transparent consequential characteristic emissions. Typically though not necessarily, embodiments may include a station adapted to detect and identify a characteristic acoustic emission (such as a musical pitch at a particular frequency), that acoustic emission being produced by a remote that is engaged or proximate to a medication container. The acoustic emission may be transparent, in that the user may not be required to take any particular action not already being performed in order to dispense or take the medication. The acoustic emission also may be consequential, in that actions performed to dispense or take the medication may produce the acoustic emission as a consequence thereof without (for example) requiring a user to make a choice, "arm" or activate an emitter, a processor to execute instructions, a secondary system to be activated, etc., in order to produce that acoustic emission. For example, the acoustic emission may be a purely mechanical consequence of dispensing medication (though other arrangements may be suitable). The acoustic emission also may be characteristic, in that the emission may be reliably recognizable as coming from the remote, distinct from background noise. In addition, the acoustic emission may be purposed, in that the remote may be configured specifically to produce the acoustic emission as a function that is not necessary to dispense the medication itself, rather than the emission being purely incidental from the operation of a type of container (for example, an unmodified "hiss" noise that an inhaler may produce expelling vapor with a puff of air).

It is noted that not all embodiments necessarily must exhibit all such features of emissions: transparent, consequential, characteristic, and purposed. Certain embodiments may not be fully user-transparent, for example, and/or other such features may not be present in all embodiments. In addition, even when present such features are not required to be absolute. For example, a characteristic acoustic emission may not be (and may not be required to be) absolutely unique, or perfectly identifiable. The presence of features and the degree to which each feature is present may vary from one embodiment to another, so long as the functionality described herein is enabled.

With reference now collectively to FIG. 1A through FIG. 3, aspects of structure and function of example arrangements for determining the dispensing and/or use of a medication are shown. As illustrated, a remote and a station cooperate in such determinations. The remote is adapted to purposefully produce a characteristic acoustic emission in user-transparent and consequential response to some action associated with taking a medication; for example, a characteristic whistle pitch may be emitted by the remote as an eyedrop is dispensed. The station then receives that acoustic emission, and registers a medication-associated event as having taken place based on that acoustic emission.

More particularly, with reference now to FIG. 1A through FIG. 1D, therein is shown an example remote and arrangements for producing an acoustic emission, illustrated in cross-section view.

In FIG. 1A, a remote 0116A is shown. The remote 0116A is shown as approximately spherical in shape, truncated at top and bottom. The example remote 0116A shown includes a wall 0122A enclosing an interior containing a volume of air. In addition, the remote 0116A includes an acoustic emitter 0118A. In the example shown the acoustic emitter 0118A is in the form of a whistle, enabling airflow through the acoustic emitter 0118A between the interior of the remote 0116A and the environment surrounding the remote 0116A. In addition, the remote 0116A has a container 0132A engaged therewith, shown disposed within an aperture of the remote 0116A. It is noted that the container 0132A may not necessarily be considered part of the remote 0116A; while a remote 0116A that includes a container 0132A as a component thereof (e.g., rather than accommodating a container therein, otherwise engaging with a container, etc.) is not prohibited, neither is such required.

Turning to FIG. 1B, an arrangement at least somewhat similar to that in FIG. 1A is shown. A remote 0116B with a wall 0122B and an acoustic emitter 0118B is shown, with a container 0132B engaged therewith. However, in FIG. 1B the wall 0122B of the remote 0116B is slightly indented to either side. Typically though not necessarily, such indentation may be a result of compression applied to the remote 0116B. The wall 0122B of the remote 0116B may be flexible so as to readily deform and return to an original shape.

In addition, attention is drawn to the shape of the container 0132B. Given a remote 0116B having a flexible wall 0122B with air enclosed therein, when pressure is applied to the remote 0116B at least some of that pressure may be transmitted to the container 0132B disposed within the remote 0116B. Thus, if the container 0132B is flexible the container 0132B also may deform to some degree. (The degree of deformation as shown is explanatory, and is not necessarily intended to reflect a real physical system; actual deformation of a flexible wall 0116B and/or a flexible container 0132B may be extremely complex, and the particulars of such deformations are not limiting.)

Moving on to FIG. 1C, again an arrangement at least somewhat similar to that in FIG. 1A and FIG. 1B is shown, with a remote 0116C having a wall 0122C and an acoustic emitter 0118C, and a container 0132C engaged therewith. However, as may be seen in FIG. 1C the wall 0122C is more extensively deformed than in FIG. 1B; the sides of the wall 0122C are visibly deeply indented. Likewise, the sides of the container 0132C are also deeply indented.

Given such deformation of the remote 0116C as shown in FIG. 1C, the volume available for air inside the wall 0122C may be reduced. Consequently, air may be communicated from inside the wall 0122C to the outside environment via the acoustic emitter 0118C. For an acoustic emitter 0118C in the form of a whistle as shown in FIG. 1C, such flow of air may cause the acoustic emitter 0118C to produce an acoustic emission 0120C (shown as radiating wave fronts for explanatory purposes; in practice acoustic emissions may not be visible). In more colloquial terms, the whistle may make a pitch if the remote 0116C is squeezed, e.g., by a user's hand.

In addition, given such deformation of the container 0132C as shown in FIG. 1C, the volume inside the container 0132C likewise may be reduced. Consequently, depending on the orientation of the container 0132C, the amount of material (if any) contained therein, etc., some of the contents of the container 0132C may be expelled. No such expelled contents are shown in FIG. 1C; given the vertical orientation of the container 0132C, and the depiction of the container 0132C as a squeeze bottle (such as an eye drop bottle), contents thereof may not necessarily be expelled.

However, in FIG. 1D an arrangement at least somewhat similar arrangement is shown that does include expelled contents of a container. As may be seen, the remote 0116D shown therein has a wall 0122D and an acoustic emitter 0118D, and a container 0132D is engaged therewith. The wall 0122D is again deeply indented, and the sides of the container 0132D also are also deeply indented. However, in the arrangement shown in FIG. 1D, the remote 0116D and the container 0132D engaged therewith are inclined approximately 135 degrees from vertical. In addition, the remote 0116D is positioned such that the nozzle of the container 0132D is disposed over the eye 0148D of a user.

Consequently, as the remote 0116D is compressed, container 0132D also is compressed, and a dispersal 0142D of medication (shown in the form of a droplet of liquid) is dispensed from the container 0132D; given the relative disposition of container 132D and eye 0148D, it may be anticipated that the medication will fall into the eye 0148D. In addition, as in FIG. 1C the compression of the remote 0116D has reduced the volume within the wall 0122D, and air passing through the acoustic emitter 0118D has produced an acoustic emission 0120D. To again use colloquial terms, as the remote is squeezed to dispense medication, and because the remote is so squeezed, the whistle sounds. (It is noted that, for an eyedrop bottle, it may not be typical to squeeze the container while in a vertical orientation. The orientation of the remote and container in FIG. 1C is shown as an example illustrating acoustic emission, rather than implying that FIG. 1C is necessarily part of a rigid sequence of events in dispensing medication.)

Several aspects of such an arrangement may be worthy of further description and/or emphasis.

First, it is noted that the acoustic emission 0120D in FIG. 1D is purposed, rather than incidental. For example, the acoustic emission 0120D under consideration in FIG. 1D is one that is produced deliberately, through the addition of an air bladder and a whistle. This may be understood as distinct from sounds that may be incidental, such as the sound of a container being compressed, of a droplet landing in a user's eye, etc. The acoustic emission 0120D in FIG. 1D is an additional noise that is produced deliberately and with purpose (and, as will be explained in greater detail subsequently herein, with a particular function), rather than being an environmental noise.

Second, given that the acoustic emission 0120D is produced on purpose, e.g., by providing the acoustic emitter 0118D in the remote 0116D and engaging the remote 0116D with the container 0132D, the nature of the acoustic emission 0120D may be selected. The acoustic emission 0120D thus may be characteristic, that is, may exhibit properties that render the acoustic emission 0120D readily identifiable. For example, the acoustic emitter 0118D may produce a whistle pitch at a particular frequency and/or volume, two or more frequencies together, etc. By selection of such properties, the acoustic emission 0120D may be recognizable from background noise, and/or unlikely to be mistaken for other sounds.

Third, production of the acoustic emission 0120D may be understood to be a consequential result of dispensing the droplet 0142D of medication. That is, it may not be necessary for the squeeze to be detected with a sensor, or for such a sensor or a processor to activate an electrical system that generates sound, etc. Rather, squeezing the remote 0116D causes the acoustic emission 0120D as a consequence of the squeeze, without other active intervention. Such an arrangement may also be described as in some sense "passive", in that the act of dispensing the medication (e.g., squeezing the remote) in itself causes a characteristic sound to be produced. However, as action typically may be taking place— e.g., an acoustic emission may be produced—the term "consequential" typically may be used herein.

Fourth, the production of the acoustic emission 0120D also may be viewed as transparent from the perspective of a user of the medication. That is, the user may not be required to take an additional action beyond dispensing the medication in order to produce the acoustic emission 0120D. In the example of FIG. 1D, squeezing the remote 0116D to dispense a droplet 0142D produces the acoustic emission 0120D without other conscious action by the user when attempting to use the medication. (And as described subsequently herein, that acoustic emission 0120D then may cause the use of the medication to also be registered without additional conscious action by the user.) Thus the user may not be required to consciously activate the acoustic emitter 0118, or to document the use of the medication, inform or report that the medication was used, etc.

Turning now to FIG. 2A, a remote 0216A is shown with a container 0232A engaged therewith. The remote 0216A is shown to be in the hand of a user 0244A, within some enclosed space (not numbered). In addition, a station 0204A is shown at some distance from the user 0244A and the remote 0216A.

As noted previously with regard to FIG. 1A through FIG. 1D, a remote 0216A such as is shown in FIG. 2A may produce an acoustic emission as the remote 0216A is manipulated in a manner associated with dispensing a medication, e.g., squeezing the remote 0216A to squeeze the container 0232A so as to dispense medication may activate a whistle.

Figure 2B:
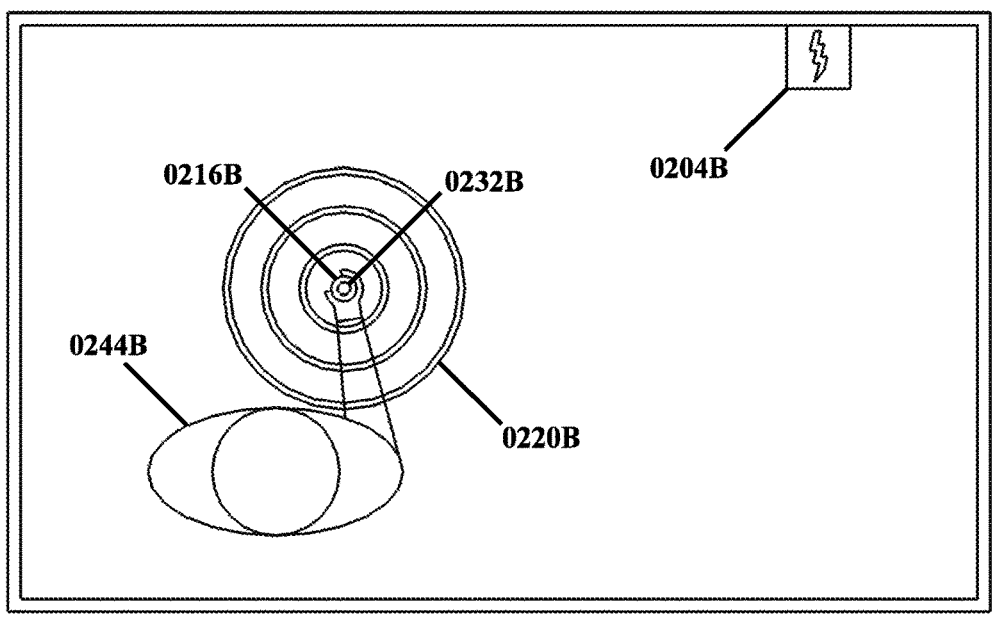

Turning to FIG. 2B, a circumstance is shown wherein such an acoustic emission is produced. At least somewhat similarly to FIG. 2A, the arrangement in FIG. 2B shows a remote 0216B in the hand of a user 0244B, and a container 0232B engaged with the remote 0216B. A station 0204B also is shown. In addition, the remote 0216B is depicted to be producing an acoustic emission 0220B (an acoustic emitter is not individually illustrated) radiating from the remote 0216B. The station 0204B is also shown to be active (indicated by the lightning bolt). More regarding stations and activation thereof is described subsequently herein, however typically the station 0204B may be understood as receiving the acoustic emission 0220B, e.g., with a microphone or similar receiver.

Thus, in the arrangement of FIG. 2B, the remote 0216B produces an acoustic emission 0220B in a transparent and consequential response to an event associated with dispensing medication from the container 0232B; and the station 0204B receives that acoustic emitter.

It is noted that the body position of the user 0244B in FIG. 2B—standing with hand partially extended and holding the remote 0216B and container 0232B—may not correspond with a typical body position for dispensing an eye drop (e.g., with the head tilted back and the bottle inclined over an eye). This is deliberate, so as to emphasize that embodiments are not limited only to eye drops or to any particular medication, and that events producing an acoustic emission 0220B are not limited only to dispensing the medication. For example, pills, ointments, etc. also may be so dispensed, from bottles, squeeze tubes, etc. Likewise, acoustic emissions may be triggered by contextual events that are not dispensing actions themselves but are otherwise associated with dispensing medication. For example, removing the cap of a container, shaking a bottle to mix a medication, etc. may trigger an acoustic emission. While removing the cap of a medication container may not constitute taking the medication, removing the cap still may be associated with taking the medication, and thus an acoustic emission upon removing the cap may be indicative that a medication has been taken.

Thus, while perhaps not typical for dispensing an eye drop, the body position in FIG. 2B may be suitable for at least some such actions.

Figure 3:
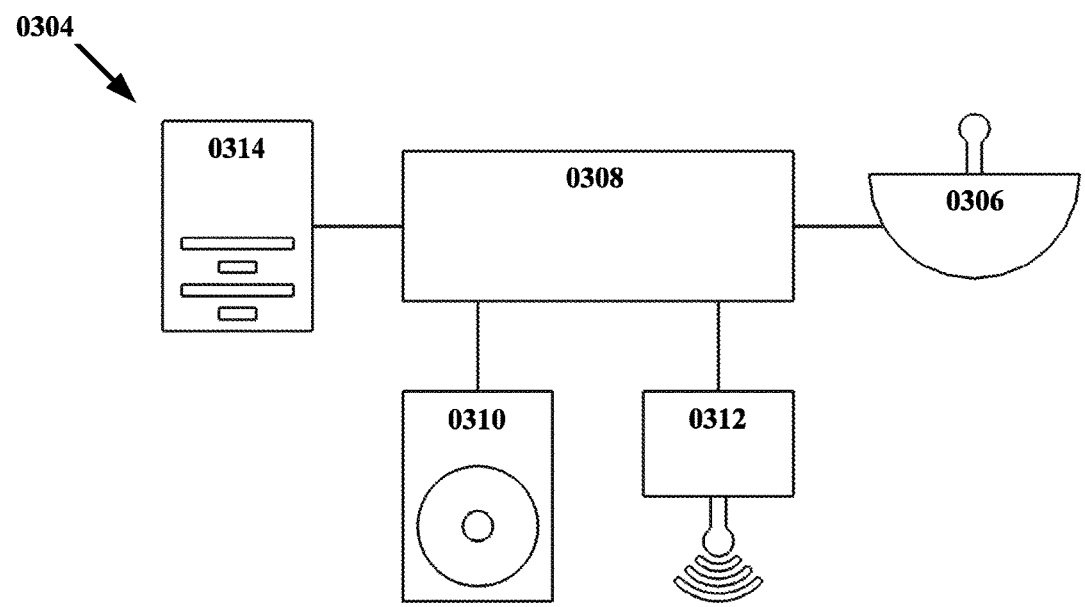
FIG. 3 depicts an example station, in schematic view.

Moving on to FIG. 3, a schematic of an example station 0304 is shown therein. The station 0304 includes an acoustic receiver 0306, adapted to receive acoustic emissions. A processor 0308 is in communication with the receiver 0306. A power supply 0314 is also shown, along with a data store 0310 adapted to store information, and a communicator 0312 adapted to communicate (e.g., send and/or receive) information with some external entity. It is noted that not all elements will necessarily be present in all embodiments, and that embodiments may exhibit other elements and/or other configurations. For example, it may not be necessary to communicate the data externally if the data may be stored, thus if a data store 0310 is present a communicator 0312 may not be present (or vice versa), etc.

So long as the station 0304 is capable of performing the necessary functions, the particulars thereof are not limited. Likewise, substantially any device and/or group of devices providing adequate functional capabilities may be suitable. For example, certain electronic devices such as desktop computers, laptop computers, tablets, smart phones, other smart devices, etc. may include a microphone and processor (and/or other elements such as a power supply, data store, communicator, etc.). Thus for at least certain embodiments a smart phone may serve as a station 0304. Typically though not necessarily, executable instructions may be instantiated onto a processor in a smart phone or other device so employed, so as to support certain functions described herein. Use of a smart phone or other portable electronic device may exhibit certain advantages, for example in that a user may already have a smart phone and routinely keep their smart phone nearby. However, use of a dedicated station 0304 also may be suitable. Dedicated stations also may exhibit certain advantages. For example, a unit adapted to plug in to a wall socket also may not be subject to issues regarding low battery, etc.

A given remote and station are not necessarily required to be engaged in a one-to-one correspondence. That is, a single remote may be used in cooperation with multiple stations, and/or a single station may be used in cooperation with multiple remotes. Thus, for example, a user may have remotes for several different medications, all of which cooperate with the user's smart phone as a station. Conversely, a user may have receivers in several rooms of a dwelling (or other space), so that acoustic emissions may be received no matter where the user is in that dwelling.

More description regarding functions of individual elements in a station 0304 such as is shown in FIG. 3 is presented below.

Figure 4:
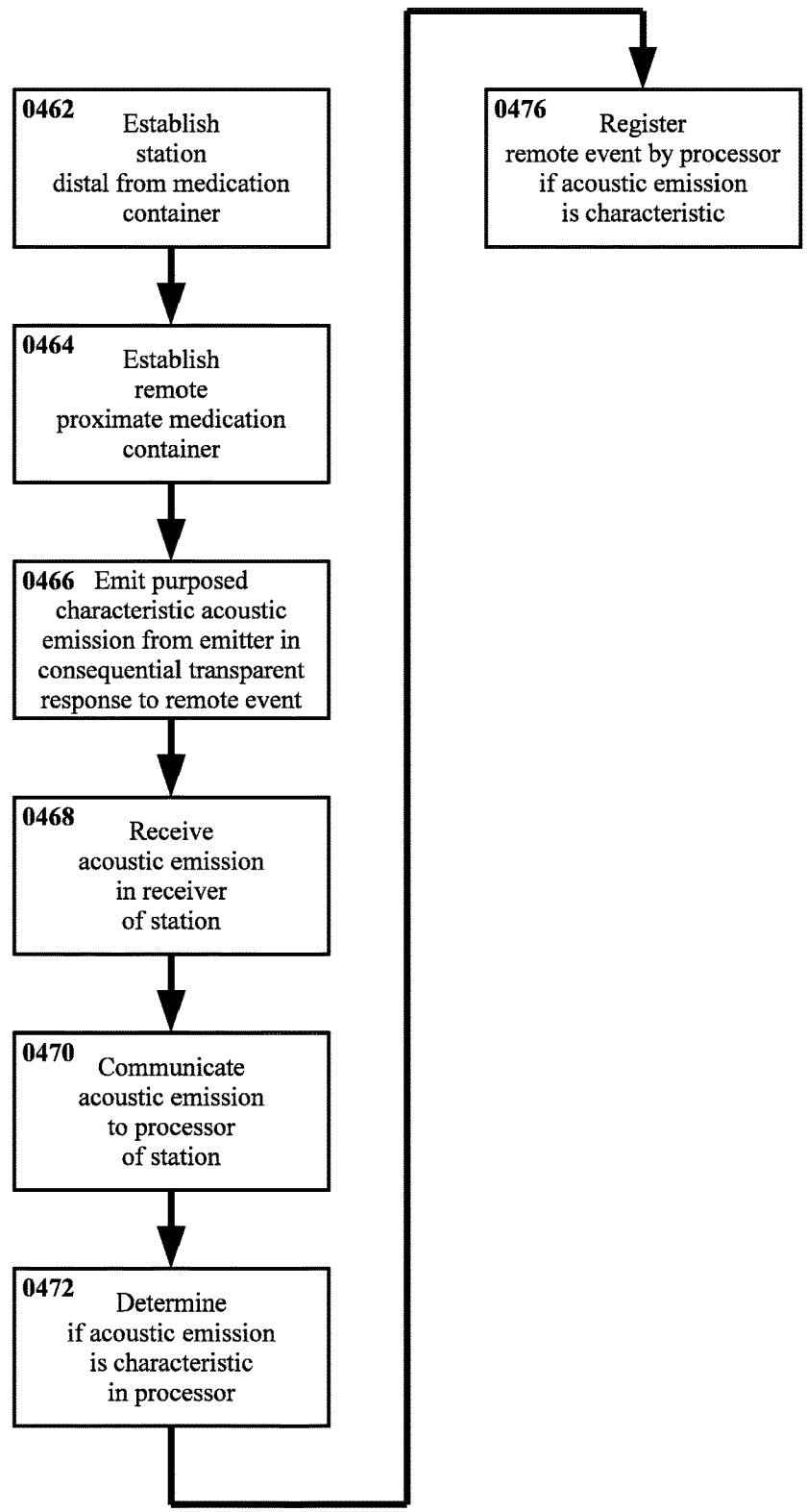
FIG. 4 depicts an example method for determining the use of a medication through transparent consequential characteristic emissions, in flow chart form.

Now with regard to FIG. 4, an example method for determining use of medication through transparent and consequential response to a remote event associated with dispensing said medication is illustrated, in flow chart form.

In the method of FIG. 4, a station is established 0462 at some location distal from a medication container. The physical distance is not limited and may vary not just for different embodiments but also over time for a particular embodiment, however typically (though not necessarily) the station may be sufficiently distant from the medication container as to not be in physical contact therewith.

A remote is established 0464 at some location proximate the medication container. Again, the physical distance is not limited, but typically (though not necessarily) the remote may be physically engaged with the medication container. For example, the medication container may be disposed within the remote, physically coupled to the remote, etc.

In a consequential and transparent response to some event affecting the remote and in association with dispensing medication, a purposed characteristic acoustic emission is emitted 0466 from the remote. For example, as described with regard to FIG. 1A through FIG. 2 a sound such as a whistle may be produced by squeezing the remote in order to expel medication from the container. The acoustic emission may be emitted 0466 as a direct result of dispensing the medication. However, as noted previously remote events (that is, events relating to the remote in some manner) that are contextual to dispensing medication also may be suitable for consideration. The acoustic emission also may be emitted 0466 in a manner that is user-transparent.

Still with reference to FIG. 4, the acoustic emission is received 0468 in the receiver of the station. For example, a microphone in a smart phone may pick up a whistle emitted from a remote. The acoustic emission (or some electronic signal representing the acoustic emission, etc.) is communicated 0470 to the processor of the station. Within the processor, a determination is made 0472 as to whether the acoustic emission that has been received (in step 0468) is indeed characteristic of the remote. A given acoustic receiver may receive numerous sounds, including but not limited to ambient noise, conversation, music being played nearby, etc. As noted, the acoustic emission emitted 0466 by the remote is in some manner characteristic, e.g., with a particular pitch or combination of pitches, etc. Thus the processor may determine 0472, for example by comparing a received sound against some standard instantiated onto the processor, whether a given sound is or is not the acoustic emission from a remote.

If the acoustic emission is determined 0472 to be characteristic of the remote, then a remote event is registered 0476 by the processor. That is, if the processor determines that the remote has made its characteristic sound, it is considered that whatever event causing that sound to be made has taken place. If the event in question is dispensing medication, then it is considered that the medication has been dispensed. If the event in question is contextual, such as removing the cap of a container, then it is considered that the cap has been removed. Further conclusions also may be determined in certain embodiments, e.g., it may be determined that if the cap has been removed, the medication also has been dispensed. Such determinations may be absolute, e.g., yes or no, or may be associated with some confidence value, e.g., high confidence, 92% confidence, class I confidence, etc.

How the event is registered 0476 is not limited. The event may be flagged for transmission to some other entity (a database, another processor, a human monitor, etc.), may be flagged for storage in a data store (such as a hard drive, solid state drive, etc.), or otherwise noted in some fashion. In addition, the precise information that may be registered 0476 is not otherwise limited. Information may be as minimal as the fact that the event was detected to have occurred (that is, that the sound was received and identified), but may also include other information. For example, the time that an event was identified as having occurred may be registered (whether with the fact of the event explicit or implicit in there being a time of occurrence), and/or may include other information such as confidence of identification of the acoustic emission, confidence that a contextual event corresponds with the medication being dispensed, the characteristic sound itself, identifying information such as an ID for the processor, station as a whole, remote, etc., patient name or reference number, the type/dose of medication, etc.

What, if anything, is done if a sound is received but not determined to be the characteristic acoustic emission of the remote is not limited. In certain instances such sounds also may be registered in some manner, e.g., as non-characteristic sounds that may be safely excluded from consideration, as potentially characteristic but with low confidence, etc. However, in other instances it may be suitable simply to ignore non-characteristic sounds and take no action in response.

Figure 5:
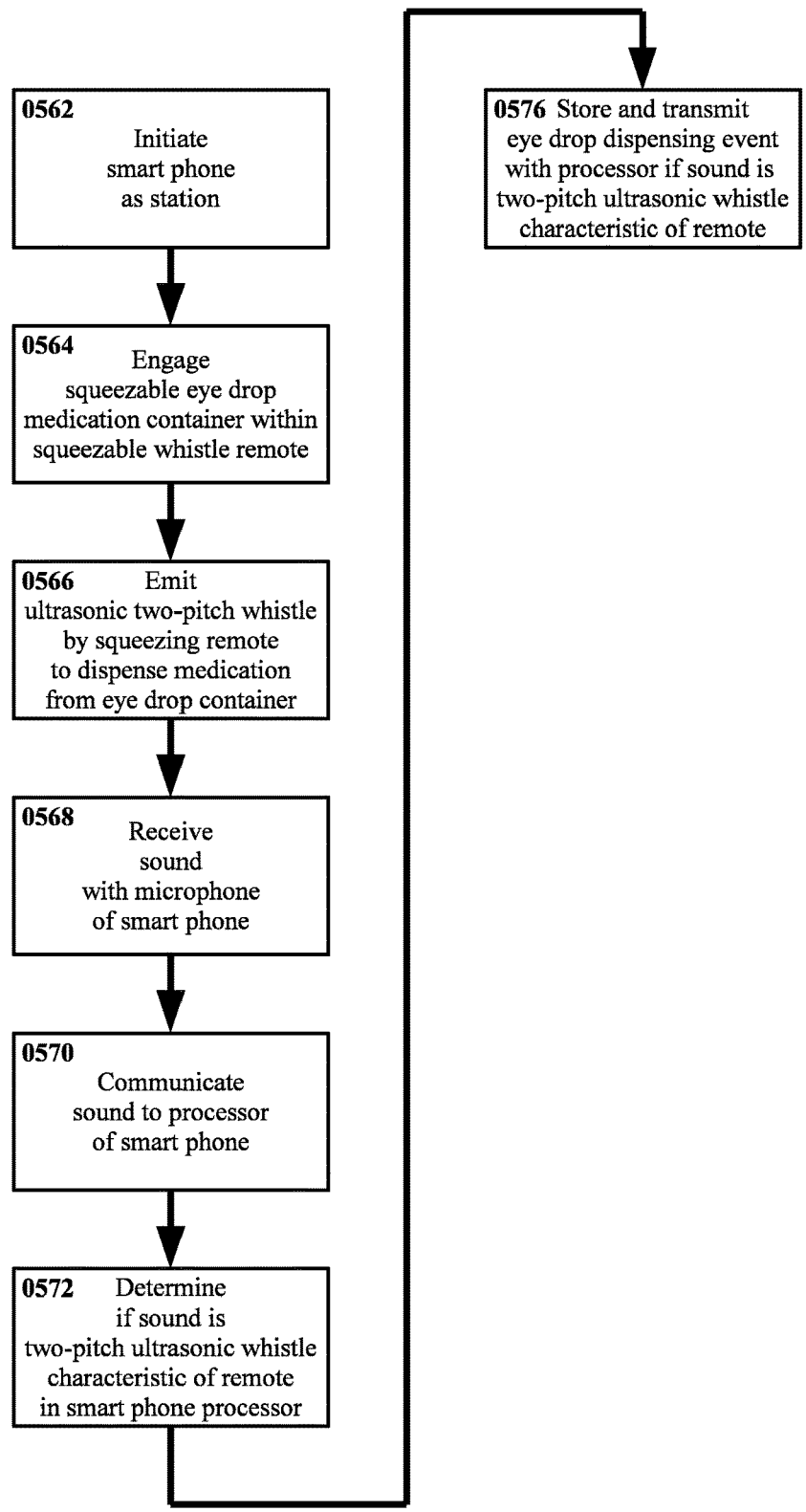
FIG. 5 depicts another example method for determining the use of a medication through transparent consequential characteristic emissions, with concrete reference to a squeezable whistling remote and a smart phone as a station, in flow chart form.

Moving on to FIG. 5, for clarity a highly concrete example method is presented that may be similar to that in FIG. 4 but that is also a more specific embodiment. Namely, the method in FIG. 5 refers to an arrangement using a squeezable remote and a squeezable eye drop container disposed therein such as illustrated in FIG. 1A through FIG. 1D, an eye drop medication, and a smart phone serving as a station. It is emphasized that such particulars are examples only, and are not limiting.

In the method of FIG. 5, a smart phone is initiated 0562 as a station. For example, executable instructions and/or data may be instantiated onto the processor of the smart phone. As a more colloquial example, a medication tracking application or "app" may be loaded onto the phone. Alternately, such an app (and/or other instructions/data) may already be present on the smart phone (e.g., having been previously installed as part of a package of basic software), in which case initiation may simply be running the app or similar.

Continuing in FIG. 5, a squeezable eye drop container is engaged 0564 within a squeezable whistle remote. For example, as shown in FIG. 1A through FIG. 1D the remote may be a flexible, roughly spheroid air-filled body with a whistle incorporated therein, and defining an aperture to accept a medication container therein.

The remote emits 0566 an ultrasonic two-pitch whistle, wherein the two pitches are at specific frequencies. Thus for this example, as the remote is squeezed the container also is squeezed; when an eye drop is to be dispensed, the remote is squeezed so as to squeeze the container. However, so squeezing the remote also causes air to pass through the whistle, the whistle being configured to produce the two ultrasonic pitches. (In practice the "whistle" may not be singular, rather two distinct mechanisms may each produce one pitch. Embodiments are not limited in this regard.) Such an acoustic emission may be considered characteristic, in that the number of phenomena that may simultaneously produce two specific pitches in the ultrasonic range may be small, and consequently detecting that particular combination of pitches may be treated as a reliable indication that the sound is coming from the remote.

A sound is received 0568 with the microphone of the smart phone that is serving as a station in the example of FIG. 5. The sound may be the acoustic emission, in this example the ultrasonic two-pitch whistle, but other sounds may be received by the microphone. The sound is communicated 0570 to the processor of the smart phone. Although the sound is referred to as being communicated, processed, etc., it is noted that sound itself may not literally be communicated or otherwise manipulated; rather, the microphone in receiving 0568 the sound may generate an electronic signal therefrom, with this signal or some portion thereof then being communicated to the processor, processed therein, etc.

In the processor of the smart phone, a determination is made 0572 as to whether the sound in question is characteristic of the remote. In the example of FIG. 5, this may include a determination of such factors as to whether two pitches are present, whether each pitch is of the proper frequency, whether the waveforms of the pitches correspond with what may be expected for a whistle (as opposed to, for example, pitches generated electronically, pitches generated by vibrations of a string, etc.), whether the two pitches were received (thus presumably produced) at approximately the same time, etc. The factors that may be considered are not limited.

If the sound in question is determined 0572 to be the two-pitch ultrasonic whistle characteristic of the remote, an eyedrop dispensing event (that is, that the medication in the container has been dispensed) is recorded 0576 in a data store by the processor, and is also transmitted 0576 to some external entity by the processor. Thus in this instance, registration of the event corresponds to both storing and communicating the event.

It is again emphasized that the arrangements in FIG. 5 are an example only, and while the particulars therein are presented for clarity those particulars do not limit embodiments. For example, medication containers may be other than eye drop bottles, including but not limited to other squeeze bottles, boxes or tubes such as may dispense pills, tubes as may dispense ointments, hypodermic syringes as may dispense injectable medications, shakers as may dispense powders, etc. Indeed, in certain embodiments the container may not contain a medication at all, but rather some other material to be dispensed. Also, at least in principle other non-medication actions may be signaled similarly, e.g., use of a device for physical therapy may be configured similarly with a remote so as to produce whistles or other acoustic emissions in a fashion similar to the remotes shown in FIG. 1A through FIG. 1D.

Likewise, the type(s) of medication (and/or other materials) as may be dispensed is not limited. The acoustic emissions are not limited, and may vary considerably. While ultrasonic emissions may be useful in certain regards (for example in avoiding distraction of a user), and the use of two distinct pitches or other components likewise may be useful (for example in make the emission more distinctive), and whistles also may be useful in generating acoustic emissions (for example being inexpensive, easily mass-produced, and reliable), other arrangements may be equally suitable. Furthermore, as previously noted, while a smart phone or similar portable electronic device may present certain advantages as a station, such as already being widely available and frequently carried on users' persons, the use of smart phones as stations also is an example only.

Now with reference to FIG. 6A through FIG. 6D, as noted previously embodiments are not limited only to eye drop bottles as containers. FIG. 6A through FIG. 6D show an example arrangement for a pill bottle as may be used to contain and dispense pills, tablets, capsules, etc. The arrangements in FIG. 6A through FIG. 6D may be at least somewhat similar to those in FIG. 1A through FIG. 1D, with a different container (and as noted previously, the container is not necessarily part of a given embodiment).

Figure 6A:
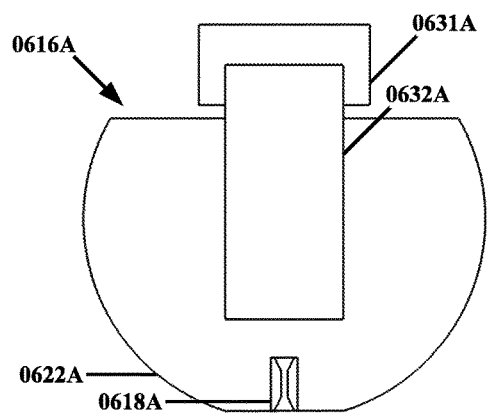
FIG. 6A through FIG. 6D depict an example remote and an example container adapted to dispense pills, in cross-section view.

In FIG. 6A, a remote 0616A is shown, approximately spherical in shape and truncated at top and bottom. The remote 0616A includes a wall 0622A enclosing an interior containing a volume of air, and an acoustic emitter 0618A illustrated in the form of a whistle (though such is not limiting). A container 0632A is engaged with the remote 0616A, disposed within an aperture of the remote 0616A. The container 0632A includes a cap 0631A therefor, as may for example engage with the container 0632A with screw threads, through a friction fit, a "child-proof" safety latch, etc.

Figure 6B:
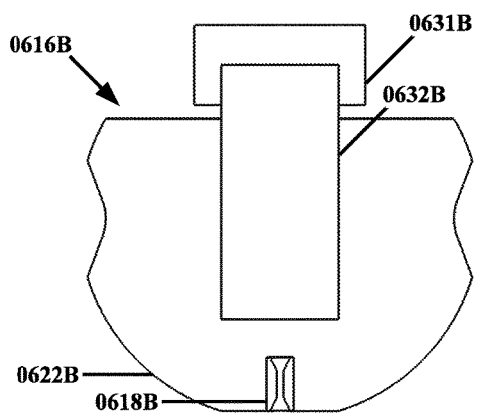

In FIG. 6B, a remote 0616B with a wall 0622B and an acoustic emitter 0618B is shown, with a container 0632B having a cap 0631B engaged therewith. The wall 0622B of the remote 0616B is slightly indented to either side, for example as may be a result of compression applied to the remote 0616B in picking up the remote 0616B.

Figure 6C:
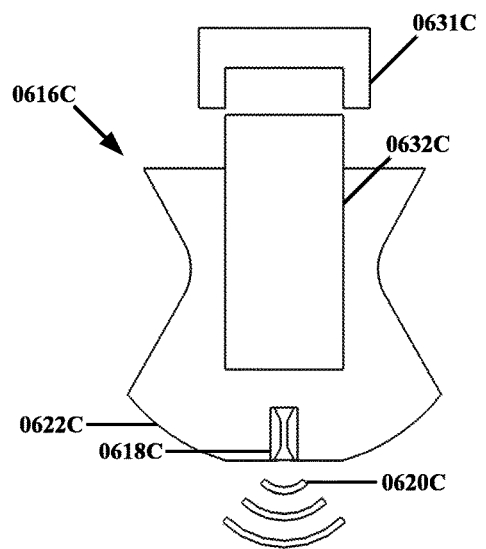

Moving on to FIG. 6C, again a remote 0616C is shown having a wall 0622C and an acoustic emitter 0618C, along with a container 0632C with a cap 0631C engaged therewith. As may be seen the sides of the wall 0622C are deeply indented. In addition, the cap 0631C is shown as separated from the container 0632C. Such deformation as shown in FIG. 6C may result for example from a user gripping the remote 0616C with sufficient strength as to unthread a cap, pop off a friction fitted cap, etc. When such deformation of the remote 0616C occurs, the volume available for air inside the wall 0622C may be reduced. Air may be communicated from inside the wall 0622C to the outside environment via the acoustic emitter 0618C, causing the acoustic emitter 0618C to produce an acoustic emission 0620C. Thus, as the container 0632C is opened the whistle may produce a pitch.

Figure 6D:
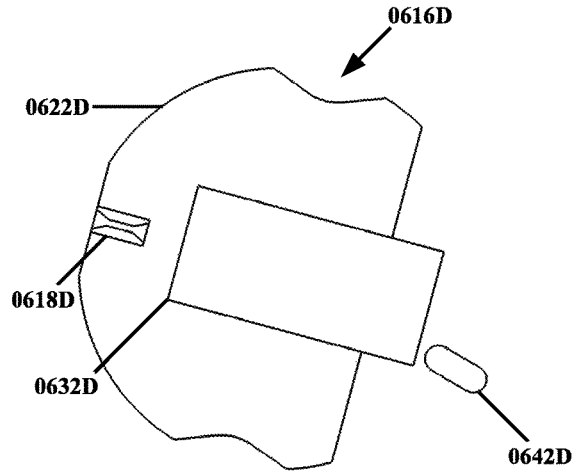

Now with regard to FIG. 6D, an arrangement is shown with a remote 0616D having a wall 0622D and an acoustic emitter 0618D, and a container 0632D engaged therewith. The container 0632D is not shown to have a cap. The remote 0616D and the container 0632D engaged therewith are inclined approximately 120 degrees from vertical. A dispersal 0642D in the form of a pill is shown near and slightly below the mouth of the container 0632D, as may occur when the container 0632D is dispensing medication. In addition, the wall 0622D is slightly indented, for example as may be produced by pressure applied by a user holding and/or manipulating the container 0632D. Thus, the arrangement of FIG. 6D may be understood to show the container 0632D dispensing a dispersal 042D of medication.

It is noted with regard to FIG. 6C and FIG. 6D, an acoustic emission 0620C is produced upon opening the container 0632C as shown in FIG. 6C, but an acoustic emission is not shown upon dispensing a dispersal 0642D of medication in FIG. 6D. Such an arrangement may be considered to address a contextual event (e.g., opening the container) rather a medication event proper (e.g., dispensing/applying the medication). Thus, for arrangements similar to those of FIG. 6A through FIG. 6D a station (not shown in FIG. 6A through FIG. 6D) may receive an acoustic emission associated with dispensing and/or using a medication, without necessarily receiving an acoustic emission that indicates the act of dispensing medication (or using medication) per se. For at least certain embodiments, a station may determine that a medication has been dispensed/used based on such contextual events, without considering medication events themselves (though receipt and/or consideration of medication events, in addition to or in place of contextual events, is not prohibited).

Moving on to FIG. 7A and FIG. 7B, another example remote 0716A is shown, including a wall 0722A and an acoustic emitter 0718A. A container 0732A is engaged with the remote 0716A, disposed within an aperture of the remote 0716A. The container 0732A as illustrated is a squeeze tube, as may contain and dispense ointments or similar medications (and/or other materials).

In FIG. 7B, a remote 0716B with a wall 0722B and acoustic emitter 0718B is shown, with a container 0732B engaged therewith. As may be seen, the wall 0722B of the remote 0716B is deformed inwardly, in turn deforming the container 0732B so as to cause the container 0732B to dispense a dispersal 0742B of medication (illustrated as ointment on an approximately flat surface, such as the palm of a user's hand). In addition, in deforming the container 0732B the volume of air enclosed by the wall 0722B is reduced, expelling air through the acoustic emitter 0718B and producing an acoustic emission 0720B.

As noted previously, remotes are not limited only to engaging with containers for eye drops or similar (although eye drop containers are shown in certain examples herein). As seen in FIG. 6A through FIG. 6D pill bottles may be suitable, and as seen in FIG. 7A and FIG. 7B squeeze tubes also may be suitable. Other suitable containers may include, but are not limited to, hypodermic syringes and inhalers (e.g., "nebulizers").

In addition, with regard to FIG. 7B it may be observed that dispensing the dispersal 0742B of medication does not necessarily equate to administering the medication. That is, where in the arrangement previously shown in FIG. 1D expelling an eye drop 0142D from the container 132D into the user's eye 0148D is at least arguably both dispensing the medication and taking the medication. (Some period may elapse during which time the drop falls from the container into the eye, but such a period typically may be short enough to ignore for at least some purposes of determining whether medication has been administered.) However, in the arrangement shown in FIG. 7B the dispersal 0742B of medication is dispensed but not necessarily applied, e.g., rubbed into the skin, etc. Thus, dispensing a medication is not necessarily equivalent to using that medication. In a strict sense a dispensing event (e.g., dispensing medication) may be considered contextual to a medication event (e.g., actually administering the medication). Nevertheless, determining that a medication has been dispensed may be seen as indicating with high confidence that the medication also has been administered; typically it may be expected that if medication is dispensed, medication may also be administered. For example, removing an ointment from a tube (as in FIG. 7B) typically may precede applying that ointment to the skin (or other location), and circumstances wherein medication may be dispensed but not applied may be considered as uncommon. While other circumstances may be imagined—e.g., dispensing a pill and then dropping or otherwise losing the pill, etc., such circumstances may not be considered likely. Thus, barring unusual circumstances (or deliberate deception), it may be useful in at least certain instances to equate dispensing a medication with taking that medication, at least with some degree of confidence. Thus while embodiments may not necessarily determine concretely that medication is taken, determining that medication has been dispensed, that medication containers have been prepared for dispensing (e.g., opened), and so forth may be sufficient to infer that medication has indeed been taken, and/or to register the medication as having been taken.

However, which event or events are determined to occur, and/or the relationship of such events to the use of a medication, is not limited. For certain examples herein, the dispensing of the medication may be considered to be a defining event, given a remote that is engaged with a medication container. However, other arrangements also may be suitable.

Now with reference to FIG. 8A, another example remote 0816A is shown. The remote 0816A includes a wall 0822A, and a container 0832A is engaged with the remote. In addition, the remote 0816A is shown to include two acoustic emitters 0818A1 and 0818A2. As may be seen in FIG. 8B, an arrangement of dispensing medication from the container 0832B is shown. The remote 0816B is inclined, the wall 0822B thereof is indented inward, and a dispersal 0842B of medication is being dispensed into an eye 0848B. In addition, the acoustic emitters 0818B1 and 0818B2 are emitting acoustic emissions 0820B1 and 0820B2, respectively. The number of acoustic emitters in a given embodiment is not limited. Where certain examples herein show one acoustic emitter, others (such as FIG. 8A and FIG. 8B) show more than one.

In addition, what constitutes an acoustic emission 0818B1 and 0818B2 may vary considerably. As shown in FIG. 8B each of the acoustic emitters 0818B1 and 0818B2 produce an individual acoustic emission 0820B1 and 0820B2. For example, acoustic emissions 0820B1 and 0820B2 may be two whistle noises at different pitches. However, while it may be useful in certain instances to consider the acoustic emissions 0820B1 and 0820B2 individually (e.g., two emissions are being produced), it may be equally suitable to consider elements 0820B1 and 0820B2 as components of a single acoustic emission. Thus, multiple components may be considered as a single acoustic emission; likewise, the product of two or more acoustic emitters may be considered as a single acoustic emission. The precise structure and/or contents of an acoustic emission is not limited.

Figure 9A:
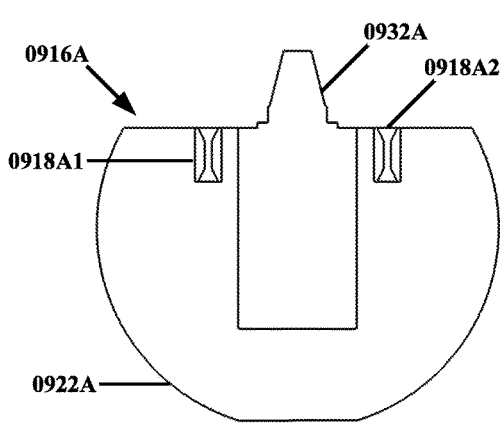
FIG. 9A through FIG. 9C depict an example remote with two sequential emitters and an example container, in cross-section view.
Figure 9B:
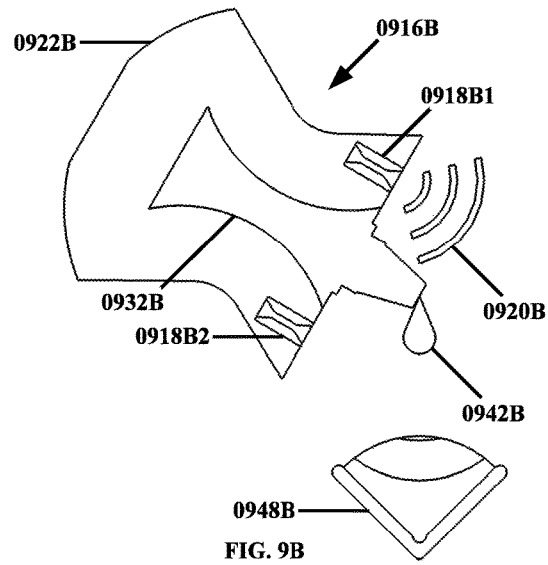

Now with reference to FIG. 9A, an arrangement at least somewhat similar visually to that of FIG. 8A is shown, with a remote 0916A that includes a wall 0922A and two acoustic emitters 0918A1 and 0918A2, and a container 0932A engaged with the remote 0916A. Turning to FIG. 9B, an arrangement wherein a remote 0916B is dispensing a dispersal 0942B of medication into an eye 0948B is shown; the remote includes a wall 922B and acoustic emitters 0918B1 and 0918B2. However, as may be seen only one acoustic emission 0920B is being produced, by acoustic emitter 0918B1; acoustic emitter 0918B2 is not producing an acoustic emission in FIG. 9B.

Figure 9C:
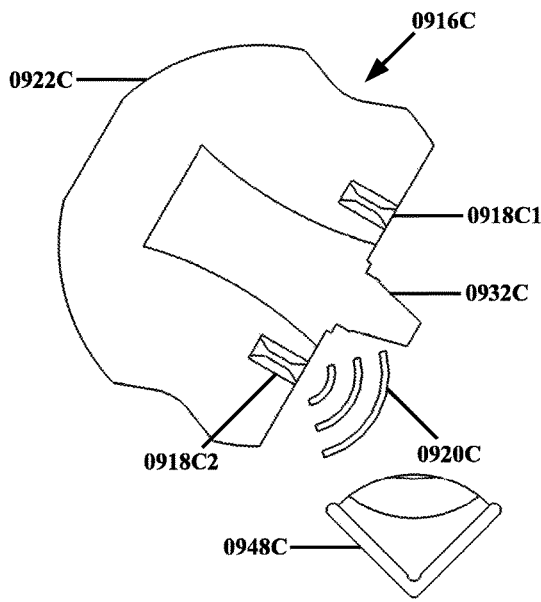

Moving on to FIG. 9C, a remote 0916C is shown including a wall 0922C and acoustic emitters 0918B1 and 0918B2, with a container 932C engaged with the remote 0916C. The wall 0922C is slightly indented, and the container 0932C is positioned over an eye 0948C, as may be the case after an eye drop has been dispensed (e.g., as shown in FIG. 9B). Thus the arrangement of FIG. 9C may represent a configuration of a remote 0916C as the wall 0922C elastically returns toward a default shape, drawing in air as the volume within the wall 0922C increases.

As may be seen, the acoustic emitter 0918C2 in FIG. 9C is producing an acoustic emission 0920C. Such an acoustic emission 0920C may be produced for example for an acoustic emitter 0918C2 such as a whistle that is configured to produce sound as air is drawn into the remote 0916C, rather than as air is expelled.

Several points are noted. First, the acoustic emission 0920C may be taken as indicating that a medication has been dispensed, even though the acoustic emission 0920C would not be coincident in time with dispensing the medication. That is, since the sound from acoustic emitter 0918C2 is produced as the remote 0916C relaxes towards a default state after being squeezed to expel medication, that sound is produced after the medication has already been dispensed. Such an arrangement—wherein acoustic emissions do not happen at (or necessarily even near) the same time as an event (in FIG. 9C, dispensing medication) that those acoustic emissions represent—may be suitable for at least certain embodiments.

Second, in viewing FIG. 9B and FIG. 9C together, two acoustic emissions 0920B and 0920C are produced one after the other. Thus, not all acoustic emissions must be produced together in time. In addition, as noted with regard to FIG. 7B, although it may be suitable to consider acoustic emissions 0920B and 0920C as distinct (e.g., as two separate sounds) it may be equally suitable to consider the combination of elements 0920B and 0920C as a single acoustic emission having two components. Moreover, it may be suitable to consider 0920B and 0920C as a single acoustic emission even if some time elapses between the production of element 0920B in FIG. 9B and element 0920C in FIG. 9C; sound need not be continuous in order to be considered as a single acoustic emission.

Third, regardless of whether acoustic emissions 0920B and 0920C are considered together or separately, not all acoustic emissions or components thereof need to be produced from the same physical action. In FIG. 9B the acoustic emission 0920B is produced as pressure is applied to the remote 0916B; in FIG. 9C the acoustic emission 0920C is produced as pressure on the remote 0916C is relaxed. Other variations and arrangements also may be suitable.

Now with reference to FIG. 10A, a remote 1016A is shown with a wall 1022A and an acoustic emitter 1018A. A container 1032A is engaged with the remote 1016A. Similarly in FIG. 10B a remote 1016B is shown with a wall 1022B and an acoustic emitter 1018B, with a container 1032B engaged therewith. The remote 1016B and container 1032B are inclined, and the container 1032B is dispensing a dispersal 1042B of medication into an eye 1048B. The acoustic emitter 1018B is producing an acoustic emission 1020B, e.g., a whistle as air is expelled from within the remote 1016B. Again in FIG. 10C, a remote 1016C is shown with a wall 1022C and an acoustic emitter 1018C, with a container 1032C engaged therewith. An acoustic emission 1020C also is being produced by the acoustic emitter 1018C, e.g., a whistle as air is drawn into the remote 1016C.

Thus in considering the examples of FIG. 10B and FIG. 10C together as different states of a single remote, an acoustic emitter 1018B and 1018C may produce more than one acoustic emission 1020B and 1020C. For example, one acoustic emission 1020B as air flows out and another acoustic emission 1020C as air flows in. Such an arrangement may be produced for example by a two-way whistle, though other arrangements may be suitable.

As noted previously, it may be equally suitable to consider the acoustic emissions 1020B and 1020C either independently or as components of a whole; acoustic emissions may be produced at different times, and/or in response to different actions, etc. In addition, it is noted that a single acoustic emitter (e.g., 1018B and 1018C assuming FIG. 10B and FIG. 10C to show the same embodiment in different states) may produce more than one acoustic emission 1020B and 1020C. Two such acoustic emissions (or components) 1020B and 1020C need not be identical, or even similar. For example, the acoustic emissions 1020B and 1020C may have different frequencies ("pitches"), waveforms, amplitudes, durations, etc. Embodiments are not limited with regard to how many acoustic emissions a given acoustic emitter may produce, the content/form thereof, or similarity among such acoustic emissions.

Figures 11A, 11B:
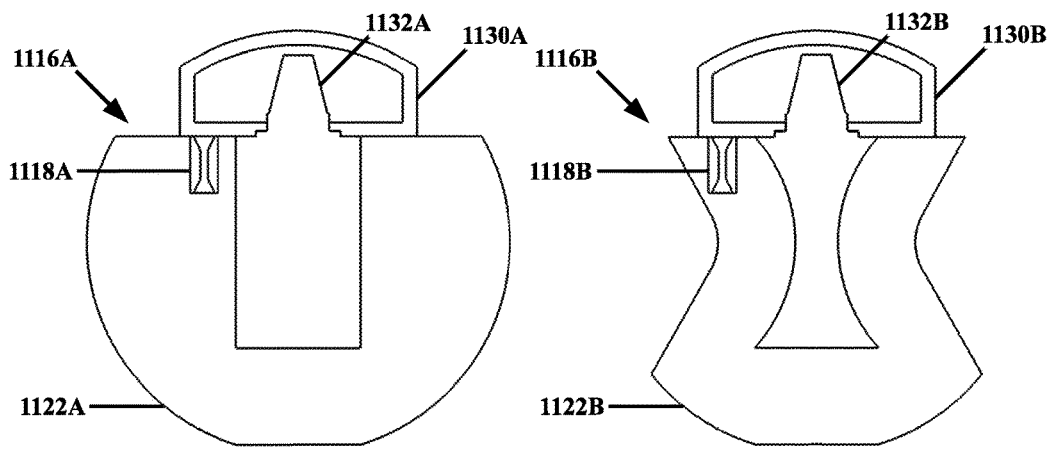
FIG. 11A through FIG. 11C depict an example remote with a controllably obstructed emitter and an example container, in cross-section view.

Turning to FIG. 11A, a remote 1116A is shown with a wall 1122A and an acoustic emitter 1118A, and a container 1132A engaged therewith. In addition, a remote cap 1130A is shown. As may be seen, the remote cap 1130A obstructs the container 1132A, so as to oppose dispensing medication therefrom. Thus, typically the remote cap 1130A may be removed to enable medication to be dispensed from the container 1132A. (Although a cap for the container 1132A proper is not shown, the presence of a container cap for the container 1132A as distinct from the remote cap 1130A is not prohibited.) In addition, the remote cap 1130A also may be seen to obstruct the acoustic emitter 1118A, so as to oppose acoustic emissions therefrom. For example, for an acoustic emitter 1118A in the form of a whistle, blocking or at least muffling air flow through the whistle may reduce or entirely prevent the emission of whistling sounds therefrom.

In FIG. 11B, certain obstruction functions of a remote cap 1130B are illustrated. The remote 1116B is shown with the wall 1122B thereof indented (with the container 1132B likewise indented). In certain instances, such indentation may cause the acoustic emitter 1118B to produce an acoustic emission. However, as may be seen the remote cap 1130B obstructs the acoustic emitter 1118B; thus, an acoustic emission may not produced, may be muffled if produced, etc.

Figure 11C:
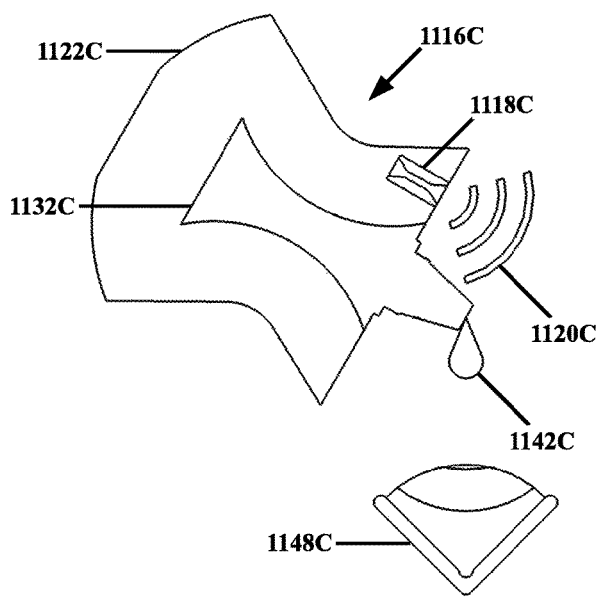

However, as shown in FIG. 11C, without the remote cap (not illustrated in FIG. 11C) in place to obstruct the acoustic emitter 1118C, compressing the wall 1122C of the remote 1116C so as to cause the container 1132C to expel a dispersal 1142C of medication into an eye may again result in the acoustic emitter 1118C producing an acoustic emission 1120C.

Thus, considering FIG. 11B and FIG. 11C together, in at least certain embodiments an acoustic emitter may be obstructed, and/or otherwise controlled, so as to avoid producing acoustic emissions in at least certain circumstances while still producing acoustic emissions in other circumstances. For example, through the use of a remote cap as shown, an acoustic emitter in the form of a whistle may be restricted from a characteristic whistling sound so long as the cap is in place. As a result, if the remote is squeezed with the remote cap in place, for example incidentally (e.g., through fidgeting by the user, compression by other objects in a pocket or bag, etc.), the characteristic acoustic emission may not be produced. In such manner, at least certain instances of "false positive" results may be avoided. The function of a remote cap in such manner as illustrated in FIG. 11B and FIG. 11C is an example only, and other arrangements for obstructing production of acoustic emissions (including but not limited to locking mechanisms for an acoustic emitter, other obstructions, etc.) in various circumstances may be equally suitable.

Now with reference to FIG. 12A through FIG. 12D, in certain previous examples a container was disposed within a remote, the remote including a wall, containing air within, etc. However, embodiments are not limited to such remotes. Indeed, so long as the remote includes at least the acoustic emitter, and/or is otherwise capable of producing a suitable acoustic emission, it may not be necessary for other structure to be present. In addition, while certain previous examples illustrated an acoustic emitter in the form of a pneumatic whistle, this too is an example only, and other arrangements for producing acoustic emissions also may be suitable.

In FIG. 12A, an arrangement is shown with a container 1232A and a cap 1240A for the container 1232A. In addition, an acoustic emitter 1218A is shown, in the form of mechanical projections and recesses, such that sliding the projections and recesses past one another, and/or pulling projections out of recesses, may produce a series of clicks and/or an apparently continuous "zip" noise. (Such mechanisms may be referred to as a "zip strip".) No distinct remote is shown to be present in FIG. 12A. Rather, the acoustic emitter 1218A is integrated into the container 1232A and/or the container cap 1240A. For simplicity, with regard to FIG. 12A the acoustic emitter 1218A may be referred to as a distinct element, as opposed to being or being part of a remote. However, it may be equally suitable to consider the acoustic emitter 1218A as being a remote, e.g., a remote that includes no components other than the acoustic emitter. So long as a remote can carry out the necessary functions, e.g., producing a suitable acoustic emission, precisely which element(s) are required to be present and/or are defined to be part of the remote (as opposed for example to being part of a container, part of some other structure, etc.) may be at least somewhat arbitrary. So long as the remote and/or acoustic emitter function suitably, embodiments are not limited with regard to what structure may be present and/or what structure may be part of a remote or may be considered to be part of a remote.

In FIG. 12B, an arrangement is shown with a container 1232B and a container cap 1240B separated slightly from the container 1232B. It may be understood that the container cap 1240B is being/has been removed from the container 1232B. As may be seen, the container cap 1240B is engaged with a portion 1218B1 of an acoustic emitter, and that the container 1232B is engaged with another portion 1218B2 of an acoustic emitter. The two portions 1218B1 and 1218B2 of the acoustic emitter have cooperated to produce an acoustic emission 1220B, e.g., in sliding past one another as the container cap 1240B was removed from the container 1232B. Thus, as the container 1232B is opened, (e.g., in preparation to dispense medication) the acoustic emission 1220B is produced.

Embodiments are not limited with regard to whether an acoustic emitter is integral or in multiple parts, or with regard to how an emitter may be engaged with a container (or a remote). For example, in FIG. 12B the portion 1218B1 of the acoustic emitter in the container cap 1240B may be an element such as a stamped or injection-molded part inserted into the container cap 1240B, while the portion 1218B2 of the acoustic emitter on the container 1232B may be molded integrally with the container 1232B itself. Other arrangements also may be suitable.

Likewise, embodiments are not limited with regard to the nature of the acoustic emission. Certain previous examples have shown acoustic emissions produced by whistles, as may include one or more whistle pitches. The example in FIG. 12B shows an acoustic emission produced by a zip strip, as may include a rapid series of clicks, etc. However, other arrangements may be equally suitable. In particular, it is noted that acoustic emissions are not required to be audible to human hearing. For example, pitches too high (or too low) for hearing, such as may be emitted by a so-called "dog whistle", may be suitable. Such acoustic emissions, being inaudible, may not distract or otherwise disturb a user, while still being detectable (e.g., by a station). However, audible acoustic emissions, while not required, also are not excluded.

Moving on to FIG. 12C, a container 1232C with a portion 1218C2 of an acoustic emitter is shown therein. The container 1232C is inclined, and a dispersal 1242C of medication in the form of a pill is visible near the mouth of the container 1232C, as may occur when the medication is being dispensed. While dispensing the medication itself may not produce an acoustic emission, it is again noted that contextual events—such as opening/closing the container 1232C—may nevertheless be considered in determining whether medication has been dispensed.

In FIG. 12D, an arrangement is shown with a container 1232D and a container cap 1240D engaged therewith. It may be understood that the container cap 1240D is being/has been engaged with the container 1232D. The acoustic emitter 1218D has produced an acoustic emission 1220D, e.g., in portions of the acoustic emitter 1218D sliding past one another as the container cap 1240D was replaced on the container 1232D. Thus, as the container 1232B is closed, (e.g., subsequent to dispensing medication) the acoustic emission 1220D is produced. It is noted that the acoustic emission 1220D produced in replacing the container cap 1240D in FIG. 12D may not necessarily be identical to the acoustic emission 1220B produced when removing the container cap 1240B in FIG. 12B (nor is it required that both acoustic emissions be identical, even if made by the same acoustic emitter). For example, a single acoustic emitter may produce different acoustic emissions when being disengaged (e.g., in FIG. 12B) than when being engaged (e.g., in FIG. 12D).

Given the arrangement in FIG. 12B through FIG. 12D, it may be understood that acoustic emissions 1220B and 1220D may be produced "bracketing" the dispensing of medication, that is, one acoustic emission 1220B before dispensing and another acoustic emission 1220D after. Depending on the particulars of an embodiment, a determination may be made (e.g., at a station, not shown) that medication has been dispensed if either such acoustic emission is detected, only if both acoustic emissions are detected, if both acoustic emissions are detected in the proper sequence (e.g., if the acoustic emissions 1220B and 1220D are distinguishable from one another), etc. Again, while the actual dispensing and/or taking of medication may not be detected for all embodiments (and may not be required to be detected), nevertheless dispensing/taking the medication may be inferred with at least some confidence based on context, e.g., acoustic emissions from opening and closing the medication container.

Turning to FIG. 13A through FIG. 13D collectively, although it may be suitable for certain embodiments to produce acoustic emissions in response to contextual events (such as opening/closing a container), and for other embodiments to produce acoustic emissions in response to medication dispensing events, embodiments are not limited to one or the other, that is, to either indicating context or dispensing. In FIG. 13A through FIG. 13D, an example arrangement is shown wherein both a dispensing event and contextual events produce acoustic emissions.

Figures 13A, 13B:
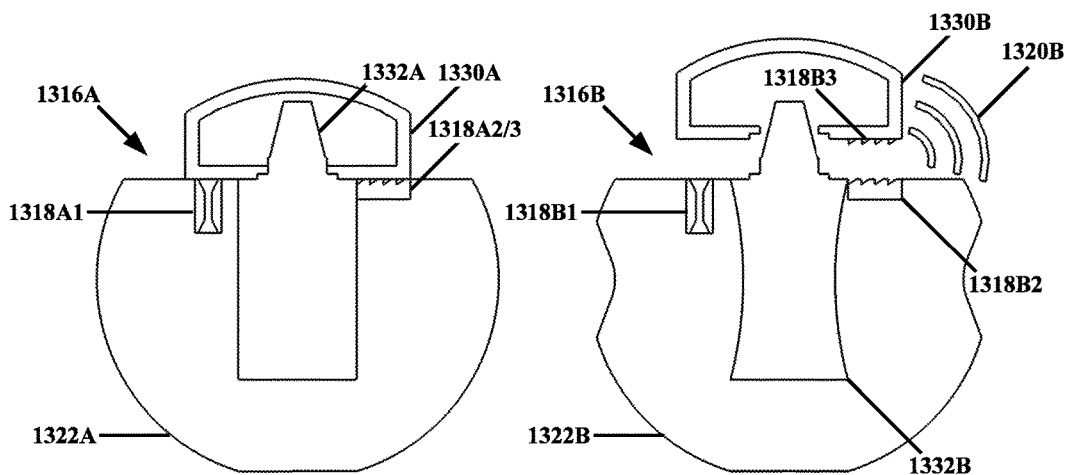
FIG. 13A through FIG. 13D depict an example remote with multiple dissimilar emitters producing emissions upon different events and an example container, in cross-section view.

In FIG. 13A, a remote 1316A having a wall 1322A is shown. Two acoustic emitters 1318A1 and 1318A2/3 are present; acoustic emitter 1318A1 is illustrated in the form of a whistle, and acoustic emitter 1318A2/3 is illustrated in the form of a zip strip (e.g., elements 1318A2 and 1318A3, not individually identified in FIG. 13A). A medication container 1332A is engaged with the remote 1316A, and a remote cap 1330A is also engaged with the remote 1332A.

Moving on to FIG. 13B, a container 1332B including a wall 1322B is shown with a container cap 1340B separated slightly from the container 1332B. It may be understood that the remote cap 1330B is being/has been removed from the remainder of the remote 1316B. The remote 1316B includes an acoustic emitter 1318B1. In addition, the remote cap 1330B includes a portion 1318B2 of another acoustic emitter; the remainder of the remote 1316B includes another portion 1318B3 of that same acoustic emitter. The two acoustic emitter portions 1318B2 and 1318B3 have cooperated to produce an acoustic emission 1320B, for example in pulling away from one another as the remote cap 1330B was removed from the remote 1316B (e.g., in preparation for dispensing medication).

Figures 13C, 13D:
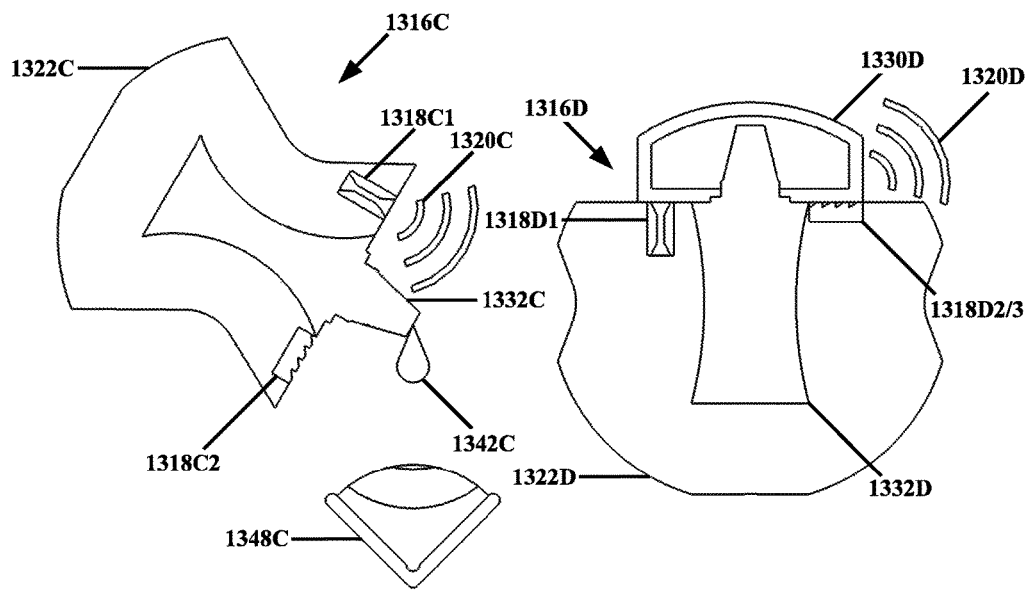

In FIG. 13C, a remote 1316C with a wall 1322C, an acoustic emitter 1318C1, and an acoustic emitter portion 1318C2 is shown inclined and disposed over an eye 1348C. The wall 1322C is indented, as is the container 1332C, such that a dispersal 1342C of medication is being dispensed from the container 1332C. The acoustic emitter 1318C1 is producing an acoustic emission 1320C.

Continuing in FIG. 13D, a remote 1316D with a wall 1322D, an acoustic emitter 1318C1, and another acoustic emitter 1318C2/3 is illustrated. A medication container 1332D is engaged with the remote 1316D. A remote cap 1330D is also engaged with the remote 1316D. It may be understood that the remote cap 1330D is being/has been replaced on the remote 1316D. In addition, the acoustic emitter 1318D2/3 is shown producing an acoustic emission 1320D, for example in engaging with one another as the remote cap 1330D was replaced on the remote 1316D (e.g., subsequent to dispensing medication).

Considering FIG. 13B through FIG. 13D as a sequence, in such instance three acoustic emissions 1320B, 1320C, and 1320D are produced, at different times and originating from different actions and different emitters. Acoustic emission 1320B is produced as the remote cap 1330B is removed; acoustic emission 1320C is produced as the eye drop container 1332C is squeezed (via the remote 1316C) to expel the eye drop 1342C; and acoustic emission 1320D is produced as the remote cap 1330D is replaced. Thus, three distinct acoustic emissions (or, considered differently, three components of one acoustic emission) occur in sequence as medication is used. Contextual events drive two acoustic emissions (1320B and 1320D), while a dispensing event (as may alternately be considered a medication event) drives another acoustic emission (1320C). As may be understood, embodiments are not limited with regard to the physical sources of acoustic emissions, the events driving acoustic emissions, uniformity of acoustic emissions (e.g., whether different emissions are different from one another, produced differently, etc.), and so forth.

Now with reference to FIG. 14A through FIG. 14D, as previously described, through receiving and considering acoustic emissions (e.g., at a station) a determination is made as to whether a medication has been dispensed, used, etc. However, information as may be conveyed through acoustic emissions is not limited only to the fact of dispensing or use. Embodiments may convey other information, such as relating to the manner in which a medication is used. For example, dosage dispensed may be determined in at least certain instances.

Figure 14A:
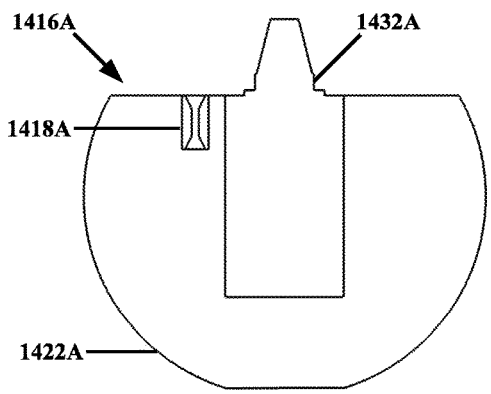
FIG. 14A through FIG. 14D depict an example remote adapted to indicate dosage dispensed and an example container, in cross-section view.
Figure 14B:
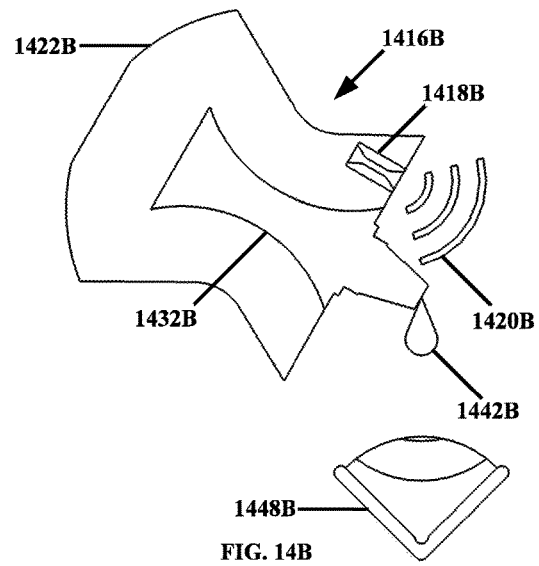

FIG. 14A depicts a remote 1416A with a wall 1422A and an acoustic emitter 1418A. A medication container 1432A is engaged with the remote 1416A. FIG. 14B also shows a remote 1416B with a wall 1422B and acoustic emitter 1418B, and a medication container 1432B engaged therewith. The remote 1416B and container 1432B are inclined and deeply indented. The container 1432B is dispensing a dispersal 1442B of medication to an eye 1448B, while the acoustic emitter 1418B is producing an acoustic emission 1420B.

Figure 14C:
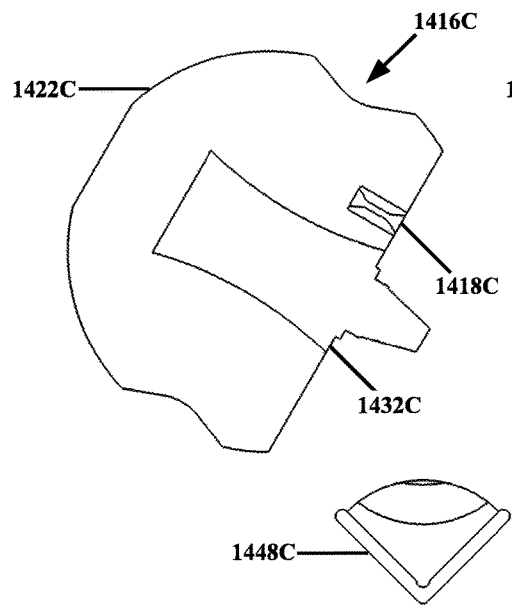
Figure 14D:
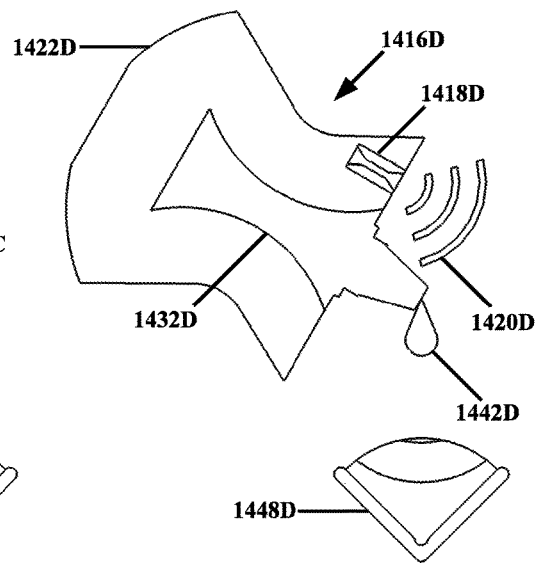

In FIG. 14C, a remote 1416C with a wall 1422C and acoustic emitter 1418C, and a medication container 1432C engaged therewith, is again shown. The remote 1416C and container 1432C are inclined similarly to FIG. 14B, but are only slightly indented. Turning to FIG. 14D, a remote 1416D is shown with a wall 1422D and acoustic emitter 1418D, and a medication container 1432B engaged therewith. Again, the remote 1416D and container 1432D are inclined and deeply indented, the container 1432D is dispensing a dispersal 1442D of medication to an eye 1448D, and the acoustic emitter 1418D is producing an acoustic emission 1420D.

If FIG. 14B through FIG. 14D are considered as a sequence of events, the events depicted therein may represent applying two droplets 1442B and 1442D of medication into a user's eye, in FIG. 14B and in FIG. 14D respectively. As may be seen, two acoustic emissions 1420B and 1420D (or considered alternatively, two components of a single acoustic emission) also are produced, associated with the two droplets 1442B and 1442D respectively. If the acoustic emissions 1420B and 1420D are received (e.g., in a station), then the number of droplets 1442B and 1442D dispensed may be determined therefrom. Thus as may be seen, for at least certain embodiments the dosage of medication dispensed may be determined based on acoustic emissions.

As has been described, embodiments may enable determination of various information regarding the dispensing, use, etc. of a medication. However, it is noted that such information is not required to be, and typically may not be, embedded into the acoustic emissions themselves. For example, a given acoustic emission typically may not be modulated in the manner of a radio or television broadcast, wherein a voice, picture, or other data is embedded into the signal itself (e.g., through actively varying the amplitude or frequency of an electromagnetic wave). Rather, the acoustic emissions of various embodiments may themselves be the information, and/or convey the information by the existence (rather than the content) of the acoustic emissions. For example, an acoustic emission in the form of a two-pitch ultrasonic whistle may serve as an indication that a medication has been dispensed, but may not have a message to that effect encoded into the whistle.

Acoustic emissions (and the remote, etc.) for various embodiments may be considered "dumb", for example, a characteristic two-pitch whistle, with no information encoded therein. A remote may not require power, computational control, "intelligence", active modulation, etc., and acoustic emissions likewise may simply be sounds with no data encoded therein. For example, for certain example embodiments presented herein, a remote may as be a purely mechanical squeezable bladder, akin to a so-called "squeaky toy", adapted to engage with a medication container. Such an arrangement may not typically be referred to as a "smart device".

Nevertheless, even though the acoustic emissions and/or the emitters thereof are themselves may reasonably be characterized as "dumb", embodiments overall (and/or parts thereof, such as a station) may be characterized as "smart", and/or exhibit smart functionality. For example, embodiments may register whether a medication was dispensed, when, where, in what dosage, etc., and/or similarly whether a medication container has been manipulated, when, where, in what manner (e.g., by removing a cap, etc.), and so forth.

Such an arrangement—"smart" functionality with a "dumb" remote—may present certain advantages. For example, smart functions may be enabled, even though the remote and/or medication container themselves may not require power supplies, processors, sensors, etc. As a more concrete example, an embodiment akin to a squeaky toy may be a purely mechanical device, insensitive to issues such as processor or software malfunctions, sensor damage, dead batteries, and so forth (because there may be no processor, software, sensor, battery, etc.). Likewise, a remote that does not rely on electromagnetic communication may not be susceptible to electromagnetic interference (whether suffering from or causing such interference), may not exhibit difficulties with communication protocols, etc. In additional, a simple mechanical device may be robust, and thus at least potentially less prone to problems due to physical damage, environmental factors (such as getting wet), and so forth. Also, avoiding electronic components in a remote may reduce the cost, weight, complexity, etc. of a remote, making widespread smart functionality (such as autonomous acquisition of authenticated medication adherence information) more feasible and/or user friendly.

However, it is emphasized that functionality as described herein that is "dumb", unpowered, not reliant on processors, etc., does not exclude other functionality that may utilize processors, and/or other "smart" features. For example, an embodiment of a remote may utilize a squeeze ball with a whistle—a purely mechanical system not requiring a processor, sensors, or power—while that same remote nevertheless may incorporate a processor, sensors, power supply, etc., carrying out other functions (e.g., using capacitive sensors to measure the medication remaining in a container engaged with that remote). Thus, while certain functions as described herein may be implemented using "dumb" approaches, the presence of smart functions even in the same system is not prohibited. In such an arrangement, even if smart systems in a remote may fail due to (for example) lack of power to the remote, other functions such as a whistle producing acoustic emissions as may indicate that the medication has been dispensed still may be carried out. Other advantages and features of "mixed" smart-and-dumb systems also may be provided.

Now with reference to FIG. 15A through FIG. 15D, although it may be useful in certain instances for acoustic emissions themselves to be a signal, rather than contain an embedded signal, nevertheless in other instances it may be useful to extract information from an acoustic emission. Even so, extracting such information from within an acoustic emission may not require the acoustic emitter (or remote overall) to be a smart device, or otherwise diminish advantages of dumb remotes/emitters as noted previously.

For example, FIG. 15A illustrates a remote 1516A with a wall 1522A and an acoustic emitter 1518A1 in the form of a whistle. The remote 1516A also includes another acoustic emitter 1518A2 in the form of a bell. In addition, a medication container 1532A is engaged with the remote 1516A.

FIG. 15B shows a remote 1516B with a wall 1522B and acoustic emitters 1518B1 and 1518B2, and a medication container 1432B engaged therewith. The remote 1516B and container 1532B are inclined, and are positioned over an eye 1548B. The acoustic emitter 1518B2 is shown to be producing an acoustic emission 1520B. For example, a bell suspended so as to ring when disturbed may make one or a series of ringing pitches. Thus, the acoustic emission 1520B may be produced as the acoustic emitter 1518B2 is inclined into an orientation as to facilitate the container 1532B dispensing an eye drop into an eye 1548B. In such instance, reception of the acoustic emission 1520B (e.g., in a station) may be taken to indicate such a change in orientation of the container 1532B. Depending on the particulars of the acoustic emitter 1518B2 (e.g., the type of bell, the manner of mounting, etc.), in addition to or instead of being produced upon a change in orientation, an acoustic emission 1520B may be produced upon a change in position (that is, movement through space rather than rotation within space).

Furthermore, for at least certain embodiments, the acoustic emission 1520B may be characteristic not only of the acoustic emitter 1518B2, but of the manipulation of the remote 1516B and container 1532B. That is, a rotation of the remote 1516B may cause the acoustic emitter 1518B2 to emit an acoustic emission 1520B exhibiting one particular pattern of tones that is identifiable as being caused by rotation, while a translation of the remote 1516B may cause the acoustic emitter 1518B2 to emit an acoustic emission 1520B exhibiting a different pattern of tones that is identifiable as being caused by translation. Certain embodiments may enable acoustic emissions 1520B that may be interpreted to indicate complex motions (e.g., being lifted, inclined, shifted to another eye, then set down), magnitudes of motion (e.g., inclination of 120 degrees), speeds, accelerations, and/or other properties. Such properties may be determined by the content of the acoustic emission itself (such as by the particular pattern of tones from a suspended bell), by environmental factors affecting the acoustic emission (such as a doppler shift in an expected series of tones), or by some combination thereof. Typically though not necessarily, such information may be extracted from an acoustic emission 1520B in a processor utilizing executable instructions instantiated thereon, for example a processor of a station.

However, although in at least certain embodiments information may be determined from the content of an acoustic emission 1520B, it is noted that the content need not be encoded into that acoustic emission 1520B in an active manner. That is, the sound of a jingling bell may be analyzed to reveal how that bell was moved, but the jingling still may be the result of natural behavior by a "dumb" system. Thus, even if such information may be extracted from an acoustic emission 1520B for a given embodiment, that embodiment nevertheless may retain advantages of a dumb remote and/or dumb emitter, as described previously.

Now with reference to FIG. 15C, a remote 1516C is shown with a wall 1522C and acoustic emitters 1518C1 and 1518C2, and a medication container 1532C engaged therewith. The remote 1516C and container 1532C are deeply indented, and the container 1532C is shown to have expelled a dispersal 1542C of medication over an eye 1548C of a user. In addition, the acoustic emitter 1518C1 is producing an acoustic emission 1520C.

Then in FIG. 15D, a remote 1516D is shown with a wall 1522D and acoustic emitters 1518D1 and 1518D2, and a medication container 1532D engaged therewith. The remote 1516D and container 1532D are slightly indented, as may occur if the remote 1516D is being gripped but not squeezed to expel medication. In addition, the acoustic emitter 1518D2 is shown to be producing an acoustic emission 1520D. Such an acoustic emission 1520D may be produced for example if a bell jingles as the remote 1516D is set down onto a surface, such as a table or shelf, after dispensing medication. Thus, depending on the particulars of a given embodiment, the acoustic emission 1520D may be interpreted to indicate motion, potentially a particular motion (e.g., being set on a surface) of the remote 1516D.

If FIG. 15B through FIG. 15D are considered as a sequence, an example embodiment of a remote therein may produce a jingling acoustic emission 1520B upon being brought into place for dispensing medication, a whistling acoustic emission 1520C upon dispensing medication, and another jingling acoustic emission 1520D upon being returned to storage after dispensing medication. As noted, some acoustic emissions such as 1520B and 1520D may include (but are not required to include) characteristic content indicating particulars of the triggers for those acoustic emissions 1520B and 1520D, for example how the remote was moved may leave an identifiable signature in the content of the acoustic emissions 1520B and 1520D. Thus, receipt and analysis of acoustic emissions 1520B, 1520C, and 1520D may reveal that the container was moved, dispensed medication, and then was moved again; and further may indicate that the container was so moved in a manner consistent with preparing for dispensing medication and recovering from dispensing medication (though this is not required, and is not limiting).

As may be understood, even if a given remote is a "dumb" device, the information as may be obtained therefrom regarding use of medication is not necessarily limited, and in particular is not limited only to binary indications of use or no use (or of dispensing or not dispensing, etc.).

Moving on to FIG. 16A through FIG. 16D collectively, the manner by which a remote may engage a container is not limited. As noted with regard to FIG. 12A through FIG. 12D, in certain embodiments a remote may take the form of elements integrated into a container, and in such instances a means of engagement may be considered moot. However, even where a well-defined and distinct remote does engage with a well-defined and distinct container, the means of engagement may vary considerably. Certain examples herein show a friction fit, wherein a remote defines an aperture therein and the container fits securely within that aperture. However, this is an example only. Other suitable arrangements may include, but are not limited to, adhesive, hook-and-loop, threading or other mechanical engagement of remote and/or container, mechanical fasteners, etc. Engagement between a remote and a container may be removable or fixed, without limit.

Figure 16A:
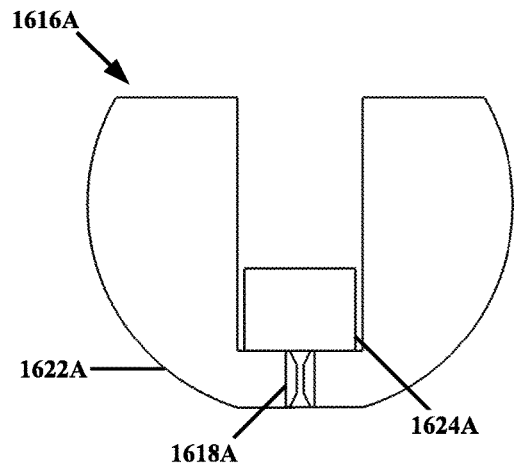
FIG. 16A through FIG. 16D depict an example remote adapted to indicate insertion and removal of a container, in cross-section view.

In addition, the manner of engagement itself may be associated with a characteristic acoustic emission. In FIG. 16A, a remote 1616A is shown with a wall 1622A and an acoustic emitter 1618A. The remote 1616A defines an aperture (not numbered) for accepting a container (not present in FIG. 16A). The remote 1616A also includes a bladder 1624A in pneumatic communication with the acoustic emitter 1618A (in the example shown, the acoustic emitter 1618A is not shown to be in pneumatic communication with the volume enclosed by the wall 1622A, as in certain other examples herein).

Figure 16B:
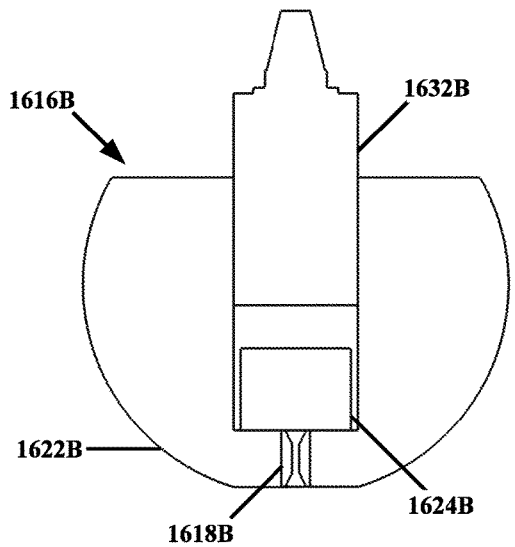

FIG. 16B shows a remote 1616B with wall 1622B, acoustic emitter 1618B, and bladder 1624B, with a container 1632B disposed partway into an aperture in the remote 1616B. Such an arrangement may occur for example as the container 1632B is being inserted into the remote 1616B.

Figure 16C:
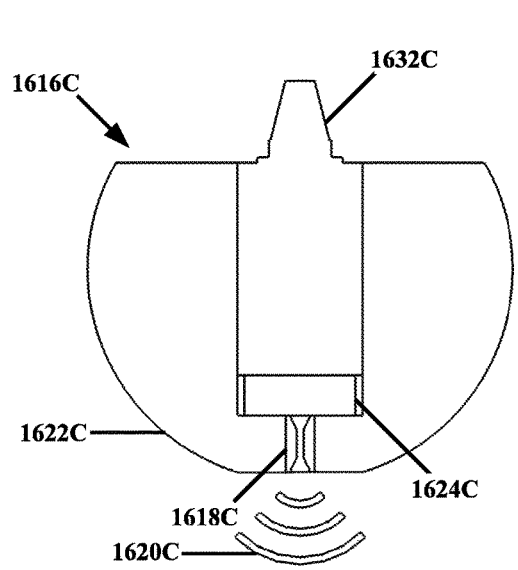

Turning to FIG. 16C, a remote 1616C is shown with a wall 1622C, acoustic emitter 1618C, and bladder 1624C. A container 1632C is disposed within the remote 1616C. As may be seen, the bladder 1624C is compressed by the container 1632C. Air thus is expelled from the bladder 1624C through the acoustic emitter 1618C, producing an acoustic emission 1620C. Such an acoustic emission 1620C may be received and interpreted to indicate that the container 1632C has been engaged with the remote 1616C, for example if a new supply of medication is being prepared for use.

Figure 16D:
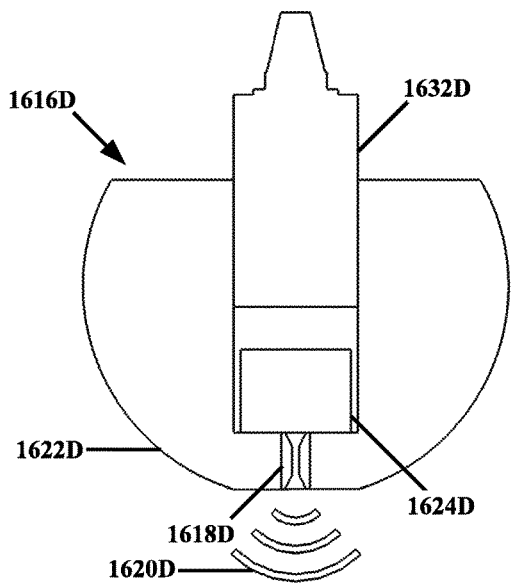

In FIG. 16D, a remote 1616D is shown with a wall 1622D, acoustic emitter 1618D, and bladder 1624D. A container 1632D is shown partly withdrawn from the remote 1616D. As may be seen, compression on the bladder 1624D by the container 1632D is relieved. Air thus is drawn into the bladder 1624D through the acoustic emitter 1618D, producing an acoustic emission 1620D. Such an acoustic emission 1620D may be received and interpreted to indicate that the container 1632D is being disengaged from the remote 1616D, for example if the container 1632D is empty and in need of replacement.

Thus as may be seen in FIG. 16A through FIG. 16D, actions/states/data not associated immediately with dispensing of a medication also may be indicated through production of acoustic emissions, and/or identified through reception and analysis thereof. For example, engaging or disengaging a medication container from a remote, which may happen well before or well after any act of dispensing the medication, may be so identified through characteristic acoustic emissions.

Now with regard to FIG. 17A and FIG. 17B, certain previous examples have shown purely mechanical mechanisms for producing acoustic emissions. Such arrangements may be transparent to the user, and/or consequential in function. That is, with regard to transparency, the user may not be required to take action other than dispensing the medication in order to produce an acoustic emission indicating that the medication has been dispensed (or that some related act has been carried out). For example, squeezing a remote may both squeeze a container to expel medication and expel air from a bladder to produce a characteristic whistle; so far as the user is concerned, in dispensing the medication no further action may be required in order for the dispensing to be registered (e.g., in a station). With regard to consequentiality in function, the remote itself may be "dumb". That is, an acoustic emission may be produced as a consequence of dispensing the medication, without relying on data processing, choices to be made by the system or user, etc. For example, squeezing an air-filled remote drives air through a whistle, producing a whistle pitch; no "intelligence" or control may be required. In such an arrangement, the whistle pitch is a purely mechanical consequence of squeezing the remote.

However, while purely mechanical approaches may provide transparent and consequential functionality, it is not required for all embodiments to utilize purely mechanical approaches.

For example, FIG. 17A shows a remote 1716A with a wall 1722A. A container 1732A is engaged with the remote 1716A. In addition, the remote 1716A includes an acoustic emitter 1718A in the form of an electrical audio speaker, and a trigger 1750A in the form of a piezoelectric pad in communication with the acoustic emitter 1718A.

In FIG. 17B, a remote 1716B and container 1732B are shown inclined over an eye 1748B. The wall 1722B of the remote 1716B and the container 1732B are indented, such that the container 1732B is dispensing a dispersal 1742B of medication. In addition, the trigger 1750B also is deformed by the indentation of the wall 1722B. Deformation of the trigger 1750B (being in this example a piezoelectric pad) produces an electrical output which is communicated to the acoustic emitter 1718B; the acoustic emitter 1718B thus produces an acoustic emission 1720B.

The arrangement in FIG. 17B for producing the acoustic emission 1720B is not purely physical. An electrical output is generated, and an electrical system—the acoustic emitter 1718B—is activated. However, the arrangement of FIG. 17B is nevertheless both transparent to the user and consequential. The user need perform no more action to cause the acoustic emission 1718B to be produced than for example if the acoustic emitter 1718B were a whistle instead of a speaker (and indeed, if the acoustic emission 1720B is not audible, such as an ultrasonic sound, the user may not even be aware that an acoustic emission 1720B has been produced). Likewise, even though the acoustic emitter 1718B is electrically activated, such activation is still a direct consequence of the user squeezing the remote 1716B. Given a configuration of a particular embodiment (such as shown in certain previous examples), squeezing an air filled wall pushes air through a whistle and necessarily produces a sound; for a different embodiment such as shown in FIG. 17B, deforming a piezoelectric pad causes an electrical output that just as necessarily drives a speaker to produce a sound. No "intelligence", choice, internal processing, etc. may be involved (or required). Thus, although strictly mechanical systems may be suitable in certain embodiments, embodiments are not limited only to strictly mechanical systems.

Now with reference to FIG. 18A and FIG. 18B, certain embodiments described herein have been specific to acoustic emissions. Acoustic emissions may be convenient for certain embodiments. For example, acoustic emissions may not necessarily be restricted to line of sight, may not necessarily blocked by fabric or similar if a receiver (e.g., in the form of a smart phone) is in a bag, a pocket, etc. However, embodiments are not necessarily limited only to acoustic emissions.

FIG. 18A shows an arrangement at least somewhat similar to that of FIG. 17A. A remote 1816A is shown with a wall 1822A. A container 1832A is engaged with the remote 1816A. The remote 1816A includes an emitter 1818A in the form of an LED (light emitting diode), and a trigger 1850A in the form of a piezoelectric pad in communication with the emitter 1818A.

In FIG. 18B, a remote 1816B and container 1832B are shown inclined over an eye 1848B. The wall 1822B of the remote 1816B and the container 1832B are indented, such that the container 1832B is dispensing a dispersal 1842B of medication. In addition, the trigger 1850B also is deformed by the indentation of the wall 1822B. Deformation of the trigger 1850B (in this non-limiting example a piezoelectric pad) produces an electrical output which is communicated to the emitter 1818B. The electrical output causes the acoustic emitter 1818B to produce a characteristic emission 1820B; for an LED, the emission typically may be in the form of light, whether visible or otherwise (e.g., infrared, etc.). (While a station is not shown in FIG. 18B, it should be understood that if non-acoustic emissions are produced by an emitter, a station cooperating with that emitter may include a receiver other than an acoustic receiver. For example, if an LED is to serve as an emitter, a station may include an optical receiver in addition to or instead of an acoustic emitter. Other similar changes may be suitable depending on the particulars of emitter(s) and/or emission(s) in a given embodiment, and embodiments are not limited with regard thereto)

It is noted that the manner in which a non-acoustic emission may be characteristic may vary, and may depend on the nature of the emitter in a given embodiment. For example, an LED may produce light of a specific frequency, frequency distribution, etc., may produce a particular series of pulses (e.g., three dots and a dash), or similar. The particulars of emissions, acoustic or otherwise, are not limited.

Figure 19A:
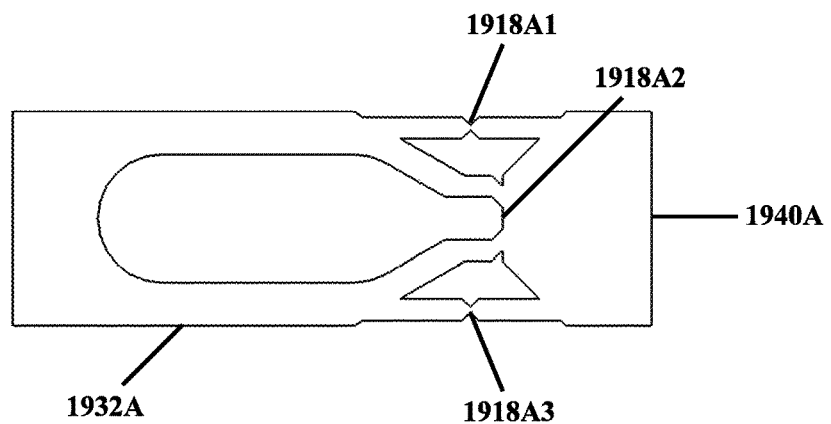
FIG. 19A through FIG. 19C depict an example of destructive acoustic emitters integrated with single-use container and executing in parallel, in cross-section view.
Figure 19B:
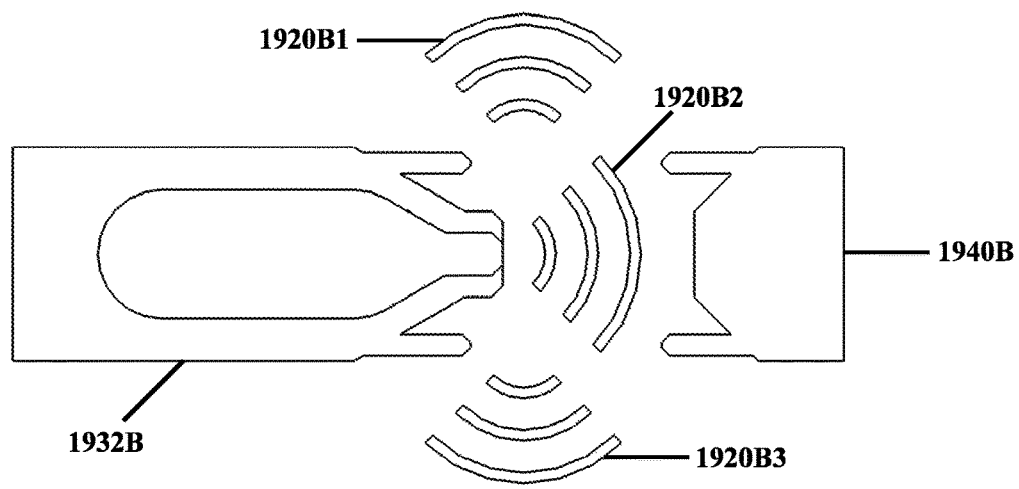
Figure 19C:
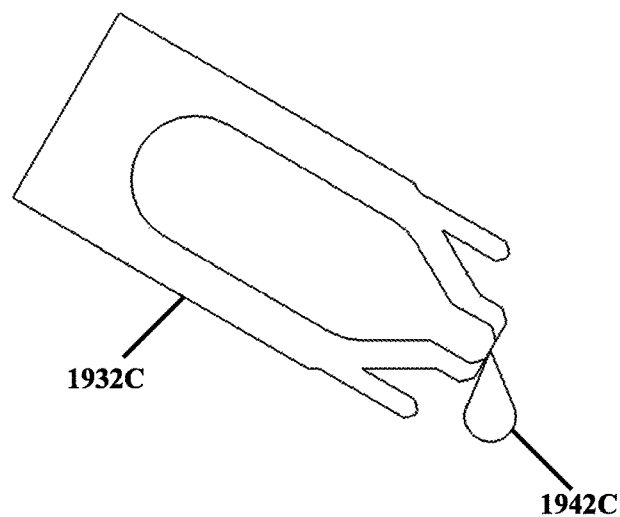

Now with reference to FIG. 19A through FIG. 19C collectively, in certain previous examples herein emissions may have been repeatable, and emitters likewise reusable. For example, in FIG. 1A through FIG. 1D the emitter therein may be considered as a pneumatic whistle, which may produce emissions more than once (assuming the wall of the remote is squeezed more than once), at least potentially being reused many times. However, such repeatability/reusability is not required, and other arrangements may be suitable. For example, emitters may be expendable, being destroyed in producing an emission, or otherwise not adapted to producing an emission more than once. Similarly, although containers in certain previous examples may be reusable, for example containing therein more than one dose of medication, this also is not required. For example, single-use or "one-shot" containers may be suitable.

In FIG. 19A, a container 1932A is shown therein, as may for example contain a quantity of liquid medication (or other material). A container cap 1940A is shown engaged with the container 1932A. Three points of connection are shown between the container 1932A and the container cap 1940A, in the form of two filaments and a nozzle for the container 1932A; these structures may serve as emitters, and are thus identified as 1918A1, 1918A2, and 1918A3. For example, the container 1932A and the container cap 1940A may be formed integrally, such as being molded out of a plastic material; in such instance, the filaments and nozzle may be frangible (and are shown in FIG. 19A as being notched to define weak points, though such notches/weak points are not necessarily required). Thus when a pulling force is applied to remove the container cap 1940A from the container 1932A so as to enable dispensing medication therein, the filaments and nozzle may separate in at locations and in a manner that are at least somewhat predictable.

In breaking emitters 1918A1, 1918A2, and 1918A3, sounds may be produced. The precise sounds made may depend on the configuration of the emitters 1918A1, 1918A2, and 1918A3. For example, physical properties such as the shape, thickness, rigidity, strength, elongation, etc., of the structure (e.g., filaments and nozzle as shown) may determine, in whole or in part, certain predictable properties of acoustic emissions produced when those structures 1918A1, 1918A2, and 1918A3 are broken. For instance, the frequency, waveform, volume, etc. of the noises as each emitter 1918A1, 1918A2, and 1918A3 is torn or snapped (or otherwise separated) may be particular to and/or predictable from the structures of the emitters 1918A1, 1918A2, and 1918A3. Consequently, through selection of suitable materials, shapes, etc., the emitters 1918A1, 1918A2, and 1918A3 may be configured so as to produce characteristic acoustic emissions when broken.

Thus, as may be seen in FIG. 19B, separating the cap 1940B and the container 1932A may produce three such characteristic acoustic emissions 1920B1, 1920B2, and 1920B3 by the destruction of the former acoustic emitters (not separately numbered in FIG. 19B, though the remains of the structures themselves may be observed). If the emitters 1918A1, 1918A2, and 1918A3 previously shown in FIG. 19A are distinct from one another, then the acoustic emissions 1920B1, 1920B2, and 1920B3 shown in FIG. 19B likewise also may be distinct from one another. As a result, the example arrangement shown in FIG. 19B may produce three different sounds at approximately the same time, thus providing three overlapping pitches, waveforms, etc. Such combination of three different acoustic emissions 1920B1, 1920B2, and 1920B3 may be both recognizable and unlikely to otherwise occur as background noise, and thus may be detected and interpreted (e.g., at a station, not shown in FIG. 19B) as evidence of a contextual event representing that the single-use container 1932B of medication has been opened.

Turning to FIG. 19C, therein a single-use container 1932C is shown dispensing a dispersal 1942C of liquid medication therefrom. While dispensing the dispersal 1942C of medication does not necessarily produce a characteristic acoustic emission in itself (though such is not prohibited), detecting and identifying acoustic emissions 1920B1, 1920B2, and 1920B3 shown previously in FIG. 19B may indicate that the single-use container 1932C has been opened in preparation for dispensing the dispersal 1942C of medication, as a contextual event associated therewith. Thus, although dispensing the dispersal 1942C of medication may not be directly detected, if characteristic acoustic emissions are detected it still may be inferred with at least some confidence that the medication has been dispensed and/or used. This may be considered similar to arrangements in FIG. 12A through FIG. 12D, wherein removal of a cap for a pill bottle was detected and considered as a contextual indication that a pill may have been dispensed and administered. In addition, a contextual acoustic emission for opening a single-use container may be interpreted as providing greater confidence of use of a medication than may be so for a reusable container; where a user may fidget with a reusable container, for example loosening and tightening or removing and replacing the container cap therefor, the container cap for a single-use container may not be replaceable (e.g., as shown previously in FIG. 19B). If opening a container in some sense destroys the container, such as may be true with a single-use container, users may be less likely to open such single-use containers except when preparing to dispense medication; thus, an indication that such a container has been opened may reliably indicate at least an intent to use the medication therein.

While the destructive acoustic emitters shown and described with regard to FIG. 19A through FIG. 19C produce acoustic emissions before medication is dispensed (in opening the container, in the example shown), arrangements wherein acoustic emissions are produced through destruction of emitters during and/or after dispensing medication also may be suitable. For example, a hypodermic injector may incorporate a frangible stem that breaks making an audible noise as the plunger is depressed and/or as the plunger is withdrawn. Such destructive acoustic emissions may for example also perform additional functions; for example, destruction of a plunger for a hypodermic injector may for example render that injector non-functional, thus making re-use of the injector impossible or at least more difficult. The single frangible element may in such manner serve both to provide an acoustic indication of adherence to a medical regimen and to restrict health concerns associated with the sharing and/or re-use of needles. Other arrangements likewise may perform multiple functions, not limited to discouraging re-use of hypodermic injectors or other systems.

However, although pairing destructive emitters and single-use containers (and/or other systems) may be suitable for certain embodiments as shown in FIG. 19A through FIG. 19C, neither one requires the other. For example, a single-use container may utilize non-destructive emitters, and/or a reusable container may utilize destructive emitters. Furthermore, in certain embodiments an emitter that is not itself damaged or destroyed (and/or only part thereof is damaged or destroyed) may be actuated through the destruction of some element or structure, either an element of the emitter or some other distinct element. For example, if a filament (e.g., similar to those shown in FIG. 19A through FIG. 19C) is fabricated so as to produce an electrical voltage when distorted and/or broken, distorting and/or breaking that filament may provide power to an LED (such as in FIG. 17A and FIG. 17B), a speaker (such as in FIG. 18A and FIG. 18B), some other element, etc.; in such case the filament may be damaged or destroyed, but the LED, speaker, etc. may remain intact (and at least potentially may be reusable).

Now with reference to FIG. 20A through FIG. 20D, as noted previously with regard to FIG. 19A through FIG. 19C acoustic emissions produced by damaging and/or destroying emitters and/or portions thereof may be substantially simultaneous, such that the acoustic emissions may overlap one another (and that such overlap of multiple sounds may represent at least a portion of the characteristicness of acoustic emissions). However, as may be seen in FIG. 20A through FIG. 20D acoustic emissions produced destructively are not required to be simultaneous or nearly so, and also may be produced in series or otherwise non-simultaneously.

Figure 20A:
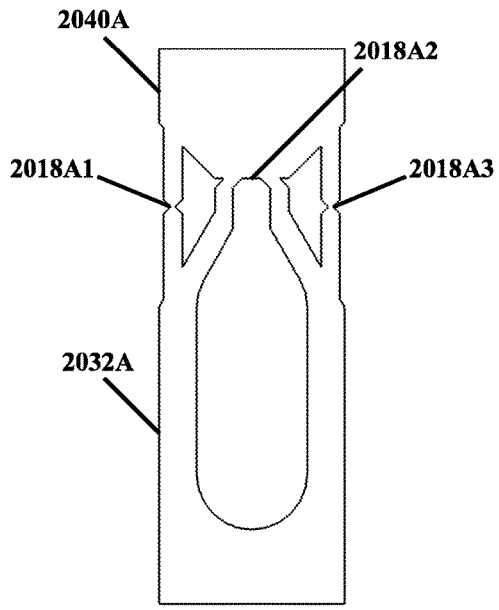
FIG. 20A through FIG. 20D depict another example of destructive acoustic emitters integrated with single-use container and executing in series, in cross-section view.

In FIG. 20A, a single-use container 2032A is shown. A container cap 2040A is also shown, and the container 2032A and container cap 2040A are shown to be engaged via three acoustic emitters 2018A1, 2018A2, and 2018A3 in the form of two filaments and a nozzle (though such structures are examples only).

Figure 20B:
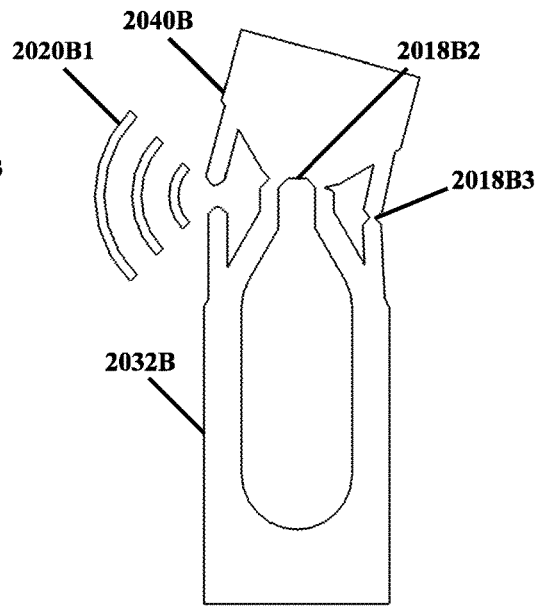

In FIG. 20B, a container cap 2040B is shown partly separated from a container 2032B, as may occur as part of a sequence of events in removing that container cap 2040B preparatory to dispensing medication from the container 2032B. One acoustic emitter in the form of a filament (no longer individually numbered) formerly extending from container 2032B to container cap 2040B is shown as having been broken, and as emitting a characteristic acoustic emission 2020B1. Two remaining acoustic emitters 2018B2 and 2020B3 are shown as deformed but as-yet intact.

Figure 20C:
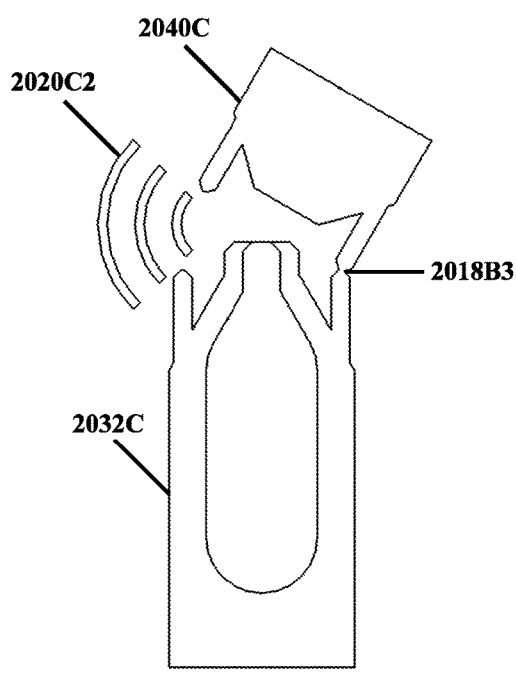

FIG. 20C shows a container cap 2040C progressively more separated from a container 2032C. A second acoustic emitter in the form of a nozzle (no longer individually numbered) is also shown as having been broken, and as emitting a characteristic acoustic emission 2020C2. One remaining acoustic emitters 2020C3 is shown intact.

Figure 20D:
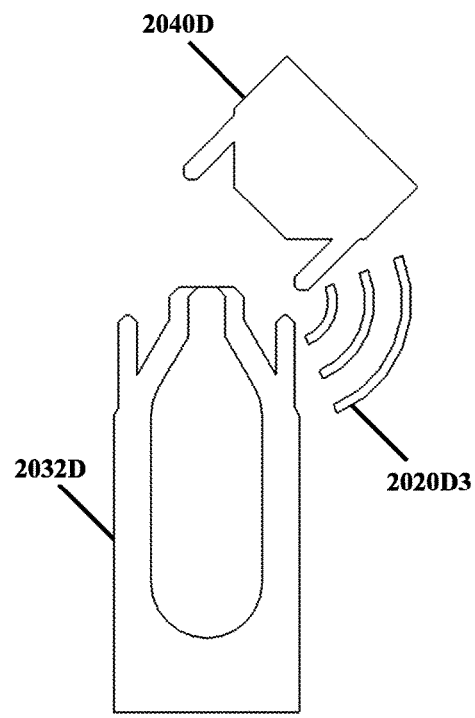

In FIG. 20D, a container cap 2040D is shown separated from a container 2032D. Three broken acoustic emitters (not individually numbered) are shown; one in the form of a filament (e.g., the most recently broken) is shown as emitting an acoustic emission 2020D3.

If FIG. 20A through FIG. 20D are considered as a series, then it may be seen that three acoustic emissions 2020B1, 2020C2, and 2020D3 are produced by the destruction of three acoustic emitters (initially numbered 2018A1, 2018A2, and 2018A3). The acoustic emitters break in series one after another, and thus the acoustic emissions 2020B1, 2020C2, and 2020D3 are produced in series one after another. Such a series of three particular noises may provide a reliable indication that a container cap has been removed from a single-use container of medication. The sequence itself—e.g., acoustic emission 2020B1, followed by acoustic emission 2020C2, followed by acoustic emission 2020D3—may be considered as a feature in determining whether sounds received (e.g., in a station, not shown) represent opening such a container, and/or in excluding background noise as false positives.

In addition, when multiple acoustic emissions 2020B1, 2020C2, and 2020D3 are produced (regardless of whether the emitters therefor are destroyed in the process or not), relationships among those multiple acoustic emissions 2020B1, 2020C2, and 2020D3 also may be considered. For example as noted, the order of the acoustic emissions 2020B1, 2020C2, and 2020D3 may be considered. Similarly, the timing of acoustic emissions 2020B1, 2020C2, and 2020D3 may be considered. For instance, for certain embodiments the interval between acoustic emissions 2020B1 and 2020C2 may be anticipated as being similar in length to the interval between acoustic emissions 2020C2 and 2020D3 (e.g., assuming a uniform rate of motion in removing the container cap and similar spacing between emitters). In addition or instead, the lengths of such intervals themselves may be considered. For example, it may be that in opening a given configuration of container the typical interval between acoustic emissions 2020B1 and 2020C2 may be approximately 50 milliseconds. In such instance, if two sounds were detected that were otherwise similar two acoustic emissions 2020B1 and 2020C2 but that exhibited an interval of significantly less than or more than 50 milliseconds, a low confidence may assigned that those two sounds actually represent acoustic emissions characteristic of opening a container. Other features, such as ratios of intervals to one another, etc., also may be considered.

Figure 21:
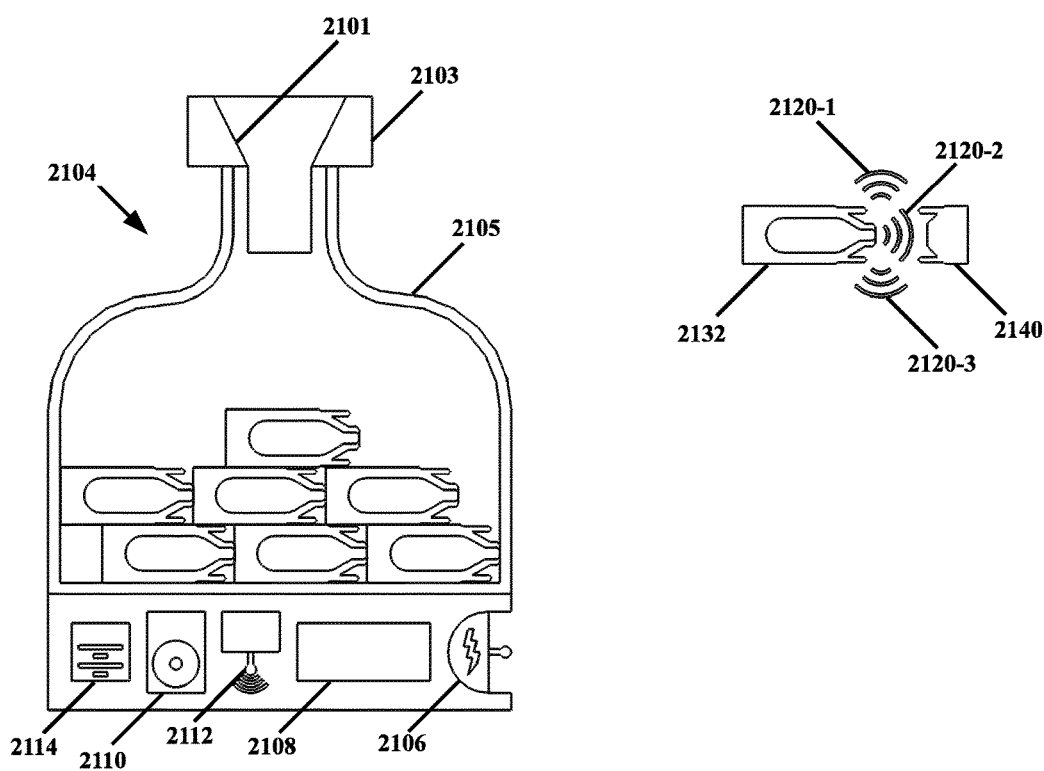
FIG. 21 depicts an example station adapted to fulfill additional functions beyond acoustic reception, in cross-section view.

Now with regard to FIG. 21, in certain previous examples reference has been made to a station as may detect acoustic emissions from a remote and/or a container lacking a remote (and/or wherein the container itself may be considered as a remote). However, while a station may carry out functions related to detecting acoustic emissions, interpreting acoustic emissions, etc., stations are not limited only to such functions. For example, a smart phone or other portable electronic device may be suitable for use as a station, and may continue to carry out functions for which that smart phone is adapted even while serving as a station. In addition, even for a station that is at least nominally dedicated to serving as a station (e.g., a device purpose-built for detecting such acoustic emissions), other functions still may be carried out thereby.

In FIG. 21 a single-use medication container 2132 is shown. A container cap 2140 is shown separated from the container 2132, and three acoustic emissions 2120-1, 2120-2, and 2120-3 are shown being produced. (Such an arrangement may be at least somewhat similar to that shown in FIG. 19A through FIG. 19C).

FIG. 21 also shows a station 2104. As in certain previous examples, the station 2104 is shown to include an acoustic receiver 2106, a processor 2108, a data store 2110, a communicator 2112, and a power supply 2114 (though as already noted, such elements are themselves examples only and may not necessarily be present or required for all embodiments). In addition, the station 2104 in FIG. 21 includes a bin 2105 in the form of a narrow-mouth jar; the bin 2105 is shown as having a number of opened medication containers therein (not individually numbered). The station 2104 also includes a bin lid 2103, and a bin chute 2101. The top of the bin chute 2101 as shown is approximately conical in shape, narrowing at the bottom thereof. Given the configuration of the bin chute 2101, bin lid 2103, and bin 2105 of the station 2104 an expended single-use container dropped into the bin chute 2101 may be deposited within the bin 2105.

The acoustic receiver 2106 may detect acoustic emissions 2120-1, 2120-2, and 2120-3 as produced by the container 2132; as may be understood from the lightning bolt depicted on the acoustic receiver 2106, in FIG. 21 the acoustic receiver 2016 is active in receiving the acoustic emissions 2120-1, 2120-2, and 2120-3. Consequently, the station 2104 as a whole may identify the acoustic emissions 2120-1, 2120-2, and 2120-3, may register events, take further action based thereon, etc.

However, the station 2104 also may perform additional functions. As shown in FIG. 21 the bin 2105 of the station 2104 accepts and accommodates therein expended single-use medication containers. In at least certain instances, it may be desirable to retain and/or to segregate "the empties" in some fashion. For example, during clinical testing of a new medication, a new single-use container, etc., it may be useful to examine used containers to evaluate matters such as how much medication was dispensed, how effectively the containers opened (e.g., did a frangible nozzle tear in the intended manner), etc. Such features may be performed passively; that is, no additional active components may be required in a station 2104 that merely collects and stores expended containers, and no additional functions may be required of components already present in the station 2104.

However, in other embodiments additional active functions may be performed. For example, if an expended container deposited in the bin 2105 makes a detectable sound (e.g., upon hitting the bottom of the bin 2105), the acoustic receiver 2106 may be utilized to receive that sound. In certain embodiments the sound of disposing of the empty container may be considered as an acoustic emission unto itself (in place of or in addition to acoustic emissions produced by opening a container, dispensing medication, etc.). "Container disposal" may be utilized and considered as yet another form of contextual event, associated with the use of at least certain medications.

Furthermore, it may be suitable to include additional active components in some embodiments. As may be seen in FIG. 21, the station 2104 therein already includes a power supply 2114, communicator 2112, data store 2110, and processor 2108; such elements may serve as infrastructure in supporting additional sensors and/or other components. For example, a weight sensor or impact sensor in the base of the bin 2105 may serve to determine the weight of expended containers deposited in the bin 2105; if the empty weight of the containers is known, the weight of medication remaining may be determined. Alternately, the simple presence of an impact may serve as an indication that an expended container has been deposited in the bin, serving as a contextual indication of medication use (though not necessarily being passive in the same sense as a whistle produced when a user squeezes a medication container, etc.). Similarly, photo-sensors, capacitive sensors, etc. disposed in and/or near the bin lid 2103, the bin chute 2101, etc., may be used to determine whether empty containers are being deposited, other information about those containers such as how much medication remains therein (e.g., through light transmission through the container), etc.

Such additional active and/or functions may be supported by already-existing elements of at least some stations. However, while such functions are not prohibited, neither are additional functions necessarily required for any given embodiment.

Figure 22:
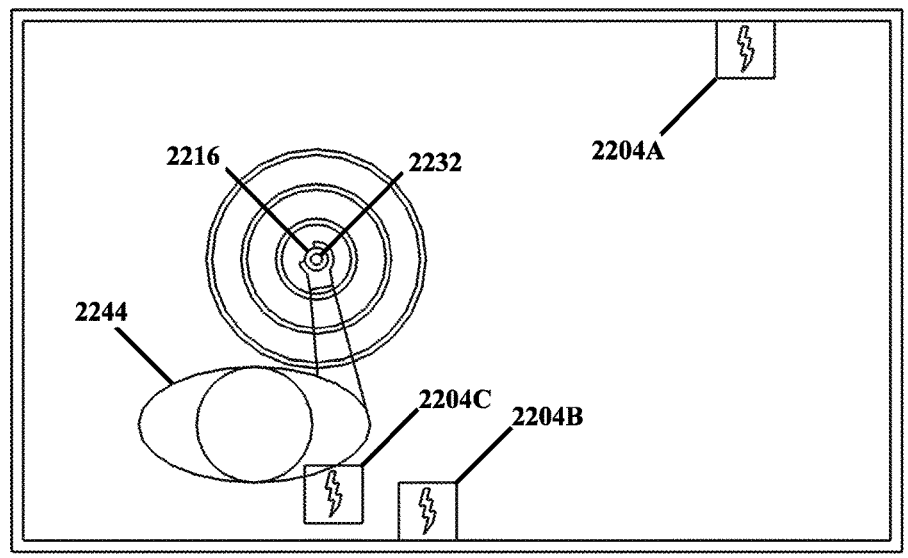
FIG. 22 depicts multiple stations and an example remote as may be utilized, in top-down view.

Now with reference to FIG. 22, embodiments are not limited with regard to the form and/or number of stations that may cooperate with a remote. For example, the example arrangement of FIG. 22 depicts a remote 2216 in the hand of a user 2244, and a container 2232 engaged with the remote 2216. The remote 2216 is depicted to be producing an acoustic emission 2220. In addition, three stations 2204A, 2204B, and 2204C are shown. Stations 2204A and 2204B are shown at some distance from the user 2244; for example, stations 2204A and 2204B may be dedicated systems, such as electronic devices adapted to be deployed within a room or other space specifically for the purpose of detecting and processing an acoustic emission 2220. Alternately, stations 2204A and 2204B may be multi-purpose devices as may incidentally be present, such as a desktop PC, laptop PC, game system, smart television, etc.; so long as the necessary functionality is enabled, the types of devices as may serve as stations are not limited.

Station 2204C is shown in contact with the user 2244, for example as may be disposed within a pocket or bag, otherwise carried by the user, etc. Such stations may include, but are not limited to, phones, smart watches, other portable electronic devices, etc. While portable and/or user-carried/worn stations such as 2204C may be non-dedicated, such as devices that a user 2244 may carry for other purposes (such as a phone), the use of dedicated portable stations 2204C specifically adapted to function as stations also may be suitable. In addition, while FIG. 22 shows only one station 2204C disposed on a user 2244, the use of two or more portable stations disposed on the user 2244 and/or on some other person also may be suitable. For example, if two people are present, each carrying a phone as may be suitable as a station, one or both such phones may function as a station in cooperation with a remote. In particular, systems on the person of individuals other than the user 2244 may serve as stations, in addition to or instead of a system on the person of the user himself/herself.

As may be seen in FIG. 22, the stations 2204A, 2204B, and 2204C are active (as indicated by the lightning bolts shown thereon). Thus, 2204A, 2204B, and 2204C may be understood as receiving the acoustic emission 2220, processing that acoustic emission, attempting to detect the acoustic emission, etc. The use of multiple stations 2204A, 2204B, and 2204C as shown in FIG. 22 may facilitate certain functions. For example, if one such station does not receive or identify the acoustic emission 2220 (e.g., due to distance, intervening sound-absorbing obstacles, background noise, etc.) another station may do so, providing redundancy. Similarly, if two or more stations do receive a given acoustic emission 2220, then the confidence that an acoustic emission 2220 has been produced (and thus that the relevant medication has been dispensed) may be greater than for only one station. In addition, if multiple stations receive an acoustic emission 2220, such stations may cooperate to determine features such as the location of the remote 2216 when the acoustic emission 2220 was produced. For example, if the stations 2204A, 2204B, and 2204C shown in FIG. 22 have receivers adapted to determine a relative direction of the source of the acoustic emission 2220 relative to those receivers, then the position of the source (i.e., the remote 2216) may be triangulated. Similarly, if the time of receipt at each station 2204A, 2204B, and 2204C may be determined with sufficient precision, it may be possible to determine where the acoustic emission 2220 originated based on time-of-flight. Other functions also may be enabled.

In addition, for at least certain embodiments multiple stations may cooperate. For example, stations may communicate wirelessly or via other avenues, sharing information, combining received data regarding acoustic emissions to make determinations as to whether an emission is characteristic, comparing received data to reject background noise (e.g., stations at different locations may not receive the same background noise), registering events and/or other information in multiple stations even if an acoustic emission was only determined at one station, etc. Other cooperative functions also may be suitable, and cooperation among stations (or likewise among remotes) is not limited.

Figure 23:
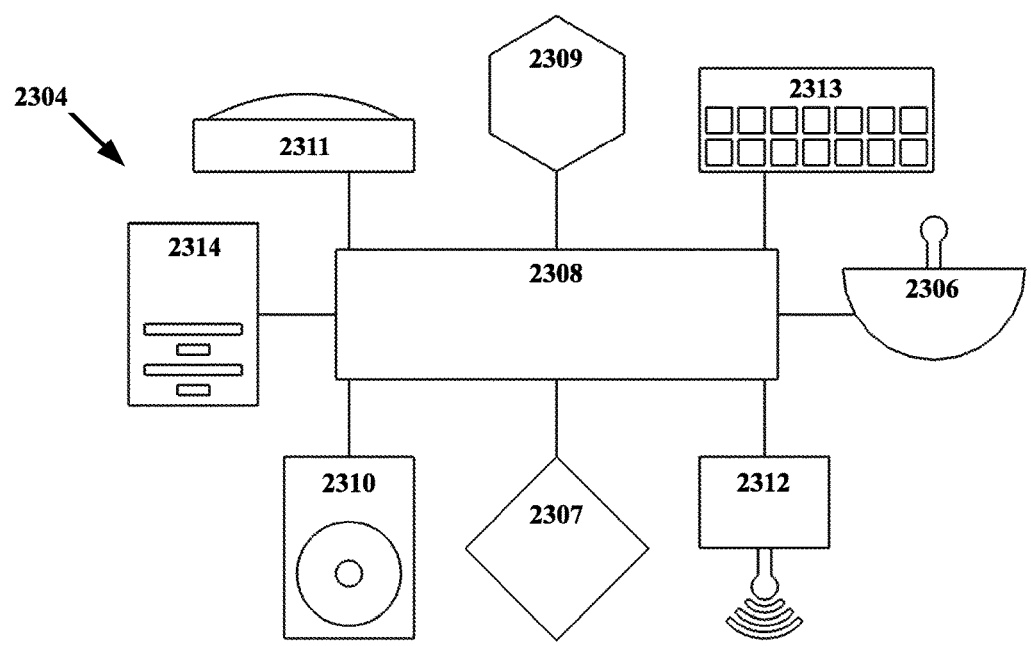
FIG. 23 depicts another example station, in schematic view.

Turning to FIG. 23, while certain elements as may be present in a station 2304 have been shown and described previously, for example in FIG. 3, other elements also may be present, and embodiments are not limited with regard to what elements are (or are not) present within a given station 2304. FIG. 23 shows certain additional elements as may be (but are not required to be) present in a station 2304.

The station 2304 as illustrated includes an acoustic receiver 2306, adapted to receive acoustic emissions, and a processor 2308 in communication with the receiver 2306. A power supply 2314, data store 2310, and communicator 2312 also are shown.

In addition, the example station 2304 includes a GPS 2307, adapted to determine a location of the station 2304 at a given time. For example, the location at which a user dispenses medication (as determined by the location at the time a characteristic acoustic emission is received) may be determined through the GPS 2307. Also, data from the GPS 2307 may be considered for other purposes. For example, typically it may be expected that a user may dispense eye drops while at least approximately stationary, such as sitting, standing, etc. If the GPS 2307 were to indicate that a user is moving at a walking or running pace, it may be unlikely that the user is dispensing eye drops at that time, regardless of what acoustic emissions may have been received. Thus, environmental factors may be considered in determining confidence as to whether a medication has been properly dispensed. Other determinations of position/motion (e.g., from receivers adapted to determine the direction from which an acoustic emission was received) likewise may be considered. Similarly, output from accelerometers, gyros, temperature or humidity sensors, etc., may be considered as well in determining whether a medication has been dispensed.

The station 2304 as shown also includes a direction finder 2309. For example, the direction finder 2309 may be adapted to determine the direction from which an acoustic emission originated, relative to the station 2304. It is noted that in at least certain instances a direction finder 2309 may be integrated into a receiver 2306, for example in the instance of a directional microphone. However, while such integration is not prohibited, neither is such integration required.

The station 2304 may include a display 2311. For example, the display 2311 may show information related to the dispensing of medication. The display 2311 may show confirmation that an acoustic emission has been detected, a listing of previous acoustic emissions, a visual reminder that a user is due for their next dose of medication, an advisory that medication is running low, etc. The type and extent of information as may be displayed is not limited. In addition, the nature of the display 2311 is not limited, either with regard to form or complexity. For example, a display may be a simple tell-tale such as an LED that flashes green to indicate that medication has been dispensed. However, suitable displays may be more sophisticated, including but not limited to alpha-numeric displays, CRT or LED screens, etc. In addition, while the term display 2311 may suggest visual output, suitable displays are not limited only to visible displays; for example, an audio speaker that provides a reminder chime to take medication, or that plays a voice message confirming that medication has been taken, etc., also may be suitable.

In addition, the station 2304 may include a user interface 2313 as shown in FIG. 23. For example, the user interface 2313 may enable input from a user to the station 2304. Thus for at least certain embodiments a user may add or delete characteristic emissions of interest (e.g., if the user begins taking a new medication or ceases to take an old one), to call up data for review, to change user preferences, etc. As with displays 2311, user interfaces 2313 may be simple (such as one or more individual buttons) or complex (such as a touch screen or voice input system), and are not limited with regard to form, complexity, etc.

It is noted that certain existing systems, including but not limited to smart phones, may already include some or all of the elements shown in FIG. 23. For example, a smart phone may include a processor, directional microphone, power supply, data store, communicator, GPS, display, user interface, etc. While use of such devices as stations in cooperation with remotes is not prohibited, and in at least certain instances may be advantageous (e.g., being already available to or in possession of certain patients), neither is it required to use smart phones as stations.

Thus, it may be useful in at least certain instances to consider remotes (and/or emitters, for embodiments that may not include a distinct remote such as shown in FIG. 12A through FIG. 12D) and stations separately. Different remotes and stations may be "mixed and matched"; it is not necessary for a given remote to be exclusively in cooperation with a given station, or vice versa. A single station may detect acoustic emissions from many remotes, and likewise may remotes may detect acoustic emissions from a single remote.

Figure 24:
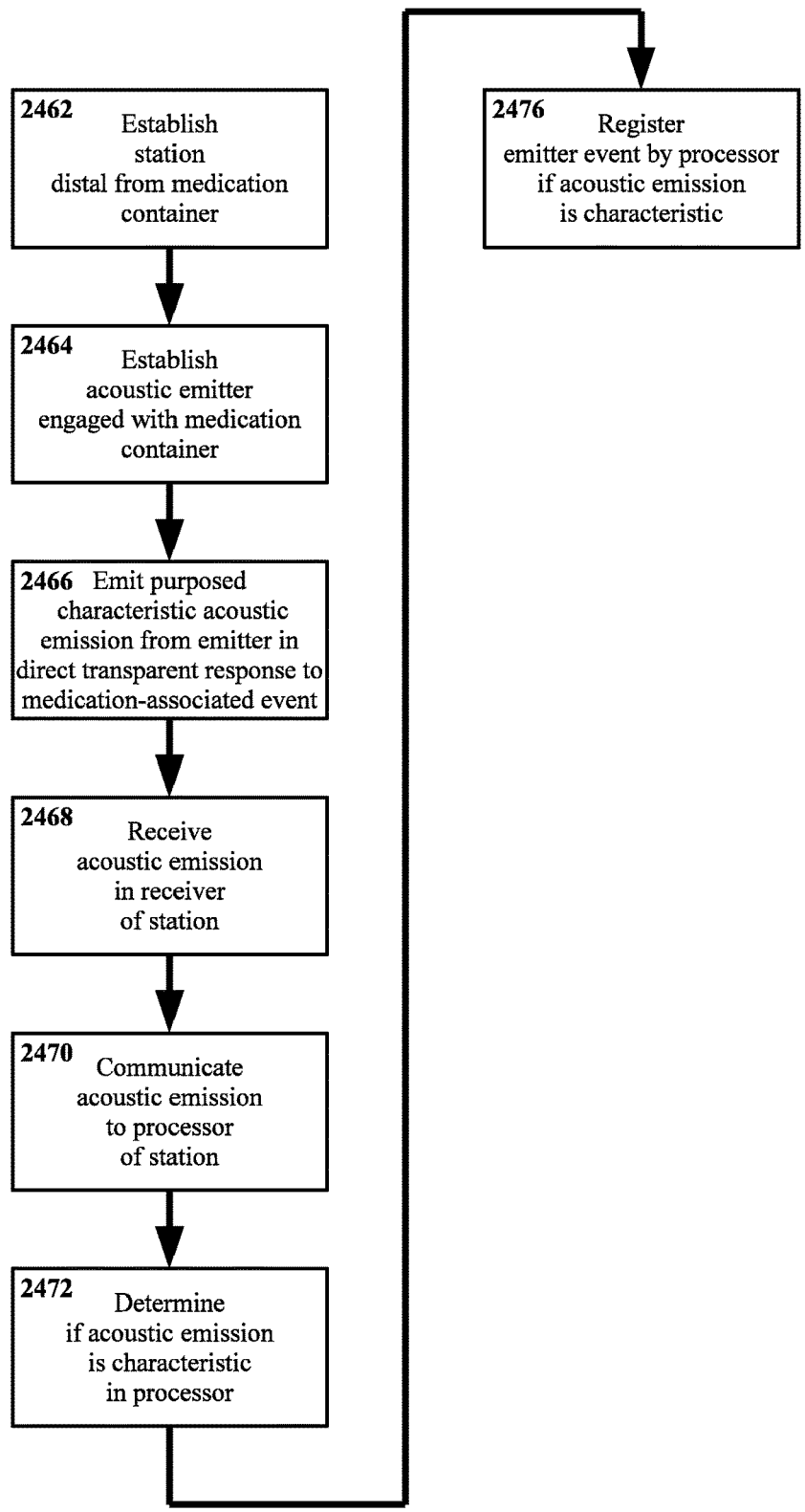
FIG. 24 depicts an example method for determining the use of a medication through transparent consequential characteristic emissions absent a remote, in flow chart form.

Now with reference to FIG. 24, as previously noted (e.g., with regard to FIG. 4) example methods may utilize remotes to determine the dispensing and/or use of medication through transparent and consequential response to some event. Certain previous examples herein have addressed the use of remotes for producing evidence of the event, such as an acoustic emission caused by compressing a remote equipped with a whistle. Such events, being associated with a remote, may be referred to as "remote events". (It is noted that the term "remote event" does not necessarily refer to remoteness in the sense of distance, but may instead refer to the use of a mechanism referred to herein as a remote. Nevertheless, a remote producing an acoustic emission may indeed be at some distance from, for example, a station receiving that acoustic emission.)

However, while the use of a remote may be suitable for certain embodiments, use of a remote is not necessarily required. For example, as shown in FIG. 12A through FIG. 12D, an acoustic emission may be produced without a remote that is distinct from a container. An acoustic emitter may be integrated into a container, so that functionality is obtained without the use of a remote. An example method for such an arrangement is shown in FIG. 24.

In the method of FIG. 24, a station is established 2462 at some location distal from a medication container. An acoustic emitter is established 2464 at some location proximate the medication container. As shown and described previously herein, establishing an acoustic emitter 2464 may include establishing a remote and engaging that remote with the medication container; however, not all embodiments necessarily require a remote as such.

In a consequential and user-transparent response to some event affecting the acoustic emitter (and typically the medication container), and in association with dispensing medication, a purposed characteristic acoustic emission is emitted 2466 from the acoustic emitter. Such an event may be referred to as an emitter event; an emitter event may be considered as similar to a remote event, and indeed certain remote events may also be emitter events. For example, if a whistle is used as an acoustic emitter, and an acoustic emission therefrom is to be received and considered, it may be reasonable to refer to the event producing that acoustic emitter as an emitter event (being produced due to an event happening to the emitter) or in some instances equivalently as a remote event (being produced due to an event happening to the remote, and thus also to the emitter). However, where reference to a remote event may assume the presence of a remote, reference to an emitter event does not so presume that a remote exists.

As with remote events, emitter events may be produced as a result of dispensing or using a medication, or as a result of some contextual action. For example, in the arrangement of FIG. 12A through FIG. 12D acoustic emissions are produced as the cap of a medication container is removed and replaced, rather than as medication is dispensed per se; such acoustic emissions may be understood as contextual to dispensing medication.

Still with reference to FIG. 24, the acoustic emission is received 2468 in the receiver of the station. The acoustic emission is communicated 2470 to the processor of the station. Within the processor, a determination is made 2472 as to whether the acoustic emission that has been received is indeed characteristic of the emitter. If the acoustic emission is determined 2472 to be characteristic of the emitter, then an emitter event is registered 2476 by the processor. That is, if the processor determines that the emitter has made its characteristic sound, it is considered that an event that would cause that sound has taken place, and the event may be stored in a data store, transmitted to some recipient, etc. Thus if the event in question is associated with dispensing medication, then it may be considered that the medication has been dispensed, etc.

In comparing FIG. 4, FIG. 5, and FIG. 24 (and certain subsequent figures herein) it is noted that embodiments of a method may similar despite variations in the specifics of the emitter and/or station. For example, whether a remote is present (e.g., FIG. 4 and FIG. 5) or not (e.g., FIG. 24), or whether a station is a smart phone (e.g., FIG. 5) or not (as is unspecified by but encompassed within FIG. 4 and FIG. 24), embodiments of methods may be carried out regardless. Thus, embodiments may be independent of at least certain particulars of emitter/remote and station; a given station may function regardless of whether a remote or an emitter is present (or what sort of remote or emitter is present), a given remote or emitter may function regardless of whether a station is a smart phone or a dedicated device, etc.

Figure 25:
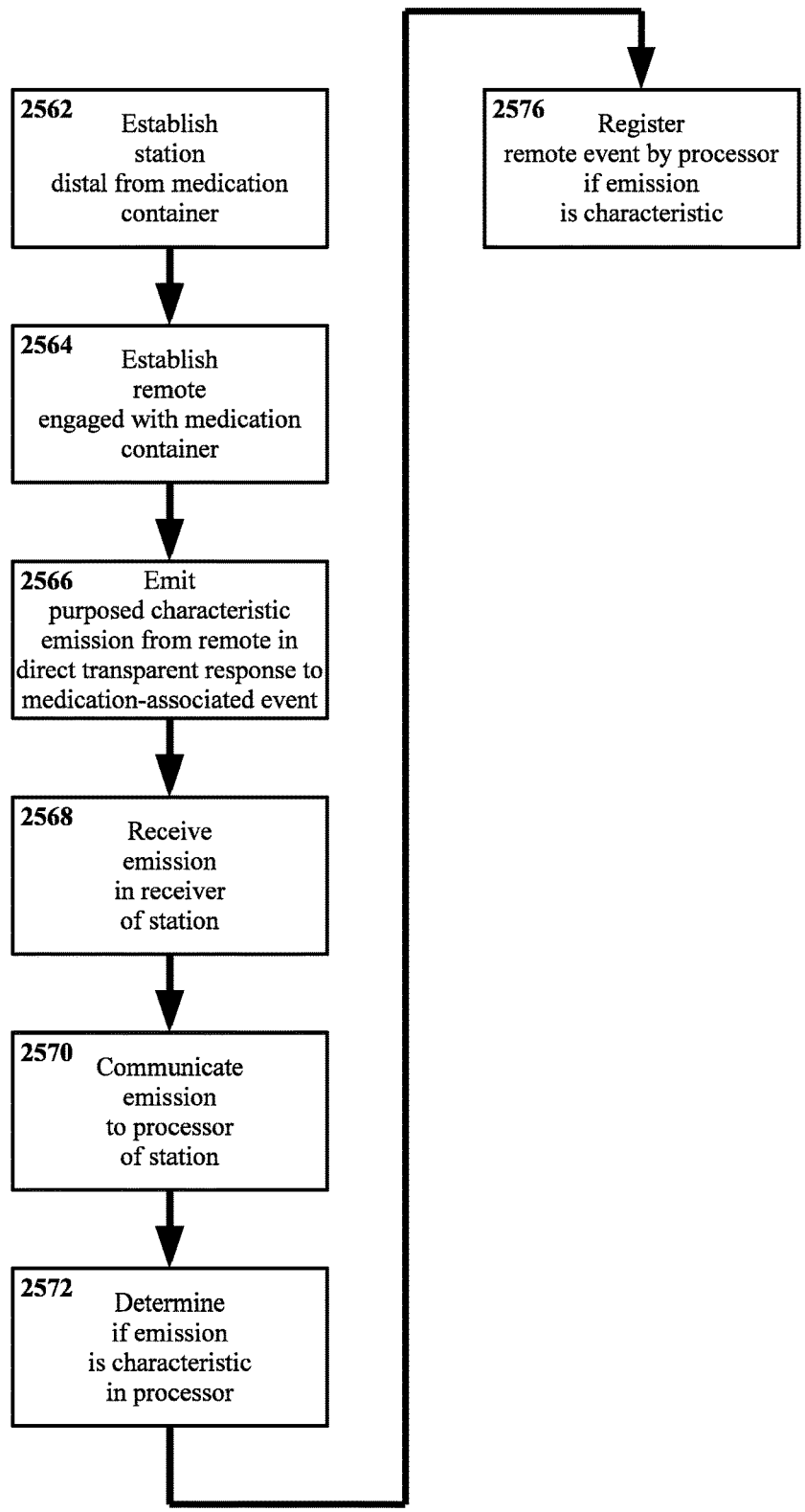
FIG. 25 depicts an example method for determining the use of a medication through transparent consequential characteristic non-acoustic emissions, in flow chart form.

Now with reference to FIG. 25, methods may utilize acoustic emissions in determining the dispensing and/or use of medication through transparent and consequential response to some event. However, for example as noted with regard to FIG. 18A and FIG. 18B, non-acoustic emissions, including but not limited to optical emissions such as visible light, infrared light, etc., also may be suitable In the method of FIG. 25, a station is established 2562 at some location distal from a medication container. A remote is established 2564 at some location proximate the medication container. (As noted previously with regard to FIG. 24, for certain embodiments it may be suitable to establish an emitter without a remote.) In a consequential and user-transparent response to some event affecting the remote, and in association with dispensing medication, a purposed characteristic emission is emitted 2566 from the remote. The characteristic emission may be entirely acoustic, but other arrangements also may be suitable. For example, an emission may include both acoustic and optical portions. Such an arrangement may for example enable a convenient determination of distance between a remote and a station. For example, if a light component of an emission and a sound component of an emission are produced together in time, the distance between the remote producing the emission and a station receiving that emission may be determined through measuring the time elapsed between receipt of the light component and receipt of the sound component. (This may be analogous to approximating distance to a lightning strike through counting the seconds between the visible flash and the audible thunder.) Alternately, all-optical emissions may be suitable, as may other non-acoustic emissions. The type of characteristic emissions are not limited.

Still with reference to FIG. 25, the emission is received 2568 in the receiver of the station. The emission is communicated 2570 to the processor of the station. A determination is made 2572 as to whether the emission is characteristic of the emitter. If the emission is determined 2572 to be characteristic of the emitter, then a remote event is registered 2576 by the processor.

Figure 26:
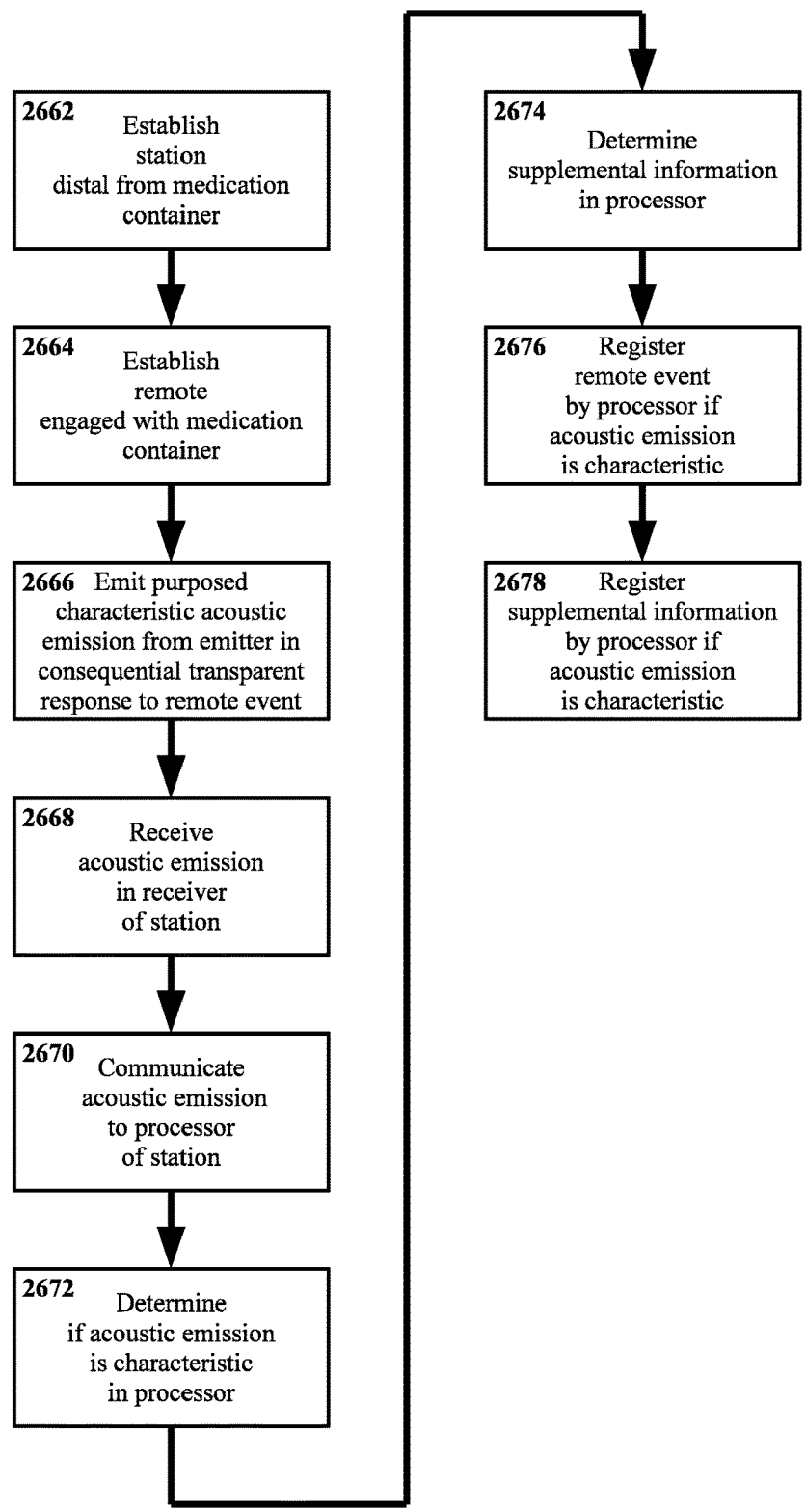
FIG. 26 depicts an example method for determining the use of a medication through transparent consequential characteristic emissions and determining supplemental information, in flow chart form.

Now with reference to FIG. 26, as described previously embodiments may include registration of events, such as recording that a medication has been dispensed in a data store, displaying that the medication has been dispensed on a screen, etc. However, the information registered is not limited only to the fact of the event, and other information also may be registered.

In the example of FIG. 26, a station is established 2662 at some location distal from a medication container. A remote is established 2664 at some location proximate the medication container. In a consequential and user-transparent response to some event affecting the remote, and in association with dispensing medication, a purposed characteristic acoustic emission is emitted 2666 from the remote. The acoustic emission is received 2668 in the receiver of the station, and is communicated 2670 to the processor of the station. A determination is made 2672 as to whether the emission is characteristic of the emitter.

In addition, supplemental information also may be determined 2674 in the processor. For example, the time at which the acoustic emission—in this example, referred to as the remote event—was received by the station may be determined (e.g., from a clock on-board the processor, from some external source in communication with the processor, etc.). This time may be referred to as the remote event time. The precise manner in which a remote event time is determined is not limited; a remote event time may be defined as the time that the acoustic emission was detected, the time that the acoustic emission was confirmed as being characteristic of the remote/emitter, or in some other manner. Similarly, additional supplemental information regarding the dispensing of medication may be determined, such as the dosage dispensed (e.g., as noted with regard to FIG. 14A through FIG. 14D).

Other supplemental information regarding the acoustic emission may be determined. For example, the wave form of an acoustic emission may be measured and communicated to the processor. Such an action may not require additional steps; determination of whether the acoustic emission may for example be based in whole or in part on consideration of the wave form, whether that wave form matches some standard therefor, etc. However, performing additional steps in acquiring such supplemental information, while not required, is not prohibited.

Supplemental information regarding processing of the acoustic emission also may be determined. For example, if a confidence value is computed for or otherwise assigned to a given acoustic emission (e.g., 92% confidence that the received acoustic emission is characteristic), that confidence value also may be regarded as supplemental information.

Furthermore, information not immediately related to the remote event may be determined. For example, environmental information such as the temperature, humidity, light level, level of background noise, etc., may be determined. Information regarding the user also may be determined, such as how the user is moving, the user's body temperature, etc. Such supplemental information may be determined using sensors on the station. For example, considering a smart phone as a station, certain smart phones may include sensors adapted to measure temperature, background noise, etc. If a smart phone is employed as a station, and may be determined (or assumed) to be on the person of the user, then such a station also may measure properties of the user such as body temperature, other biometrics, the position, speed, etc. of the user (e.g., through on-board gyros and accelerometers), and other phenomena. However, such supplemental information is not limited to being determined only by a smart phone, only from a station disposed on the person of a user, or by any station.

The content of supplemental information and manner of determining supplemental information is not limited.

Continuing in FIG. 26, if the emission is determined 2672 to be characteristic of the emitter, then a remote event is registered 2676 by the processor. Similarly, if the emission is determined 2672 to be characteristic some or all of the supplemental data may be registered 2678. Like registration 2676 of the remote event, registration 2678 of supplemental information is not limited, and may include but is not limited to display, storage, and communication. In addition, it is noted that not all supplemental information determined 2674 necessarily must be registered 2678 in a given embodiment. For example, a waveform for an acoustic emission may be determined as supplemental information and a confidence level assigned thereto, but this does not impose any requirement for the waveform or confidence level to be outputted to a display, recorded in a data store, or otherwise registered.

In addition, as previously noted with regard to registering remote events, registration of supplemental information if an acoustic emission is characteristic does not exclude the possibility of registering supplemental information even if an acoustic emission is received but found not to be characteristic, or if no acoustic emission is received. For example, considering a smart phone as a station, it may be suitable to record the degree of motion of the smart phone over time on an ongoing basis regardless of whether an acoustic emission is received. If the smart phone is completely stationary for some period, it may be considered that the smart phone is not being worn or carried by the user during that time. In such instance, it may be inferred that the user may be away from their phone and that medication may have been dispensed during the period even though that dispensing of medication was not detected, that the user may be asleep, etc. While such information may not directly indicate that medication was or was not dispensed, nevertheless such information may still be of use in evaluating the overall usage of medication over a period of time. Thus, information may be registered even if no emission is received that is determined to be characteristic of a given remote.

Figure 27:
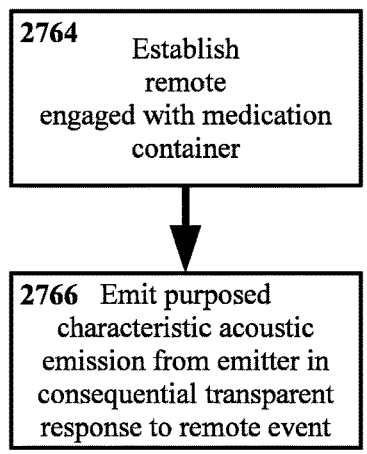
FIG. 27 depicts an example method for indicating use of a medication through producing transparent consequential characteristic emissions, in flow chart form.
Figure 28:
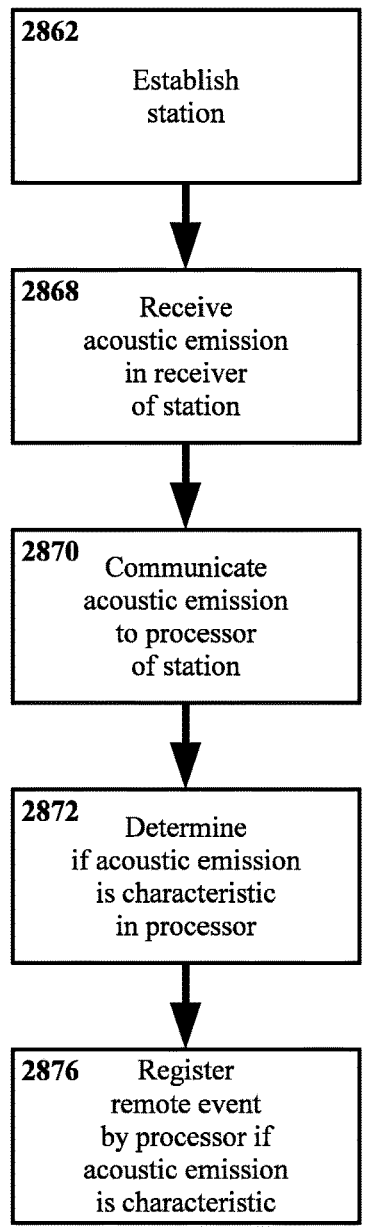
FIG. 28 depicts an example method for identifying use of a medication through receiving characteristic emissions, in flow chart form.

Turning to FIG. 27 and FIG. 28, as noted previously (e.g., with regard to FIG. 23 and FIG. 24) embodiments are not necessarily required to match a given remote with a given station, or vice versa. Indeed, embodiments of a remote may be considered as distinct devices from any station as may cooperate therewith, and embodiments of a station likewise may be considered as distinct devices from any remote as may cooperate therewith. Similarly, producing the acoustic emission (e.g., dispensing medication) and evaluating the acoustic emission (e.g., registering that medication has been dispensed) may be considered separately from one another.

Specifically with reference to FIG. 27, therein an example method for indicating use of a medication through producing transparent consequential characteristic emissions is shown. In the example method shown an acoustic emission indicative of some event such as a medication being dispensed is produced, however the interpretation of that acoustic emission is not shown. Thus FIG. 27 may be considered as addressing use of a remote (or similarly an emitter) as a distinct device.

In the example of FIG. 27, a remote is established 2764 engaged with (or at least in proximity to) a medication container. In a consequential and user-transparent response to some event affecting the remote, and in association with dispensing medication, a purposed characteristic acoustic emission is emitted 2766 from the remote.

Typically though not necessarily, the acoustic emission then may be received, evaluated, etc. elsewhere, such as in a station. However, it may be suitable for at least some embodiments to focus on the production of an acoustic emission that indicates medication has been dispensed, used, prepared for use, etc., without also considering in detail the subsequent processing of that acoustic emission.

Conversely with reference to FIG. 28, therein an example method for determining use of a medication through receiving characteristic emissions is shown. In the example method shown an acoustic emission is received and interpreted, however the production of that acoustic emission is not shown. Thus FIG. 28 may be considered as addressing use of a station as a distinct device.

In the example of FIG. 28, a station is established 2862. A characteristic acoustic emission is received 2868 in the receiver of the station, and is communicated 2870 to the processor of the station. A determination is made 2872 in the processor as to whether the emission is characteristic. For example, the station may have some standard for evaluating acoustic emissions, some algorithm for comparing emissions to that standard, etc. However, the particulars of what may have generated any given acoustic emission may or may not be addressed by the station. Continuing in FIG. 28, if the emission is determined 2872 to be characteristic, then an event is registered 2876 by the processor. Again, the nature of the event (e.g., medication being dispensed) may not be specified or even considered with regard to the station.

Typically though not necessarily, characteristic acoustic emissions as received may be anticipated to have been produced by some characteristic source, such as an emitter and/or a remote incorporating an emitter. However, it may be suitable for at least some embodiments to focus on the receipt and evaluation an acoustic emission without concern as to how, why, etc., that acoustic emission may have been produced.

Figure 29:
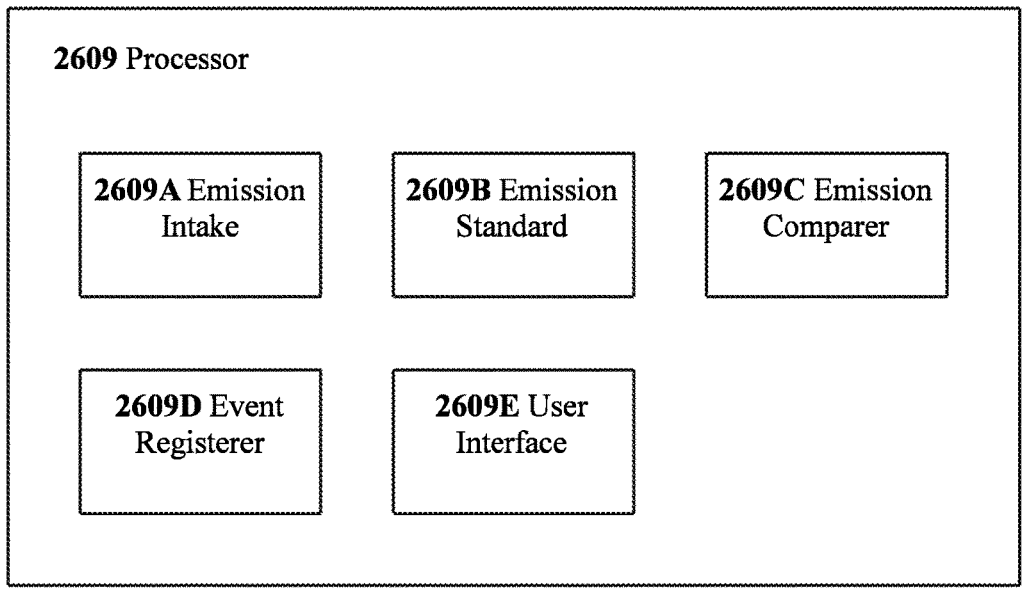
FIG. 29 depicts an example processor adapted for identifying use of a medication through receiving characteristic emissions via data entities instantiated thereon, in schematic view.

Now with reference to FIG. 29, as has been described previously certain functions may be carried out within/by a processor, such as determining whether a received acoustic emission is characteristic of a given emitter. One example approach (though not necessarily the only approach) for implementing such functionality is shown in FIG. 29. Therein, a processor 2908 is shown, as may be similar to processors shown elsewhere herein as being in/on various stations. In addition, the processor 2908 in FIG. 29 is shown with several data entities disposed thereon: an emission intake 2908A, an emission standard 2908B, an emission comparer 2908C, an event register 2908D, and a user interface 2908E. Such data entities may for example include digital data and/or executable instructions instantiated onto the processor 2908. In more colloquial terms, some or all of the data entities 2908A through 2908E may be programs or portions thereof installed onto a processor, such as the processor of a smart phone, etc. (though this is not limiting). Steps of establishing a station may include, for example, instantiating data entities 2908A through 2908E onto a processor, though other arrangements also may be suitable.

In the example of FIG. 29, the emission intake 2908A is adapted to accept an acoustic emission, and/or some signal representing an acoustic emission, into the processor from some external source, such as a microphone or other receiver. For example, the emission intake 2908A may represent one or more device drivers for communicating input from a microphone to a processor, etc.

The emission standard 2908B is adapted to provide guidance in some form as to what may constitute a characteristic acoustic emission. For example, the emission standard 2908B may specify frequency ranges for one or more pitches (e.g., whistle pitches), wave forms, etc. The emission standard 2908B may in at least some sense be considered as a target or template that a received acoustic emission must match in order to be identified as being a characteristic acoustic emission (e.g., characteristic of a particular whistle, etc.) as opposed to background noise, a false positive, etc.

The emission comparer 2908C is adapted to determine whether a given acoustic emission is a characteristic acoustic emission. For example, the emission comparer 2908C may compare frequency ranges of a two-tone whistle pitch to frequency ranges as specified in the emission standard 2908B, may carry out an algorithm to determine whether a waveform for a sound sufficiently matches a specified waveform in the emission standard 2908B to identify that sound as characteristic, etc.

The event register 2908D is adapted to register an event as having taking place if the emission comparer 2908C determines that a received acoustic emission is characteristic. Thus, the event register 2908D may record data indicating that the event (such as dispensing a medication) took place into a data store, may output data regarding the event to a display, may transmit data for the event to some recipient, some combination thereof, etc. Not all embodiments necessarily will exhibit all such functions, for example a station with no display may not benefit from an event register 2908D capable of outputting information to a display, etc.

The user interface 2908E is adapted to accept input from a user, for example regarding functions performed by the station. As a more concrete example, the user interface 2908E may enable a user to enter a query to display all events in the past 30 days, to install a new emission standard 2908B (e.g., for a new remote and/or a new medication), to manually register an event that was erroneously not registered or manually delete an event that was registered by mistake, etc. Again, not all embodiments necessarily will have or must have a user interface, even among those embodiments which utilize data entities as shown in FIG. 29 (which configuration itself is not limiting).

Similarly, various embodiments may have additional data entities and/or other elements. For example, an embodiment may include a data entity adapted to compare the usage of a medication (as determined through receiving acoustic emissions from an emitter on/in the container) against a prescribed regimen for that particular medication and patient, a data entity to communicate such adherence information to some external party such as a medical care provider or clinical research supervisor, a data entity to remind the user to take a medication, a data entity to automatically request a refill of a prescription based on time or quantity remaining, etc. Other arrangements also may be suitable.

Figure 30:
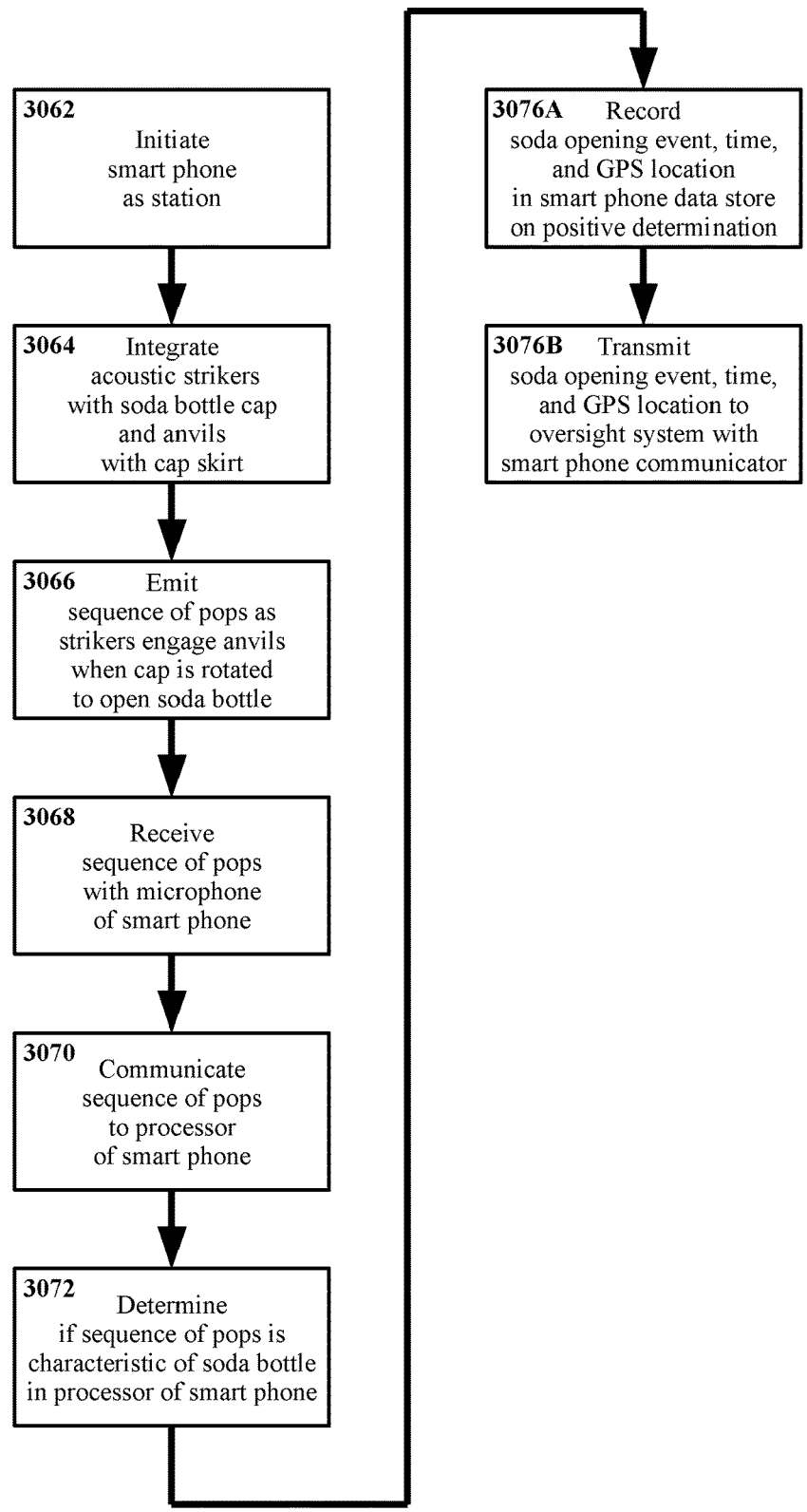
FIG. 30 depicts an example method for identifying use through receiving acoustic emissions, with reference to a soda bottle, in flow chart form.

Now with reference to FIG. 30, certain previous examples herein have referred to medication, medication containers, tracking the use of medication, etc. However, embodiments are not limited only to arrangements that address medication or medical treatment. So long as a suitable acoustic emission is produced (and received, etc.), embodiments may include a broad range of enclosures, emitters, processes, physical objects or products, etc. FIG. 30 shows an arrangement as may be at least somewhat similar to certain previous examples, but which is not specific to a medication container (or indeed specific to any other container).

In FIG. 30, an example method is presented with reference to a container not specified as being a medication container. For purposes of clarity, FIG. 30 is relatively concrete, referring to specific devices and features, e.g., a smart phone, strikers and anvils making acoustic emissions, etc. It is emphasized that such particulars are examples only, and are not limiting.

In the method of FIG. 30, a smart phone is initiated 3062 as a station. For example, executable instructions and/or data may be instantiated onto the processor of the smart phone. Such instantiation may take the form of a tracking application or "app" being loaded onto the smart phone. Alternately, such an app (and/or other instructions, data, etc.) may already be present on the smart phone (e.g., having been installed earlier), in which case initiation may simply be loading/running the app, or similar.

Continuing in FIG. 30, acoustic strikers are integrated 3064 with a plastic twist-off cap of a soda bottle, and anvils are integrated 3064 with a skirt ring of that cap. As described subsequently herein, the strikers and anvils may cooperate to serve as an acoustic emitter. (Example arrangements of such a cap and skirt ring are shown subsequently herein.) As noted previously, the ordering of steps is not necessarily limited to what is shown in the various examples herein. As a particular example, the integration 3064 of strikers and anvils into a soda bottle cap assembly may take place before, simultaneously with, or after initiation 3062 of the smart phone as a station. For instance, a cap may be injection-molded with suitable strikers and anvils in place, then applied to a soda bottle, etc. (Though other emitters, production methods, containers, etc. all may be equally suitable. Further, it is not required that emitters must be integral with a cap or other element, though such arrangement is presented as an example herein.)

Typically, to open the soda bottle the cap is rotated while the skirt ring remains in place. The strikers engage the anvils, emitting 3066 a series of "popping" noises as the bottle is opened. In such instance, the user need not perform any particular action to consciously or deliberately cause the sequence of pops to be emitted 3066; the pops are emitted 3066 as a consequence of the cap being twisted relative to the skirt ring in opening the bottle. It is noted that the number, size, shape, material, arrangement, spacing, etc. of the various strikers and anvils may vary considerably and may affect the pitch, volume, duration, etc. of each pop emitted 3066. Thus, such an acoustic emission may be made to be characteristic, in that the number of other phenomena that may produce that particular sequence of pops is small. Consequently, detecting that particular series of pops may be treated as a reliable indication that the sound is coming from the cap while being opened on the container.

Continuing in FIG. 30, the sequence of pops (in this example serving as an acoustic emission) is received 3068 with a microphone of the smart phone (serving as a station). The series of pops (and/or some electronic or other analog thereof) is communicated 3070 to the processor of the smart phone. In the processor of the smart phone, a determination is made 3072 as to whether the series of pops is characteristic of the soda bottle under consideration (or perhaps more strictly, the opening of the cap of that soda bottle). This may include a determination of such factors as to how many pops are present, at what pitches, with what timing, in what order, with what waveforms, etc. The factors that may be considered are not limited.

In response to a positive determination—that is, it is determined 3072 that the series of pops corresponds with the soda bottle—a soda opening event is recorded 3076A in a data store of the smart phone by the processor, along with the time of that soda opening event and the GPS location of the smart phone during the soda opening event (which may be inferred as approximating the location of the soda bottle at the time of opening). In addition, the soda opening event, time thereof, and GPS location of the smart phone are transmitted 3076B to an oversight system via a communicator (e.g., wifi) of the smart phone. The oversight system may be understood as some system as may receive and at least potentially take further action with the data transmitted thereto (e.g., soda opening event, time, and GPS location). The form and nature of oversight systems is not limited. However, for example an oversight system may include a processor and/or memory adapted to record soda opening events, times, and locations and determine distributions in time, space, etc. for the consumption of the soda in question. Such information may be logged for future reference, or may be used to drive other actions; for example, if a particular soda company were to sponsor a concert, then smart phone users whose smart phones registered the opening of that brand of soda at the time and location of the concert may be contacted to assign a "badge" thereto, distribute consumer loyalty points, etc. Such follow-up actions are not limited.

It is noted that both steps 3076A and 3076B in FIG. 30 may be understood as representing aspects of registration. That is, data may be recorded 3076A and also transmitted 3076B. In certain previous examples multiple forms of registration are presented as a single step, e.g., in FIG. 5 both storing and transmitting an eye drop dispensing event are referenced as step 0576. As noted elsewhere, steps may be subdivided, combined, etc. without limit within the range of logic and function. In certain examples, it may be useful to subdivide the registration in particular; as shown subsequently herein for example, some embodiments may include different registration steps in different situations.

It is again emphasized that the arrangements in FIG. 30 are an example only, and while the particulars therein are presented for clarity those particulars do not limit embodiments.

Figure 31:
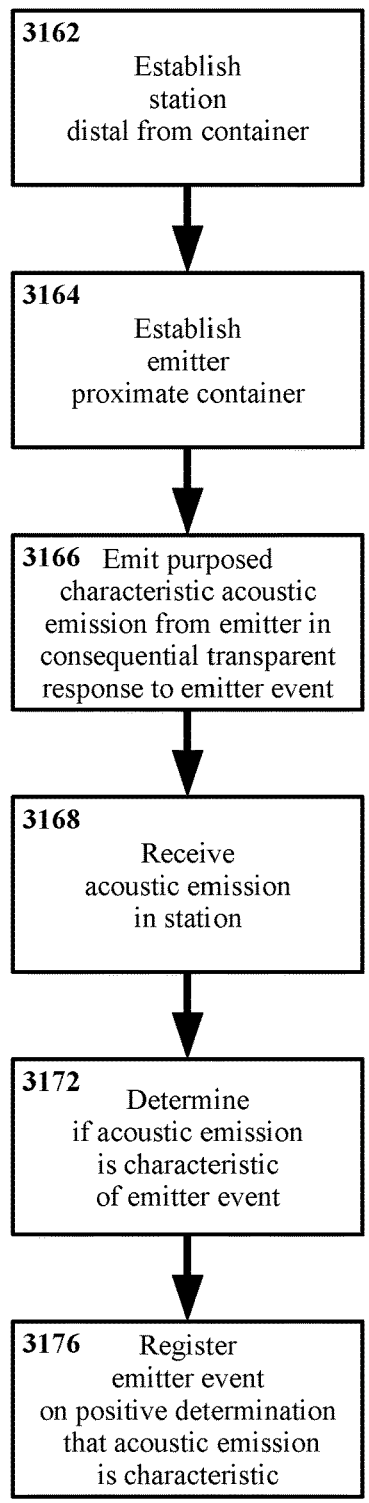
FIG. 31 depicts an example method for identifying use through receiving acoustic emissions in flow chart form.

Turning now to FIG. 31, a less concrete example otherwise at least somewhat similar to the arrangement in FIG. 30 is presented. As noted, containers and/or other enclosures, acoustic emissions, etc. may vary considerably and are not limited to various examples presented herein. The arrangement in FIG. 31 is not specific as to a container, emitter, etc.

In the arrangement of FIG. 31, a station is established 3162 distal from a container. The station is not limited and may vary widely; however, as described previously herein suitable stations may include but are not limited to smart phones, other portable or stationary electronic devices, and a dedicated device. Similarly, the container is not limited and may vary widely. As also described previously herein, suitable containers may include but are not limited to various forms of medication container, such as squeeze bottles, pill bottles, etc. It is emphasized that non-medication containers may be suitable, for example bottles or cans adapted for containing soda, water, or other liquids, bags adapted for containing chips, nuts, or similar snacks, boxes adapted for transportation (e.g., by mail) for storage of goods, etc. In addition, it is noted that "containers" may include mechanisms that may function as part of an enclosure without necessarily being or including a complete container in themselves. For example, a packing tape that produces a suitable acoustic emission when cut or torn may not literally be a container; however, insofar as such packing tape may be suitable for closing a box (or other container) such that the packing tape is cut or torn to open the box, as so used (or similarly used) the packing tape should be understood as being encompassed by the term "container" herein.

Continuing in FIG. 31, an emitter is established 3164 proximate a container. Emitters have been described previously herein (and additional examples are presented subsequently). It is noted that certain previous examples may have referred to a step of establishing a remote, with an emitter therein, thereon, etc. While it is not prohibited to establish 3164 an emitter in cooperation with a remote, an emitter may be established 3164 even if no remote exists, or if the only feature of a remote is considered to be the emitter. For example, a plastic emitter molded as an integral part of a plastic container certainly may be understood as having been established (since the emitter exists), but aside from the emitter itself there may be no structure or other feature that could be identified distinctly as a remote. Alternately, it may be considered that for a plastic container with an emitter integral thereto the container itself represents the remote; that is, the remote and the container may be considered to be one and the same. Thus the emitter and/or remote may be considered "proximate" a container in the sense that the emitter and/or remote are part of the container itself. Establishing 3164 an emitter thus encompasses (though is not necessarily limited to) emitters that are distinct as well as emitters integral to a container or other element, whether with or without a remote.

In addition, as noted previously certain steps shown in FIG. 31 (and other examples) may be carried out in an order differently than is illustrated. For example, depending on the particulars of station and remote steps 3162 and 3164 may be reversed. As a more concrete example, considering a smart phone as a station and an emitter molded into a soda bottle cap, the bottle may be manufactured well before the smart phone is manufactured (or before suitable executable instructions are instantiated onto the processor of the smart phone); in such case the station may not even physically exist at the time that the emitter and/or container are established.

Similarly, the emitter may be established 3164 before the container exists. Considering an emitter in the form of a packing tape that emits a series of acoustic pops when cut or torn, the tape may be produced long before a given container (such as a cardboard box) exists. This also is not prohibited. In such instance, it may be useful to consider the act of "establishing" the emitter to be the application of the tape to the box, rather than necessarily being the manufacture of the tape. Thus, unless physically impossible or specified herein, the reordering of steps and/or portions thereof may be understood to encompassed within various embodiments.

Still with reference to FIG. 31, a purposed characteristic acoustic emission is produced by the emitter, as a transparent (at least to the user) consequence of some emitter event. Typically though not necessarily, the emitter event may correspond with opening the container with which the emitter is associated, dispensing product therefrom, or otherwise manipulating the container. (Certain previous examples reference a "remote event" in a similar function; however as noted above with regard to steps 3162 and 3164 a remote may not necessarily be present in all cases, nor is a remote necessarily required.) For example, a bottle cap may produce a series of pops from strikers on a cap interacting with anvils on the skirt ring, as a consequence of the user opening the bottle and without requiring the user to take action (beyond opening the bottle) to produce such sounds.

Features such as purposed emission, characteristic emissions, transparency, and consequentiality have been described previously herein. However, as an aside it is noted that the absence of certain such features may be suitable for at least certain applications of certain embodiments, and may indeed provide additional functionality. More regarding such variations may be described subsequently herein.

Still with reference to FIG. 31, the acoustic emission is received 3168 in the station. For example, a microphone in, on, or in cooperation with the station may pick up sounds, etc., though other approaches also may be suitable. A determination is then made 3172 as to whether the acoustic emission is characteristic of the emitter event. To continue the example of the striker-and-anvil arrangement, does a given acoustic emission exhibit properties as would correspond with that striker-and-anvil arrangement? Typically though not necessarily, such determination is made in an electronic processor (whether in the station, in communication with the station, etc.), and/or is made through comparison to some emitter event standard setting out what the particulars of the characteristic sound may be.

On a positive determination (e.g., in step 3172) that the acoustic emission is characteristic of an emitter event (e.g., opening a bottle of soda), an emitter event is registered 3176. For example, the fact that an emitter event has taken place may be recorded in a data store, possibly along with additional information such as the time, the GPS location (e.g., of the station, and/or if known or determined, the emitter), the acoustic waveform of the emission, etc. In addition or instead, the emitter event may be displayed to the user (and/or some other person), communicated to some recipient, etc. As another alternative, the emitter event itself may not be displayed or communicated at all; for example, considering a smart phone as a station registration may include loading or running some program or function in the processor, or some other action(s) internal to the smart phone. As a more concrete example, registering 3176 opening a bottle of soda may load a cola promotion program on a smart phone, as may track cola consumption in different times and places so as to earn awards, prizes, etc. As a different example, registering 3176 opening a bottle of soda may load a health tracking program to log calorie intake, time and location of a cola being consumed, etc. Similarly, registering opening a jar of pasta sauce may load a data tracking program to log when various food items (or other perishables whether consumable or not, e.g., paints or nail polish as may dry out, etc.) were opened, so as to provide a record that the user may consult to see how long the pasta sauce has been in a refrigerator, etc. (Such arrangements may utilize, but are not required to utilize, unique first-opening acoustic emissions as distinct from subsequent opening emissions.) It is noted that loading such a program as a form of registration may be internal to the smart phone (or other station). That is, registration of when a food product in a user's kitchen was opened may not include or require communication with another system, device, etc. While such external communication is not prohibited, for at least certain embodiments it may be sufficient for the user to know (or be able to look up) when a product was opened, closed, etc. The manner and form of registration may vary widely, and is not limited.

Figure 32:
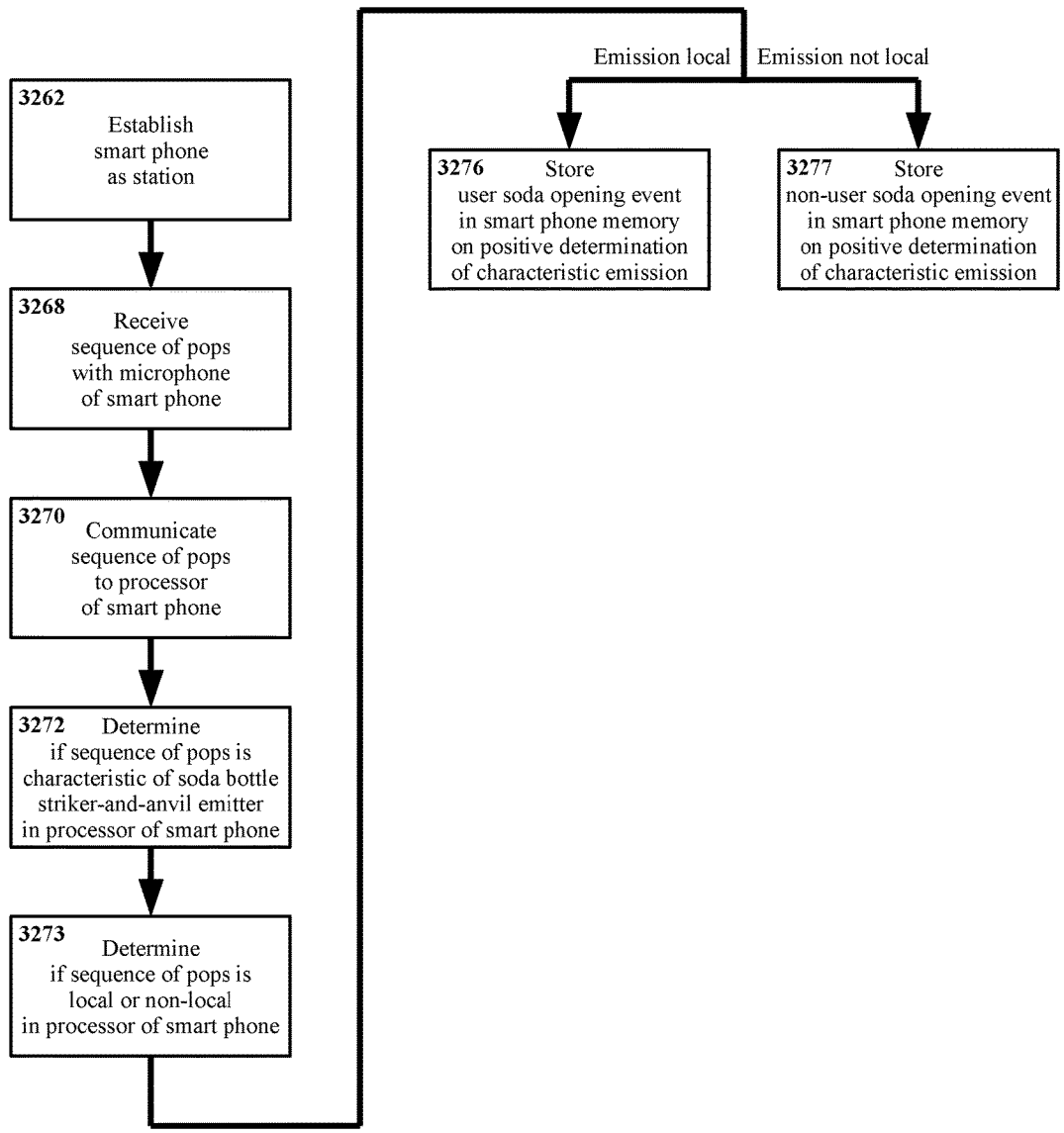
FIG. 32 depicts an example method for identifying use through receiving acoustic emissions, with non-linear registration distinguished by location, in flow chart form.

Indeed, turning to FIG. 32 it is noted that registration need not be a singular or "linear" operation. Rather, different registrations may take place under different conditions (or no registration at all) for a single embodiment. The example of FIG. 32 refers again to a smart phone as a station and a soda bottle as an emitter (somewhat similar to FIG. 30) but this is not limiting.

In FIG. 32, a smart phone is established 3262 as a station. The smart phone receives 3268 a series of pops with a microphone thereof, and communicates 3270 the sequence of pops to the processor of the smart phone.

It is noted that the emitter is not shown to be established or to produce the emission in the example of FIG. 32. For at least certain embodiments it may be suitable to consider a method mainly or entirely from the perspective of the station. For example, if a characteristic acoustic emission is received then that acoustic emission presumably was produced, which in turn implies the existence of an emitter. An arrangement at least somewhat similar also was shown previously in FIG. 25.

Continuing in FIG. 32, a determination is made 3272 as to whether the sequence of pops is characteristic of a striker-and-anvil emitter for a soda bottle. In addition, a determination is made 3273 in the smart phone processor as to whether the sequence of pops is local or non-local with respect to the smart phone. This may be determined for example based on the volume of the sound, e.g., a given design of emitter on a given container may produce an acoustic emission with at least a somewhat consistent level of volume. In such instance, the actual volume measured (e.g., acoustic wave magnitude) may be compared against some standard such as the expected volume at one meter. Other approaches also may be suitable, and the manner by which the determination of locality is not limited. In addition, what constitutes "local" vs. "non-local" is not limited and may vary from one embodiment to another. For example, an emission may be defined as being local if the source thereof may be determined to be not more than 1 meter distant, and non-local otherwise. However, an emission may be defined as local based on non-numerical considerations, e.g., is the emission from a soda bottle held by a person holding/carrying the smart phone? (In turn, such a determination may in itself utilize numerical analysis, though such an approach is not limiting.) Moreover, absolute certainty is not required in determining locality; it may be suitable to identify an acoustic emission as local with 95% confidence, 75% confidence, etc.

For at least some embodiments, the matter of locality may be described in colloquial terms as addressing the question: is the person opening the soda bottle (or other container) the person carrying the smart phone? Such a determination may be useful, since at least in principle two or more similar containers with similar emitters may be present in a given area, and/or two or more smart phones or other stations likewise may be present. If the aim is to determine whether a specific person may have opened a soda, determining locality may be one way to distinguish opening events for that person as opposed to opening events from some other person in the vicinity (though other approaches for distinguishing such matters also may be suitable, and are not limited).

Still with reference to FIG. 32, the example method therein then divides into two options, depending on the outcome of the determination 3273 regarding locality of the acoustic emission. If the emission is local, then a user opening event is stored 3276 in the memory of the smart phone on a positive determination of a characteristic emission (e.g., previously in step 3272). However if the emission is non-local, then a non-user opening event is stored 3276 in memory on a positive determination of a characteristic emission. In more colloquial terms, the characteristic emission is registered as having occurred, but may be either attributed to a user (e.g., the person owning/carrying the smart phone) or to someone other than the user. Such an approach may be useful, for example in subsequent evaluation and/or intervention. If the smart phone is executing an app to track consumption of a brand of cola, for example, distinguishing whether the user or some other person nearby has opened a cola may be relevant in tracking cola consumption. Likewise, considering medication use, it may be useful to distinguish between acoustic emissions associated with the user dispensing medication as opposed to background events in the environment (e.g., other people dispensing their medication).

Figure 33:
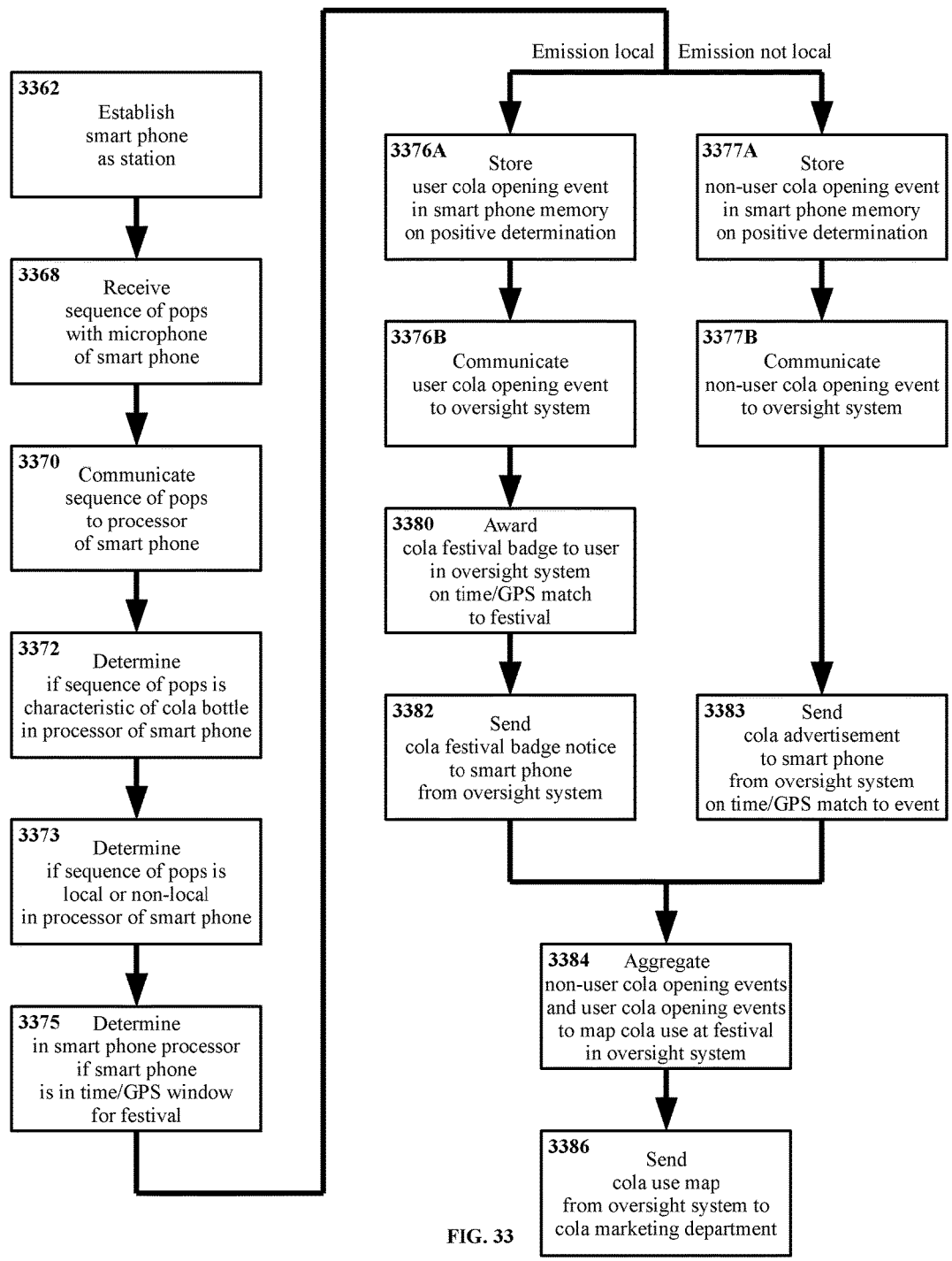
FIG. 33 depicts an example method for identifying use through receiving acoustic emissions, with intervention via registration and with reference to soda use, in flow chart form.

In the arrangement of FIG. 32 no such follow-up (e.g., intervention) is shown; characteristic emissions are registered as local (associated with the user) or not, but no specific action is referenced. Turning to FIG. 33, another example showing one (though by no means the only) form of subsequent intervention is presented. For the purposes of FIG. 33, it may be useful to consider an arrangement where a cola company is conducting a promotional campaign, wherein persons consuming the company's brand of cola at a specific festival (street fair, concert, etc.) may be awarded a digital "badge" commemorating those persons' presence at the festival. Potentially other benefits might attach, e.g., accumulation of "cola points", drawings for prizes, etc. The particulars are examples only and are not limiting.

In FIG. 33, a smart phone is established 3362 as a station, the smart phone receives 3368 a sequence of pops and communicates 3370 those pops to the smart phone processor, which determines 3372 whether the sequence of pops is characteristic of opening a bottle of a specific company's brand of cola. A determination is also made 3373 as to whether the acoustic emission (the sequence of pops) is local to the smart phone or non-local.

In addition, a determination is made 3375 in the smart phone processor as to whether the smart phone is within a time and position window defined for the festival under consideration. For example, the time may be determined by a chronometer of the smart phone, while a GPS function may supply information regarding the position of the smart phone. Thus, with information regarding time and space it may be viable to determine whether the smart phone (and presumably the user thereof) is at the festival, e.g., in the right place at the right time. Different, fewer, and/or more conditions may be applied (including no conditions at all); defining a festival and delineating that festival in time and space is presented as an example only.

The example method in FIG. 33 then divides, based on whether a received acoustic emission is local or non-local.

For local emissions, a user cola opening event is stored 3376A in the data store of the smart phone, and the user cola opening event also is communicated 3376B to an external recipient, referred to for this example as an oversight system. Collectively steps 3376A and 3376B may be understood as at least somewhat similar to registration of other events as presented in other examples herein, e.g., event data may be stored and communicated.

The recipient of the communication step 3376B as noted is an oversight system. Such a term is not limiting, and may for example be a database, network, computer system, technician or group of technicians, etc. as may collect, process, consider, and/or act upon cola opening events reported thereto. In addition, while for explanatory purposes functions may be referred to herein to carried out by distinct elements, e.g., a station and a separate oversight system, it is not required for all embodiments to separate such functions in practice. For example, a station may carry out certain functions of an oversight system, an oversight system may carry out certain functions of a station, etc. Indeed, a single device may carry out the functions referred to regarding both a station and an oversight system. For example, a smart speaker may receive acoustic emissions as well as aggregate registered information (more regarding aggregation is described subsequently herein).

Regardless of nature, in the example of FIG. 33 the oversight system then awards a badge to the smart phone and/or the user thereof, given a time/GPS match between the smart phone and the festival window (step 3380). Such a badge may indicate that the phone/user was present at the festival during the appropriate time and place, possibly also indicating that the user consumed the cola company's brand of product at the festival as well. Although a badge is awarded within the oversight system in step 3380, this is an example only and oversight system management is not limited. Other forms of data processing, comparisons, plotting, etc. also may be suitable.

The oversight system also sends 3382 a notice to the smart phone that a badge has been awarded 3380. Again, the interventions that an oversight system may perform are not limited. To continue the example of awarding a badge, other oversight system interventions with the smart phone/user such as communicating the badge to the user's social media account, forwarding messages to persons on a contact list, etc. also may be suitable. In addition, oversight system interventions other than notifications also may be suitable. (The nature of oversight interventions as may be carried out may depend to at least some extent on the oversight system management, type of information registered, etc. for a given embodiment.)

Returning to the local/non-local divide in FIG. 33, for non-local emissions a non-user cola opening event is stored 3377A in the data store of the smart phone, and the non-user cola opening event also is communicated 3377B to the oversight system. Again, collectively steps 3377A and 3377B may be understood as being (or at least resembling) forms of registration.

In addition, given a time/GPS match between the smart phone and festival window the oversight system sends 3381 a cola advertisement to the smart phone. For example, an advertisement might reference the detection of a non-user cola opening event, e.g., "Someone close to you just had a Kali Cola, why not have one yourself?" However, this advertisement (and indeed sending an advertisement at all) is an example only. It is noted that no oversight system management step comparable to 3380 is shown for non-local emissions; oversight system management (e.g., internal processing of registered data) is not required for all embodiments. However, although no such step appears in the non-local branch in FIG. 33, this is an example only and such steps also are not prohibited.

Continuing in FIG. 33, the method then unifies once again after steps 3380 and/or 3383. In the example as shown, non-user cola events and user cola events for the festival are aggregated 3384 in the oversight system so as to produce a map of cola use, e.g., where colas were opened, when, how many active non-user smart phones picked up the opening of those colas, etc., whether a given advertisements were followed by colas being opened, etc. Such a map may be useful so as to reveal patterns of consumption, effectiveness of advertising, clustering/interactions of people during consumption, etc. Other approaches for processing information, and/or other actions, also may be suitable. It is noted that collating 3384 to form a map may bear at least some resemblance conceptually to awarding 3380 the cola festival badge, e.g., in that both may involve management of information by the oversight system. However, a distinction may be drawn in that awarding 3380 a badge to a specific phone/user may require only data from/about that individual, where collating 3384 data to form a man may require data from multiple users and/or multiple instances of colas being opened. (Described in different terms, in at least some sense the arrangement shown in FIG. 33 and/or step 3384 individually may be considered to be a form of networked or distributed data processing.) It is noted that although FIG. 33 shows a specific ordering of such oversight system management—namely individual management happening before collective management—this is an example only. Collective management may be carried out first, collective and individual management may be carried out simultaneously, one may be carried out without the other, etc. Sequencing of oversight system management is not limited (similar variability has already been noted with regard to certain other example steps herein).

Still with reference to FIG. 33, the cola use map is sent 3386 from the oversight system to a marketing department for the cola company producing/distributing the cola under consideration. Such a step may be at least somewhat similar to 3382 and/or 3383, in that information is being communicated from the oversight system to some recipient. However, as noted with regard to step 3384, in step 3386 the oversight system communication may include combined information from multiple inputs. Also as noted with regard to step 3384, the ordering of individual vs. collective communication by the oversight system is not limited (nor is such communication necessarily required for all embodiments).

With regard to FIG. 33 as a whole, it is noted that certain logical/functional possibilities are not explicitly addressed therein. For example, in principle sounds may be received that are not found to be characteristic of the cola bottle; no actions are specified in such instances for FIG. 33. This should not be understood as an indication that actions are prohibited in such instances; for example, non-characteristic sounds may still be registered, may be analyzed, etc. (though such sounds also may be ignored). Similarly, characteristic sounds may be received while the smart phone is not in the designated time/GPS window for the festival. In such case various actions may be taken, including but not limited to actions by the oversight system. Alternately, no action may be taken, e.g., even a characteristic sound indicating a cola being opened may not even be registered if outside the time/GPS window. A wide range of variations and options may exist, so that in practice method trees may be almost arbitrarily complex. For simplicity not all possible options are addressed herein, but it should be understood that other options than those explicitly shown may be carried out and may be suitable.

Figure 34:
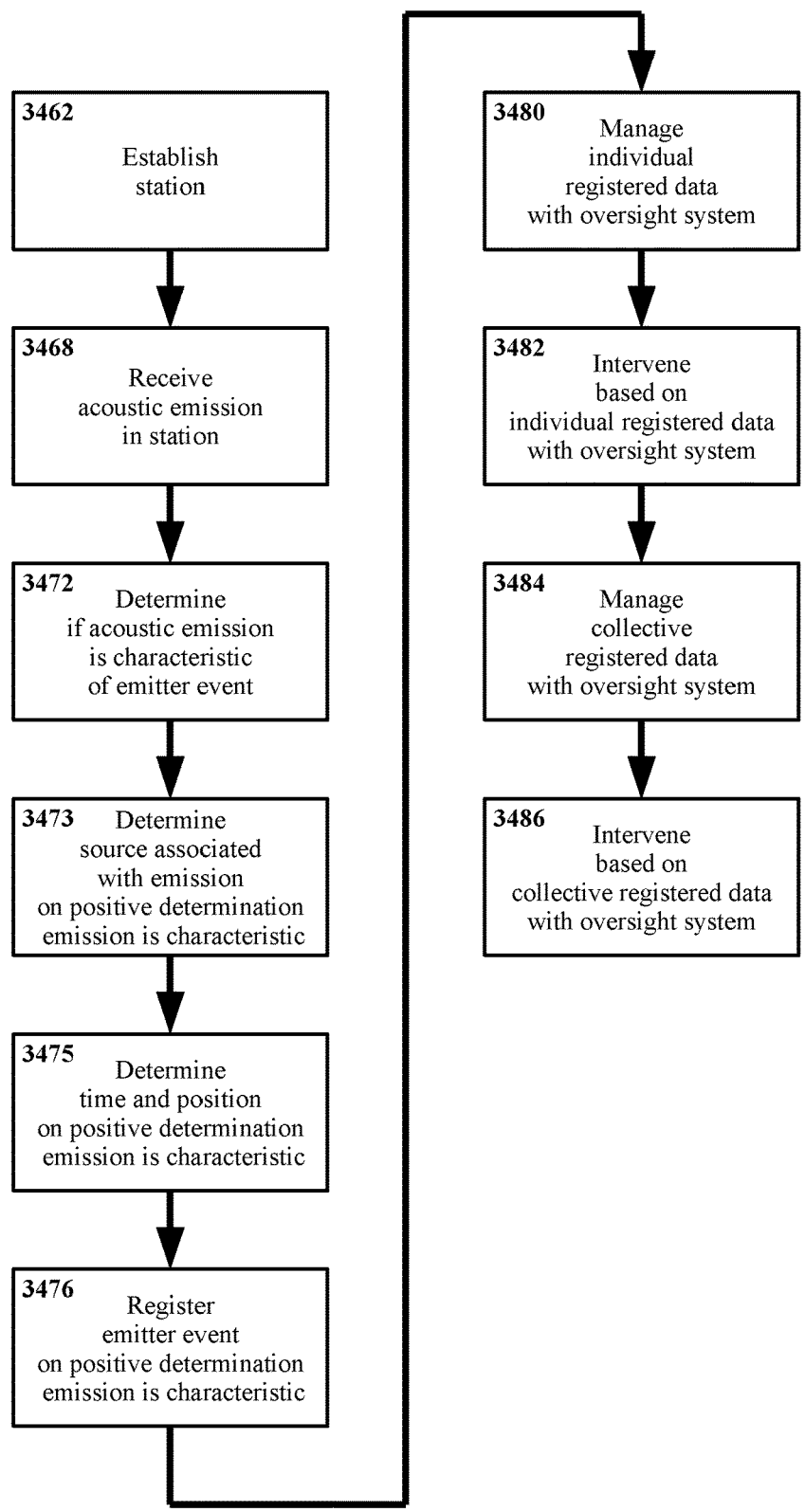
FIG. 34 depicts an example method for identifying use through receiving acoustic emissions, with intervention via registration, in flow chart form.

Now with reference to FIG. 34, an example at least somewhat similar to the arrangement in FIG. 33 is presented. However, the example in FIG. 34 is not specific as to a station, container, emitter, registration, management and intervention, etc.

In FIG. 34, a station is established 3462. An acoustic emission is received 3468 in the station, and a determination is made 3472 as to whether that acoustic emission is characteristic of an emitter event, e.g., opening a container having a particular configuration of emitter, etc.

For a positive determination of a characteristic emission—that is, in 3472 it is determined that the acoustic emission is indeed characteristic—a determination is also made 3473 as to which user the emission is associated with. Such a determination may be made in a variety of ways, based on a variety of factors. For example, referring back to the example of FIG. 33 the station was a smart phone, and it was determined whether a given characteristic emission was local to the station or non-local, based for example on volume. Such a local/non-local determination may be essentially binary, e.g., the acoustic emission either was or was not associated with a particular smart phone or user. However, other arrangements also may be suitable. For example, it is useful to uniquely identify an individual responsible for an acoustic emission in some fashion. Even for a binary "user" vs. "not the user" determination, other approaches than volume may be suitable, for example determining the direction from which a sound came. For a smart phone carried in a pants pocket, a soda bottle being opened by the person carrying that smart phone typically may be horizontally close but some vertical distance above the smart phone; thus the source of the acoustic emission may be expected to be at a relatively steep angle to the horizontal when the source is associated with a user, but at a shallower angle when the source is some other person (who may be farther away horizontally but of similar vertical elevation).

Returning to FIG. 34, again for a positive determination of a characteristic emission in step 3472, the time and position of the emission are determined 3475. The manner by which determining time and position may be implemented may vary among embodiments. Again referring back to the example of FIG. 33 the time at which the acoustic emission was produced (and/or the time at which the emission was received, etc.) may be determined from a chronometer on a smart phone, while the position from which the acoustic emission was emitted (and/or the position at which the emission was received, etc.) may be determined by a GPS receiver in a smart phone. However, numerous options may be feasible for determining time and/or position, and other arrangements may be equally suitable.

With regard to FIG. 34, it is noted that steps 3473 and 3475 in particular are presented as examples only, and may be optional or absent in some embodiments. That is, not all embodiments necessarily will or must determine which person, object, etc. is associated with a given acoustic emission. (As noted elsewhere herein, other steps likewise may be omitted, reordered, combined, subdivided, etc.) Similarly, not all embodiments necessarily will or must determine the time and position of the emission. While such information regarding characteristic acoustic emissions may be useful, the exact information obtained and the manner in which that information may be obtained may vary considerably among embodiments. Such information as may (or may not) be determined (whether computed, sensed directly, approximated, inferred, etc.) is not limited.

In addition, while steps 3473 and 3475 in the example of FIG. 34 are presented as contingent on a positive determination that a given acoustic emission is characteristic, embodiments are not limited in gathering data only for such positive determinations of characteristic emissions. For example, for some embodiments it may be suitable to determine the time and date of some or all non-characteristic emissions, to register such information, and/or to manage such information.

Continuing in FIG. 34, on a positive determination that the emission is characteristic (in step 3472), an emitter event is registered 3476. For certain embodiments, the source, time, and/or position, as well as other information may be registered also. In the example of FIG. 34, it may be assumed that registration includes (but is not limited to) communicating the emitter event and/or additional data to an oversight system, since certain subsequent steps as illustrated refer to actions taken with/based on such data. However, not all embodiments necessarily will or must communicate with an oversight system (nor is an oversight system even required to exist for at least some embodiments).

An oversight system manages 3480 individual registered data. For example, as described with regard to FIG. 33 an oversight system may assign badges or otherwise process, manipulate, etc. registered information. The form of management is not limited; while assigning badges/awards may be suitable, other acts of management also may be suitable.

The oversight system intervenes 3482 based on the individual registered data. Such intervention may include but is not limited to contacting the user, station, or other personal entity (e.g., thanking the user for using the product/service in question), reporting the use of the product/service to some third party (e.g., informing a physician, pharmacy, etc. that some medication has been opened), assigning products, services, cash value, game "points", etc. in response to the user of the product or service, and so forth.

Still with reference to FIG. 34, the oversight system also manages collective registered data. For example, a history of product use over time may be compiled for a particular user (e.g., so as to assist a user in determining their overall caffeine consumption, or their use of sunscreen, etc.). Alternately, patterns of use for multiple users may be compiled, such as the cola consumption map referenced for FIG. 33, or an analysis of the frequency of use of a given product such as sunscreen or opiate painkillers within an area or a population. To expand on the previous cola example a competition may be carried out wherein individuals may be assigned "cola points" for consumption of a given brand of cola at different locations, during different events, while performing different tasks, as purchased from different vendors, etc., with the "scores" of multiple individuals and/or groups being logged and updated over time. Regardless of form, collective management may be almost arbitrarily complex (particularly as the amount of available data increases), and the management of such collective data (step 3483) is not limited.

It is noted that neither individual nor collective management of data in steps 3480 and 3484 are limited only to registered data. For example, a plot tracking the use of sunscreen in an area over time may also include information on the temperature, cloud level, UV index, etc., even if that information is not registered (perhaps being obtained through weather reports, etc.).

Continuing in FIG. 34, the oversight system intervenes 3486 based on collective registered data. As with intervention 3482 from individual registered data, intervention 3486 relating to collective data is not limited and may take many forms. To continue the cola competition example, ads or updates may be sent to participants, a running score may be posted to social media sites, special time-limited offers may be presented, badges or titles assigned, real-world prizes bestowed, etc., for a potentially very large number of participants in the competition.

It is noted that the form of intervention for a given embodiment may depend at least in part on the nature of data as may be encoded in an acoustic emission, registered, etc. Considering detecting the use of a medication as an example of vehicle detection (e.g., the acoustic emission may be characteristic for detection but may not carry information per se), intervention may include contacting the user of the medication if it is detected that they have missed a dose, taken too much, etc. Considering communicating what type of soda that has been opened as an example of vehicle information (e.g., the acoustic emission may include information about the container to which the emitter is engaged, its contents, etc.), intervention may include changing marketing strategies for a given area. Considering determining whether a replacement part was manufactured by a given company or is a "knock-off" as an example of vehicle validation (e.g., the acoustic emission carries data as may indicate whether the packaging to which the acoustic emitter is engaged was made by someone with access to a security algorithm or not), intervention may include advising the user that the part cannot be verified with the manufacturer (or alternately, that the part is confirmed as genuine).

It is noted that even for acoustic emissions audible and recognizable to a user (e.g., a brand "jingle"), certain types of information therein may still be received, registered, intervened in response, etc. That is, while user recognizable data may be intended to be heard by live persons, such user recognizable data is not necessarily exclusive thereto and need not be ignored by a station (or oversight system, etc.). For example, consider a brand jingle configured to be recognized by a user, but for a company with which the user has not signed up for intervention (e.g., a different brand of cola). While other data encoded in an acoustic emission may be unreadable and/or uninformative, the station may still recognize the jingle of the competing cola brand, the oversight system may note that the user also consumes that other cola, etc.

As also noted elsewhere, acoustic emissions are not limited to only one type of data/function (e.g., detection, information, validation, audible). A given acoustic emitter may encode two or more such types of data, without limit. Also, data as may serve one function may also serve another, for example an audible jingle may include a lot number for the product in question "buried" within that audible jingle ((e.g., in spacing variations between notes). Other arrangements also may be suitable.

Considering steps 3480 through 3486 collectively, it may be suitable for some embodiments to address only individual data or only collective data, to manage but not intervene (or vice versa), etc. The arrangement shown in FIG. 34 is an example, and is not limiting.

Further, as shown in FIG. 33 a given method may fork, rejoin, run multiple branches in parallel, etc. This should be understood as applicable to FIG. 34 as well (and to other examples herein unless logically prevented or stated otherwise).

At this point it may be useful to point out at least one advantage as may be associated with various embodiments for determining use of enclosures, e.g., dispensing medication from containers, opening soda bottles, etc. A distinction may be made between determining point of sale for a product, and point of use. Where certain other approaches—for example, tracking bar codes printed on a product or packaging when that product is sold—may provide and/or utilize data on when, where, etc. a product is acquired. However, while embodiments encompassed herein may likewise serve to track point of sale, in addition or instead various embodiments encompassed herein may provide and/or utilize information on when a product is used (or at least opened/accessed for use), where the product is used, etc.

Considering prescribed medication as an example, medication may be prescribed to a patient and obtained by that patient from a pharmacy. However, in practice that medication may not be used at all, may not be used as prescribed, etc. Thus, point of sale data may not be revealing for at least certain types of data. Objective data indicating that a patient has used a medication (or dispensed the medication, opened the medication for dispensing, etc.), along with when, where, etc. may be more illuminating than simply knowing that the patient at some point procured the medication. Such point of use data thus may facilitate more effective medical treatment, more efficient medical research, etc. when considered instead of or in combination with point of purchase data. (It is emphasized that collection and/or consideration of point of purchase data is not excluded.)

As another example, consider cola consumption. A bottle of cola (or another soft drink, etc.) may be purchased in one place at a given time, and then consumed hours or days later at a location that may be many miles from the point of purchase. Obtaining data on when and where customers consume a given cola (or other medical and/or non-medical product) may illuminating e.g., from a marketing standpoint. In addition to or instead of merely determining where and when the cola was at some point purchased, various embodiments may reflect where, when, etc. the cola was opened, consumed, and so forth. Data regarding dispensing and/or use may be obtained differently from point of sale data, may reflect different phenomena (e.g., consumption habits of customers as opposed to buying habits), may be useful in different analyses and/or for determining different conclusions and/or following up in different ways, etc. Thus, while use data may superficially resemble point of sale data in certain aspects—e.g., both representing an event at a particular time and place—use data and/or consideration thereof may be qualitatively different in practice.

Now with reference collectively to FIG. 35 through FIG. 40, an example arrangement illustrative of the production of acoustic emissions is shown. The example in FIG. 35 through FIG. 40 is relatively concrete, e.g., reflecting a twist-off cap for a soda bottle generating acoustic emission through the interaction of flexible striker blades on the cap with anvils on the skirt ring. It is emphasized that such an arrangement is presented for explanatory purposes, and is not limiting.

Figure 35:
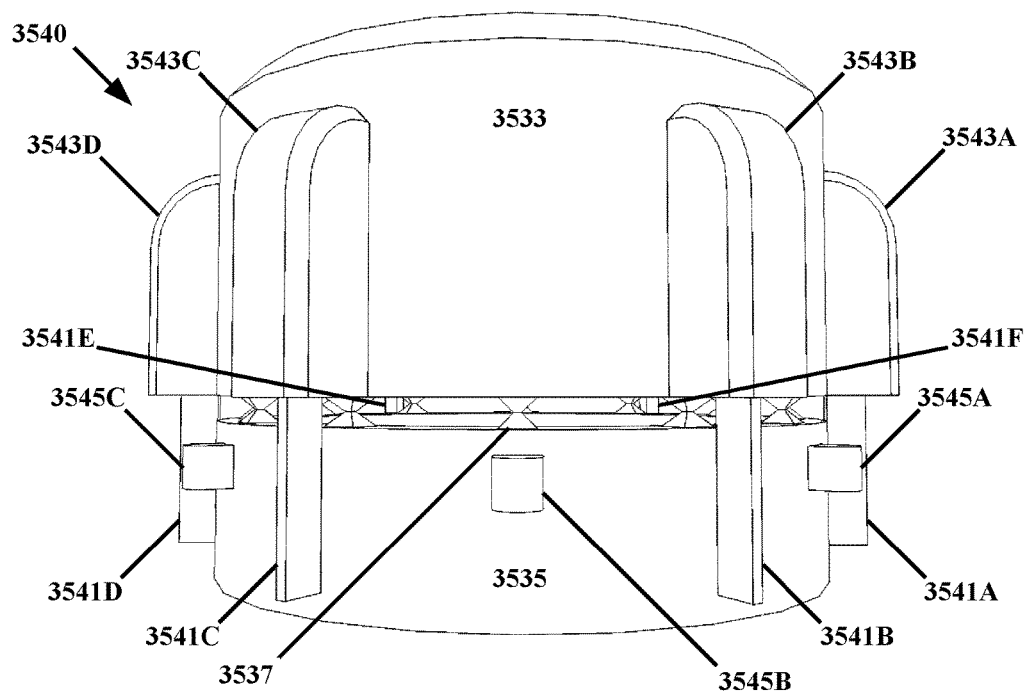
FIG. 35 through FIG. 41 depict example arrangements for producing acoustic emissions with regard to a twist cap, in perspective view.
Figure 36:
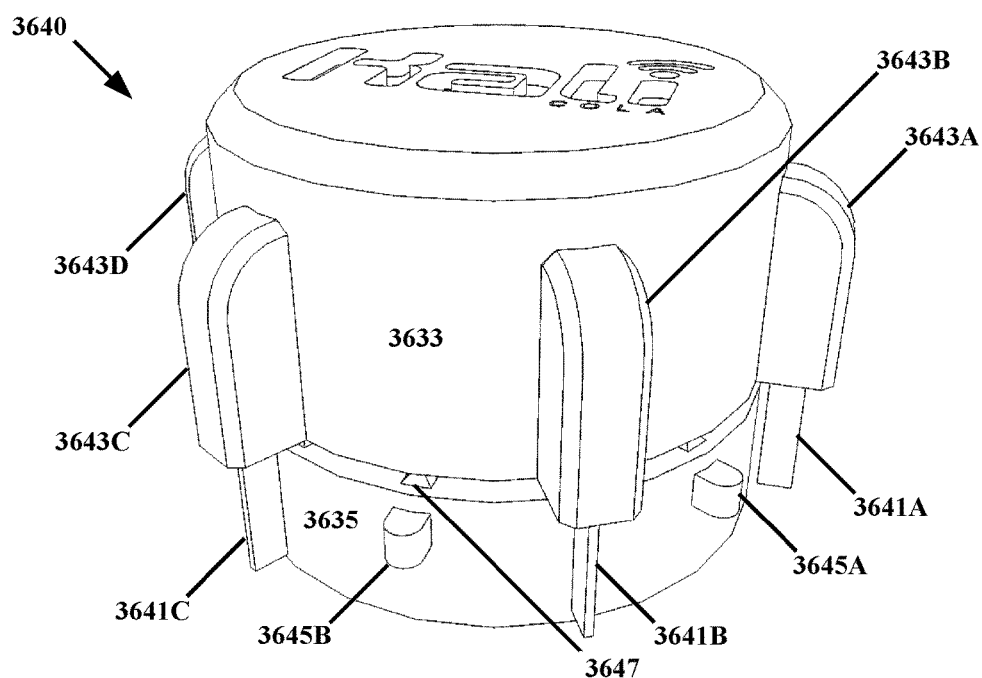

Specifically with regard to FIG. 35, a cap assembly 3540 for a soda or similar beverage container is shown in perspective view. (A container is not shown, though in use such a cap assembly 3540 may be engaged with such a container.) As may be seen, the cap assembly includes a cap 3533 and a skirt ring 3535. The cap 3533 and skirt ring 3535 are engaged via breakaways 3537 (only one breakaway is individually identified in FIG. 35 for illustrative purposes, though several may be observed). Typically for such a cap assembly 3540 the cap 3533 may be rotatable with respect to the skirt ring 3535, while the skirt ring 3535 may be adapted to remain approximately stationary with respect to the container (not shown) with which the cap assembly 3540 is engaged.

Several pedestals 3543A, 3543B, 3543C, and 3543D are shown to extend radially outward from the cap 3533. In addition, a striker 3541A, 3541B, 3541C, and 3541D is shown to extend downward from each of the pedestals 3543A, 3543B, 3543C, and 3543D. As may be seen the strikers 3541A, 3541B, 3541C, and 3541D are shown to exhibit a relatively long, thin, blade-like configuration; in at least certain embodiments the strikers 3541A, 3541B, 3541C, and 3541D may be flexible. However, rigid strikers also may be suitable. In addition, in at least some embodiments it may be suitable for some or all strikers to be frangible, e.g., such that the strikers are disabled or destroyed in producing acoustic emissions and thus only produce such acoustic emissions once, e.g., the first time medication is opened. In addition, several anvils 3545A, 3545B, and 3545C are shown to extend radially outward from the skirt ring 3535. The anvils 3545A, 3545B, and 3545C are shown to exhibit a compact blocky configuration, and in at least certain embodiments the anvils 3545A, 3545B, and 3545C may be at least somewhat rigid so as to serve as obstacles to the strikers 3541A, 3541B, 3541C, and 3541D (though again other arrangements may be suitable).

In addition, though not necessarily readily visible, additional strikers and/or anvils may be present. Small portions of strikers 3541E and 3541F may be observed in FIG. 35, on the far side of the cap 3533; similarly additional pedestals, anvils, etc. also may be present, though not necessarily visible. Not all elements as may be present necessarily are readily visible in FIG. 35 due for example to limits of perspective, etc.

As will be shown and described in more detail with regard to FIG. 36 through FIG. 40, as the cap 3533 is rotated with respect to the skirt ring 3535 and the bottle (not shown) to remove the cap 3533 and open the bottle, the strikers 3541A, 3541B, 3541C, and 3541D rotate therewith and engage the anvils 3545A, 3545B, and 3545C so as to produce acoustic emissions. Thus collectively the strikers 3541A, 3541B, 3541C, and 3541D and the anvils 3545A, 3545B, and 3545C may be considered as to function as one or more acoustic emitters. However, in the arrangement shown there may be no single physical element as may be distinctly and exclusively identified as "the" acoustic emitter. It may be suitable to consider all strikers and all anvils collectively as a single acoustic emitter, each striker and a corresponding anvil to be considered as individual acoustic emitters, strikers to be considered as acoustic emitters exclusive of the anvils, etc. The precise organization of structure is not limiting, so long as the functions of an acoustic emitter are provided.

In addition, it is noted that certain features as may appear in FIG. 35 may be optional (e.g., given that the arrangement in FIG. 35 is an example only). For example, breakaways 3537 or analogs thereto may not appear in all embodiments. However, when present breakaways 3537 such as are shown in FIG. 35 may perform a variety of functions. For example, the breakaways 3537 may be continuous but frangible, e.g., at the narrow portion shown approximately midway between the cap 3533 and the skirt ring 3535 in FIG. 35. When the cap 3533 rotates with respect to the skirt ring 3535, the breakaways 3537 may break or otherwise separate. Thus, the condition of the breakaways 3537 may provide an indication as to whether the cap 3533 has been removed (even if the cap 3533 were to be subsequently replaced). As another example, breakaways 3537 may serve to retain the cap 3533 in place to at least some degree. In such case, if forces applied to the cap 3533 are not of sufficient magnitude and direction as to break the breakaways 3537, the cap 3533 may not rotate and thus may not be unscrewed from the bottle. Thus the breakaways 3537 may inhibit the container from being opened due to incidental stresses, such as routine handling, while still enabling the cap 3533 to be removed with application of suitable force.

In addition, in at least certain embodiments breakaways 3537 may produce acoustic emissions when broken. The arrangement shown in FIG. 35 through FIG. 40 illustrates the production of acoustic emissions via the strikers 3541A, 3541B, 3541C, and 3541D and the anvils 3545A, 3545B, and 3545C, however other arrangements, including but not limited to production of acoustic emissions from breakaways 3537 or other sources, also may be suitable.

Moving on, collectively FIG. 36 through FIG. 40 may be understood as illustrating a sequence showing the production of acoustic emissions given a bottle cap at least somewhat similar to that shown in FIG. 35. Specifically with regard to FIG. 36, as may be seen a cap assembly 3640 is shown therein, with a cap 3633 and a skirt ring 3635. The cap 3633 exhibits several pedestals 3643A, 3643B, 3643C, and 3643D and strikers 3641A, 3641B, 3641C, and 3641D. The skirt ring 3635 in turn exhibits anvils 3645A and 3645B. Portions of breakaways 3647 (only one uniquely numbered, though others may be observed) also are visible. In addition, it is noted that the cap 3635 exhibits impressed text (not numbered); while not necessarily providing a function with regard to producing acoustic emissions, the impressed text may serve as an indication of rotation of the cap 3635, e.g., as the cap 3635 is twisted to be removed from a bottle (not shown, as previously noted).

Figure 37:
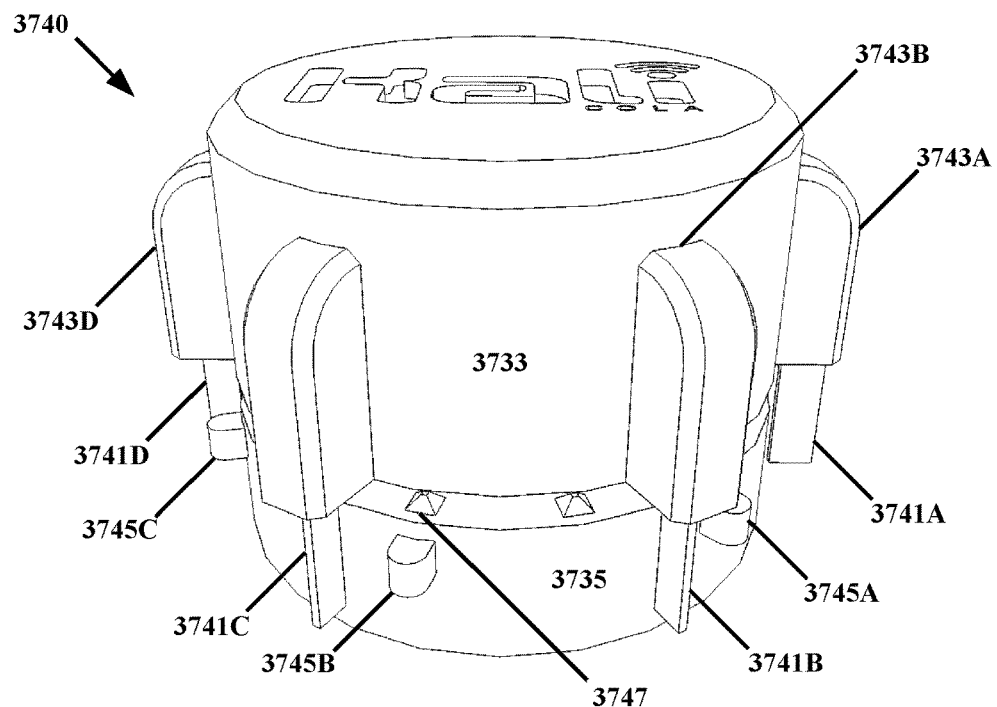

Turning to FIG. 37, a cap assembly 3740 is visible, with a cap 3733 that exhibits pedestals 3743A, 3743B, 3743C, and 3743D and strikers 3741A, 3741B, 3741C, and 3741D, and a skirt ring 3735 that exhibits anvils 3745A, 3745B, and (newly visible) 3745C. As may be seen (e.g., from the impressed text) the cap 3733 has rotated somewhat compared with FIG. 36. As may also be observed, the cap 3733 has risen slightly away from the skirt ring 3735, e.g., due to threads (not shown) on the cap 3733 engaging with corresponding threads on a bottle as the cap 3733 turned. Breakaways 3747 also are visible; however, where in FIG. 36 the breakaways therein were shown as being whole, in FIG. 37 the breakaways 3747 (or at least the portions thereof visible) are visibly separate, e.g., having broken at the narrow portions thereof as the cap rotated and rose vertically. As noted previously, such breakage may in at least some embodiments produce acoustic emissions, though such acoustic emissions are not presented in FIG. 37.

Figure 38:
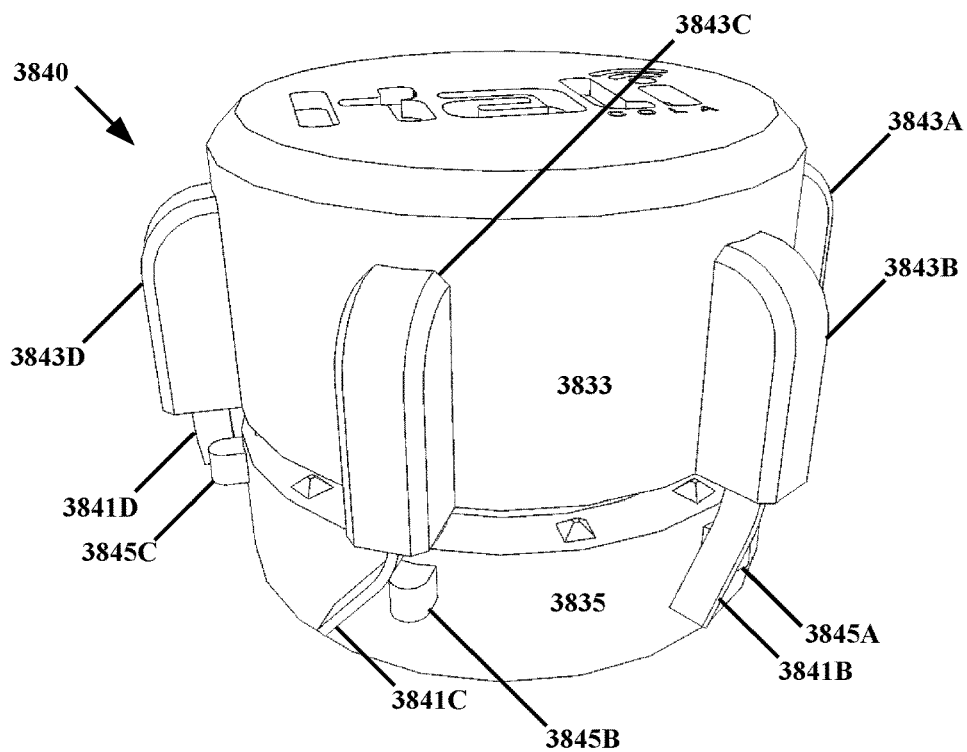
Figure 39:
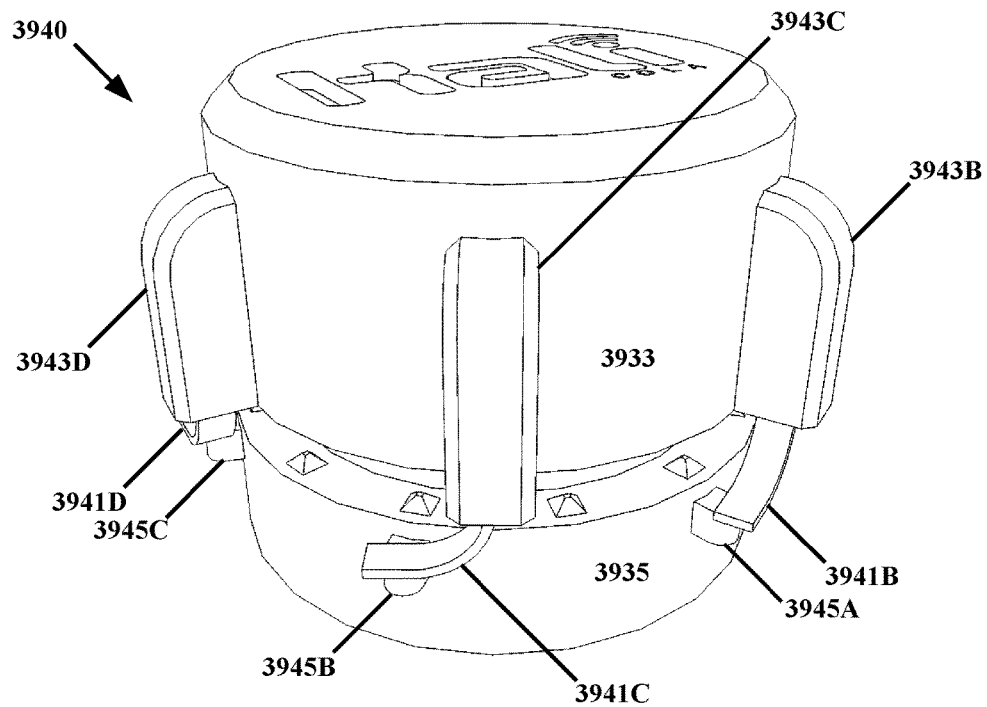

In FIG. 38, a cap assembly 3840 is shown with a cap 3833 exhibiting pedestals 3843A, 3843B, 3843C, and 3843D and strikers 3841B, 3841C, and 3841D (a striker corresponding to striker 3741A in FIG. 37 is no longer visible in FIG. 38). The cap assembly 3840 also is shown with a skirt ring 3835 that exhibits anvils 3845A, 3845B, and 3845C. (Breakaways remain visible in FIG. 38, but are not numbered.) As may be observed, the cap 3833 has continued to rotate and rise. In FIG. 38, the rotation of the cap 3833 relative to the skirt ring 3835 is such that strikers 3841B, 3841C, and 3841D are physically in contact with anvils 3845A, 3845B, and 3845C respectively. Indeed, the strikers 3841B, 3841C, and 3841D are visibly bent; the anvils 3845A, 3845B, and 3845C have obstructed the motion of the strikers 3841B, 3841C, and 3841D as the cap 3833 has rotated. For strikers 3841B, 3841C, and 3841D as may be elastic, such deformation may represent potential energy within each such striker 3841B, 3841C, and 3841D.

Moving on to FIG. 39, again a cap assembly 3940 is shown with a cap 3933 exhibiting pedestals 3943B, 3943C, and 3943D (a pedestal corresponding to striker 3843A in FIG. 38 is no longer visible in FIG. 39) and strikers 3941B, 3941C, and 3941D, and with a skirt ring 3935 that exhibits anvils 3945A, 3945B, and 3945C. Compared with FIG. 38 the cap 3933 in FIG. 39 has continued to rotate and rise relative to the skirt ring 3935. Strikers 3941B, 3941C, and 3941D have continued to deform against the anvils 3945A, 3945B, and 3945C, being bent until the tips of strikers 3941B, 3941C, and 3941D approach right angles with the undeformed direction of the strikers 3941B, 3941C, and 3941D (e.g., as shown in FIG. 37). However, as also may be seen the strikers 3941B, 3941C, and 3941D are turning to a point where the strikers 3941B, 3941C, and 3941D may move past the anvils 3945A, 3945B, and 3945C such that the anvils 3945A, 3945B, and 3945C no longer interfere with the strikers 3941B, 3941C, and 3941D.

Figure 40:
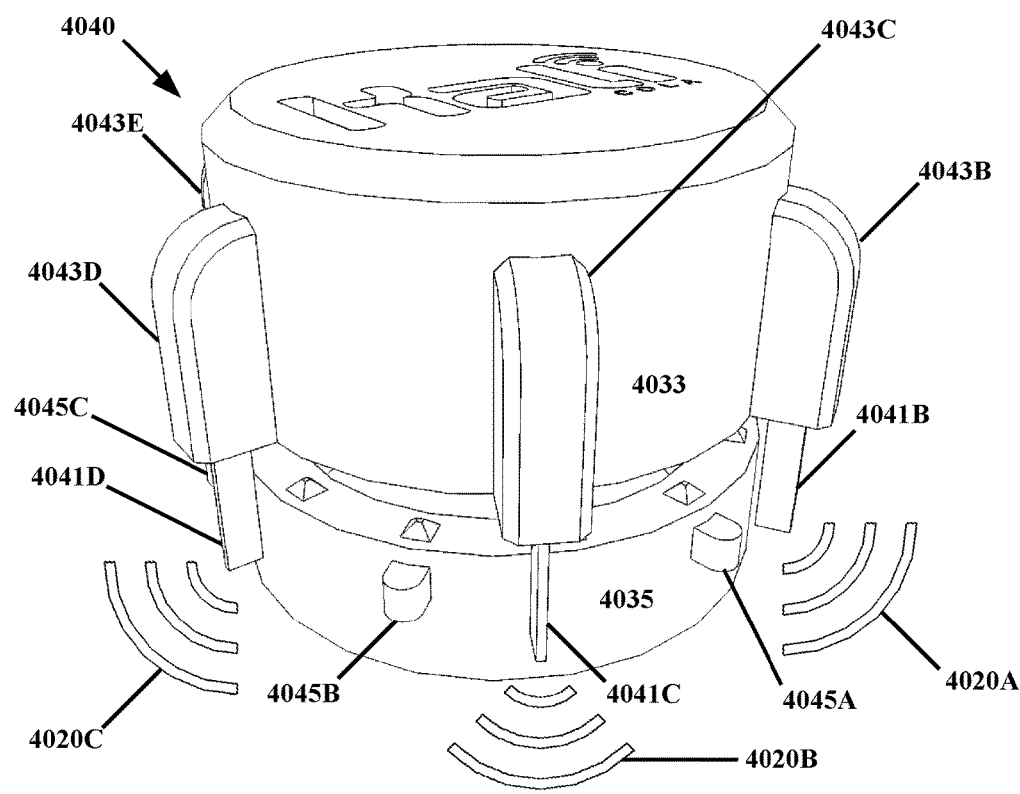

Continuing in FIG. 40, a cap assembly 4040 is shown with a cap 4033 exhibiting pedestals 4043B, 4043C, 4043D, and (newly visible) 4043E and strikers 4041B, 4041C, and 4041D, and with a skirt ring 4035 that exhibits anvils 4045A, 4045B, and 4045C. Compared with FIG. 39 the cap 4033 in FIG. 40 has continued to rotate and rise relative to the skirt ring 4035. As may be seen, the strikers 4041B, 4041C, and 4041D have disengaged from the anvils 4045A, 4045B, and 4045C, e.g., via the strikers 4041B, 4041C, and 4041D rotating past the anvils 4045A, 4045B, and 4045C as the cap 4033 has rotated with respect to the skirt ring 4035. As noted previously (e.g., with regard to FIG. 38) in deforming the strikers 4041B, 4041C, and 4041D may accumulate potential energy; as the strikers slip past the anvils 4045A, 4045B, and 4045C that potential energy may be released at least in part as acoustic emissions 4020A, 4020B, and 4020C. In more colloquial terms, a "pop", "snap", "click", etc. may be emitted as the strikers 4041B, 4041C, and 4041D return to a vertical configuration.

Thus, for an arrangement such as may be shown in FIG. 40, several acoustic emissions 4020A, 4020B, and 4020C may be produced at least approximately in unison. Additional acoustic emissions likewise may be produced from strikers and anvils not visible in FIG. 40. Thus, multiple acoustic emissions may be produced by such an arrangement, enabling consideration of those multiple acoustic emissions (e.g., as distinct from producing and considering only one).

The production and/or consideration of multiple acoustic emissions may be useful for at least certain embodiments. For example, the strikers 4041B, 4041C, and 4041D and anvils 4045A, 4045B, and 4045C as shown are identical or at least similar; given such an arrangement several identical or similar acoustic emissions may be produced together; the production of multiple similar/identical acoustic emissions in unison (or nearly so) may be detected with greater confidence, e.g., the chances of a single "pop" being received as noise may be significant, but the chances of receiving three (or six, etc.) simultaneous "pops" of the same volume and frequency happening at the same time by random coincidence may be lower.

Alternately, acoustic emitters may be configured so as to produce different acoustic emissions, and/or to produce acoustic emissions at different times. For example, the frequency of a noise made by a long, slender emitter (e.g., the strikers 4041B, 4041C, and 4041D in FIG. 40) may be a function of the length of the emitter (among other possible factors). While the strikers 4041B, 4041C, and 4041D illustrated in FIG. 40 are of similar length, providing strikers of different lengths may result in different pitches being produced by each striker. As another option, the spacing of the strikers and/or anvils may be made non-uniform, so that not all acoustic emissions are produced synchronously, e.g., resulting in a sequence of "pops" (possibly also of differing pitches). Other arrangements also may be suitable.

Thus as may be understood, through varying the arrangement and/or configuration of acoustic emitters, relatively complex signals may be produced, for example a sequence of "pops" at various particular frequencies, in a particular order, with a particular relative or absolute time gap between "pops", etc. However, even with such a range of possible signals, the signals may be made to be predictable. That is, a given configuration of length, spacing, etc. of strikers as resembling those in FIG. 40 may produce a given sequence of "pops"; even if the resulting combined acoustic emission may be complex overall, a specific configuration of the physical structure(s) producing that acoustic emission (e.g., where the strikers and anvils are, the size thereof, etc.) may produce a reliable and/or predictable acoustic emission. In more colloquial terms, if the shape of the hardware is known, the sounds to be produced may be known. For example, the arrangement in FIG. 40 may consistently produce a given acoustic emission (or, as may also be considered, a combination of acoustic emissions); that acoustic emission may be specific to the arrangement of strikers and anvils as illustrated.

Thus, a connection may be established between a structure of emitter and a (possibly complex) sound produced thereby. While not necessarily perfectly unique, a sufficiently complex sound may facilitate the identification of the structure that produced that sound with high confidence. To continue the example of a soda bottle cap, one acoustic emission may indicate (and be identifiable as) a first type of soda, a second acoustic emission may indicate a second type of soda, and so forth. Thus products may be identifiable based at least in part on the particulars of an acoustic emission produced in opening those products (or otherwise manipulating the products, etc.).

Indeed, although as noted previously it is not required to encode information into a particular acoustic emission, in at least certain embodiments it may be suitable to do so. For example, with a sufficiently large number of "pops" of different pitches in a specific order, it may be useful to configure the emitter(s) generating those acoustic emissions so that the emission itself includes data encoded therein, e.g., the name of a particular type of cola, the manufacture date of a given medication, etc. While such encoding is not necessarily required for all embodiments, neither is encoding data within an acoustic emission necessarily prohibited.

Figure 41:
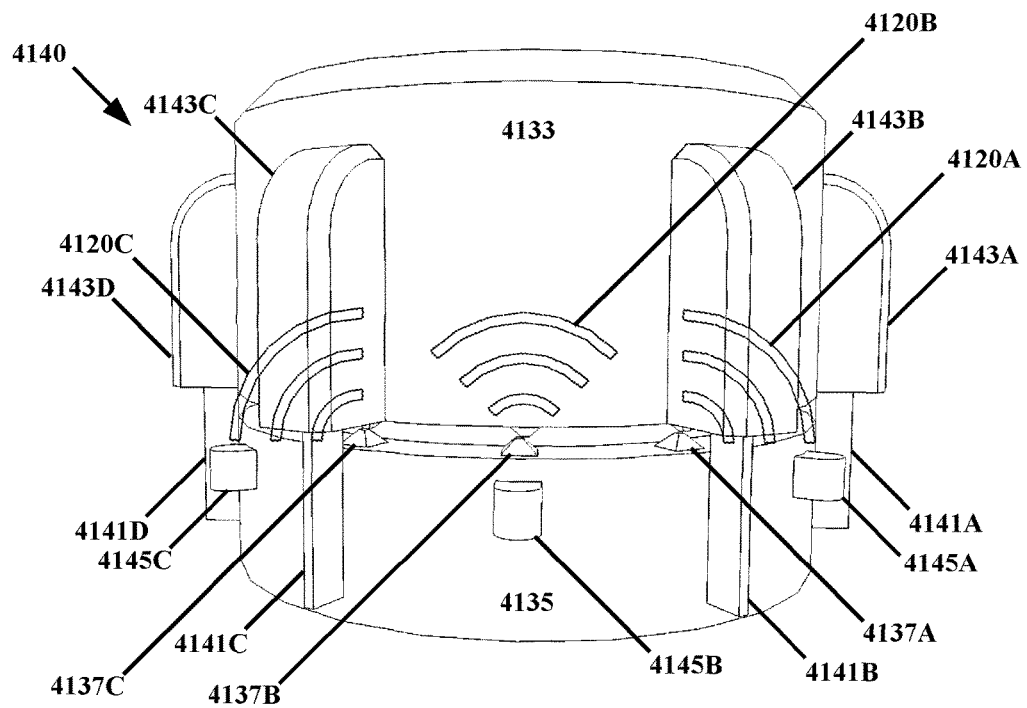

Turning now to FIG. 41, it may be suitable in at least certain embodiments to utilize more than one structure for producing more than one type of acoustic emission. For example, a potential for producing acoustic emissions from breakaways as a cap is turned was noted previously with regard to FIG. 37. Where FIG. 36 through FIG. 40 are presented sequentially so as to illustrate operation of the example striker-and-anvil arrangement described with regard thereto, FIG. 41 also is presented to illustrate an example wherein a second type of acoustic emitter may produce a second type of acoustic emission.

As may be seen in FIG. 41, a cap assembly 4140 is shown, with a cap 4133 exhibiting pedestals 4143A, 4143B, 4143C, and 4143D and strikers 4141A, 4141B, 4141C, and 4141D, and with a skirt ring 4135 that exhibits anvils 4145A, 4145B, and 4145C. In addition, three breakaways 4137A, 4137B, and 4137C are identified individually, each approximating two truncated pyramids connected at small ends thereof, and with the bases thereof connected to the cap 4133 above and the skirt ring 4135 below. A cap assembly and breakaways at least somewhat similar previously were illustrated in FIG. 35; however compared to FIG. 35 the cap 4133 in FIG. 41 is rotated and elevated slightly, e.g., as when beginning to unscrew the cap 4133 to open a soda bottle (not shown). As may be seen, the breakaways 4137A, 4137B, and 4137C have broken or otherwise separated at a narrow portion thereof. In addition, acoustic emissions 4120A, 4120B, and 4120C are illustrated as emanating from breakaways 4137A, 4137B, and 4137C respectively (the depiction of the acoustic emissions being illustrative; in practice such emissions may not be visible). Such acoustic emissions 4120A, 4120B, and 4120C may represent sounds emitted as the breakaways 4137A, 4137B, and 4137C crack, break, distort inelastically to the point of failure, etc. The structure of the breakaways 4137A, 4137B, and 4137C is visibly different from the structure of strikers 4141A, 4141B, 4141C, and 4141D and anvils 4145A, 4145B, and 4145C. Likewise, the breakaways 4137A, 4137B, and 4137C may function differently in producing acoustic emissions 4120A, 4120B, and 4120C than the strikers 4141A, 4141B, 4141C, and 4141D (e.g., by breaking rather than by elastically distorting and recovering). Consequently, as may be understood the acoustic emissions 4120A, 4120B, and 4120C themselves as produced in FIG. 41 may differ from acoustic emissions produced by strikers and anvils (e.g., as shown in FIG. 40).

Production of multiple acoustic emissions through the use of multiple emitters may be useful. In certain embodiments, multiple emissions may be considered so as to provide greater confidence that some event has occurred, e.g., a soda bottle has been opened. Given such an arrangement, multiple types of emissions may be understood as performing a similar function to one another.

However, it is noted that two or more emissions or types of emissions also may serve different functions. For example, considering an arrangement wherein both breakaways and strikers provide acoustic emissions, it may be observed that the conditions for producing acoustic emissions from breakaways may not be identical to those for producing acoustic emissions from strikers. Notably, a frangible breakaway that produces acoustic emissions through breaking typically may only produce such an emission once. Thus, such breakaways may produce acoustic emissions the first time a cap is removed from a bottle, but not on subsequent openings. Such an arrangement may be referred to as being "variant" with regard to instances of the acoustic emissions, e.g., the acoustic emissions vary notably from one opening to the next. Conversely, arrangements wherein acoustic emissions remain at least approximately consistent from one opening to another.

Considered together, providing acoustic emissions by both breakaways and strikers in such an arrangement may not only facilitate determining when the cap has been removed from the bottle, but also may facilitate distinguishing the first such opening from other, later openings. Continuing the example of a soda bottle, the first time such a bottle is opened both a series of fracture noises may be emitted as breakaways break and a series of pops may be emitted as strikers move past anvils; while the second time (and subsequent times) the bottle is opened only the pops from strikers and anvils may be emitted. Reception of pops alone may be interpreted to determine that a bottle has been re-opened after having already been opened once, while reception of pops and fracture noises may be interpreted to reveal that a bottle is being opened for the first time. Knowing when a bottle (or other enclosure) is first opened, as distinct from subsequent openings, may in turn be useful in tracking use patterns for a product, logging when a package has been delivered (e.g., picking up "first open" emissions for a shipping box using a smart speaker), and/or for other applications.

More broadly, provision of two or more types of acoustic emitters may provide data that does not merely duplicate existing data or increase the overall quantity of data, but that provides data that may be distinct in kind and that enables distinct additional functionality. In the case of an arrangement such as is shown in FIG. 41, provision of breakaways and strikers may enable a distinction to be made between when (and/or where, etc.) a bottle of soda is first opened as opposed to being re-opened. However, it is emphasized that the arrangement shown in FIG. 41 is an example only, and is not limiting. Likewise, embodiments are not limited to distinguishing "first opening" vs. "subsequent openings"; for example, different types of acoustic emissions (whether from the same or different emitters) may reflect different actions being carried out (as opposed to repetition of one action), such as opening packaging as opposed to dispensing medication, etc.

Now with reference to FIG. 42 through FIG. 50, certain examples of variations in striker-and-anvil acoustic emitters are shown as may be useful in demonstrating various characteristics of and/or options for acoustic emissions. In FIG. 42 through FIG. 50 arrangements are illustrated showing strikers and anvils or analogs thereof, similar at least on concept to those already described and illustrated in FIG. 35 through FIG. 41. This is done for explanatory purposes, e.g., so as to show different manners by which acoustic emissions may be made characteristic, may be made to carry data, etc. However, it is emphasized that these are examples only, and that arrangements are not limited only to strikers and anvils, nor to only the variations (e.g., in pitch, sequence, spacing, etc.) as shown in FIG. 42 through FIG. 50.

Figure 42:
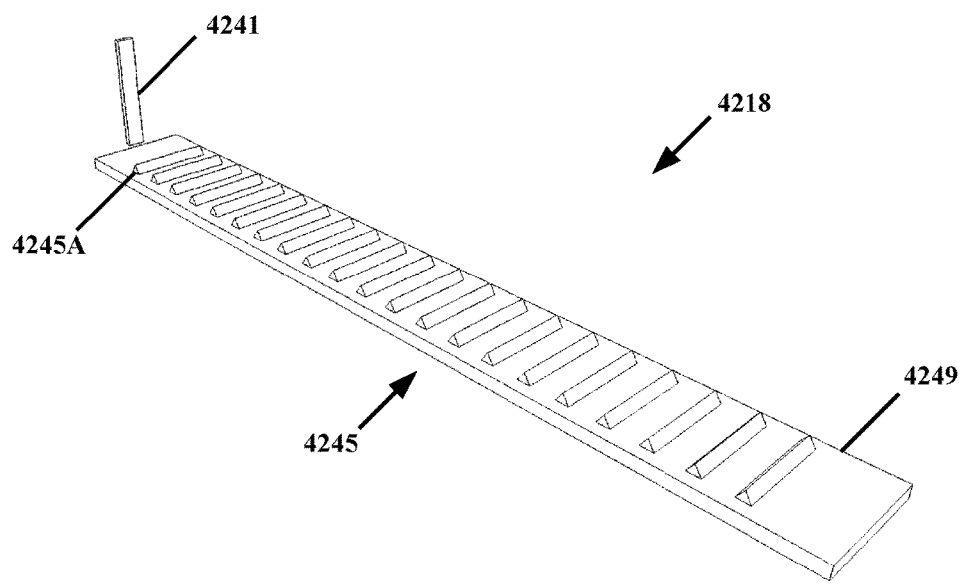
FIG. 42 through FIG. 50 depict example arrangements for striker-and-anvil acoustic emitters, in perspective view.

With regard specifically to FIG. 42, an emitter 4218 is shown therein. The emitter 4218 includes a striker 4241, along with a series of anvils 4245. The anvils are identified as a group, referred to herein as element 4245; one anvil 4245A is uniquely identified for explanatory purposes. The anvils 4245 are disposed on a platform 4249, which in the arrangement shown in FIG. 42 is a long, flat strip of material. Such a configuration is an example only, and anvils (or other features) may be disposed differently and/or elsewhere (for example, in FIG. 41 anvils are shown distributed around the approximately cylindrical outer surface of the skirt ring rather than on a flat strip). For purposes of simplicity the emitter 4218 (and the striker 4241, platform 4249, etc.) are not shown to be engaged with any larger physical structure, such as a container. However, it may be suitable to engage the emitter 4218 and/or portions thereof with various enclosures, other structures, etc.

If the striker 4241 were to be moved along the platform 4249 (or the platform 4249 moved with respect to the striker 4241), the striker may engage first anvil 4245A and subsequently other anvils 4245 of the emitter 4218. Such interaction between striker 4241 and anvils 4245 may produce a series of acoustic emissions, e.g., one acoustic emission for each anvil 4245 with which the striker 4241 interacts. The precise geometry of interaction may vary, and is not limited; as shown in FIG. 36 through FIG. 40 strikers may deform elastically when obstructed by anvils and then produce acoustic emissions when that deformation is released once the striker passes the anvil, and a similar arrangement may be suitable for the example in FIG. 42. However, it also may be that sound is produced by simple contact between the striker 4241 and each anvil 4245, by abrasion of the tip of the striker 4241 against a roughened surface of each anvil 4245, and/or by other approaches.

Regardless of the precise manner by which acoustic emissions may be produced, the acoustic emitter 4218 as shown typically (though not necessarily) may produce a series of similar well-defined noises such as clicks, chimes, pops, etc. Given the arrangement shown in FIG. 42 wherein the anvils 4245 are at least approximately similar in size, shape, configuration, and spacing, the acoustic emission produced from the striker 4241 interacting with each anvil 4245 may be similar and evenly spaced. In more colloquial terms, the acoustic emitter 4218 may produce a regular series of similar sounds in succession, with little variation between sounds. While technically it may be accurate to refer to the entirety of the sounds so produced as a single acoustic emission, for illustrative purposes it may be useful to envision an "acoustic phrase" made up of a series of such sounds, with each such sound referred to as an acoustic emission (or portion thereof). However, such descriptive language should not be taken to imply that a given acoustic emission may be either singular or plural (e.g., one distinct sound or multiple).

Regardless of illustrative terminology (e.g., acoustic phrase vs. acoustic emission) such an acoustic phrase (or equivalently an acoustic emission) as may be generated by the emitter 4218 thus may be characteristic in terms of features such as the frequency, volume, waveform, etc. of each emission, the spacing thereof, etc., but may not necessarily be characteristic in terms of variations in frequency, volume, waveform, spacing, etc. Nevertheless, considerable specificity may be achieved through selection of such factors, even if uniform within a given acoustic phrase. (It is also noted that certain properties not visible in FIG. 42 may affect acoustic emission, e.g., the hardness and/or elasticity of the various anvils 4245 may vary, which in turn may result in varying acoustic emissions for each anvil 4245. Such factors are not limited.)

As a further matter, it is noted that the striker 4241 as shown is not necessarily limited to an artificial structure as may be part of an enclosure, etc. For certain embodiments it may be suitable for a fingernail to serve as a striker (and/or an anvil, some other part of an acoustic emitter, etc.). For example, a series of anvils may be disposed on an accessible surface of a product, device, etc. so that a user may run a fingernail along the anvils to produce acoustic emissions (or conversely, the fingernail may be considered an anvil, etc.). Such an arrangement may for example be useful in time/location tracking, e.g., as an "acoustic bar code"; acoustic emissions produced at different locations may be registered with those locations (e.g., as determined through GPS in a smart phone or other station). A series of locations at various times could be registered in the station (and/or communicated externally) to facilitate tracking of where the item bearing the acoustic emitter is and when. Regardless of applications, in such case the striker (e.g., a user's fingernail) may or may not necessarily be considered to be literally part of an apparatus per se. Nevertheless, a fingernail or similar may be suitable, so long as the functionality of the acoustic emitter is supported, and strikers are not otherwise limited. (Likewise, acoustic emitters are not limited to strikers generally, and not all embodiments will have or necessarily must have or utilize strikers.)

Figure 43:
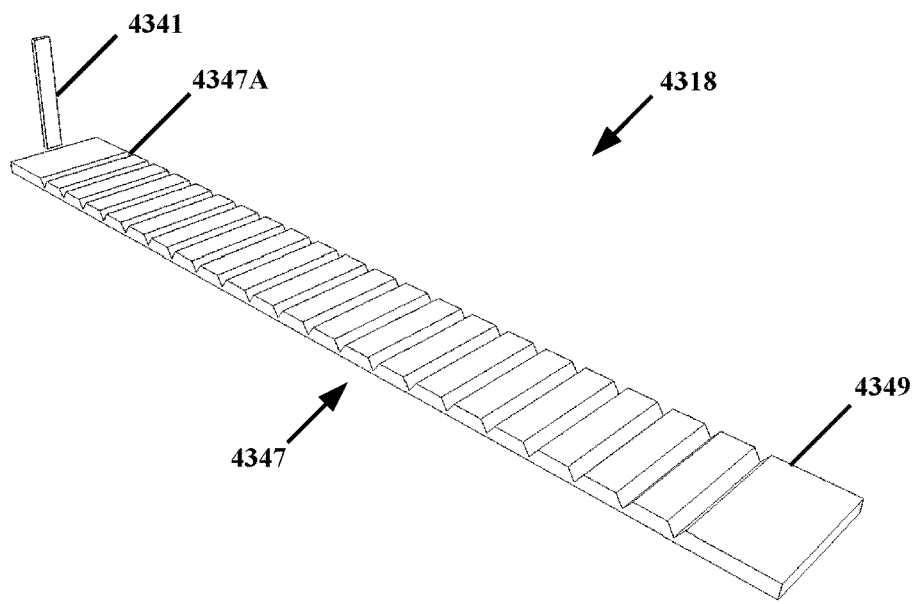

Moving on to FIG. 43, another acoustic emitter 4318 is shown including a striker 4321 and a platform 4349. However, rather than anvils the platform 4329 defines voids 4347 therein (in the form of lateral grooves of wedge-shaped cross-section, though this is an example only); again, one void 4347A is uniquely identified for illustrative purposes, while the voids collectively are referred to by 4347. As in FIG. 42, the voids 4345 are at least approximately similar in width, depth, shape, spacing, etc., and may (though not necessarily must) manifest similar and/or regular acoustic emissions when interacting with the striker 4341.

Attention is drawn to several points with regard to FIG. 43. First, even for an arrangement utilizing a striker or similar structure, positive (e.g., physically projecting) anvils are not necessarily required. That is, the voids 4347—gaps or grooves recessed into the surface of the platform 4349—may be equally suitable as and/or may function similarly as projecting anvils. Given that the voids 4347 are illustrated as visibly "negative" rather than visibly "positive" anvils shown in certain other examples, for explanatory purposes a different term—voids 4347—is used with regard to FIG. 43 (and certain similar structures as may appear in other examples). However, it may be reasonable to consider the voids 4347 as being or at least providing anvils, at least insofar as the voids 4347 may function similarly, e.g., providing a target with which a striker 4341 may engage to produce an acoustic emission.

Second, although voids 4347 may serve similarly to anvils it is not required that voids 4347 serve as anvils per se. For example, the surface of the platform 4349 may be roughened such that the striker 4341 produces acoustic emissions in the form of scratching or dragging noises, leaving gaps (e.g., silence or near-silence) as the striker 4341 passes over the voids 4347. Third, and in connection with the notion of gaps as just noted, it may be suitable to define an acoustic emission or phrase at least partially in terms of gaps therein, in addition to or instead of in terms of the sound itself. Indeed, for certain embodiments an acoustic emission may be characteristic entirely in terms of the gaps therein. For example, an acoustic emission standard may be defined to enable recognition of an unspecified sound that exhibits a specified series of gaps therein and/or other negative aspects thereof, e.g., a certain number of gaps, a certain duration, a certain absolute or relative spacing, etc. Thus, it may be suitable for a sound to be characteristic by silence.

Figure 44:
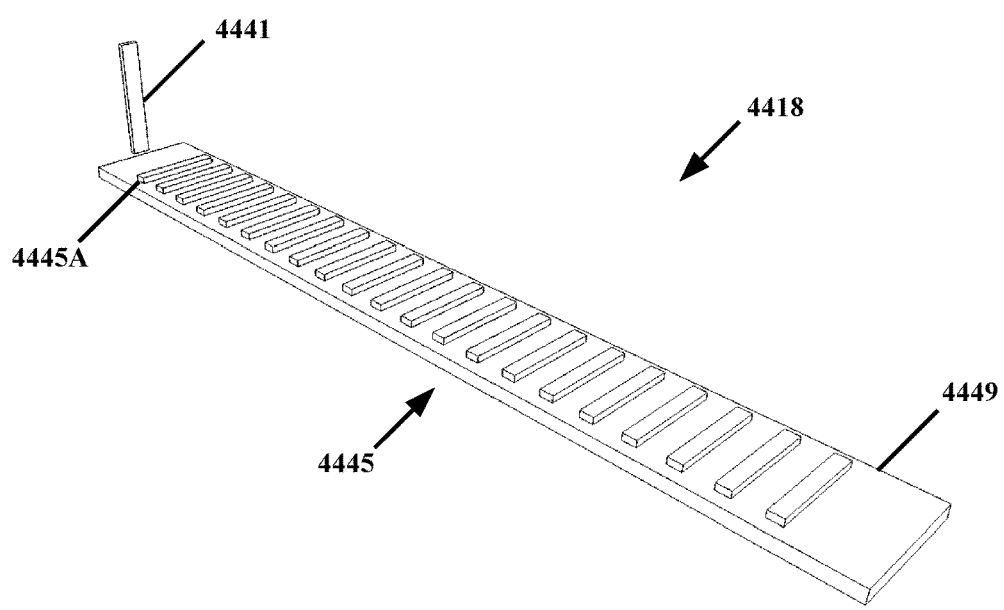

Continuing to FIG. 44, therein an arrangement at least somewhat similar to that in FIG. 42 is shown. An acoustic emitter 4418 is illustrated with a striker 4441 and a platform 4449 with anvils 4445 thereon (one anvil 4445A being uniquely identified). However, it is noted that the anvils 4445 in FIG. 44 differ in shape from those in FIG. 42 (and in certain previous illustrations), being essentially "blocks" with vertical sides rather than slopes, radii, etc. It is noted that the nature and/or shape of anvils is not limited.

Figure 45:
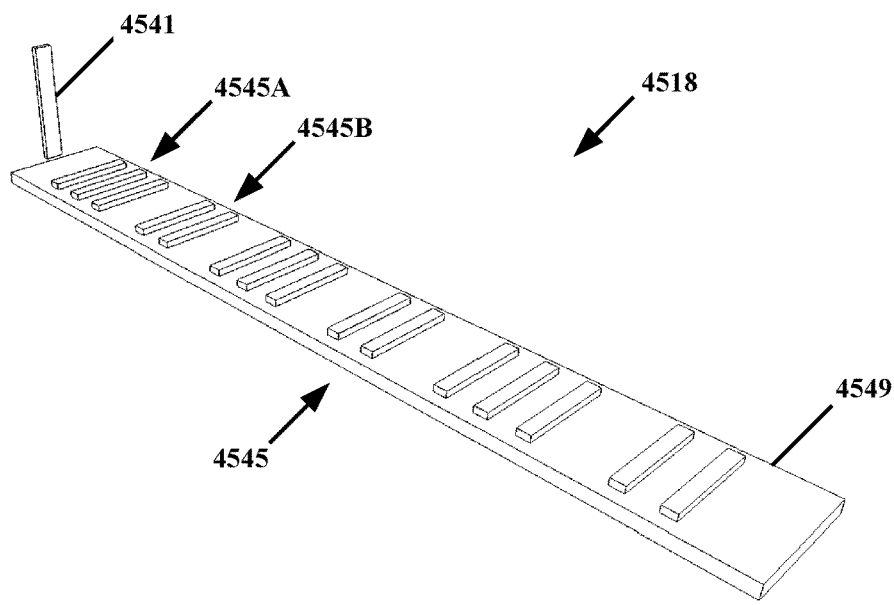

Turning to FIG. 45, an acoustic emitter 4518 is shown with at least some similarity to that in FIG. 44. The acoustic emitter 4518 includes a striker 4541 and a platform 4549 with anvils 4545 thereon. As may be seen, the anvils 4545 are clustered together in groups of two and three; a three-anvil group is uniquely identified as 4545A, and a two-anvil group as 4545B. Thus, acoustic emissions as may be produced by the striker 4541 interacting with the anvils 4545 likewise may exhibit patterns with features in groups of two and three. The precise nature of the patterns may vary, for example depending on the manner in which acoustic emissions are produced, e.g., contact between striker 4541 and anvils 4545, release of elastic deformation of the striker 4541 after passing anvils 4545, acoustic vibration of the striker 4541 due to contact with anvils 4545 (e.g., as may be similar to a struck tuning fork), friction between the striker 4541 and anvils 4545, etc.

However, regardless of such particulars, grouping anvils 4545 as shown in FIG. 45 may enable production of acoustic emissions that reflect such grouping in some fashion. Thus, at least certain data regarding the organization, shape, distribution, etc. of anvils 4545 (and/or other elements of an acoustic emitter 4518) may be incorporated into the acoustic emissions produced therewith. For example as visible in FIG. 45, the anvils 4545 exhibit patterns of twos and threes, and a series of acoustic emissions (e.g., an acoustic phrase) likewise may exhibit patterns of twos and threes. Thus in some sense data may be incorporated into acoustic emissions based at least in part on the physical configuration and/or properties of a given acoustic emitter 4518.

It is noted that such incorporated data may or may not be considered as an aspect of how the acoustic emissions are characteristic. To continue with FIG. 45 as an example, an acoustic emission may be made characteristic through the particular pitch, waveform, etc. produced each time the striker 4541 interacts with an anvil 4545. The acoustic emission produced by one interaction of striker 4541 and anvil 4545 may in itself be characteristic, e.g., an individual acoustic emission may be sufficient (and/or utilized) for recognizing that a container has been opened. However, even for such self-sufficient acoustic emissions, patterns within a group of such acoustic emissions may carry additional data. For example, if a given acoustic emission from a striker 4541 against an anvil 4545 may be sufficiently characteristic as to enable identification that a brand of cola has been opened, a pattern of such acoustic emissions then may indicate other information such as whether the cola is diet or regular, cherry or plain, the month and/or year of bottling, the bottling plant identity, etc.

Thus, in some sense such pattern data within a phrase of acoustic emissions may be considered as being distinct from the function of the acoustic emissions for detecting and/or characterizing an event. Consider as an example a bar code, printed in a particular color of ink. The color of the bar code may be characteristic to a particular product, container, etc.; however, the bar code itself may incorporate information in addition to and/or distinct from the color. The two features—color as employed to identify a container, and bar code configuration as employed to carry other data—may be viewed as distinct, and/or may perform distinct functions.

To return to acoustic emissions, a series of acoustic emissions may similarly be understood as comparable in at least some sense to a bar code. The individual emissions may be characteristic in frequency (e.g., comparable to light frequency or ink color), while the pattern of emissions may carry information as well similarly to how the pattern of lines in a bar code may carry information. Thus, it may be useful to consider patterns of/within acoustic emissions as being "acoustic bar codes", for illustrative purposes if not necessarily in a literal sense.

However, although such acoustic bar code data may be encoded into patterns/arrangements of acoustic emissions, it is not required that such encoding be performed (or even possible) for all embodiments. Moreover, while in some embodiments pattern information may be distinct and/or perform distinct functions from characterization of individual acoustic emissions, in other embodiments it may be suitable for patterns to be part of what makes an acoustic emission characteristic. That is, a group or phrase of acoustic emissions may be characteristic due to the properties of the individual emissions, the pattern of the emissions (and/or a pattern of gaps in emissions), or some combination thereof.

More regarding acoustic bar codes is described subsequently herein.

Figure 46:
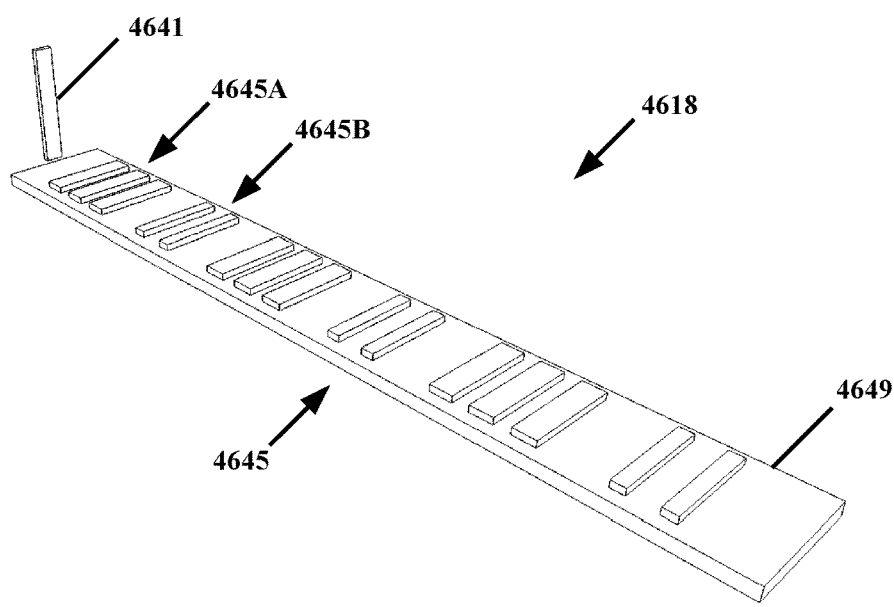

Turning now to FIG. 46, a wide range of physical variations may be utilized to configure and/or modify acoustic emissions, e.g., so as to encode acoustic bar code data therein. In FIG. 46 an acoustic emitter 4618 is shown with at least some similarity to that in FIG. 45. The acoustic emitter 4618 includes a striker 4641 and a platform 4649 with anvils 4645 thereon. As may be seen, the anvils 4645 are clustered together in groups of two and three, similarly to FIG. 45; a three-anvil group is uniquely identified as 4645A, and a two-anvil group as 4645B. However, where in FIG. 45 the anvils therein were all at least approximately similar in width and spacing, in FIG. 46 the anvils 4645A in groups of three are visibly broader than and more closely spaced than the anvils 4645B in groups of two. Differences in width may for example affect volume (e.g., causing a striker 4641 to deform elastically to a greater degree before releasing), duration (e.g., longer frictional contact between the striker 4641 and a given anvil 4645), etc., while differences in spacing may for example affect timing (how close together or far apart in time sequential acoustic emissions may be), sustenance of acoustic emissions (e.g., how long a striker 4641 may travel while emitting resonating "tuning fork" pitch before the pitch is stopped through contact with the next anvil 4645), etc. As may be understood, a wide variety of factors may affect individual acoustic emissions and/or patterns thereof.

Figure 47:
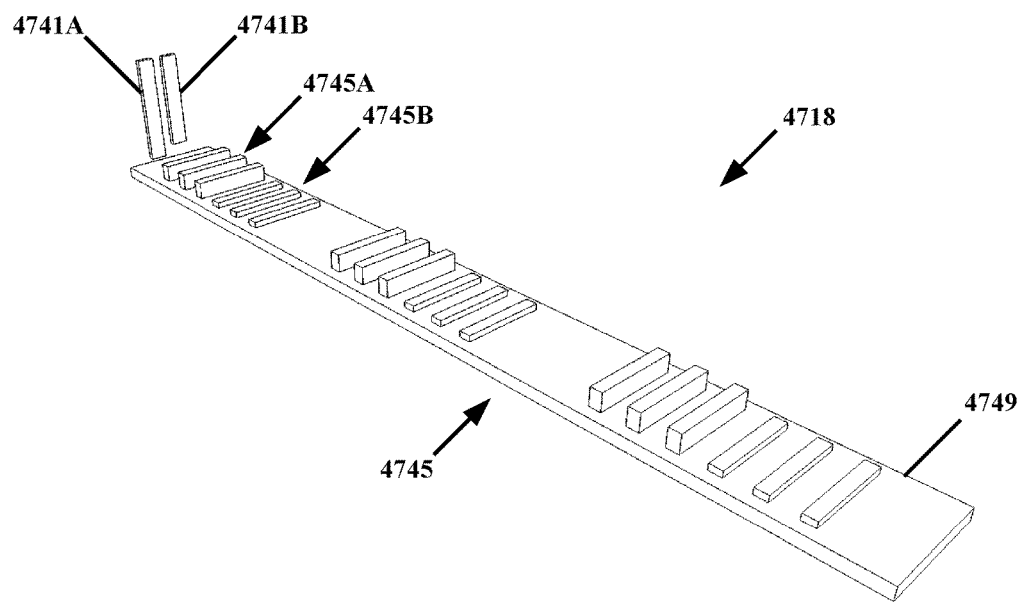

With reference now to FIG. 47, an acoustic emitter 4718 is shown that includes two strikers 4741A and 4741B and a platform 4749 with anvils 4745 thereon. As may be seen, the anvils 4745 are clustered together in groups of six; three anvils 4745A in each such group exhibit a first height, while the other three anvils 4745B are exhibit a second height shorter than the first height. The strikers 4741A and 4741B also are of differing dimensions, with striker 4741A being longer than and extending farther downward than striker 4741B.

Thus, if the strikers 4741A and 4741B move down the platform 4749 across the anvils 4745 (or the platform 4749 moves, etc.), the longer striker 4741A will engage both the taller anvils 4745A and the shorter anvils 4745B, but the shorter striker 4741B will engage only the taller anvils 4745A but will not reach far enough down to engage with the shorter anvils 4745B. In addition, it is noted that acoustic properties in at least some instances may be a function of the length of an object emitting the sound, e.g., longer strings on a piano produce lower pitches. Likewise, the longer striker 4741A may produce a lower (or at least different) pitch than the shorter striker 4741B. Consequently, such an acoustic emitter 4718 may produce three two-pitch chords (one pitch from each striker 4741A and 4741B engaging the taller anvils 4745A approximately in unison) followed by three single-pitch notes (one from the longer striker 4741A for each shorter anvil 4745B), repeating with each group of six anvils 4745.

As shown and described, the use of two or more strikers 4741A and 4741B may provide for multiple pitches or other variations in acoustic emissions. Likewise, varying height of anvils 4547A and 4745B may provide for variations in acoustic emissions. In addition, combinations of variations in strikers 4741A and 4741B and/or anvils 4547A and 4745B may enable further variations, e.g., a given striker engages with some but not all anvils.

Further, any one acoustic emission, or any combination thereof, may serve to be characteristic; any one or combination may serve to carry acoustic bar code data. For example, the presence of two pitches (one each from strikers 4741A and 4741B) may be characteristic, while three two-pitch chords followed by three on-pitch notes followed by a gap may carry acoustic bar code data. Alternately, six repetitions of a first pitch from striker 4741A may be characteristic, while three repetitions of a second pitch from striker 4741B may serve as an acoustic bar code. Other arrangements also may be suitable. The distinction between what is characteristic and what constitutes an acoustic bar code may vary considerably; so long as both functions are carried out, precise definitions and distinctions are not limited. (In addition, it is noted that not all embodiments necessarily must carry out both functions, e.g., an acoustic bar code may not be present in at least some embodiments.)

Figure 48:
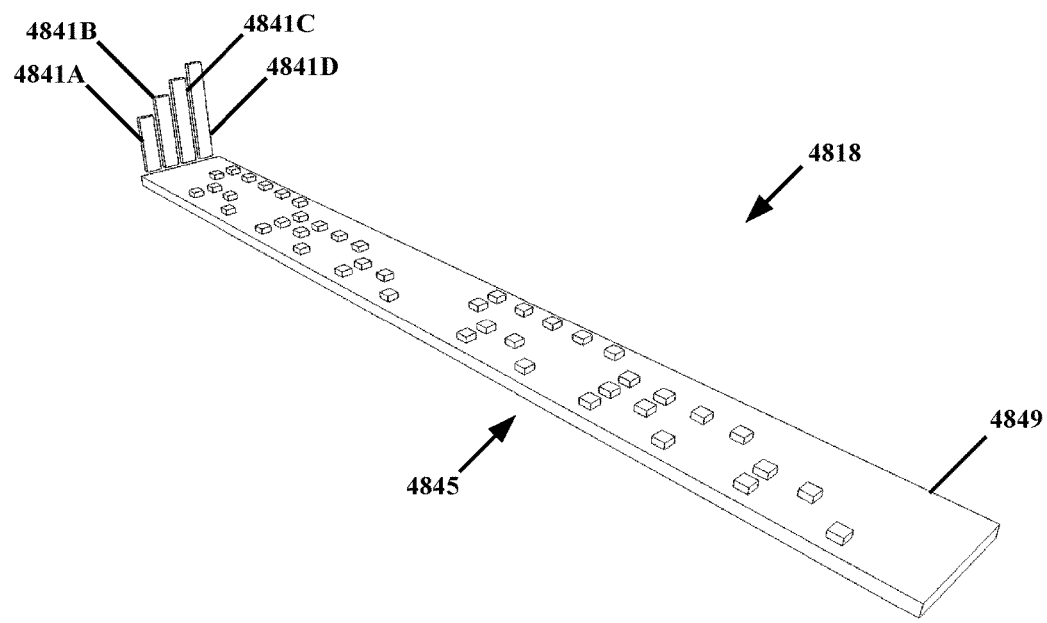

Turning to FIG. 48, certain previous examples have presented a single series or "trace" of anvils, with one or more strikers. However, it may also be suitable to have multiple traces of anvils, whether in one-to-one correspondence with strikers (e.g., each striker engages one trace) or otherwise (e.g., two strikers engage one trace as shown in FIG. 47). In FIG. 48 an acoustic emitter 4818 is shown. Four strikers 4841A, 4841B, 4841C, and 4841D are shown, each of different length, with striker 4841A being the shortest and striker 4841D being the longest. Other factors being equal, the strikers 4841A, 4841B, 4841C, and 4841D may produce different individual acoustic emissions (e.g., different pitches), for example striker 4841A may produce the highest pitch and striker 4841D the lowest.

The acoustic emitter also includes anvils 4845 disposed on a platform 4849. As may be seen, the anvils 4845 are arranged in four columns, or traces, along the length of the platform 4849; if the strikers 4841A, 4841B, 4841C, and 4841D move down the length of the platform 4849 each striker 4841A, 4841B, 4841C, and 4841D may engage one such trace. Consequently, each striker 4841A, 4841B, 4841C, and 4841D may interact with anvils 4845 arranged in a different pattern, and thus the acoustic emissions from each such interaction may be different for each striker 4841A, 4841B, 4841C, and 4841D. The combination of all such acoustic emissions produced may be considered and/or utilized in a variety of manners. For example, the series of acoustic emissions for each striker 4841A, 4841B, 4841C, and 4841D may be considered as a separate phrase overall, thus the acoustic emitter 4818 may produce four such distinct phrases (e.g., at different pitches) in parallel. Alternately, all acoustic emissions from all strikers 4841A, 4841B, 4841C, and 4841D may be considered together as a single phrase (e.g., with chords of multiple pitches but also with single pitches). Either may be suitable, as may other variations. Likewise, any one or more acoustic emission or pattern thereof may be utilized as characteristic (e.g., for indication/recognition), while others may be utilized as an acoustic bar code (e.g., as may encode additional data).

Further, it may be that the entirety of all sounds produced by the acoustic emitter 4818 (e.g., from all four strikers 4841A, 4841B, 4841C, and 4841D engaging all four traces of anvils 4845) may serve as both a characteristic acoustic emission and an acoustic bar code as well. For example, the arrangement of anvils 4845 may correspond to a binary countdown from 12 to 1, considering the left-most trace as 1, then 2, 4, and 8 for traces increasingly farther right. Such a numerical sequence may be considered to be an acoustic bar code, while the individual pitches thereof may be considered as characteristic (e.g., if all four pitches are present a characteristic acoustic emission is deemed to be present); however, it also may be suitable to consider the entire countdown in the specified pitches as being both characteristic, and also carrying encoded information (e.g., a specific number sequence, with a countdown from 12 to 1 being only an example).

The amount of information as may make up a characteristic acoustic emission, and/or the amount of information as may be encoded as an acoustic barcode, are not limited. As shown in certain previous examples arrangements may be simple, e.g., a single striker engaging a uniform series of anvils (with acoustic emissions being correspondingly simple). However, as shown with regard to FIG. 48 phrases of acoustic emissions may include multiple different pitches (or other acoustic properties), sounding in multiple patterns (e.g., one for each of several pitches), encoding considerable information (numerical or otherwise). In principle the sounds produced (and/or the acoustic emitters producing such sounds) may be arbitrarily complex; for example, a suitable groove and needle may provide for emission of human speech, perhaps even recognizable to a particular individual, and/or similarly complex sounds. The type, complexity, and generation of acoustic emissions is not limited.

In addition, it is noted that acoustic emissions, individually or in combination, may be "styled" so as to be conveniently recognizable for less formal applications, e.g., so as to provide a sound associated by human users with a particular product, brand, etc. For example, an acoustic emitter may produce an audible musical sequence or "jingle" when a container is opened, such as a user may hear and recognize as being associated with a product, service, etc. It is noted that such audible styling may represent yet another distinct aspect of acoustic emissions: a given acoustic emission or phrase may include characteristic features, data encoded in an acoustic bar code, and/or an acoustic style, without limitation. The characteristic features, encoded data, and style may be associated with distinctly different acoustic emissions or portions/aspects thereof, or such features may be intermingled. For example, a container may produce an audible and recognizable phrase of music as a style feature, followed by an acoustic bar code exhibiting characteristic features (which may or may not be audible or recognizable to the user).

Audible styling is not necessarily a purely cosmetic feature. For example, an acoustic phrase with a recognizable style therein that is produced when a container is opened may serve to audibly reinforce to users that the correct container is being opened. An acoustic phrase may be more readily recognized, distinguished, and/or remembered in at least some circumstances than a printed pharmacy label, for example. In addition, since an acoustic emission may permeate some volume of space (e.g., may be heard throughout one or several rooms), a recognizable acoustic phrase may serve as an indicator not only to the person opening a given container but also at least potentially to others. For example, if a container is configured to emit a recognizable audible style phrase, a parent may be alerted that the container is being opened, e.g., by a child. Even if the parent did not hear the style phrase, if a station (e.g., a smart speaker) detects the acoustic emission (whether the style phrase or some other portion) the parent then may be warned as part of registration of that acoustic emission. Such acoustic advisory features are not limited only to medications; household cleaning agents or other potentially dangerous chemicals likewise could be audibly "alarmed". Furthermore advisory emissions are not limited only to dangers; a cookie jar might be equipped with acoustic emitters that produce an easily recognizable acoustic phrase, for example, which may be heard by a parent not in the room. Similarly, a lunch box kept in a workplace refrigerator might be equipped with acoustic emitters as an acoustic identifier, e.g., if someone opens someone else's lunch an audible sound may be produced.

Whether used as warnings or otherwise, style phrases may be specific for example to each medication or other product, but alternately may be implemented consistently across many products/containers as a general warning. As a more concrete example, an easily recognizable 8-note sequence may be incorporated into many containers of potentially dangerous medication, household chemicals, etc. to serve as a broad warning; such an arrangement may be considered analogous to common "danger" symbols as may be printed on labels, warning signs, etc., though being made audible rather than visible. As with warning symbols, different style phrases may indicate different risks, e.g., toxic, alkaline, acidic, flammable, etc.

In addition, it is noted that persons who may not be able to read printed warnings, including children, the vision impaired, and so forth, nevertheless may recognize and respond to audible warnings. For example, a child too young to read may be taught that a particular sound means "danger" or "don't touch" when associated with a container.

Figure 49:
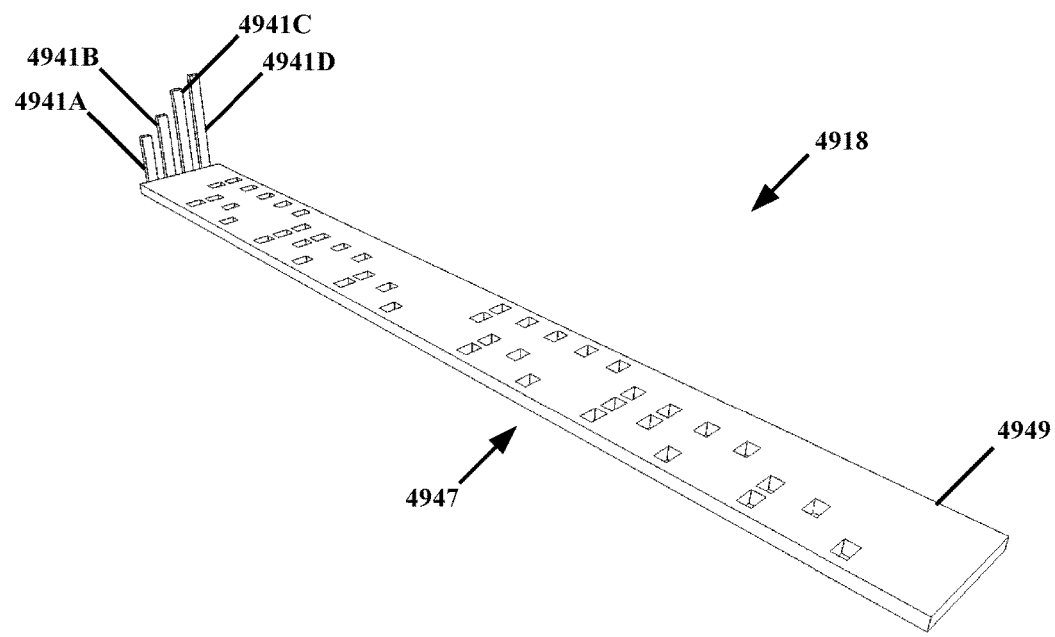

Now with reference to FIG. 49, another example acoustic emitter 4918 is shown. Four strikers 4941A, 4941B, 4941C, and 4941D are shown, each of different length, with striker 4941A being the shortest and striker 4941D being the longest. As noted with regard to FIG. 48, such an arrangement may produce a range in pitch or other properties among the strikers 4941A, 4941B, 4941C, and 4941D. The acoustic emitter 4918 also a platform 4949, with voids 4947 defined therein in four columnar traces. As noted previously with regard to FIG. 43 voids and/or other features may be suitable for cooperation with strikers in producing acoustic emissions; the complexity of such also is not limited (just as the complexity of anvils, or of other arrangements whether or not including strikers, is not limited). For the arrangement shown in FIG. 49, each striker 4941A, 4941B, 4941C, and 4941D may interact with voids 4947 (or perhaps more strictly with the table 4949 in which the voids 4947 are defined) arranged in a different pattern, and thus the acoustic emissions from each such interaction may be different for each striker 4941A, 4941B, 4941C, and 4941D, at least somewhat similarly to what has already been described with regard to FIG. 48.

Figure 50:
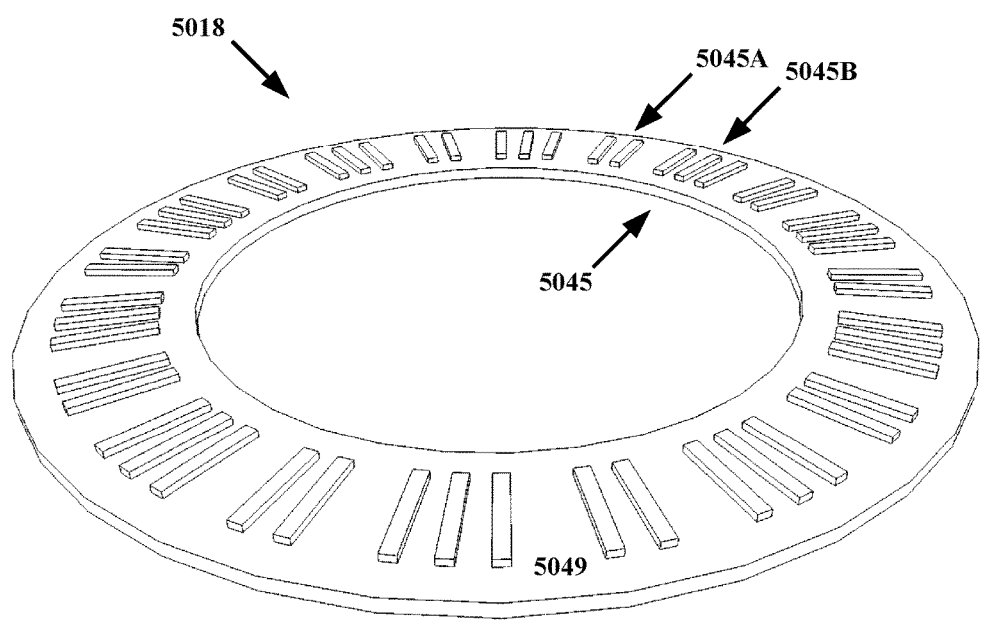

In FIG. 50, an arrangement of a platform 5049 is shown, with anvils 5045 arranged thereon in groups of two 5045A and three 5045B. Where certain previous platforms have been illustrated as linear, the platform 5049 in FIG. 50 is annular in shape, e.g., such that anvils 5045 thereof may interact with a striker (not shown) as the striker and/or platform 5049 rotates. As noted, a striker is not explicitly shown in FIG. 50. As has been previously mentioned, not all embodiments that use a "striker and anvil" approach necessarily will or must include a striker per se, for example, a fingernail may function as a striker with a suitable anvil. It may be arguable as to whether a structure lacking a striker but requiring a striker to produce acoustic emissions may be, in the most literal sense, an acoustic emitter. However, such a distinction may be academic at best, so long as the functions of an acoustic emitter may be carried out; thus at least for purposes of explanation, the arrangement shown in FIG. 5018 may be referred to as an acoustic emitter 5018 regardless.

With regard to FIG. 50, it is emphasized that the configuration of acoustic emitters is not limited. While linear acoustic emitters may be suitable for some embodiments, annular emitters may be suitable for other embodiments, and other shapes/arrangements may be suitable for yet other embodiments. Suitable arrangements are not limited only to those shown. In particular arrangements for producing acoustic emissions are not limited only to striker-and-anvil arrangements as shown in certain previous examples.

Figure 51:
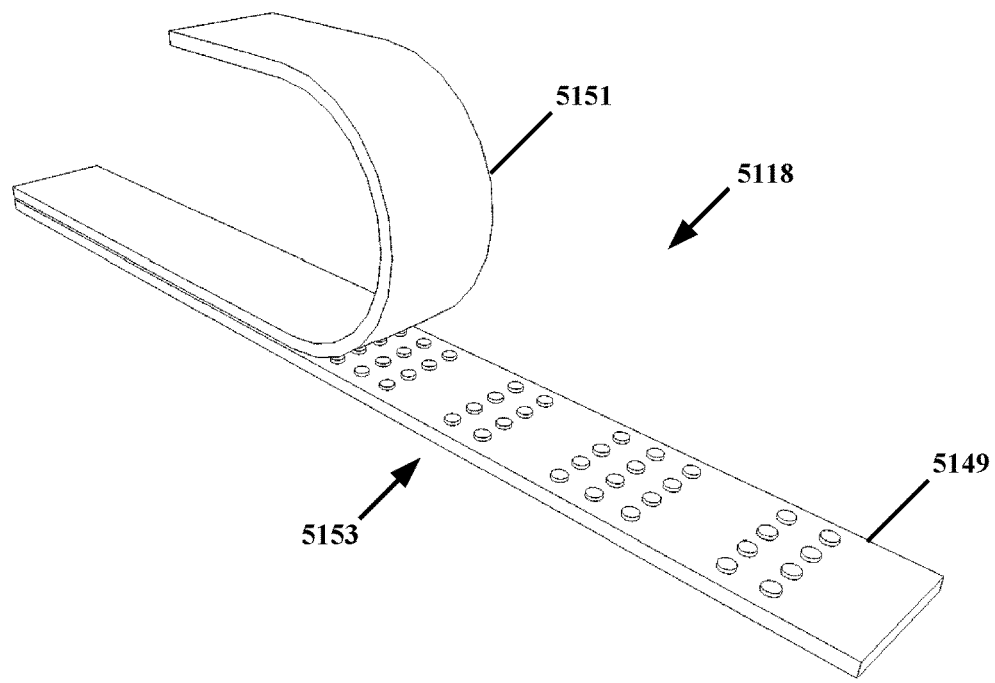
FIG. 51 through FIG. 53 depict example arrangements for adhesive peel acoustic emitters, in perspective view.

Turning to FIG. 51, an example acoustic emitter 5118 as may not utilize a striker-and-anvil arrangement is shown therein. The acoustic emitter 5118 includes a platform 5149 in the form of a long strip of relatively thin material, such as a tape, a section of cardboard, etc. (It is noted that a "platform" as the term may be used herein may not be necessarily either flat or rigid, although certain examples may illustrate a flat and/or rigid platform. The structure and/or composition of a platform, where present, is not limited.) As may be seen, beads 5153 of material are shown disposed on the platform 5149. Such beads 5153 may for example represent droplets of adhesive on the surface of the platform 5149. The beads 5153 show a pattern, namely, rows of four beads 5153 in alternating groups of two and three rows. Beads 5153 of adhesive (or other material) may be applied to a platform 5149 in such configuration through a variety of approaches, for example by deposition with a numerically controlled gluing system, deposition through a template, manual positioning, etc.; the manner by which beads 5153 may be laid down is not limited.

FIG. 51 also shows a blanket 5151, in the form of layer of material partially engaged with the platform 5149 via the beads 5153, the blanket 5151 having been partly peeled back from the platform 5149 and beads 5153, e.g., as when being removed to unseal some enclosure. As may be seen, the beads 5153 remain engaged with the platform 5149 but not the blanket 5151; for example, the blanket 5151 may be a release film (or have a release film or release agent as a portion thereof), such that the beads 5153 adhere less strongly to the blanket 5151 than to the platform 5149.

Regardless, when a blanket 5151 is peeled away from an array of adhesive beads 5153, acoustic emissions may be produced. For example, considering each bead 5153 individually, as the bond between that bead 5153 and the blanket 5151 separates some sound may be produced. The particulars of such an acoustic emission may depend on many factors, such as the composition of the blanket 5151 and/or the beads 5153 (e.g., what sort of release and/or adhesive are used), the surface texture of the blanket 5151, the size of the beads 5153, etc. Such factors may for example serve to render the acoustic emissions characteristic for purposes as described herein. Also, it is noted that where peeling away a tape that may be more-or-less uniformly covered in adhesive may produce a continuous sound (which, while not illustrated in FIG. 51, is not prohibited), an arrangement of adhesive beads 5153 may produce a series of sounds, e.g., four "pops" approximately simultaneously for each row (one for each bead 5153 in each row of four), with the pattern and spacing of the rows (groups of two and three rows as shown) defining the pattern and spacing of such pops. In practice such acoustic emissions for an arrangement as shown in FIG. 51 may audibly take the form of a punctuated stuttering sound (possibly a "multi-channel" sound due to beads 5153 in a given row possibly separating in groups of four, by row). However, regardless of the particular acoustic emissions produced, such patterning may for example carry encoded information, e.g., an acoustic bar code (and/or an audible style, etc.).

Figure 52:
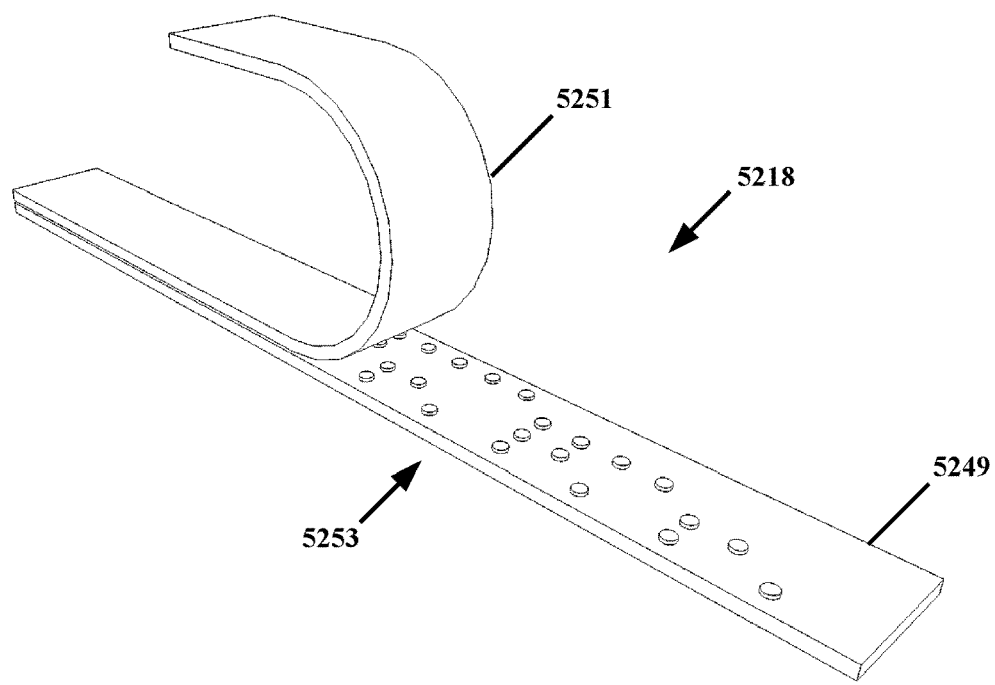

Turning to FIG. 52, as with striker-and-anvil arrangements, glue bead arrangements may exhibit considerable variation in structure, as may reflect and/or cause variations in acoustic emissions. An acoustic emitter 5218 is shown including a platform 5249 with a pattern of adhesive beads 5253 disposed thereon, with a blanket 5251 partially peeled away. As may be seen different rows of beads 5253 have different numbers of beads 5253 and in different positions, e.g., a single bead 5253 in the far left column (or trace) of the bottom most row, a single bead 5253 in the second-to-left column in next row up, etc. Different numbers of beads in different positions may alter the properties of acoustic emissions even with no other changes, e.g., an acoustic emission produced as the blanket 5251 separates from three beads 5253 may be louder than an acoustic emission produced as the blanket 5251 separates from only one bead 5253.

In addition, other factors may affect acoustic emissions, without necessarily being immediately visible. For example, if each of the four columns/traces of beads 5253 are formed from different compositions of adhesive, the sound made when the blanket 5251 separates from beads 5253 in different traces may be of different pitch, or otherwise differ. Such an arrangement may enable a four-pitch phrase of acoustic emissions, singly and/or as chords, as may be highly characteristic, encode considerable data, be readily recognized by users, etc. Thus even though beads 5253 may be visually similar (or even indistinguishable), differences in acoustic emissions among beads and/or traces, rows, etc. thereof still may be enabled. Likewise, if the blanket 5251 were formed with different properties across the width thereof, even if all beads 5253 were identical different pitches, volumes, etc. may be produced. For example, a blanket 5251 may be provided with "stripes" of material or surface properties such that separation of the blanket 5251 from a bead 5253 on one such stripe may produce a different acoustic emission than on another such stripe. As a more concrete example, lengthwise stripes of different textures or release strengths on a blanket 5251 may facilitate production of different acoustic emissions for each column/trace of beads 5253 shown in FIG. 52.

Figure 53:
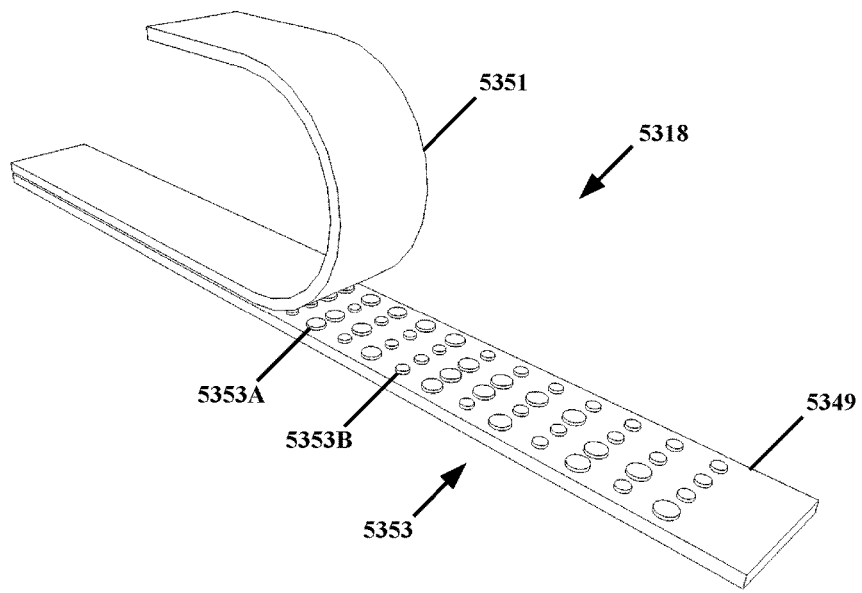

Turning to FIG. 53, in at least certain instances variations in adhesive beads may be visible. For example, as shown therein an acoustic emitter 5318 includes a platform 5349 with adhesive beads 5353 patterned thereon, and a blanket 5351 partially peeled away. As may be seen, some beads 5353A are larger than other beads 5353B. Such an arrangement may correspond with a literal difference in the size of the beads 5353A and 5353B, but also may be understood to illustrate (conceptually if not literally) other differences such as differences in adhesive composition, etc. Given the arrangement in FIG. 53, peeling the blanket 5351 from the beads 5353 may produce a pattern of differing acoustic emissions depending at least in part on whether large beads 5353A or small beads 5353B are separating, how many of each, in what positions, etc. Changes in the shape, height, etc. of adhesive beads 5353 also may produce variations in acoustic emissions. Combination with other features such as varying surface properties on the blanket 5351 may produce still other variations in acoustic emissions. For example, if the blanket 5351 were provided with longitudinal stripes with different degrees of adhesion to the beads 5353, each column of beads 5353 may produce a different pitch as the blanket 5151 may be peeled away.

In addition, it is noted that an arrangement such as is shown in FIG. 53 may be understood to illustrate a possibility for distinguishing a first time that the blanket 5351 is peeled from subsequent instances that the blanket 5351 is peeled (as previously described with regard to breakaways in FIG. 41). Consider an arrangement wherein the large beads 5353A represent an adhesive as may bond and release repeatedly, such as a silicone pressure sensitive adhesive (or PSA), while the small beads 5353B represent an adhesive as may not rebond after having once separated, such as a curable epoxy resin adhesive. In such instance, when the blanket 5351 is first peeled both the large and small beads 5353A and 5353B may produce acoustic emissions; however thereafter, if the blanket 5351 is replaced and then again peeled, only the small beads 5353B may produce acoustic emissions (e.g., since the large beads 5353A may not rebond when the blanket is replaced). Thus, first use (or opening, etc.) again may be distinguished from subsequent use, in arrangements not limited to the use of breakaways, soda caps, etc.

Now with reference to FIG. 54 through FIG. 57 collectively, another group of configurations for acoustic emitters is presented, in the form of a tape or panel as may produce acoustic emissions in response to being cut, torn, etc. For example, such tape may seal a package, and when that package is opened cutting or tearing the tape (as opposed to peeling or twisting structures for example, as shown in certain previous figures) may produce acoustic emissions as may be considered in manners as already described herein.

Figure 54:
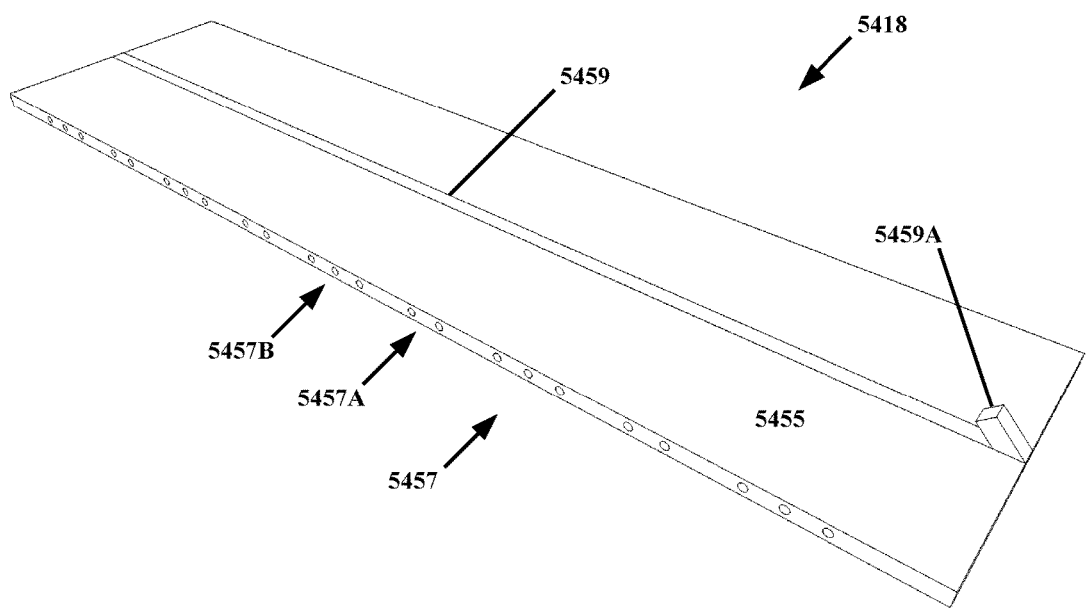
FIG. 54 through FIG. 58 depict example arrangements for filament tap acoustic emitters, in perspective view.

With reference specifically to FIG. 54, an acoustic emitter 5418 is shown. The acoustic emitter 5418 includes a mantle 5455 illustrated in the form of a long strip or sheet of material (though such form is not limiting). In addition, the ends of filaments 5457 are visible along an edge of the mantle 5455, embedded within the mantle 5455. A separator 5459 is shown extending lengthwise along the mantle 5455 and at least approximately flush therewith, with a small tab 5459A extending outward from the mantle 5455 at one end thereof. As may be seen, the filaments 4547 are arranged in groups of two 5457A and three 5457B.

Figure 55:
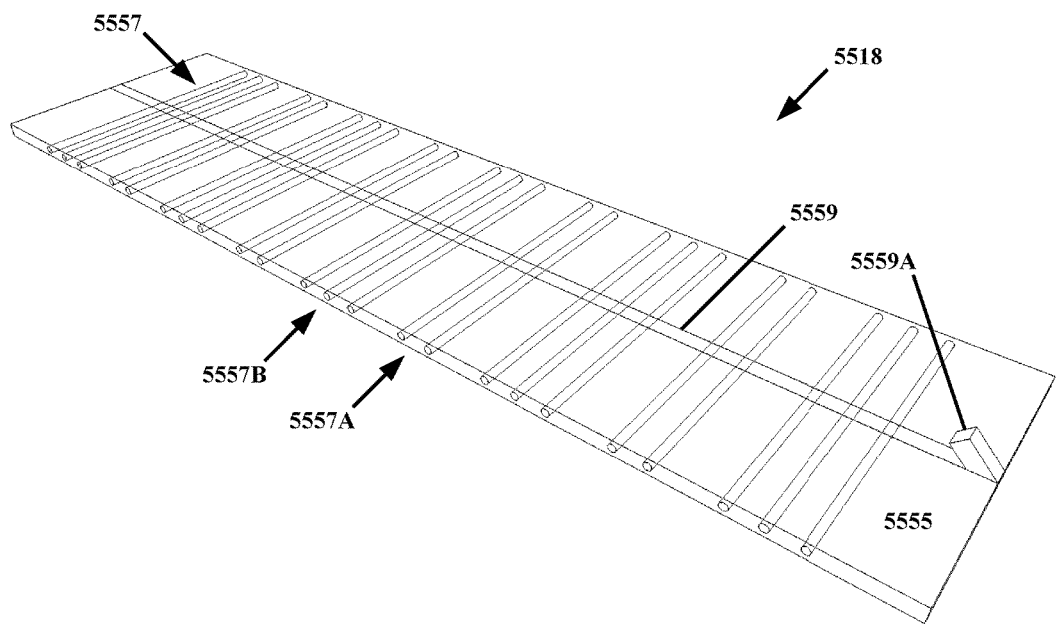

Turning to FIG. 55, an example arrangement of an acoustic emitter 5518 at least somewhat similar to that in FIG. 54 is shown, however in FIG. 55 the mantle 5555 is illustrated as transparent, such that the filaments 5557 therein (still in groups of two 5557A and three 5557B) are more readily visible. In practice a mantle 5459 may not literally be transparent (though transparency is not prohibited). Regardless, as may be seen in FIG. 55 the filaments 5557 extend approximately laterally across the mantle 5555; the separator 5559 may be seen to cross (e.g., intersecting) the filaments 5557. Thus, if the separator 5559 were pulled away from the mantle 5555 (e.g., by applying tension to the tab 5559A) the filaments 5557 may be severed.

Figure 56:
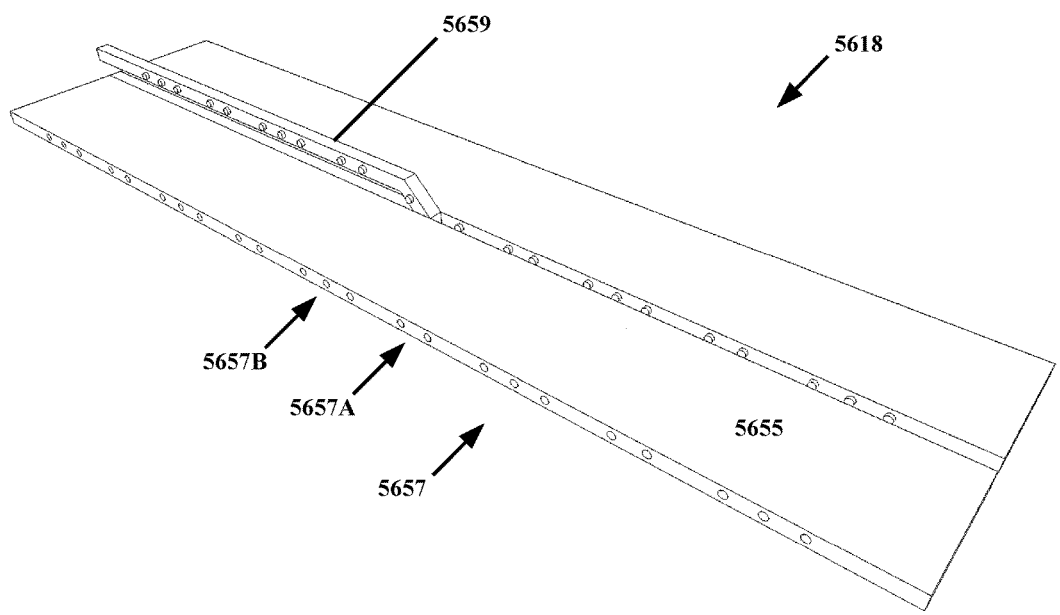

Moving on to FIG. 56 an arrangement of an acoustic emitter 5618 at least somewhat similar to that in FIG. 54 and FIG. 55 is shown, wherein the separator 5659 has been partially pulled. As may be seen, the mantle 5655 is separated (e.g., cut/torn into two narrower portions where the separator 5659 has been removed), and some of the filaments 5657 (still in groups of two 5657A and three 5657B) have been severed. In severing the filaments 5657, an acoustic emission may be produced therefrom. For example, if the filaments 5657 are under tension (or are placed under tension as the separator 5659 is removed) the release of that tension as the filaments 5657 separate may produce a "pluck" or "twang" sound, etc. Pitch, waveform, and/or other properties may vary depending on thickness, material, tension, etc., and as noted with regard to certain previous examples properties of the filaments 5657 and/or the arrangement thereof (e.g., some thick and some thin, groups of two and three, etc.) also may be varied. Thus acoustic emissions for cut/broken filaments may be characteristic, may encode acoustic bar code data, etc., in manners as may correspond to other arrangements already described (e.g., with regard to variations in striker-and-anvil embodiments).

Figure 57:
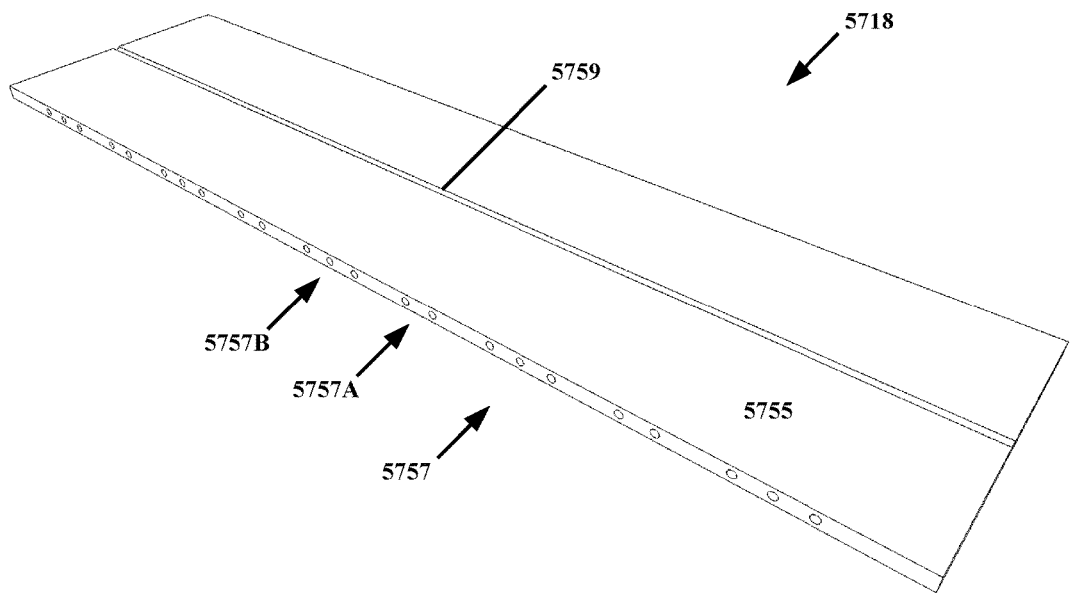

Now with reference to FIG. 57, another example acoustic emitter 5718 is shown. The emitter 5718 again includes a mantle 5755 with filaments 5757 therein (again in groups of two 5757A and three 5757B). A separator 5759 is again shown, however were certain previous separators were positive structures, e.g., a pull line, the separator 5759 as shown in FIG. 57 is a groove defined along the length of the mantle 5755. Such a groove 5759 may serve as a weak point in the mantle 5755, so that the mantle 5755 may be readily cut or torn along the separator 5759. Other arrangements for facilitating separation also may be suitable.

Figure 58:
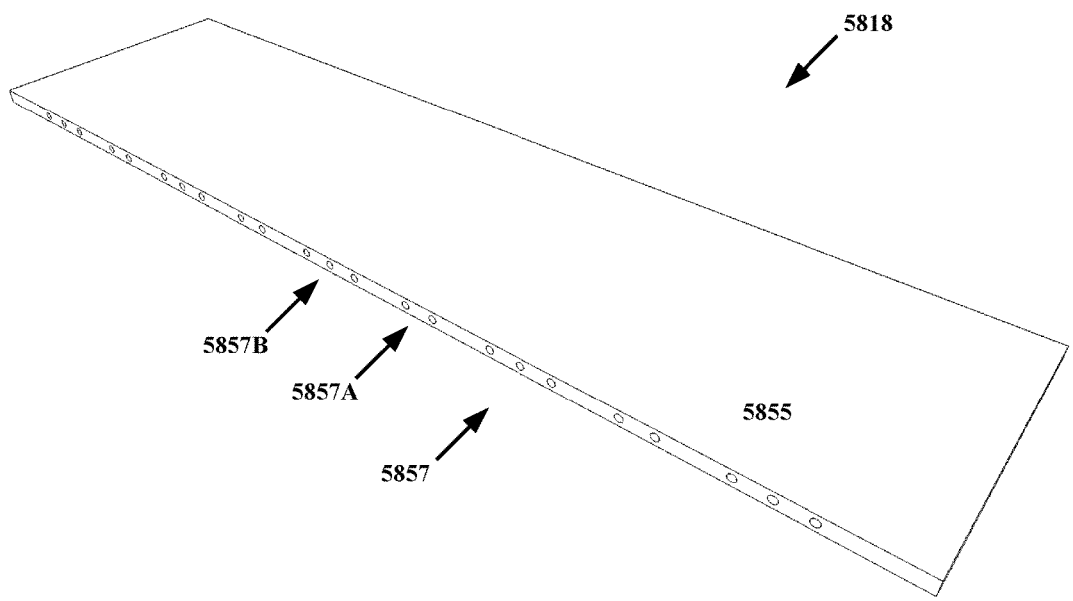

In addition, it may be suitable in certain embodiments to provide no particular arrangements to facilitate separation. In FIG. 58 an acoustic emitter 5818 is shown with a mantle 5855 and filaments 5857 therein in groups of two 5757A and three 5757B. No separator is shown to be present; while the mantle 5855 may be torn, cut, etc., no guidance, weakening, physical mechanism, etc. for separation is provided. A user may for example cut or tear the mantle 5855 at his or her own discretion. As a more concrete example, considering a mantle 5855 in the form of a strip of adhesive tape, such tape may be used to close a seam between edges of a cardboard box or other packaging; a user then may be expected to cut or tear the mantle 5855 along that seam so as to open the box. Other arrangements also may be suitable.

As may be understood for example from FIG. 35 through FIG. 58, a wide variety of vehicles/enclosures may be configured to produce acoustic emissions, via a large variety of mechanisms (e.g. strikers on twist caps, frangible filaments in adhesive tape, etc.) as may be disposed on enclosures (e.g., bottles, boxes, etc.), closures therefor (e.g., caps, sealing tapes, etc.) and/or both. The types of enclosures, closures, emitters, and mechanisms are not limited.

In addition, acoustic emitters and the operation thereof are not limited only to literal enclosures, e.g., boxes, bottles, etc., and/or to literal closures therefor such as caps, seal tapes, etc. At least in principle, any element as may be moved or otherwise actuated to produce some effect may be provided with acoustic emitters. For example, a light switch may be configured to produce suitable acoustic emissions when turned on (and/or when turned off), a laptop computer when opened, a cable when plugged in or unplugged, a printer tray when loaded with paper, a water tap when turned, etc. Indeed, the mechanism producing the acoustic emissions may not even be required to have a function other than producing the acoustic emissions. For example, a ticket for a film, a theme park ride, etc. may be equipped with acoustic emitters in the form of a peel strip and beads of adhesive similar to what is shown in FIG. 53. Rather than tearing off the top half of a ticket and then logging the ticket (e.g., by scanning a printed bar code thereon), the peel strip could be pulled away producing an acoustic emission that causes the ticket to be registered in a single step.

Thus, while as a concrete example it may be useful to refer to a container, an enclosure, etc., in a more general sense it may be useful to consider a "vehicle" with some or all of the acoustic emitters disposed thereon, integral therewith, etc. For example, with regard to arrangements such as are shown in FIG. 1A through FIG. 1D the container 132C may be considered to be the vehicle, with the acoustic emitter disposed in a remote into which the vehicle (container) is inserted. Alternately, a bottle, packing box, light switch, water tap, etc. as may be provided with acoustic emitters likewise may be referred to as a vehicle therefor.

Typically, but not necessarily, a vehicle may be an enclosure such as a medication container, soft drink bottle, etc. as described in various examples herein; however, other forms of vehicle also may be suitable, and are not limited so long as suitable functionality may be implemented therewith.

Regardless of the particulars of a given vehicle, through the use of acoustic emitters, stations, etc., smart sensing functionality may be provided (and/or retrofitted) for many devices, systems, etc., while those devices, systems, etc. themselves remain "dumb". The aforementioned water tap may not have and/or require a processor, sensors, power supply, wireless transceiver, etc. thereon, and arguably may not be a smart device per se; nevertheless, by monitoring acoustic emissions from emitters engaged with the tap, it may be possible to register when the tap was turned, how far, for how long, etc. A single station thus may support smart functionality for a large number of devices anywhere within the "hearing" of that station, even without any smart components being disposed to those devices or elsewhere within the environment. (In at least some sense, it may be reasonable to consider the combination of acoustic emitters and station for receiving acoustic emissions as a smart device or smart system, though in practice emitters and station typically may be physically distinct from one another.)

Now with reference to FIG. 59 through FIG. 69, in certain previous examples acoustic emitters have been described at least somewhat in abstraction, for example shown as engaged with soda bottle caps but without a bottle being visible. While such examples may be useful for illustration, it also may be illuminating to examine an arrangement as may include a complete enclosure, with an acoustic emitter engaged therewith, as to provide a more concrete example as to implementation. It is emphasized that the arrangements in FIG. 59 through FIG. 69 are examples only, and are not limiting.

Figure 59:
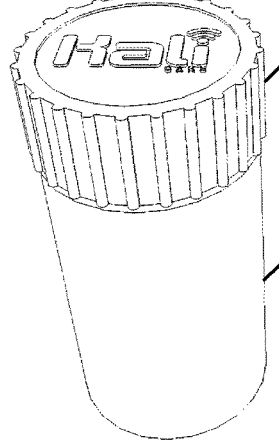
FIG. 59 through FIG. 63 depict example arrangements for striker-and-anvil acoustic emitters as may engage with an example container, in perspective view.
Figure 60:
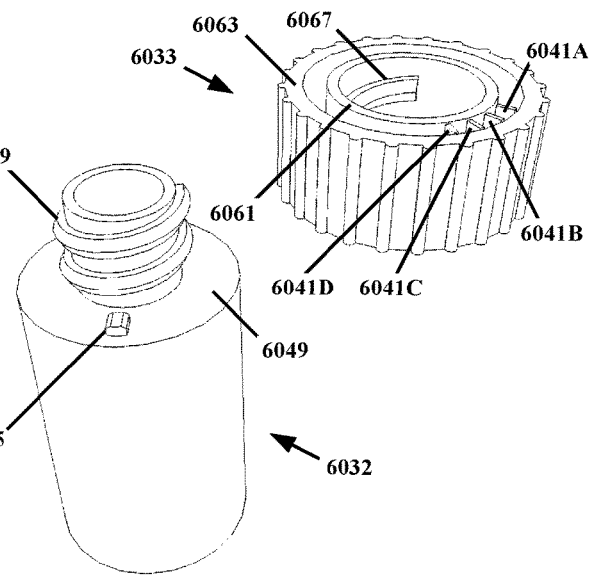

In FIG. 59, a screw top container 5932 is shown, as may be adapted to hold medication (e.g., pills, capsules, liquids, etc.) or other materials. A cap 5933 is also shown engaged with the container 5932. It is noted that no acoustic emitters or components thereof are visible in FIG. 59; while the arrangements shown in certain previous examples (e.g., FIG. 36) may present acoustic emitters as may be externally visible, for other examples acoustic emitters and/or other features may be present without being readily visible.

Turning to FIG. 60, again a screw top container 6032 is shown, as may be at least somewhat similar to the arrangement shown in FIG. 59. However, where the cap in FIG. 59 is shown engaged with the container therein, in FIG. 60 a cap 6033 is shown disengaged from the container 6032 and inverted, such that certain features of the container 6032 and cap 6033 may be visible. For example, as may be seen an anvil 6045 is present on the container 6032, along with a container thread 6069 as may engage the cap 6033 (e.g., on the cap thread 6067 thereof). The anvil 6045 is disposed on an approximately flat and circular "shoulder" surface of the container 6032 as may serve as a platform 6049 (though in practice anvils, when present, need not be disposed on such a platform). In addition, the cap 6033 includes an inner wall 6061 with a cap thread 6067 thereon, and an outer wall 6063 (shown knurled, e.g., to provide texture for a user to grip the cap 6033 when engaging and/or disengaging the cap 6033 and container 6032). Portions of four strikers 6041A, 6041B, 6041C, and 6041D also are visible, disposed between the inner and outer walls 6061 of the cap 6033.

Figure 61:
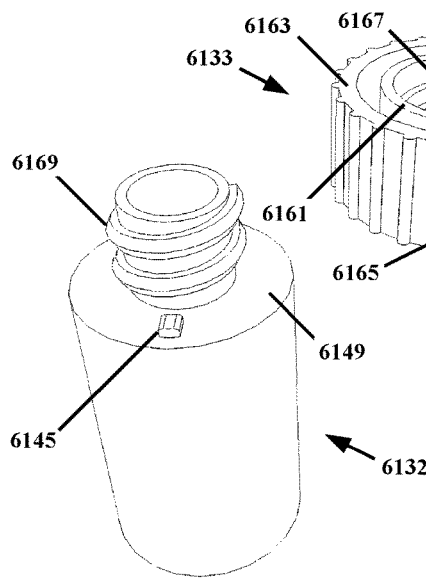

Moving on to FIG. 61, another example illustration is provided showing a screw top container 6132. Again, a cap 6133 for the container 6132 is disengaged and inverted. In addition, a portion of the outer wall 6163 is cut away; the cutaway is presented for illustrative purposes, and should not be taken to imply that such an aperture does or must be defined in all embodiments (though apertures also are not prohibited). As may be seen through the cutaway, four strikers 6141A, 6141B, 6141C, and 6141D are present, each striker 6141A, 6141B, 6141C, and 6141D extending from a pedestal 6143A, 6143B, 6143C, and 6143D that in turn extends from a channel floor 6165 of the cap 6133 (e.g., a floor of channel as defined by the presence of the outer and inner walls 6163 and 6161 of the cap 6133). The cap also includes a cap thread 6169, and the container 6032 likewise includes a container thread 6169. The container also has an anvil 6145 disposed thereon.

A cap 6133 such as shown in FIG. 61 may be produced in a variety of manners. For example, such an arrangement of inner and outer walls 6163 and 6161, channel floor 6165, pedestals 6143A, 6143B, 6143C, and 6143D and strikers 6141A, 6141B, 6141C, and 6141D, and cap thread 6167 may be produced as an integrally molded piece, e.g., injection molded out of a polymer or similar material. Alternately, the cap 6133 may be produced in several parts molded (or otherwise produced) separately and then assembled, overmolded, etc. For example each pedestal 6143A, 6143B, 6143C, and 6143D and each respective striker 6141A, 6141B, 6141C, and 6141D may be molded as a separate piece, all of the pedestals 6143A, 6143B, 6143C, and 6143D and strikers 6141A, 6141B, 6141C, and 6141D may be made as a single piece but separate from a remainder of the cap 6133, etc. Approaches other than injection molding and/or materials other than polymers may be suitable. For example, a cap 6133 may be made of metal, whether machined, cast, etc. As another example, a cap 6133 may be produced via additive manufacturing ("3D printing") out of a variety of suitable materials such as polymers, elastomers, metals, etc. Given the arrangement shown in FIG. 61 it may be useful for the strikers to exhibit some degree of flexibility (e.g., so as to pass over the anvil 6145 when the cap 6133 is turned), but so long as the functions described herein as facilitated by the structure, manufacturing technique, and/or materials, such features are not limited.

Similarly, a container 6132 as shown in FIG. 61 also may be produced with various structures, manufacturing techniques, and/or materials, and such features are not limited. However, as a particular example, it is noted that a container 6132 as shown may be produced in two or more pieces and then assembled. More concretely, an anvil 6145 may be fabricated separately from the remainder of the container 6132, and then attached thereto. For instance, an annular adhesive disc of paper, polymers, etc. may be produced with an anvil 6145 integral thereto and/or attached thereto, then applied to the container 6132 over the neck and container thread 6169 so as to adhere to the platform 6149. In such fashion, an existing bottle that is not already adapted for acoustic emissions may be retrofitted so as to provide an arrangement similar to that shown in FIG. 61 (and/or some other structure as to facilitate production/use of acoustic emissions). At least in principle, a suitable cap also might be so retrofitted.

It is also noted that although the cap 6033 and container 6032 are shown paired together in FIG. 61 (and/or certain other examples herein), embodiments of caps and containers are not necessarily limited to a one-to-one correspondence. That is, a given cap may be suitable for engagement with two or more different bottles of varying shapes, sizes, configurations, materials, etc., and/or vice versa. A single cap (or design of cap) thus might be suited for producing acoustic emissions via engagement with many different containers (or designs of containers).

An additional feature with regard to FIG. 61 is noted, in that as may be seen the acoustic emitter—in the example shown, the strikers 6141 on the cap 6133 and the anvil 6145 on the container 6132—are not themselves in a dispensing path for the contents of the container 6132. That is, whatever liquid, pills, etc. may be present in the container 6132, neither the strikers 6141 nor the anvil 6145 are in positions such that those contents may be required or expected to touch the strikers 6141 or the anvil 6145 (though the contents may touch other portions of the container 6132 and/or cap 6133). Thus, where contact with foreign bodies may be of concern for a given product (such as sterile medications, corrosive chemicals, etc.), as may be seen in FIG. 61 in at least certain embodiments an acoustic emitter may be configured so that such a product may not physically contact the acoustic emitter. Consequently, concerns regarding matters such as contamination of the product by the acoustic emitter (or vice versa) may be avoided, at least insofar as there may be no contact between the product and the acoustic emitter. While the arrangement in FIG. 61 may show a particular example configuration such that the acoustic emitter (and/or portions thereof) are not in the dispensing path for the container 6132, other such arrangements also may be suitable.

Figure 62:
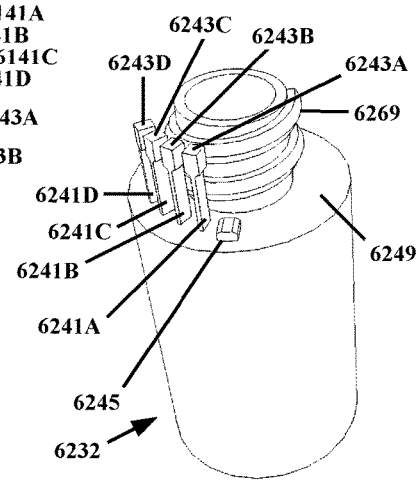

Turning to FIG. 62, therein a container 6232 is shown, along with certain elements as may be present on a cap (e.g., a cap as shown in FIG. 59): namely, pedestals 6243A, 6243B, 6243C, and 6243D and respective strikers 6241A, 6241B, 6241C, and 6241D. The pedestals 6243A, 6243B, 6243C, and 6243D and strikers 6241A, 6241B, 6241C, and 6241D are shown arranged at least approximately as if such a cap were in place and engaged with the container 6232. However, for purposes of illustration, the remainder of such a cap itself is not illustrated. Thus, the respective configuration of the strikers 6241A, 6241B, 6241C, and 6241D and the anvil 6245 on the platform 6249 of the container 6232 may be more readily observed.

Some structural similarity with strikers as shown and described previously may be observed in FIG. 62, e.g., with comparison to strikers and anvils in FIG. 36 through FIG. 40. Functionally, the strikers 6241A, 6241B, 6241C, and 6241D shown in FIG. 62 may perform similarly, e.g., distorting elastically when engaging the anvil 6245 as the cap 6233 rotates and producing acoustic emissions as the strikers 6241A, 6241B, 6241C, and 6241D return to a neutral configuration after passing the anvil 6245. As examples of physical behaviors by which acoustic emissions may be produced have already been shown and described herein, such description is not reiterated here in detail. However, as may be understood if the strikers 6241A, 6241B, 6241C, and 6241D were engaged with a cap, as that cap were turned to disengage and/or to engage the container 6232 for example so as to open and/or close the container 6232 to access contents therein (e.g., via a cap thread and the container thread 6269), the strikers 6241A, 6241B, 6241C, and 6241D may rotate to engage the anvil 6245 and thus acoustic emissions may be produced. Such acoustic emissions then may be detected, considered, etc. as described elsewhere herein.

It is noted that given the arrangements shown in FIG. 59 through FIG. 62, the acoustic emitters may engage the anvil whether the cap is being unscrewed to open the container or screwed to close the container. Such an arrangement may produce acoustic emissions both when removing the cap and when replacing the cap. Such an arrangement, while not required, also is not prohibited. However, it is noted that at least certain such arrangements may produce acoustic emissions in a different order while replacing a cap compared to removing that cap; for FIG. 59 through FIG. 62 the acoustic emissions from strikers engaging with an anvil may be produced in reverse order but otherwise unchanged, for example. However, even for arrangements wherein acoustic emitters operate in two or more directions (e.g., while a cap is being removed and replaced), not all embodiments necessarily will produce the same acoustic emissions in both instances. For example, the acoustic emitters shown in FIG. 61 exhibit a symmetrical cross-section, e.g., a flat rectangle as engaging the anvil 6145. However, if the cross section thereof was not symmetrical in such fashion, e.g., a semicircular cross-section, different shaped faces may engage the anvil 6145 depending on whether the cap 6133 is being removed or replaced. To continue the semicircular example, a flat face of each striker 6141 may engage the anvil 6145 as the cap 6133 is removed while a curved face may engage the anvil 6145 as the cap 6133 is replaced. Similarly, an anvil 6145 that is shaped differently at either end may yield different acoustic emissions depending on which end the strikers 6141 engage. Other arrangements also may produce dissimilar acoustic emissions when opening vs. closing a container.

Further, while in certain examples herein attention may be focused on acoustic emissions produced as a container is opened, in at least some embodiments it may be useful to consider acoustic emissions produced as a container is closed, even to the exclusion of considering acoustic emissions produced as that container is opened. For example, consider a storage container, such as a glass or plastic tub used for storing food. Acoustic emitters may be engaged therewith so as to produce an acoustic emission (e.g., characteristic of that particular container) when the container is closed, whether or not an acoustic emission is also produced when the container is opened. It may be of interest to know when that container was closed, e.g., "how long has this meatloaf been in the refrigerator?" Potentially knowing when a food container was closed may be of equal or even of more use than knowing when the container holding that food was last opened. Other arrangements similarly may produce acoustic emissions upon closing, in addition to or instead of on opening. Moreover, acoustic emissions are not necessarily limited only to being produced on opening or closing, nor are acoustic emitters limited to being engaged with containers only.

To continue the example of products in refrigerators, it is noted that refrigerators and/or other enclosures relating to perishables may themselves serve as stations, e.g., being equipped with an acoustic receiver (as may also accept voice commands), a processor, a communicator, etc. In such instance, tracking perishable items noted above (e.g., the aforementioned meatloaf) whether by opening and/or closing of containers may be suitable. Registration may include reporting that an item is nearing an expiration date, automatically placing a reorder for some product as is running low (e.g., five cans from a six-pack of soda have been opened), etc. Such functions also may be carried out with regard to other consumables and/or perishables, e.g., medication may be reordered when low or nearing expiration, etc.

Figure 63:
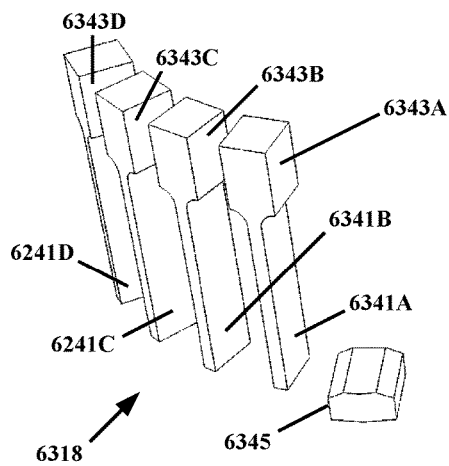

Moving on to FIG. 63, a closer view of an acoustic emitter 6318 with pedestals 6343A, 6343B, 6343C, and 6343D, strikers 6341A, 6341B, 6341C, and 6341D, and anvil is shown therein, as may be similar to a portion of the arrangement shown in FIG. 62. For purposes of simplicity, FIG. 63 does not show a cap, container, etc. (nor do certain subsequent examples herein), rather emphasizing an example structure for the acoustic emitter 6318 itself. As may be observed, the strikers 6341A, 6341B, 6341C, and 6341D are and anvil 6345 are arranged in an arc around a central axis (the axis not being illustrated). Rotating the strikers 6341A, 6341B, 6341C, and 6341D with respect to the anvil 6345 may cause the strikers 6341A, 6341B, 6341C, and 6341D to engage the anvil 6345, so as to produce acoustic emissions.

Figure 64:
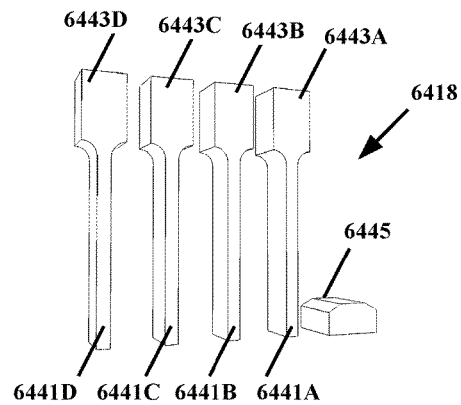
FIG. 64 through FIG. 70 depict example arrangements for striker-and-anvil acoustic emitters, in perspective view.

Turning to FIG. 64, an arrangement at least somewhat similar to that in FIG. 63 is shown, however in FIG. 64 pedestals 6443A, 6443B, 6443C, and 6443D, strikers 6441A, 6441B, 6441C, and 6441D, and an anvil 6445 are shown in a linear arrangement as opposed to being arranged in an arc, for simplicity of illustration. Certain subsequent illustrations herein also present a linear arrangement, with variations on configuration also shown therein. However, it is emphasized (as has been illustrated previously in FIG. 63) that a linear configuration is not required for all embodiments (even those embodiments that utilize a striker-and-anvil arrangement, which itself is not required). Other arrangements may be suitable.

Figure 65:
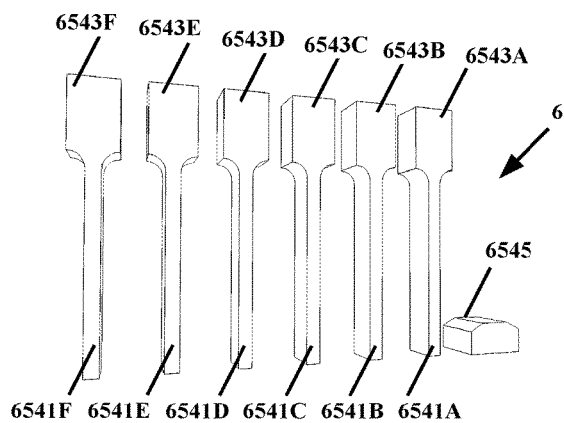
Figure 66:
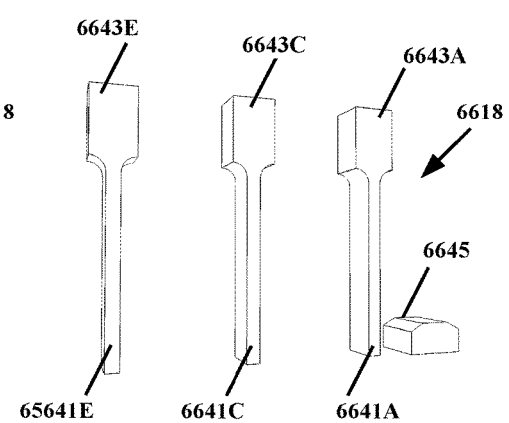
Figure 67:
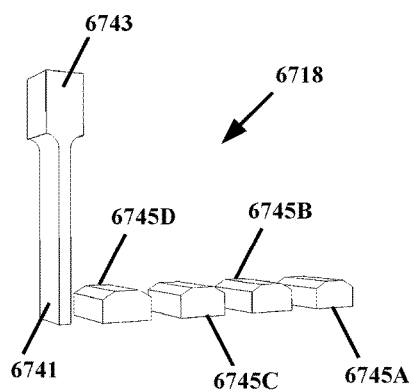

The number of strikers and/or other elements as may contribute to generating acoustic emissions, is not limited. For example, FIG. 65 shows an example acoustic emitter 6518 wherein six pedestals 6543A, 6543B, 6543C, 6543D, 6543E, and 6543F and strikers 6541A, 6541B, 6541C, 6541D, 6541E, and 6541F are present as may engage an anvil 6545, rather than four as in FIG. 64. Similarly, FIG. 66 shows another example acoustic emitter 6618 wherein three pedestals 6643A, 6643B, and 6643C and strikers 6641A, 6641B, and 6641C are present as may engage an anvil 6645; as may be seen in FIG. 66 the spacing between strikers 6641A, 6641B, and 6641C is visibly greater than in FIG. 65, as well. The spacing likewise is not limited. Also, as seen in FIG. 67 another example acoustic emitter 6718 is shown that includes only a single pedestal 6743 and striker 6741, but four anvils 6745A, 6745B, 6745C, and 6745D. As may be understood, the number, spacing, and/or arrangement of anvils 6745A, 6745B, 6745C, and 6745D likewise is not limited.

However, although the number of strikers (or other elements) and anvils and/or the spacing and/or arrangement thereof is not limited, neither are such features necessarily irrelevant. Certain advantages may be achieved with certain such arrangements in at least some circumstances. For example, a large number of strikers may provide redundancy, while a small number may more readily fit into a compact structure (e.g., a small cap for a small container). Likewise, close spacing may provide a more "dense" signal (e.g., more sounds per unit time) while broad spacing may facilitate distinct identification of individual acoustic emissions, sufficient room for a large degree of elastic deformation of strikers (which in turn may facilitate greater acoustic volume), etc. It is also noted that variations in spacing may provide acoustic emissions wherein the spacing of those emissions may be characteristic, etc., in addition to instead of the emissions themselves. In practice, the number, spacing, arrangement, etc. of strikers and/or anvils may vary considerably, based at least in part on the particular constraints for a given embodiment.

Figure 68:
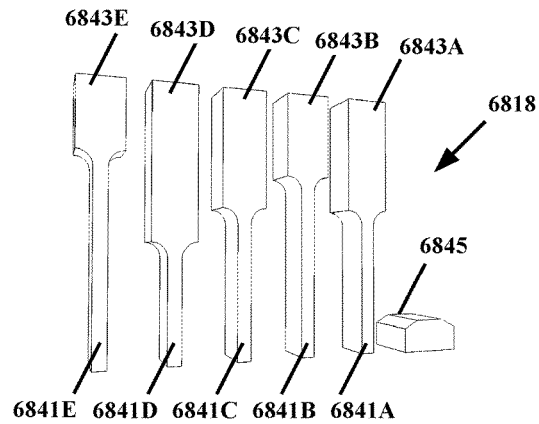

Continuing with FIG. 68, an example acoustic emitter 6818 is shown that includes an anvil 6845, five pedestals 6843A, 6843B, 6843C, 6843D, and 6843E, and five corresponding strikers 6841A, 6841B, 6841C, 6841D, and 6841E. As may be observed, pedestals 6843A, 6843B, 6843C, 6843D, and 6843E are of unequal height, and strikers 6841A, 6841B, 6841C, 6841D, and 6841E also are of unequal height (although combined, each pedestal 6843A, 6843B, 6843C, 6843D, and 6843E and corresponding striker 6841A, 6841B, 6841C, 6841D, and 6841E may be of at least approximately equal height). As noted previously, for at least certain embodiments the pitch of an acoustic emission produced by a striker engaging an anvil may be determined at least in part by the length of the striker (e.g., a longer striker may produce a lower pitch). Consequently, the strikers 6841A, 6841B, 6841C, 6841D, and 6841E may produce different pitches, and thus overall the acoustic emitter 6818 shown in FIG. 68 may produce a series of five different pitches at regular intervals, as each striker 6841A, 6841B, 6841C, 6841D, and 6841E interacts with the anvil 6845 in turn.

Such a five-pitch phrase may be suitable for a variety of applications. For example, the likelihood that five particular pitches may be produced in a particular sequence as background noise may be relatively low, thus such a five-pitch phrase may serve as characteristic for purposes as described herein (e.g., determining whether a container has been opened or closed, etc.). As another example, for five different pitches the number of possible five-pitch combinations thereof may be relatively large, e.g., 120 possibilities without repeating any such pitch or 3,125 possibilities if any such pitch may be used more than once. Thus, significant amounts of data may be encoded into such an acoustic phrase; for example one five-pitch phrase may indicate which of several medications may have been opened, or the manufacturing date of a production lot of soda, etc. As still another example, a five-pitch phrase may be sufficient for reliable user recognition (it is noted that the opening to Beethoven's Fifth Symphony is only four notes and only two pitches, yet even so may be widely recognized).

Furthermore, larger numbers of strikers and/or a greater variety of striker lengths than are shown in FIG. 68 may be suitable for various embodiments, and may correspond to accordingly longer phrases and/or greater ranges of pitch. Thus, phrases of acoustic emissions may be almost indefinitely in length and/or range, facilitating the communication of large amounts of information (whether characteristic, encoded data, user-recognizable, some combination thereof, etc.). For example, considering again an arrangement of strikers as shown in FIG. 62, a cap with strikers at 15 degree spacings in a single loop could include up to 24 such strikers; for 2 possible pitches (e.g., striker lengths) the number of possible 24-pitch combinations may exceed 16,000,000. Given such large numbers of possible phrases, individual identification of containers by unique serial number may not be impractical. (It is further noted that other factors as have been mentioned, such as variation of the spacing between individual acoustic emissions, also may increase the number of possible variations, and/or facilitate communication of additional data, etc.)

Still with reference to FIG. 68, it is noted that maintaining an approximately consistent overall height for combinations of pedestals and strikers 6843A and 6841A, 6843B and 6841B, 6843C and 6841C, 6843D and 6841D, and 6843E and 6841E, the length of the strikers 6841A, 6841B, 6841C, 6841D, and 6841E and thus the pitch emitted therefrom may be varied while the bottom ends of the strikers 6841A, 6841B, 6841C, 6841D, and 6841E remain at approximately similar heights. In such fashion, a given anvil 6845 may engage strikers 6841A, 6841B, 6841C, 6841D, and 6841E of various heights. As a counterexample, if the relatively short striker 6841D were on a pedestal the same height as the relatively long pedestal 6843E, the lower end of the resulting striker may not reach to the anvil 6845 at all and thus may produce no acoustic emission. Thus maintaining similar overall heights may be useful for at least certain embodiments, e.g., so as to facilitate production of different pitches while still engaging an anvil of fixed height.

However, such an arrangement is an example only, and other arrangements may be suitable. For example, it may be suitable to dispose an anvil such that strikers do not engage at the lower end thereof. An anvil placed laterally (e.g., on the neck of a container similar to that shown in FIG. 62 rather than on the platform thereof as illustrated) may engage strikers at various heights.

In addition, even for an anvil of fixed height, it may be useful to vary the length of a combined pedestal and striker. As may be understood, a screw cap rises when being turned for removal from a container, and falls when being turned for reattachment to that container. Thus, the distance between the channel floor on which pedestals and strikers are disposed may increase as the cap is removed, and decrease as the cap is replaced. It may be suitable to gradually adjust the combined height of pedestals and pedestals throughout the circumference of an array thereof, so that the bottom end of each striker engages a given fixed anvil in a similar fashion. (Otherwise, the first striker may engage the anvil, but later strikers may pass above the anvil without engaging. For relatively short arrays of three to six strikers as shown in certain examples herein, such change in height may not be notable, but sufficiently long arrays, sufficiently steep thread pitches, etc. may exhibit such "missed strikes".)

Thus, while it may be useful in at least certain embodiments to maintain some degree of consistency in the height of the bottom ends of various strikers, absolute consistency is not required, and indeed deliberate and systematic variation in such height may be suitable in at least certain embodiments.

Figure 69:
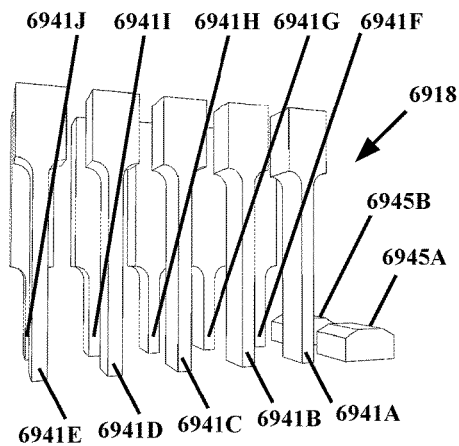

Now with reference to FIG. 69, an acoustic emitter 6918 is shown therein with two anvils 6945A and 6945B, the anvils 6945A and 6945B being disposed side-by-side. The emitter 6918 also includes two rows of five strikers emitters each (pedestals are no longer individually identified in FIG. 69 for simplicity): strikers 6941A, 6941B, 6941C, 6941D, and 6941E are aligned with anvil 6945A, while strikers 6941F, 6941G, 6941H, 6941I, and 6941J are aligned with anvil 6945B. As may be seen, the strikers 6941A, 6941B, 6941C, 6941D, and 6941E aligned with anvil 6945A are longer than the strikers 6941F, 6941G, 6941H, 6941I, and 6941J aligned with anvil 6945B, and thus may produce a lower pitch; however strikers 6941A, 6941B, 6941C, 6941D, and 6941E are of approximately equal length compared to one another, as are strikers 6941F, 6941G, 6941H, 6941I, and 6941J. Thus, if the strikers 6941A, 6941B, 6941C, 6941D, 6941E, 6941F, 6941G, 6941H, 6941I, and 6941J are moved to engage the anvils 6945A and 6945B a phrase of five similar two-pitch chords may be produced. In effect, the use of two rows of strikers 6941A, 6941B, 6941C, 6941D, and 6941E and 6941F, 6941G, 6941H, 6941I, and 6941J and two anvils 6945A and 6945B may produce acoustic emissions that are multiple both in parallel (e.g., two pitches at a time or two traces of pitches as shown in FIG. 69) and/or in series (five pitches in series for each trace). Such arrangements may enable very complex signals, e.g., signals that are highly characteristic, encode large amounts of data, etc.

Figure 70:
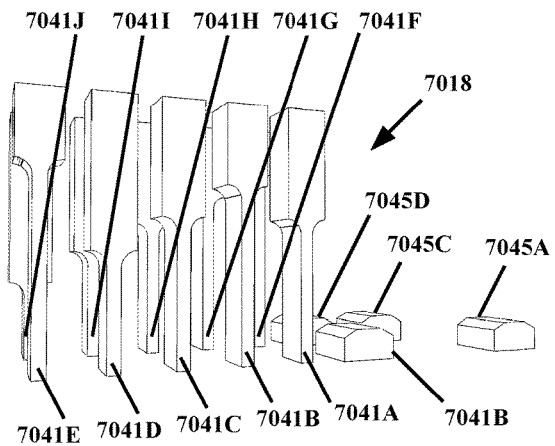

Furthermore, as shown in FIG. 70 other features also may be varied in order to produce still richer phrases of acoustic emissions. An acoustic emitter 7018 is shown therein, again with two traces of five strikers each: strikers 7041A, 7041B, 7041C, 7041D, and 7041E in one trace (closer to the viewer of the illustration, as presented) and strikers 7041F, 7041G, 7041H, 7041I, and 7041J in another trace (behind the first trace, as illustrated). The acoustic emitter 7018 also includes two traces of anvils: anvils 7045A and 7045B aligned with strikers 7041A, 7041B, 7041C, 7041D, and 7041E and anvils 7045C and 7045D aligned with strikers 7041F, 7041G, 7041H, 7041I, and 7041J. As may be seen, the strikers along each trace vary in length both within traces and between traces. Furthermore, the anvils also vary: the closer trace of anvils has anvil 7045A on the right, then a gap, then anvil 7045B on the left; whereas the more distant trace of anvils has an anvil 7045C aligned with the gap the closer trace of anvils, and also has an anvil 7045D aligned with anvil 7045B. Thus in FIG. 70 the spacing and position of anvils are varied, the pitches produced by the various strikers are varied, multiple traces may produce pitches at once, etc., at least potentially producing an extremely rich phrase of acoustic emissions. Indeed, as well as being almost arbitrarily long (as previously noted) phrases of acoustic emissions may be almost arbitrarily complex, with multiple traces of strikers, variations in striker height, multiple traces of anvils, etc. as shown. In addition other properties may vary even though not shown to vary in FIG. 70, such as striker spacing, anvil shape/size, etc. Other variations also may be suitable.

In addition, with reference to FIG. 70 as an example, another feature as may be facilitated through varying striker and/or anvil configurations (and/or other variations in acoustic emitters/acoustic emissions) may be noteworthy. As has been shown previously, anvils of a given acoustic emitter may be disposed on one physical entity (e.g., a container) while strikers of that acoustic emitter may be disposed on a different physical entity (e.g., a cap). Thus, combining different caps with a particular container, or different containers with a particular cap, may produce very different acoustic emissions. However, mathematically the two variables in question—the arrangement of strikers and the arrangement of anvils—still may be discernible. That is, it may be possible to distinguish whether a cap (with a particular array of strikers) may be characteristic even if applied to a different container, and/or vice versa. (Depending on the particulars, it may be necessary or at least useful to know one such arrangement when identifying another, e.g., to know the arrangement of strikers when evaluating an unknown arrangement of anvils.)

Such features may be useful. For example, each array may provide different information. A container may have anvils coding for the identity of the product therein (e.g., a given medication), while the cap packaged with that container may have strikers coding for the production date of the medication. Or, a container may have anvils relating to the product, but the cap may be 3D printed specifically for a given user, with an array of strikers specific to that user. Such arrangements may for example make it feasible to determine not only when a medication is taken (or some other product is opened, etc.) but also to verify acoustically which individual that medication belongs to. Such information may be useful in situations wherein many people may be taking medications (even the same medication), such as hospitals, nursing homes, etc. Even in a single-family setting, knowing whether a particular acoustic emission indicates that one person has taken their medication as opposed to another (e.g., if both persons are on such medication) may be of interest.

Additionally, it may be feasible to recognize that a user has engaged a cap with the wrong container. Whether mixing up caps may be significant in itself may depend on circumstances, however, detecting that such a mix-up has taken place may be considered as an indication that the user is having difficulty remembering which medication to take when, that someone has tampered with medication (e.g., a child has removed caps and replaced them incorrectly), etc., and/or may provide other information of note.

As an additional consideration, the complexity of data as may be enabled through various embodiments may be useful in addressing counterfeiting of medications and/or other products. While hard data regarding the rate of counterfeiting of products may be by nature difficult to obtain, counterfeit medication is at least alleged to be a significant risk in at least some markets. Regardless of frequency, the potential harm from counterfeit medication may be severe. Even if the "medication" is not in itself toxic or otherwise harmful, in taking a counterfeit a user is not taking the prescribed medication in the prescribed dose and form. As a more concrete example, while administering distilled water eye drops may not aggravate glaucoma, the lack of proper medication may allow the patient's condition to worsen (even if the patient is conscientiously and correctly taking what is believed to be the proper medication).

Thus, it may be useful in at least certain embodiments to validate enclosures, products therein and/or associated therewith, etc. through the use of acoustic emissions. At least certain aspects of validation may be at least somewhat similar to determining use (and/or other approaches as may be enabled herein). For example, acoustic emissions may be utilized in a similar fashion, e.g., being produced as an enclosure is opened, received by a station, etc. Indeed, in at least some embodiments similar or even identical hardware may be suitable for validation, such as a striker-and-anvil arrangement as previously shown and described herein.

However, it may be useful to distinguish validation of an enclosure/product from (for example) detection of use/dispensing of that enclosure product, at least conceptually. Detection may be summarized as an approach for answering the question: "Is a container being opened?" Producing, receiving, evaluating, etc. an acoustic emission as that container is opened thus may provide indication that the container in fact is being opened (and may enable inference that the contents of the container are being dispensed, used, etc.). By contrast, validation may be summarized as an approach for answering the question: "Is this enclosure 'the real thing'?" In such case it may be presumed that a container is being opened, and instead producing, receiving, evaluating, etc. an acoustic emission as that container is opened may provide indication as to whether the container (and/or the contents thereof) is genuine, e.g., that a given sample medication container presents a valid acoustic signature corresponding with known medication containers as manufactured by a reputable supplier (and/or so that it may be inferred that medication therein is genuine medication as produced by a reputable supplier, etc.).

It is noted that certain examples presented herein address the production of acoustic emissions specifically via physical interactions, e.g., strikers engaging anvils, adhesive beads separating from blankets/enclosures, filaments breaking, etc. It is emphasized that such physical interactions are examples only, and that other physical interactions also may be suitable. For example, resonating bells as may produce acoustic emissions when struck, shape-locking structures as may produce acoustic emissions upon engaging and/or disengaging, hook-and-loop tape or similar structures as may produce acoustic emissions as hooks engage/disengage loops, etc.

In addition, it is emphasized that acoustic emissions are not limited only to being produced via physical interaction. For example, as noted previously whistles and/or other pneumatic approaches also may produce suitable acoustic emissions. For example, with regard to producing non-uniform acoustic emissions (e.g., a sequence of different pitches) it may be suitable to configure a plunger within a hollow shaft, with tone holes disposed in one or both; as the plunger moves and the volume of air therein changes air is driven out through the holes producing tones, with air flowing through different holes at different times (e.g., by blocking/unblocking holes along the travel path of the plunger) and thus producing different tones at different times.

Also, at least certain acoustic properties such as resonance, pneumatic flow, etc. as may serve in producing acoustic emissions also may facilitate other functions. For example, for a container as may resonate in response to an acoustic emission (e.g., as strikers engage an anvil), such resonance may differ depending on what product is in the container and how much product remains therein. As a more concrete example, a nearly-empty container may produce acoustic emissions at least somewhat different from those produced by that same container when full; likewise a container with pills therein may produce acoustic emissions at least somewhat different from those produced by that same container with liquid therein.

For arrangements wherein such differences are substantial, it may be useful to accommodate such changes, for example by defining standards for recognizing acoustic emissions in a station in such manner that a container may be recognized whether full, half-full, nearly empty, etc. However, such changes also may be evaluated as indications regarding whether a container is full, half-full, etc. For example, if the acoustic emissions for a given container are known/anticipated to decrease in pitch as the container is emptied, detecting that decrease in pitch and/or tracking that decrease over time may facilitate determination of the amount of product present in the container. In such manner, acoustic emissions—even if nominally fixed by the geometry and composition of the emitters—may be analyzed to determine when a container is empty or nearly so, so as to facilitate automatic reordering of the product in question (e.g., renewing a prescription as part of registration of the acoustic emissions, etc.). Other interventions or actions than automatic reorder also may be suitable.

Figure 71:
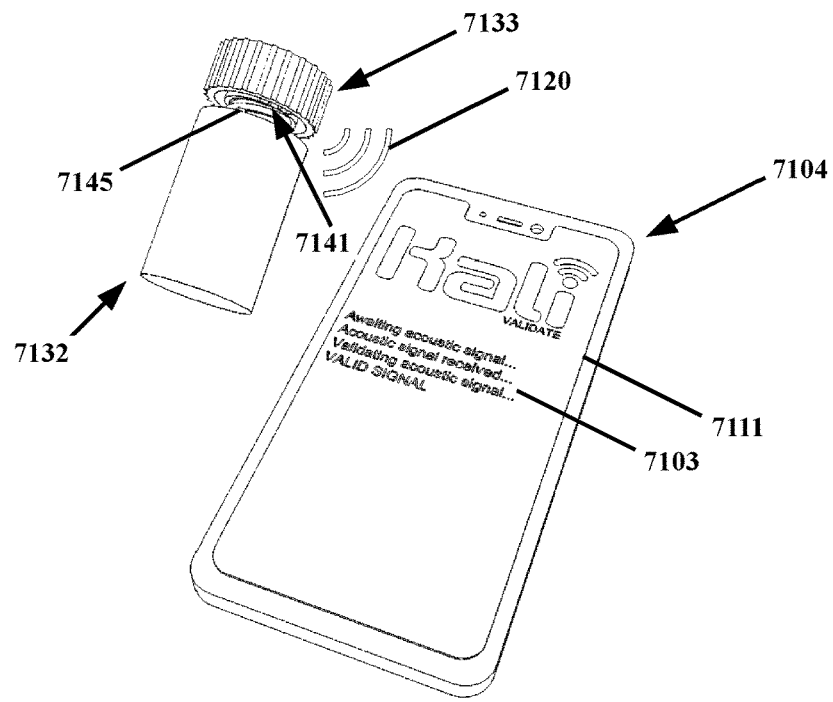
FIG. 71 and FIG. 72 depict example systems for validation via acoustic emissions, in perspective view.

Turning to FIG. 71, an example arrangement showing validation of a container through acoustic emissions therefrom is presented. Therein, a container 7132 with a cap 7133 is shown, as may be similar to certain previous arrangements already shown and described herein (e.g., FIG. 59 through FIG. 62). Portions of strikers 7141 and an anvil 7145 are visible (partially obstructed by the bodies of the cap 7133 and container 7132 respectively), and the cap 7133 is shown to be partially unscrewed from the container 7132. Consequently, the strikers 7141 and anvil 7145 (as may collectively be considered an acoustic emitter) as shown may produce an acoustic emission 7120.

As an aside, in certain previous examples strikers have been presented as flexible, e.g., so as to produce an acoustic emission each time a medication bottle is opened for tracking medication use. However, in particular though not exclusively for validation, frangible strikers also may be suitable for some embodiments. Typically once a container of medication (or other enclosure) is validated as genuine the container may not then spontaneously become counterfeit, thus a single validation and thus a single instance of producing acoustic emissions may be suitable. In addition, if the strikers (or some other portion of an acoustic emitter) are destroyed in producing acoustic emissions for validation, it may render the system less susceptible to reverse engineering of counterfeit containers using genuine containers as a model. In such case, once a container is opened the acoustic emitters may no longer be intact for convenient study and counterfeiting.

Still with reference to FIG. 71, a smart phone 7104 is shown (e.g., serving as a station) with a display 7111 thereon. As may be seen, a logo (not numbered) is shown as may indicate that the smart phone 7104 has been primed, e.g., that a validating app has been loaded, etc. In addition, as may be seen an output message 7103 is presented on the display 7111. The output message 7103 includes several statements, e.g., "Awaiting acoustic signal . . . " as may also indicate that the smart phone 7104 has been primed, "Acoustic signal received . . . " as may correspond with a step of receiving an acoustic emission 7120 within the smart phone 7104, and "Validating acoustic signal" as may correspond with a step of determining validity of an acoustic emission 7120 within the smart phone 7104. The output message 7103 as shown concludes with: "VALID SIGNAL". Such statement thus may refer to the container 7132 having been recognized as genuine, based on receipt and validation of the acoustic emission 7120 therefrom. (It is noted also that such presentation of an output message 7103 may constitute registration, as has been described previously herein.)

Thus, the arrangement in FIG. 71 may be understood to provide an example for successfully validating a container, and/or medication therein, etc.

As may be seen the container 7132 to be validated in FIG. 71 is depicted as being relatively close to the smart phone 7104. As has been noted previously herein, when determining whether a container has been opened is an aim (e.g., so as to track medication use), it may be suitable for such a container and/or emitter to be distal from a station. For example, such an arrangement may facilitate a "transparent" experience for users, in that no special action need be taken by users to prime a station, place a container near a station, etc. Rather, the user may simply use the medication, and the station (whether a smart phone in a pocket, a dedicated station plugged into a bathroom wall socket, etc.) may detect an acoustic emission and register an enclosure event. (Though such priming, placing containers in proximity, etc. also is not prohibited.)

However, for validation of a container (as opposed to determining various openings/uses thereof) different considerations may apply. While it is not necessarily required for a container 7132 to be close to a smart phone 7104 for validation as is shown in the example of FIG. 71 (any more than for detection), in at least certain embodiments it may be suitable for a container 7132 (and/or an acoustic emitter thereon) to be placed in proximity with the smart phone 7104 when validating the container 7132. As already noted, validation is not necessarily identical to detection, at least in that different questions may be under consideration. For example, in determining whether a container 7132 is valid (as opposed for example to being counterfeit), the user of that container (and/or medication, etc.) may be consciously asking a question, e.g., is this the real medication? Thus it may not offend transparency for a user to prime a smart phone 7104, place a container 7132 near the smart phone 7104, etc. so as to facilitate reception of (potentially complex/subtle) acoustic emissions; the user is already deliberately attempting to determine whether medication is valid. Further, when validating a container it may be that a user wishes to receive the results of validation, e.g., wants to see a message from the smart phone 7104 that a medication container 7132 is genuine. Thus the user may already be inclined to ready the smart phone 7104 so that results displayed therefrom may be readily seen. In addition, typically (though not necessarily) containers may be validated only once; where detecting use in a single instance may provide data only about that particular use, if a container is validated once it may be reasonable to presume that the container is valid indefinitely (e.g., a valid container may not spontaneously become counterfeit).

Thus, while the arrangement in FIG. 71 is not necessarily limiting, in practice in at least certain embodiments it may be that containers 7132 may in fact be disposed in proximity to smart phones 7104 (and/or other enclosures to other stations) as shown therein, that smart phones 7104 may be primed (e.g., a validation app thereon may be activated), etc.

Figure 72:
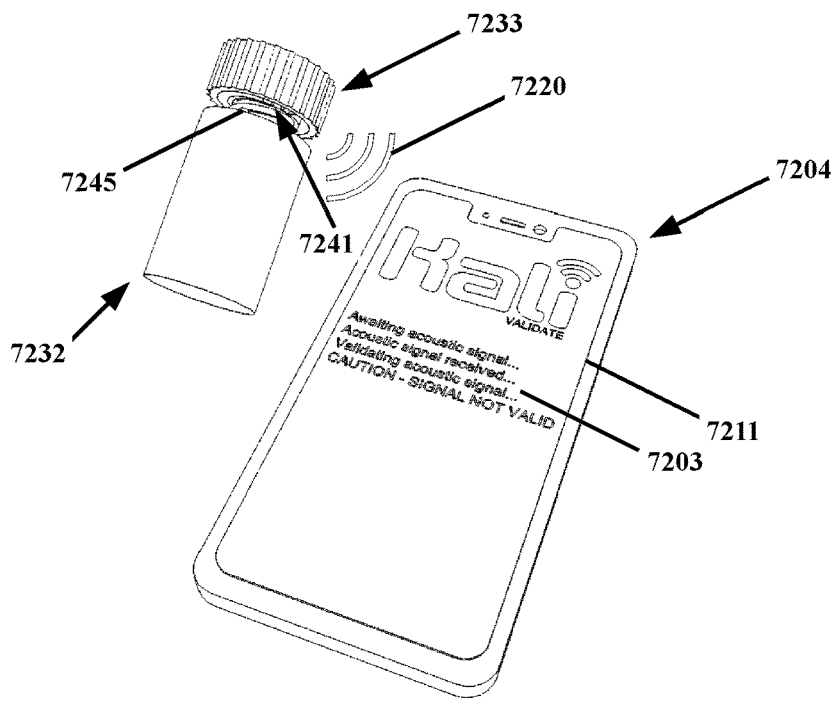

Now with reference to FIG. 72, another example arrangement is shown for validating a container through acoustic emissions therefrom. Therein a container 7232 with a cap 7233 is shown. Portions of strikers 7241 and an anvil 7245 visible and the cap 7233 partially unscrewed from the container 7232. The strikers 7141 and anvil 7145 (as may collectively be considered an acoustic emitter) may produce an acoustic emission 7220 as shown.

A smart phone 7204 is also shown with a display 7211 thereon. An output message 7203 is presented on the display 7211, at least somewhat similar to the output message in FIG. 71. However, in FIG. 72 the output message 7203 is shown to conclude with: "CAUTION—SIGNAL NOT VALID". Such a statement thus may refer to the container 7232 being determined as not genuine based on receipt and validation of the acoustic emission 7220 therefrom. (Such presentation of an output message 7203 again may constitute registration.) Thus, the arrangement in FIG. 72 may be understood to provide an example for invalidating a container, medication therein, etc.

It is noted that a variety of other output messages may be suitable, presenting a variety of other possible states and information. For example, an output message may be presented indicating errors, inconclusive results, etc., and/or may include information such as the date, time, location, etc. Output messages also may include follow-up information, whether static (e.g., a phone number as may be used to report an invalid container) or interactive (e.g., a question-and-answer interface for reporting the invalid result directly, ask for information regarding where the container was purchased, etc.). In addition, certain output messages may include implied but non-explicit information, e.g., the output message 7203 in FIG. 72 may include the possibility that the acoustic emission was inconclusive; thus the container 7232 may not necessarily be counterfeit, but validation was not successful.

Figure 73:
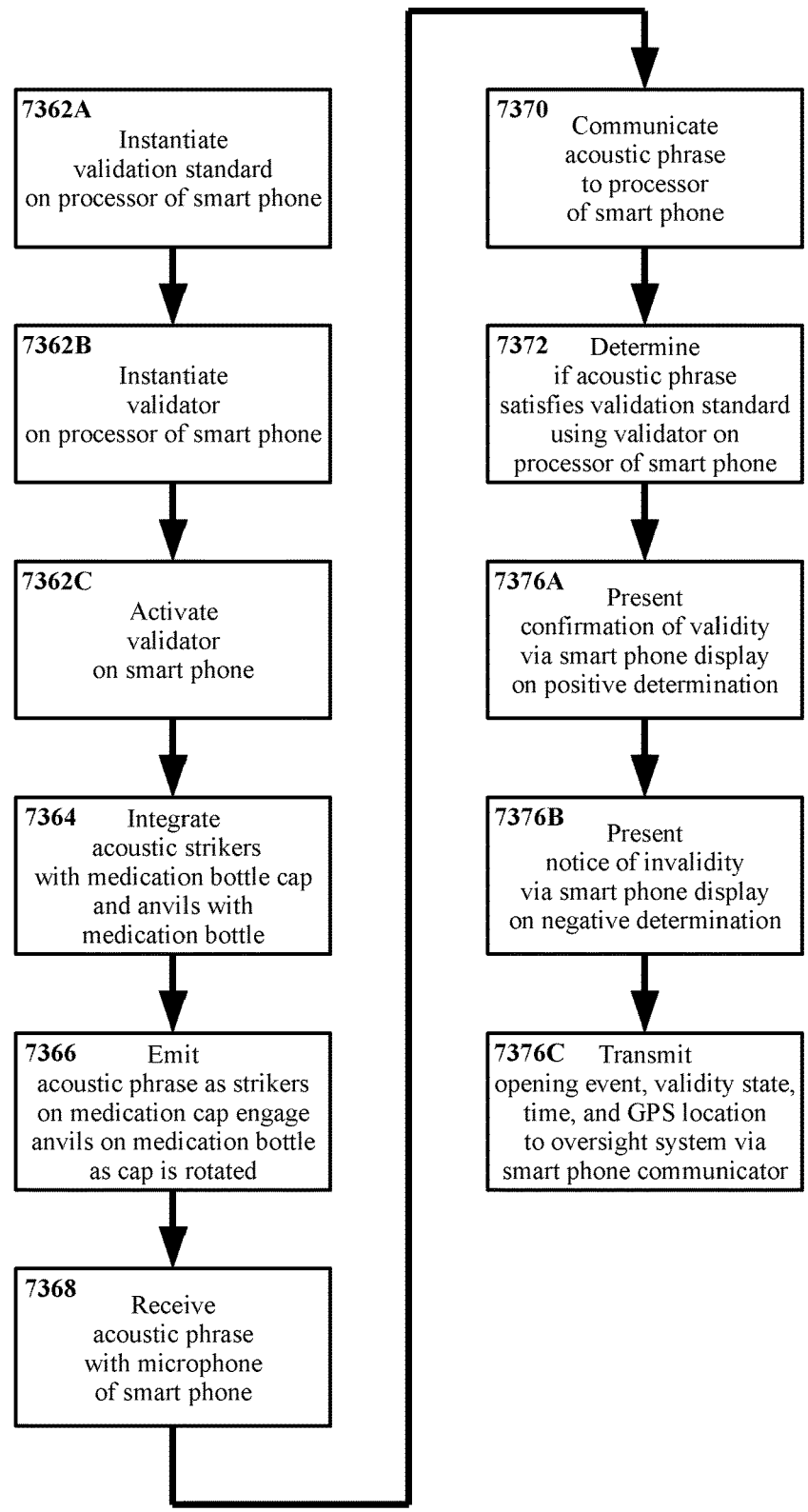
FIG. 73 depicts an example method for validation via acoustic emissions, with reference to a soda bottle, in flow chart form.

Now with reference to FIG. 73, an example method for validating a medication bottle is presented. For clarity the arrangement in FIG. 73 is presented in relatively concrete terms, e.g., a specific container, acoustic emitter structure, use of a smart phone as a station, etc. It is emphasized that this is an example only, and other arrangements may be suitable. Further, more general (though again not necessarily limiting) examples also are presented subsequently herein.

In FIG. 73, a validation standard is instantiated 7362A onto the processor of a smart phone. Typically though not necessarily, the validation standard may be a mathematical description of acoustic emissions as may be expected from a particular arrangement of acoustic strikers and anvils. For example, a validation standard may specify a series of eight "pops" exhibiting a given waveform typical of anvils and strikers of specific dimensions and materials, with each of those pops exhibiting a different frequency, the pops being received in a particular order. The complexity or simplicity of the validation standard is not limited. For example, at least in principle a validation standard may be as simple as a single "pop" (or other acoustic emission) with no other requirements as to frequency, waveform, etc. However it is noted that more complex validation standards typically may facilitate acoustic emissions that carry more data, and that larger amounts of data may facilitate greater resistance to counterfeiting.

For example, consider a series of 16 pops each selected from among 10 possible pitches, providing some 10 quadrillion potential combinations. Such an arrangement may be understood as conceptually similar to a 16 digit decimal number. Even if each instance (e.g., a bottle of medication) produces a unique series and 1 billion authentic instances exist (e.g., 1 billion bottles are sold), the chances that a given counterfeit series would match an authentic series may be expected to be on the order of one in 10 million. Thus, even if a counterfeiter is aware that acoustic emissions for a given product utilize a 16-pop acoustic phrase with 10 possible pitches, it may be extremely unlikely that a randomly chosen acoustic phrase would be authentic.

In addition, such an example may illuminate an additional dimension as may be present in at least some validation standards, namely that some discrimination may be present as to distinguish valid from counterfeit acoustic emissions. To continue the example above, if those 1 billion authentic acoustic phrases are selected using a mathematical algorithm, then the validation standard may include the algorithm itself, so as to facilitate determining whether a given unknown acoustic phrase corresponds with the output of that algorithm. Alternately, certain mathematical algorithms may produce acoustic phrases that may be recognizable (e.g., mathematically) as being produced by an algorithm, without requiring the original algorithm for such recognition. Given such an arrangement the originating algorithm may not be required by the validation standard (in which case, "hacking" the validation standard may not reveal the algorithm for defining valid acoustic phrases).

However, other arrangements, including but not limited to a validation standard that is or includes a predetermined list of valid and/or invalid acoustic phrases, also may be suitable. Some combination also may be suitable; mathematical descriptions of what may be expected from acoustic phrases produced through an originating algorithm may be present to address incoming acoustic phrases generally, while specific acoustic phrases known to have been used as counterfeits (even if matching what would be produced by the originating algorithm) may be present and tagged as invalid. The particulars of mathematical analysis, security, cryptography, etc. are not limited in regard to validation as described herein, and may vary considerably among embodiments. Likewise, the structure, form, etc. of the validation standard overall also is not limited.

In addition, it is noted that validation may be based on a variety of factors. In certain examples herein striker-and-anvil arrangements are shown wherein strikers of different effective lengths may produce different pitches when interacting with a given anvil. For such an arrangement, it may be suitable to consider whether an acoustic phrase exhibits the correct pitches in the correct order for determining validity. However, other acoustic features, including features as may not be readily apparent, also may be considered. For example, by varying the effective length of the strikers it may be possible not only to encode different recognizable pitches into an acoustic phrase, e.g., C, C#, etc., but also to encode variations in those pitches.

For example, in an arrangement where the individual pitches are nominally tones on a musical scale, it may be suitable to make certain tones slightly off-pitch, so that certain pitches may be sharp, others flat, still others on-key. Given such an arrangement, validation may be indicated not by the nominal pitches (or at least not only by the nominal pitches) but by whether each pitch in sequence may be sharp, on-key, or flat. A sequence of six tones thus may be nominally A-B-C-D-E-F, with those tones being slightly sharp, sharp, on-key, flat, on-key, and flat respectively. Thus validity may be defined by the sequence of sharp/on-key/flat (in this particular example, a six-place code with three options for each place, representing 729 possible combinations); the nominal pitches may affect validity, or may be entirely irrelevant. Use of other concealed acoustic (or non-acoustic) features also may be suitable, such as variations in waveform, relative spacing between pitches, etc.

Such "concealed" encoding (as also may be referred to as a form of steganography) may be useful, for example in resisting counterfeiting. A counterfeit container may produce the correct nominal pitches, but be detectable in not exhibiting the correct series of sharp/on-key/flat alterations to those nominal pitches. Small alterations may be identifiable for validation, even if not readily detectable by a typical listener. In such manner, counterfeiters may be duped into attempting to counterfeit the wrong properties.

It is noted that validation as described herein may not be, and may not be required to be, perfect or impossible to overcome. While a perfectly uncounterfeitable measure may on some level be considered ideal, in practice even imperfect measures may be useful. Increasing the effort required to produce viable counterfeits, and/or decreasing the likelihood that counterfeits may be accepted as authentic, may be useful in opposing counterfeiting even if such measures are less than 100% effective. Further, it is noted that multiple measures as may be overcome individually may be used in conjunction, in a sort of "layered defense" wherein successful counterfeiting would require defeating two or more individual systems (e.g., some combination of acoustic validation of the container, acoustic validation of the exterior packaging, characteristic appearances of containers, labels, packaging, etc., holographic seals, and so forth). Thus, for at least certain embodiments acoustic validation may be useful even if a particular instance thereof in itself may not present a particularly high bar to counterfeiting.

Still with reference to FIG. 73, a validator is instantiated 7362B onto the processor of the smart phone. Typically though not necessarily, the validator may take the form of executable instructions for determining whether a given acoustic phrase as is received satisfies the validation standard. Thus, the particulars of the validator may depend at least in part on the validation standard. For example, if a validation standard may take the form of a required mathematical outcome when processing a received acoustic phrase with some recognition algorithm, (similar to an example given above) the validator then may include the recognition algorithm, along with such executable instructions as may be needed to cause the processor to carry out a mathematical analysis of acoustic phrases using that recognition algorithm. However, as with the validation standard, the validator may vary considerably and is not limited.

Who carries out steps 7362A and 7362B may vary. For example, a smart phone may be sold with a validation standard and validator already instantiated thereon, e.g., as a standard app, integrated with an OS, etc. In such case a smart phone manufacturer may carry out such steps. Alternately, a user might download and install 7362A and 7362B a validation standard and validator on the smart phone, so that instantiation 7362A and 7362B at least arguably may be performed by the user.

In at least certain instances, the validation standard and validator may be instantiated 7362A and 7362B together rather than as two distinct steps. For example, a smart phone app may include both data that serves as a validation standard and executable instructions that cause a processor to carry out the functions of a validator, with the app being loaded onto the processor as an integral assembly rather than as two distinct parts (e.g., validation standard and validator). Such combination of elements and/or steps is not required, but also is not excluded.

Moving on in FIG. 73, the validator 7362C is activated on the smart phone. For example, a user who wishes to know whether a medication bottle is valid or counterfeit may run an app on the smart phone with a validator and a validation standard therein. In principle it may be equivalent to refer to activating the validation standard, but for simplicity a single step for such is presented herein. In addition, not all embodiments necessarily must have a distinct step of activating 7362C the validator. For example, a smart phone processor may load a validation standard and run a validator as a background process. However, given that validating medication may be a relatively uncommon event, e.g., once a month as a new prescription refill is obtained, dedicating resources to constant validation monitoring may not be efficient for all embodiments (and is not required).

Also in FIG. 73, acoustic strikers are integrated 7364 with the cap of a medication bottle, and anvils are integrated 7364 with the medication bottle proper. Typically such integration may be performed as a manufacturing step, e.g., when producing the cap and bottle. Thus although step 7364 is shown after steps 7362A, 7362B, and 7362C, chronologically steps 7362A, 7362B, and 7362C may be performed after the strikers and anvil are integrated 7364 into the cap and bottle respectively. Such variations in ordering are not excluded (though also not required).

An acoustic phrase is emitted 7366 as the cap is rotated, due to the strikers engaging the anvils. For example, the user of the smart phone may unscrew the cap of the medication bottle in proximity to the smart phone, such that the acoustic phrase is emitted 7366 as a consequence of opening the bottle.

The acoustic phrase is received 7368 with the microphone of the smart phone. The acoustic phrase is communicated 7370 to the processor of the smart phone. A determination is made 7372 in the smart phone processor as to whether the acoustic phrase satisfies the validation standard. The particulars of the determination 7372 may vary considerably, and may depend to at least some extent on the validation standard and/or validator. For example, given a validation standard that considers a sequence of pitches the determination 7372 may address whether the correct pitches are present in the correct order, while a validation standard that considers whether pitches are sharp, on-key, or flat may address whether such pitches as are received exhibit the correct series of sharp, on-key, and flat deviations from nominal.

In addition, it is noted that the determination 7372 may not be absolute in all embodiments. For example, a determination 7372 may be carried out in such fashion as to accommodate some degree of error. As a more concrete example, for a 16-pitch acoustic phrase the determination 7372 may accommodate instances wherein one pitch is missing, e.g., because a striker has been damaged, was malformed in manufacturing, etc. Accommodations also may be made in anticipation of differences in how different users may cause an acoustic phrase to be produced, e.g., applying great force in unscrewing the cap of a medication bottle may produce some difference in the acoustic properties of strikers and anvils thereon as compared to unscrewing that cap more gently. Similarly, validation determination 7372 may accommodate deviations in nominal pitch as may be expected to due variations in environmental conditions e.g., if the strikers may exhibit different acoustic properties at different temperatures. (Such accommodations also may be carried out in defining the validation standard, etc.)

Continuing in FIG. 73, upon a positive determination in 7372—that is, the acoustic emissions are determined 7372 to be valid—a confirmation of validity is presented 7376A via the smart phone display. For example, a text message (as shown in FIG. 71) may be presented, though other indications including but not limited to graphical icons, images, videos, animations, etc. may be suitable. Upon a negative determination in 7372—that is, the acoustic emissions are determined 7372 to be invalid (or at least are not confirmed with confidence as being valid)—a notice of invalidity is presented 7376B via the smart phone display. For example, a text message (as shown in FIG. 72) may be presented, though again other indications including but not limited to graphical icons, images, videos, animations, etc. may be suitable.

Further in the example of FIG. 73, regardless of whether the validity determination 7372 was positive or negative, the opening event (e.g., the fact that the medication container has been detected as being opened/tested for validity), the state of validity for the container (positive or negative), the time of the opening event, and the GPS location of the opening event are transmitted 7376C to an oversight system via the communicator of the smart phone. In such manner information regarding validity may be logged, processed to discern patterns (e.g., an unusually high ratio of invalid to valid medication containers proximate some geographical region, as may indicate a possible location at which counterfeit medication is being sold), reported to various authorities (such as the FDA or similar), made available to the public (e.g., so as to inform users of that medication of a high number of counterfeits detected in a given area), etc.

As noted, the arrangement in FIG. 73 is an example only, presented in relatively concrete form for purposes of explanation. Moving on to FIG. 74, a less concrete (though still not necessarily limiting) arrangement is presented for validating an emitter.

Figure 74:
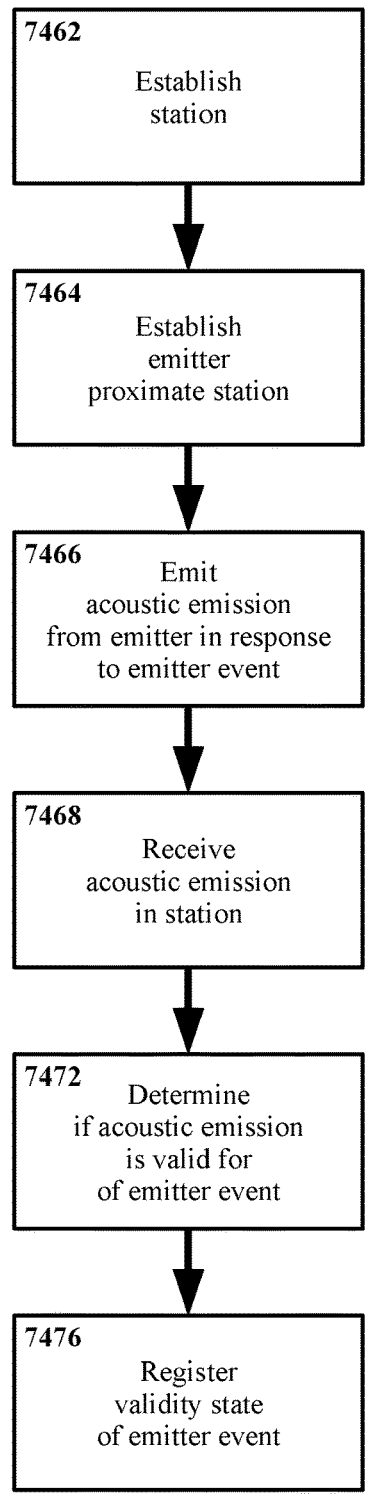
FIG. 74 depicts an example method for validation via acoustic emissions, in flow chart form.

In the arrangement of FIG. 74, a station is established 7462. For example, as in FIG. 73 a station may be a smart phone or an app running thereon, although other stations may be suitable including but not limited to a dedicated device, a smart speaker (e.g., as may support a virtual assistant), etc.

An emitter is established 7464 in the proximity of the station. Such an emitter may for example be a striker-and-anvil arrangement of a screw-cap container, but emitters may take many other forms (certain examples of which have already been described elsewhere herein). As noted with regard to FIG. 73, in practice emitters may be established 7464 before or after stations, and/or by entities other than the user. In addition, while the arrangement in FIG. 74 refers to establishing 7464 the emitter proximate the station, the degree of proximity as may be suitable may vary from one embodiment to another. For certain embodiments it may be suitable for an emitter to be placed in physical contact with the station, or very nearly so, while for other embodiments it may be suitable for an emitter to simply be within the same room as the station, etc.

Continuing in FIG. 74, an acoustic emission is emitted 7466 from the emitter in response to some emitter event, typically though not necessarily opening a container or other enclosure. The acoustic emission is received 7468 in the station, and a determination is made 7472 as to whether the acoustic emission is valid for the emitter event in question (e.g., through comparing the acoustic emission to some validation standard with a validator, though other arrangements may be suitable).

The validity state of the emitter event is registered 7476, as determined in step 7472. As noted previously, registration 7476 may vary, and may include but is not limited to displaying the validity state (e.g., valid, invalid, indeterminate), communicating the validity state to some external party, storing the validity state, etc. Likewise, registration 7476 may include information other than the validity state, including but not limited to the time, location, identity of the user conducting validation, etc. In some embodiments only invalid emitter events may be registered 7476 (e.g., reporting counterfeit containers but treating valid containers as presumed), only invalid events, some mix of valid, invalid, and/or indeterminate events (and/or other potential states), and so forth.

Figure 75:
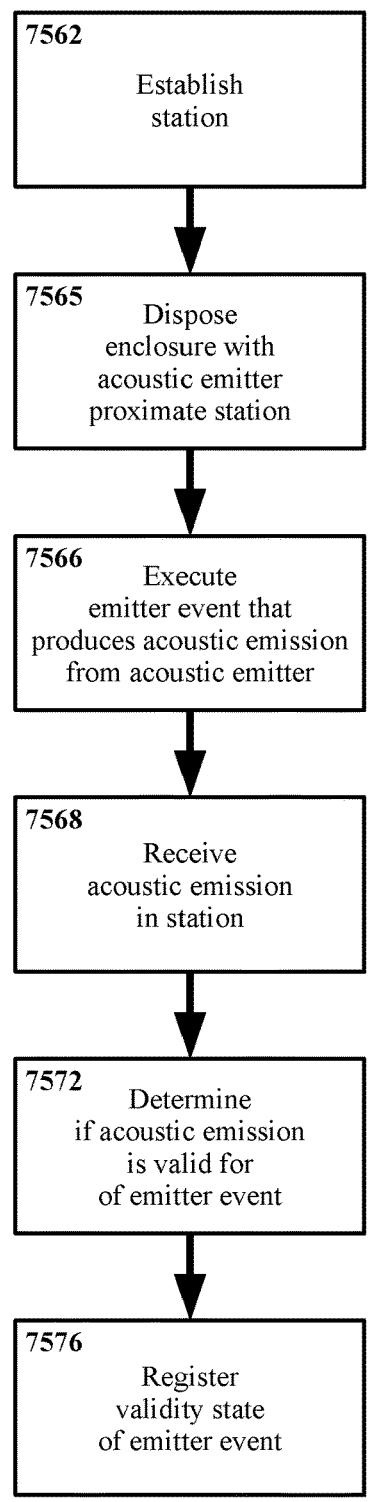
FIG. 75 depicts an example method for validation via acoustic emissions from a perspective of a subject determining validity, in flow chart form.

Turning to FIG. 75, as noted certain previous examples have addressed a method as may consider events both for an end user attempting validation and a provider of certain systems, such as the container, the station (and/or validation standard and validator thereon, etc.), and so forth. In FIG. 75 an example method for determining validity is presented as may be from the perspective of the subject determining validity, e.g., a medication consumer who has purchased medication and seeks to know whether the medication therein is counterfeit or not.

In FIG. 75, a station is established 7562. For example, a user may purchase a dedicated station, may instantiate executable instructions onto an existing smart phone, smart speaker, desktop computer, etc., or similar. An enclosure is disposed 7565 proximate that station. For example, the user may purchase a container of medication, then position the medication container adjacent a smart phone serving as a station, so as to facilitate detection by that station of an acoustic emission as may be produced from the container. (It may be suitable to consider purchasing a container with suitable emitters to be encompassed within a notion of establishing that container. Indeed, it is not prohibited for a user to be involved in fabricating a container, e.g., a factory worker may validate a container that he or she produced themselves (though the worker may or may not know this). However, for explanatory purposes in FIG. 75 the user may be considered as merely acquiring the emitter already engaged with a container.)

An event is executed 7566 that produces an acoustic emission from the acoustic emitter. For example, a user may unscrew a screw cap from a container having strikers and anvils, such that in unscrewing the cap the strikers and anvils produce a series of pitches. In such instance the emitter event may be considered to be unscrewing the cap (though "opening the container", "engaging strikers with anvils", etc. also may be considered). Thus unscrewing the cap produces the acoustic emission.

The acoustic emission is received 7568 in the station. A determination is made 7572 as to whether the acoustic emission is valid for the emitter event in question. For example, does the series of pitches exhibit a pattern as may be produced by a particular algorithm utilized by the legitimate manufacturer to define the striker geometry, suggesting that the container is authentic? With the validity state determined 7572, the validity state is registered 7576 for the emitter event. For example, a smart phone may display (or present audibly, etc.) that the container is valid or invalid, may store the validity, communicate the validity to an oversight system, etc.

It is noted that while FIG. 75 addresses a method from a user perspective, the user may not personally carry out all aspects of all steps, e.g., a smart phone may carry out the determination 7572 with at least some degree of autonomy, may register 7576 the validity state likewise, etc. However, in the example shown the user is considered to be deliberately attempting validation, and thus the station carrying out tasks in the service of the user and/or having been provided 7562 by the user may be considered in at least some sense as being a user action at least with regard to FIG. 75.

Figure 76:
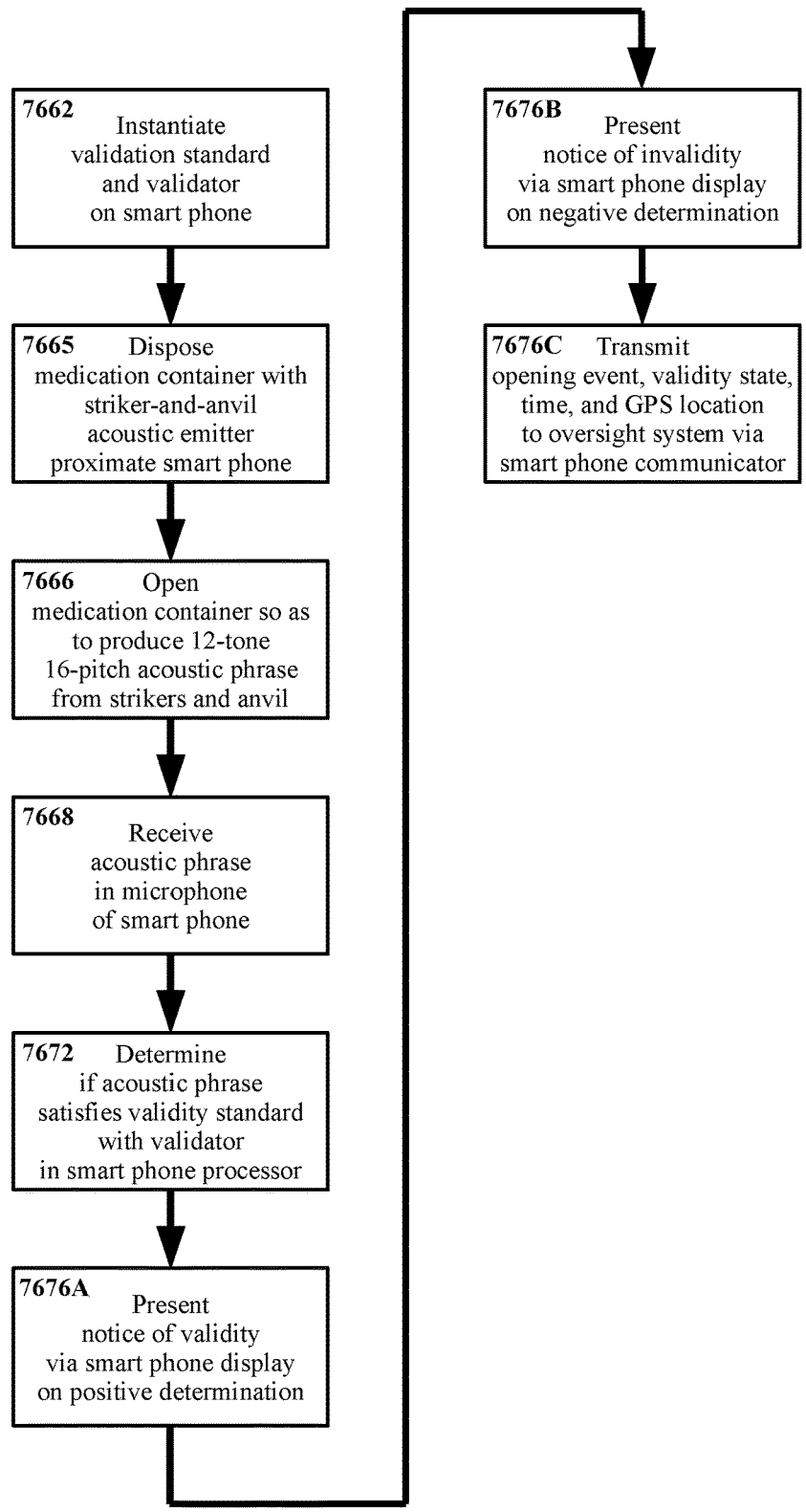
FIG. 76 depicts an example method for validation via acoustic emissions from a perspective of a subject determining validity, with reference to a medication container and smart phone, in flow chart form.

Moving on to FIG. 76, another relatively concrete example is presented at least somewhat similar overall to the arrangement in FIG. 75, but specific to a smart phone, striker-and-anvil medication container, etc.

In the arrangement of FIG. 76, a validation standard and validator are instantiated 7662 onto a smart phone. For example, a user may load suitable data and/or executable instructions as an app onto the smart phone, etc. A medication container with a striker-and-anvil acoustic emitter is disposed 7665 proximate the smart phone, e.g., the user may hold the container adjacent the smart phone. The medication container is opened 7666 so as to produce an acoustic phrase of 16 sequential pitches selected from 12 tones (e.g., a full 12-tone octave) from the strikers and anvil. For example, in an arrangement wherein the strikers are disposed partially circumscribing a screw cap and an anvil may be disposed on a shoulder of the container proper, unscrewing the cap to open the container may cause the strikers to engage the anvil in sequence.

The acoustic phrase is received 7668 in the microphone of the smart phone. (Communication of the acoustic phrase from the microphone to the processor of the smart phone is not explicitly shown in FIG. 76; certain steps likewise may be understood as implicit in at least certain examples herein.) A determination is made 7672 by the validator on the processor of the smart phone as to whether the acoustic phrase satisfies the validity standard. For example, do the 16 sequential pitches received 7668 exhibit an arrangement of tones as corresponds with that sequence of 16 pitches having been generated by an algorithm used to determine striker height when manufacturing authentic containers? Alternately, do the 16 sequential pitches exhibit a suitable arrangement of sharp, on-key, and flat states with respect to the nominal tones thereof?

For positive determinations of validity (in step 7672), a notice of validity is presented 7676A via the smart phone display; for negative determinations of validity, a notice of invalidity is presented 7676B via the smart phone display. In addition the event of the medication container having been opened, the validity state based on the acoustic phrase, the time at which validation was determined (or the acoustic phrase was received, etc.), and the GPS location (e.g., of the phone, though given a container proximate the smart phone the location of the container may be inferred or determined in addition or instead) are transmitted via the smart phone communicator (e.g., using a text message sent through a cellular network) to an oversight system.

Figure 77:
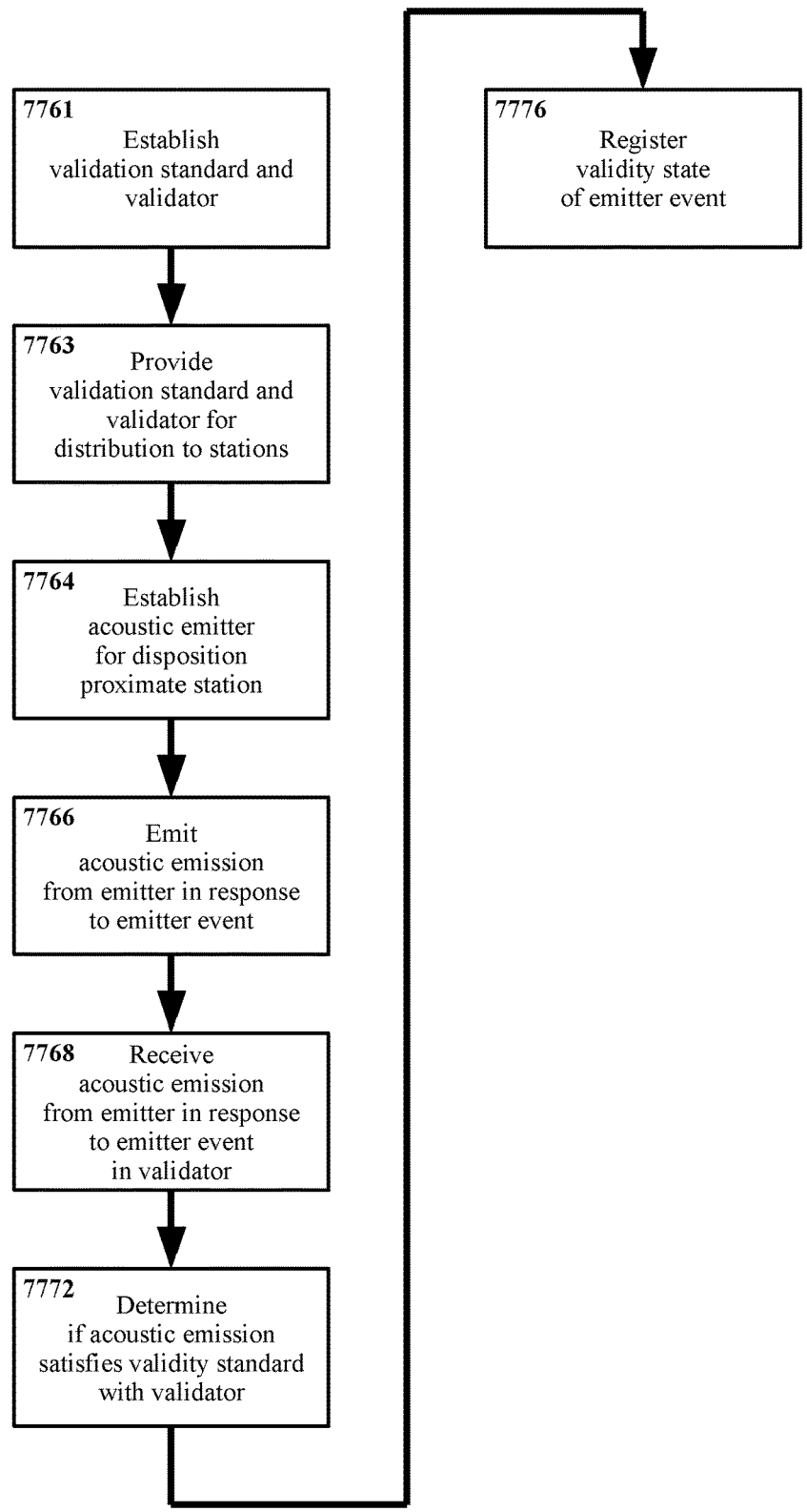
FIG. 77 depicts an example method for validation via acoustic emissions from a perspective of an authority supporting validation, in flow chart form.

Turning to FIG. 77, an example method for determining validity is presented as may be viewed from the perspective of some authority providing, enabling and/or supporting validation, e.g., a medication manufacturer so as to support consumer confidence in a medication, a software provider so as to facilitate consumer awareness regarding counterfeit medications, etc. As noted with regard to FIG. 75, no single party necessarily may be required to carry out all aspects of all steps, e.g., a software provider may not manufacture containers with acoustic emitters. Nevertheless, such tasks may be viewed overall as in at least some sense being validation provider actions at least with regard to FIG. 77.

In FIG. 77, a validation standard and validator are established 7761. For example, data entities (data, executable instructions, etc.) as may serve functions of a validation standard and validator may be encoded, etc. The validation standard and validator are provided 7763 for distribution to stations. For example, the aforementioned data entities may be provided for download from a web site or other source. It is noted that the arrangements in events 7761 and 7763 may differ from arrangements in certain previous examples. For example, in FIG. 76 a validation standard and validator as may already exist are instantiated onto a smart phone for (possibly by) a user to perform validations therewith. However, event 7761 in FIG. 77 may refer to the creation of the validation standard and validator proper, e.g., to the coding of the data entities as may carry out the necessary functions. As noted, the arrangements in FIG. 77 address a method from the point of view of a provider; where a provider may for example code an application and/or distribute the application, that provider may not necessarily download that application onto a smart phone, prepare the smart phone for use, etc. (Similarly, for a dedicated station a provider may manufacture physical hardware, offer that hardware to users, etc.)

Continuing in FIG. 77, an acoustic emitter is established 7764 for disposition proximate a suitable station. For example, a manufacturer may injection mold containers with acoustic emitters integrated therewith, some party may apply acoustic emitters as a retrofit to existing containers, etc. (It is noted that multiple providers may be involved in certain embodiments. For example, a smart phone app serving functions of a validator and validation standard as referenced in events 7761 and 7763 may be provided by a different party than manufactures medication containers as referenced in event 7764. It is not required that all such actions be carried out for example by a single individual.)

An acoustic emission is emitted 7766 from the emitter in response to an emitter event. For example, in the event of opening a container, an acoustic emitter engaged therewith may produce an acoustic emission in response to that container being opened. (It is noted that it may be reasonable to consider two or more parties as being responsible for a given phenomenon. For example, from the point of view of a user the acoustic emission may be considered as being provided by the user, e.g., because the user is the one opening the container and thus driving the creation of the acoustic emission therefrom. Alternately, from the point of view of a provider the acoustic emission may be considered as being provided by the provider, e.g., because the provider is the one that manufactured a container with an acoustic emitter that produces an acoustic emission when the container is opened. Thus, certain similar steps may appear in examples from both a user point of view and a provider point of view. A precise philosophical consideration of "who is responsible for what" may prove to be obfuscating rather than illuminating with regard to understanding the structure and function of various embodiments, and so is not presented herein. However, it is noted that at least certain steps may not be limited to being performed by certain parties, and that examples shown herein where certain parties perform certain steps are not limiting.)

Continuing in FIG. 77, the acoustic emission is received 7768 in the validator. For example, a validator instantiated on a processor may receive the acoustic emission as data from a microphone in communication therewith, or a validator in the form of dedicated device may receive the acoustic emission in hardware, etc. A determination is made 7772 with the validator as to whether the acoustic emission satisfies the validity standard. The validity state—valid/invalid/indeterminate (or genuine/counterfeit, etc.)—is registered 7776, for example by the validator (whether a data entity, hardware, etc.).

Figure 78:
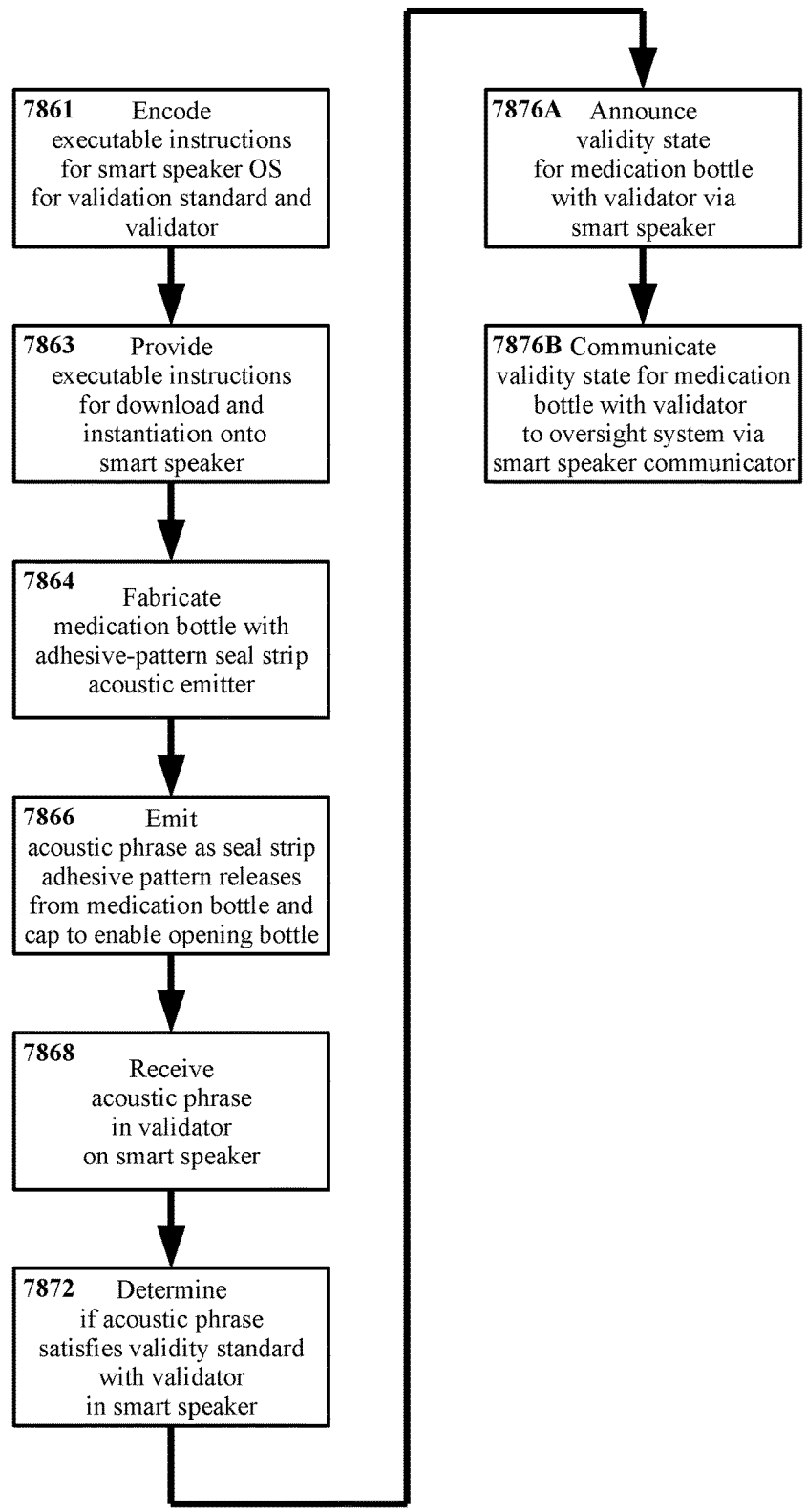
FIG. 78 depicts an example method for validation via acoustic emissions from a perspective of an authority supporting validation, with reference to a medication bottle and smart speaker, in flow chart form.

Moving on to FIG. 78, an arrangement at least somewhat similar to that in FIG. 77 but somewhat more concrete is shown, being specific to a smart speaker serving as a station and a strip with patterned adhesive thereon serving to seal a medication bottle and cap thereof.

Executable instructions are encoded 7861 for execution within a smart speaker operating system, such that the executable instructions are adapted serve functions of a validator and validation standard. The executable instructions are provided 7863 for download and instantiation onto smart speakers, for example by end users.

A medication bottle is fabricated 7864 with an adhesive pattern seal strip (e.g., as may be similar to arrangements shown in FIG. 51 through FIG. 53). Such a seal strip for example may be wrapped around a container and screw cap, such that the container may be opened after the seal strip is peeled away. An acoustic phrase is emitted 7866 as the adhesive pattern on the seal strip releases from the medication container and cap (e.g., individual dots of various sizes and/or compositions producing individual "pop" sounds as the seal strip is peeled away, with the array of adhesive dots producing an acoustic phrase suitable for enabling validation), enabling the container to be opened.

The acoustic phrase is received 7868 in the validator as instantiated on a smart speaker (e.g., having been so instantiated by a user). A determination is made 7872 with the validator on the smart speaker as to whether the acoustic phrase satisfies the validity standard. The validity state is announced 7876A for the medication container via the smart speaker. For example, a synthetic or pre-recorded message may announce "validation successful" for instances wherein the acoustic phrase satisfies the validation standard, or "caution—container could not be validated" for instances wherein the acoustic phrase does not satisfy the validation standard.

In addition, the validity state (valid, invalid, indeterminate, etc.) is communicated 7876B to an oversight system via the smart speaker communicator. As noted in certain previous examples, information so communicated may also include the time, location, medication name, user ID, a recording of the acoustic emission itself and/or data regarding the acoustic properties of the emission, etc.

Figure 79:
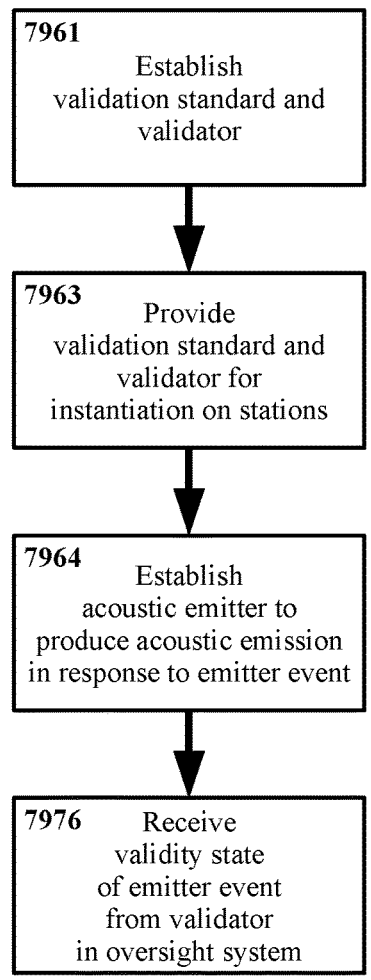
FIG. 79 depicts an example method for validation via acoustic emissions from a perspective of an oversight system, in flow chart form.

Turning to FIG. 79, an example method is shown from another perspective, that of an oversight system and/or operator thereof. For example, while a user may use a medication and/or determine whether a container is valid, and a provider may provide a validation standard, validator, acoustic emitter, etc., an oversight system may for example provide oversight regarding validity once validity is determined. Rather than inquiring as to the validity of a container or confirming the validity of that container, an oversight system may evaluate validity states, e.g., how many containers have been determined to be valid or invalid, in what areas, over what time period, etc. In some sense an oversight system may be considered to address validation on a collective scale, rather than necessarily the validity of a single instance of emitter, container, enclosure, etc. (However, it may be that at least certain actions relating to an oversight system may duplicate or be the same as actions relating to providing validation, etc. For example, while validation oversight may not inherently or necessarily include creating a validation standard, a validation standard may be relevant in addressing information on validation states, and thus in some sense may be considered relevant to, if not necessarily part of, oversight.)

In FIG. 79, a validation standard and validator are established 7961. The validation standard and validator are provided 7963 for instantiation onto a station. An acoustic emitter is established 7964 adapted to produce acoustic emissions in response to some emitter event. In addition, a validity state for the enclosure is received 7976 from the validator in the oversight system.

It is noted that additional events may take place utilizing validation state information after receipt 7976 in the oversight system. The precise nature of those oversight events is not limited, and may vary considerably. More regarding validation oversight is described subsequently herein. In addition, it is noted that certain steps as may take place—for example, the emitting of an acoustic emission—are not shown in FIG. 79. Such steps may be assumed, e.g., if a validity state is received then something (such as an acoustic emission) presumably has been determined to be valid or invalid. However, validation oversight in itself does not necessarily concern the process of determining validity per se; so long as it is made possible to determine validity (so that validation states are available to be considered), the particulars of validation is not limiting.

Figure 80:
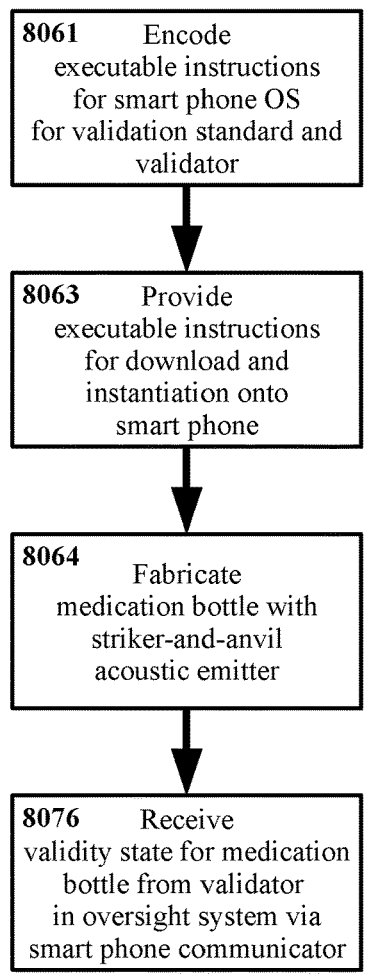
FIG. 80 depicts an example method for validation via acoustic emissions from a perspective of an oversight system, with reference to a smart phone and medication bottle, in flow chart form.

Turning now to FIG. 80, an arrangement at least somewhat similar to that in FIG. 79 but somewhat more concrete is shown, being specific to use of a smart phone as a station and a striker-and-anvil acoustic emitter on a medication container. In FIG. 80, a validation standard and validator are encoded 8061 as executable instructions adapted to be instantiated onto the processor of a smart phone. The validation standard and validator are provided 8063 for download and instantiation onto a smart phone. A medication container is fabricated 8064 with a striker-and-anvil arrangement, so as to be adapted to produce acoustic emissions in response to the cap of the container being unscrewed (thus engaging the strikers with the anvil). In addition, a validity state for the enclosure is received 8076 from the validator in the oversight system, via the smart phone communicator.

Figure 81:
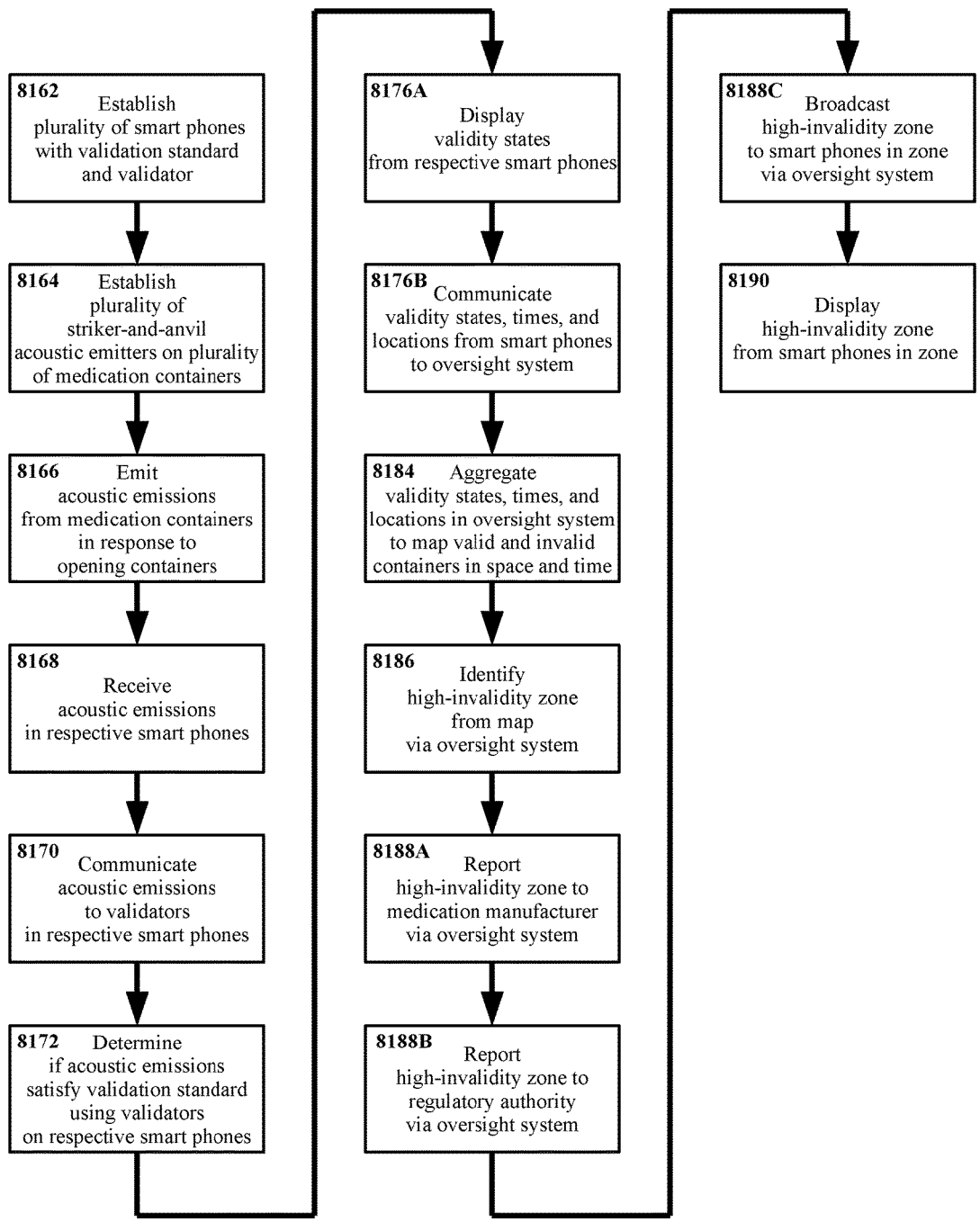
FIG. 81 depicts an example method for validation via acoustic emissions including aggregation and interpretation via an oversight system, with reference to a smart phone and medication container, in flow chart form.
Figure 82:
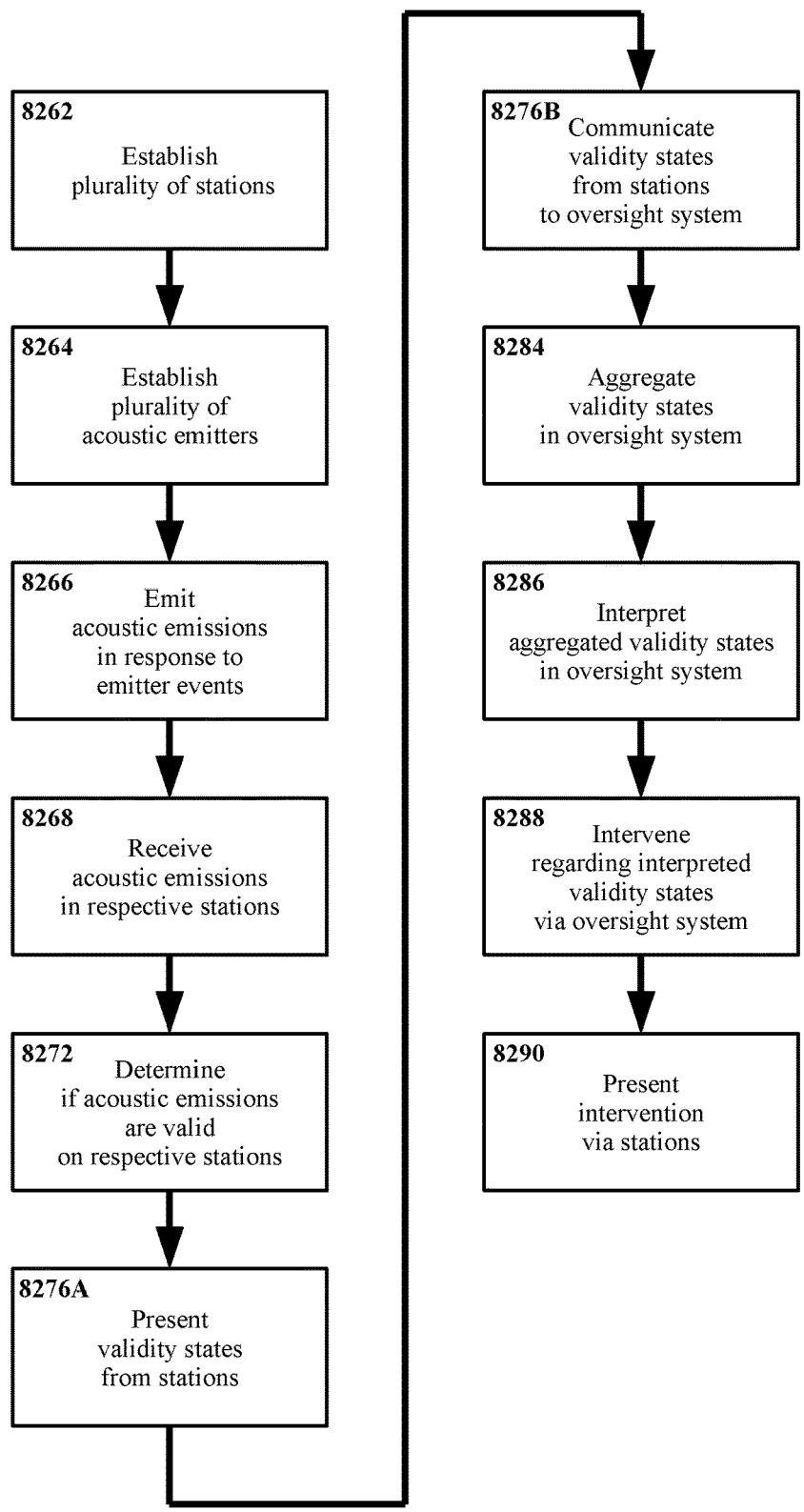
FIG. 82 depicts an example method for validation via acoustic emissions including aggregation and interpretation via an oversight system, in flow chart form.
Figure 83:
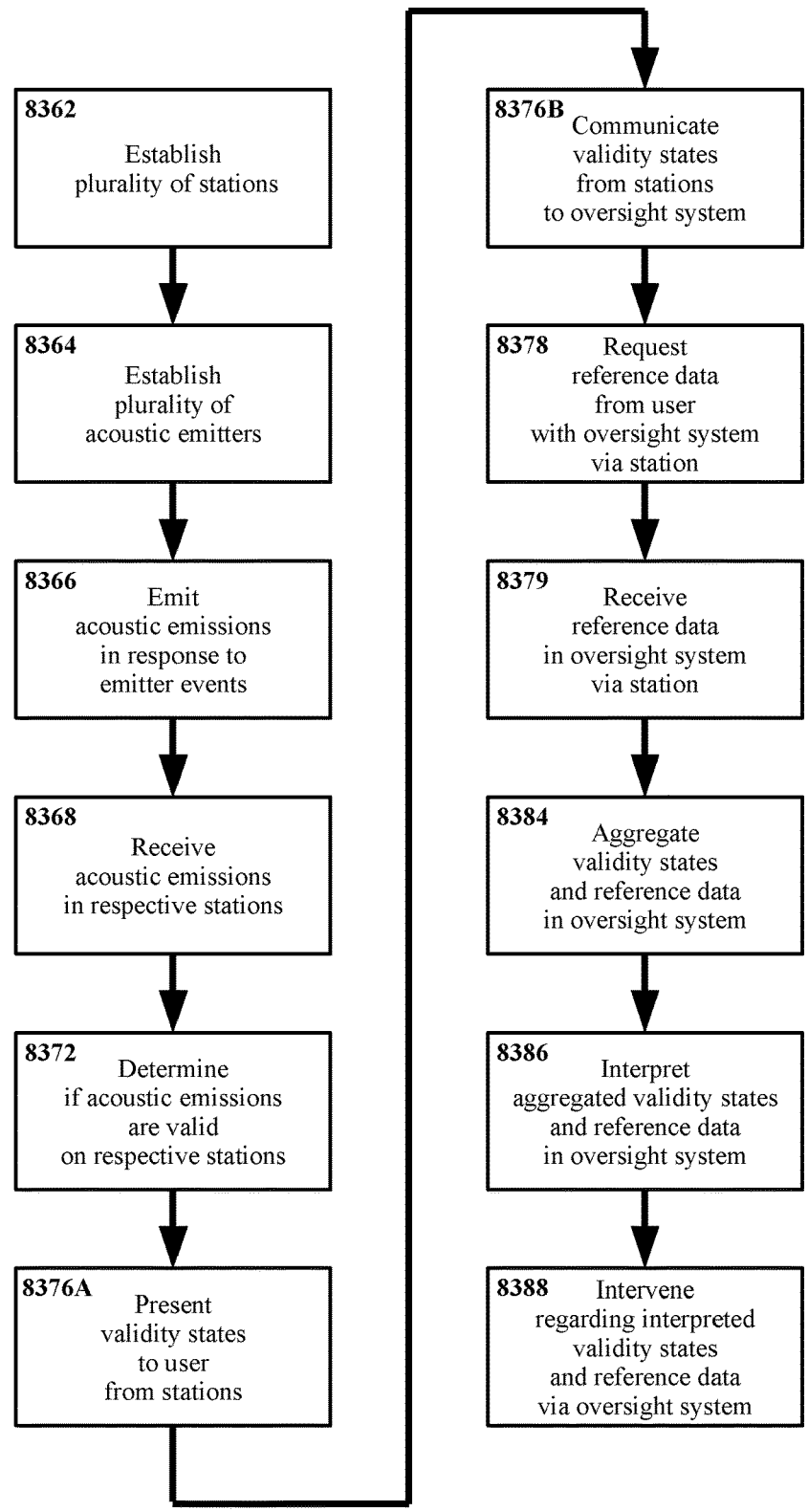
FIG. 83 depicts an example method for validation via acoustic emissions including reference data, in flow chart form.

Now with reference to FIG. 81 through FIG. 83 collectively, certain previous examples have referred to an oversight system and/or functions thereof (whether for validation or for other purposes). FIG. 81 through FIG. 83 present additional examples with regard to an oversight system.

Specifically referring now to FIG. 81, a relatively concrete arrangement is shown therein. A plurality of smart phones are established 8162 (e.g., serving as stations) with a validation standard and a validator instantiated thereon. A plurality of striker-and-anvil acoustic emitters are established 8164 on a plurality of medication containers. Acoustic emissions are emitted 8166 from multiple medication containers in response to those containers being opened.

It is noted that the example of FIG. 81 refers to multiple smart phones/stations, and likewise to multiple containers. While in principle an oversight system may operate in relation to only a single input, e.g., one validation of one acoustic emission from one container, consideration of multiple validation events (successful or not) may facilitate additional functions. Thus for illustrative purposes FIG. 81 addresses a case wherein more than one smart phone may be available to validate acoustic emissions from more than one container. However, although certain events shown in FIG. 81 are shown as single elements, e.g., one block 8166 representing multiple acoustic emissions, such events are shown collectively for simplicity. It is not required for example that the acoustic emissions all be produced together, in the same place, at the same time, etc. (Or even necessarily by the same configuration of acoustic emitters, from the same type of container carrying the same medication, etc. Moreover, not all validators and/or validation standards necessarily must be identical in all embodiments. For example, certain embodiments may address several types of container with several types of medication and several types of emitter, as evaluated by several types of smart phone or other stations with several types of validator relying on several different validation standards. While uniformity is not prohibited, neither may be uniformity required.) Continuing in FIG. 81, the acoustic emissions are received 8168 in the respective smart phones. (It is not required for example that all smart phones receive all emissions, etc.) The acoustic emissions are communicated 8170 to the validators of the respective smart phones. In the various smart phones, a determination is made 8172 by the validator as to whether the respective acoustic emissions received satisfy the validation standard.

The validity states are displayed 8176A for the respective acoustic emissions (and thus for the respective medication containers) on the respective smart phones. For purposes of FIG. 81 such display is not shown to be carried out differently according to the validation state; however as shown for example in FIG. 33, variations in methods based on whether certain determinations are positive or negative (e.g., local vs. non-local in FIG. 33, but similarly valid vs. not valid with respect to FIG. 81) may be present in at least certain embodiments.

In addition, the validity state, times, and locations are communicated 8176B from the several smart phones to an oversight system. For example, whether each acoustic emission (and thus each container) may be determined to be valid or invalid, the time of such determination, and the GPS location of the smart phone making that determination may be communicated. However, again it is not required that all such communications be uniform; some smart phones may communicate additional information, different information, and/or less information.

Moving on in FIG. 81, in the oversight system the validity states, times, and locations are aggregated 8184 so as to map valid containers and invalid containers in space and time. For example, a geographical map may be produced showing the spatial location of all valid and invalid container events during a one-week period. However, while the arrangement in FIG. 81 refers to the production of a map in block 8184, it is not necessary to produce either a literal (e.g., geographical) map for all embodiments. For example, a plot of the number of valid vs. invalid container events per day over a thirty-day period also may be suitable as a "map". Further, not all embodiments may include or require aggregation to produce features as may be interpreted as maps, as such. For example, a representation of distances from various valid and/or invalid container openings to various known points of distribution (e.g., pharmacies) may be suitable (such an arrangement may for example illuminate potential sites where counterfeit medications are being sold). As another example, a purely numerical database of validity states, times, locations, etc. may be aggregated without necessarily providing an interpretive construct such as a map, plot, etc. (though subsequent mapping, modeling, etc. is not prohibited).

Still with reference to FIG. 81, one or more zones exhibiting high levels of invalid opening events are identified 8186 from the map via the oversight system. For example, to continue the example of a literal geographical map such a map may be classified into green zones (low/no rate of invalid medications), yellow zones (moderate rates), and red zones (high rates); red zones then may be "flagged" via the oversight system for further consideration (as described below).

The high-invalidity zone is then reported 8188A to the medication manufacturer via the oversight system. For example, an automated e-mail or similar message may be sent from a computer server functioning as an oversight system to a relevant department within the company manufacturing the medication and/or containers therefor (e.g., quality control, etc.) communicating that a geographical area may be exhibiting a high rate of invalid container openings as may indicate counterfeit medication. However, other arrangements, including but not limited to prompting a live person via the oversight system who then contacts some other live person at a manufacturing company, may be equally suitable.

In the example of FIG. 81, the high-invalidity zone is also reported 8188B to a regulatory authority via the oversight system. For example, an authority such as the US Food and Drug Administration, the American Medical Association, etc., as may monitor and/or control distribution of counterfeit medications may be contacted (e.g., by email, prompt to live persons, etc.).

In addition, the high-invalidity zone is broadcast 8188C to smart phones as may be within the geographical region represented by the high-invalidity zone. For example, for a given red zone, all smart phones physically present within the area may be contacted (e.g., through a cell phone network) via the oversight system to communicate that a high level of invalid medication container openings have been detected within that area. Alternately, some portion of smart phones may be so contacted, such as smart phones that have reported openings from within that area (even if the opening reported by a particular smart phone was valid), smart phones known to have a validator and validation standard thereon, smart phones that have opted-in for validity broadcasts, etc.

Still with reference to FIG. 81, smart phones receiving the broadcast may then display 8190 the high-invalidity zone (e.g., as a graphical map showing a "red zone", as a text warning describing an area exhibiting high invalidity, as a notice of high invalidity "in this area" without necessarily specifying the area, etc.). It is noted that such notices may be displayed from smart phones regardless of whether those particular phones have themselves identified any invalid acoustic emissions. Thus, smart phones (and/or other stations, and/or users thereof) as may be informed of potential validity threats are not necessarily limited only to smart phones as have contributed to the determination that such a threat exists.

As noted the arrangement in FIG. 81 is presented as relatively concrete, for illustrative purposes. Moving on to FIG. 82, an arrangement not specific to smart phones as stations, particular types of aggregation, etc. is presented.

In FIG. 82, a plurality of stations is established 8262. A plurality of acoustic emitters is also established 8264. Acoustic emissions are emitted 8266 from at least some of those acoustic emitters (including but not limited to acoustic emissions validating medication containers), those acoustic emissions being received 8268 in respective stations. Determinations are made 8272 in the respective stations as to whether the acoustic emissions are valid (e.g., satisfy the validation standards for a given medication container).

The validity states are presented 8276A from the stations, for example as graphics, text, speech, advisory sounds, etc. The validity states also are communicated 8276B from the stations to an oversight system. Although only two such actions (as may be considered to correspond with registration of validity states) are shown, other actions also may be suitable, including but not limited to storing validity states and/or related data, etc. In addition, though in certain examples herein an oversight system is referred to for purposes of simplicity as a single physical entity, such as a processor, an oversight system also may take the form of a cloud system, wherein no particular hardware is dedicated to the functions of the oversight system (so long as those functions may be carried out). Likewise, an oversight system may be a distributed and/or peer-to-peer system. For example, considering smart phones as stations, each smart phone may communicate with several other smart phones, such that validity information, aggregated validity data, interventions, etc. may propagate through a group of such smart phones without central control (whether hardware, cloud, etc.). Such a system may for example operate independently of (or even in the complete absence of) regulatory authorities, functioning rather to notify individuals based on shared experience without relying on (or even in defiance of) official channels. For example, individual smart phones may have executable instructions thereon (possibly as part of the validator, but also possibly distinct therefrom) as may "red flag" geographical areas in response to receiving a large number of reports of invalid medication containers.

Continuing in FIG. 82, validity states are aggregated 8284 in the oversight system. The manner of aggregating 8284 may vary considerably from one embodiment to another. For example, data may simply be collected, but alternately data may be configured into geographical maps, time plots, etc. The aggregated validity states are interpreted 8286 in the oversight system. For example, areas exhibiting a high degree of invalid openings may be identified from the aggregated validity data, trends in validity state over time may be identified (such as a rising trend in the rate of invalid openings, temporary spikes of invalid openings, etc.), and/or other analytical and/or interpretive evaluations may be carried out. Typically though not necessarily such interpretation 8286 may be directed towards enabling some form of intervention, e.g., deriving "actionable intelligence" from the available validity data. However, in such instances the nature of the interpretation and/or results thereof (e.g., "red zones") are not limited and may vary considerably.

An intervention 8288 is carried out in consideration of the interpretations made regarding validity states (e.g., in event 8286). That is, some form of action is taken based on the aggregated validity states. For example, a manufacturer of a medication or medication container may be advised that a high rate of invalid acoustic emissions have been found associated with validation attempts for the medication and/or container in question, suspected counterfeiting may be reported to a regulatory agency, the public or some portion thereof (e.g., persons who have "opted in" for notifications) may be notified of a high level of possible counterfeit medication, etc., individual stores and/or management for store chains as may be distributing counterfeit medication (knowingly or not) may be advised. The form of intervention is not limited, and may vary considerably.

Still in FIG. 82, an intervention is presented 8290 via stations. For example, if an example intervention 8288 were to send notifications from the oversight system to smart phones that have opted in to receive such, presenting 8290 that intervention may including displaying a text message or graphical symbol, delivering a spoken message or caution tone, etc., from that smart phone. In at least some embodiments it may be that presentation 8290 reasonably could be considered as part of or a form of intervention 8288; for example in FIG. 82 if the intervention were to advise users via the stations then presenting such an advisory with the stations might be subsumed therein. However, not every presentation of information for every embodiment necessarily must be so subsumed, and arrangements wherein information may be presented as a result of (or in addition to, or distinct from) intervention are not excluded.

With regard to FIG. 82 overall (and at least certain other examples herein), it is noted that certain processes as may be spread out in time and/or space may be presented as well-defined event blocks. For example, determining whether acoustic emissions are valid 8272 is presented as a single block; however in practice validity determinations may take place in many devices, at many locations, during many times. Similarly, at least for certain distributed systems (e.g., peer-to-peer networks of smart devices) aggregating 8284 the validity states may not all happen in a single place, at a single time, etc. (and indeed for a peer-to-peer network not all relevant data for a given region and time period necessarily will be in any given smart device at any one time). For clarity such "distributed" actions may be shown as unitary events, but embodiments are not limited to such steps being carried out in unitary fashion in practice.

Turning to FIG. 83, another example of validation is presented therein. A plurality of stations is established 8362, and a plurality of acoustic emitters are established 8364. Acoustic emissions are emitted 8366 from various acoustic emitters in response to emitter events, and those emissions are received 8368 in respective stations. Determinations are made 8372 as to whether the acoustic emissions are valid on the respective stations. Based on the determinations, validity states (e.g., valid, invalid, indeterminate) are presented 8376A to users via the stations. Validity states also are communicated 8376B from the stations to the oversight system.

In addition, the oversight system may request 8378 reference data from users via the respective stations. For example, upon receiving a communication that a given validation attempt has been identified as invalid (e.g., because the container producing that emission may be a counterfeit), the oversight system may request 8378 additional information from the user through a cell phone network (or other communication approach). Considering a potentially counterfeit medication as an example, such information may include the time of purchase, location of purchase, the name of the user and/or the vendor, the name or other identification for the medication, etc. Typically, such reference data may be information as may illuminate the result of validation (e.g., tracing the origin of a container that has produced an invalid acoustic emission), and that may not be immediately available from the acoustic emission and/or validation process itself. For example, while validation may identify the location at which the container is validated (e.g., by GPS data from the station), the location at which the container was purchased may not be immediately apparent from validation. However, information as may at least nominally be obtained via validation also may be confirmed as reference data. For example, a genuine acoustic emission from a genuine container of medication may include a name or ID number identifying the medication; however, if the acoustic emission is considered to be invalid (e.g., counterfeit), even if the acoustic emission includes the medication name it may be that the lot number from a presumed counterfeit may not be accepted as reliable. Thus, even if the name of the medication is ostensibly obtained via an acoustic emission, a user still may be requested to enter the name (or brand, or other information) as reference data.

The type of data and/or form of request and/or reference data acquisition 8378 is not limited. For example, a user may be asked for the name of the medication, or the user may be asked to take a photograph (e.g., with a smart phone camera) of the container that may reveal the name therein. Similarly, although the requesting 8378 of reference data is shown in FIG. 83 as happening after determination 8372 of validity, in at least certain embodiments such requests may be made (and/or fulfilled) before validity is determined. For example, the user may be prompted to take a photograph of the medication at the time of purchase, to log a GPS location at that time, etc.; thus if the acoustic emission from the container is later found to be invalid, the user may not have to attempt to remember or backtrack. Alternately, requests for reference data may occur well before any purchase. For example a user may opt in at some point to allow ongoing logging of medication purchased via a smart phone from that time forward. In such case, the GPS location, time, vendor, etc. may be logged automatically by the smart phone with that information then being considered if the medication purchased is later found to be invalid.

In addition, while certain examples herein may refer to reference data being requested/acquired with regard to invalid acoustic emissions, it may also be suitable to request/acquire reference data for valid emissions. For example, it may be useful to know where genuine medication has been purchased, just as with counterfeit medication. If for instance some vendors in a given region exhibit some level of counterfeit medication but other vendors do not, it may be useful to determine (whether via validation state data, reference data, or otherwise) which vendors do not have a problem with counterfeit medication. Assuming all vendors were obtaining any counterfeit medication inadvertently, learning what is different about vendors that do not obtain counterfeit medication may be useful in avoiding the selling of counterfeit medication via the other vendors.

Continuing in FIG. 83, the reference data is received 8379 in the oversight system via the station. For example, reference data may be communicated through a cell phone network, etc. The reference data and validity states are aggregated 8384 in the oversight system. It may be that all such data is collected together, or that reference data is collected and validity state data is collected separately, or some other arrangement. The particulars of organizing validity states and reference data are not limited. Likewise, the aggregated validity states and reference data are interpreted 8386 in the oversight system. The oversight system may intervene 8388 based on the aggregated data.

Figure 84:
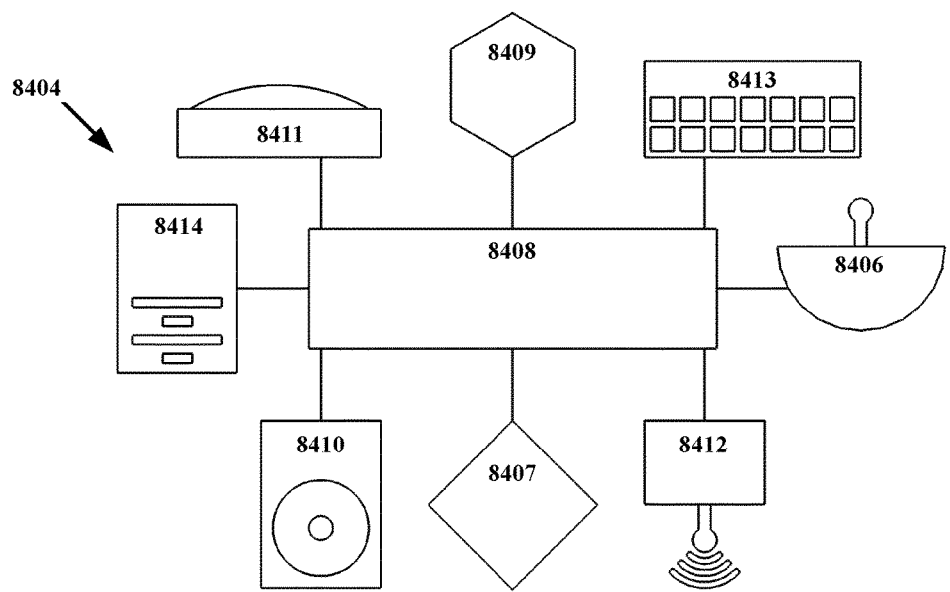
FIG. 84 depicts an example station, in schematic view.

Now with reference to FIG. 84, a station as may be suitable for acoustic validation and/or other functions is shown therein. Not all elements as shown necessarily must be present, but certain elements are shown for illustrative purposes. The station 8404 as illustrated includes an acoustic receiver 8406, adapted to receive acoustic emissions, and a processor 8408 in communication with the receiver 8406. A power supply 8414, data store 8410, and communicator 8412 also are shown. The processor 8408 is adapted to accommodate executable instructions and/or data as may include a validator and/or validation standard instantiated thereon; the data store 8410 is adapted to accommodate executable instructions and/or data as may include the validator and/or validations standard, likewise. The communicator 8412 is adapted for external communication, e.g., with an oversight system (not shown in FIG. 84).

In addition, the example station 8404 includes a GPS 8407, adapted to determine a location of the station 8404 at a given time. The station 8404 as shown also includes a direction finder 8409. For example, the direction finder 8409 may be adapted to determine the direction from which an acoustic emission originated, relative to the station 8404. The station 8404 may include a display 8411 adapted to present information, e.g., validity status. The station 8404 also may include a user interface 8413, such as a touch sensitive surface (e.g., combined with the display 8411 as a touch screen).

Figure 85:
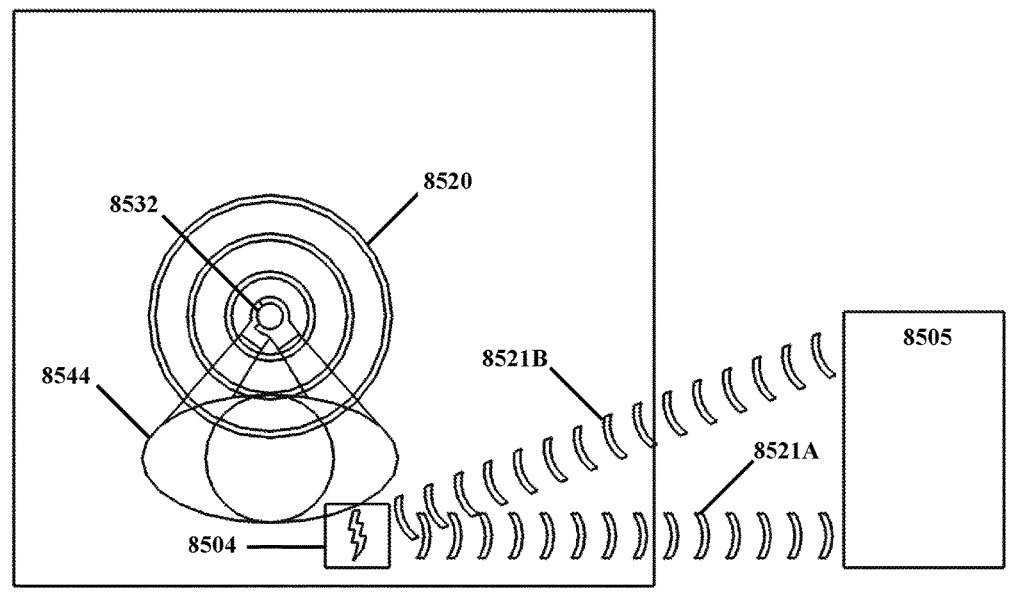
FIG. 85 depicts an example station and emitter as may be utilized by an individual, in top-down view.

Moving on to FIG. 85, an example physical arrangement of a user, container (with emitter), and oversight system as may be suitable for validation, interpretation of acoustic bar codes, etc. is shown. In FIG. 85 a container 8532 is shown in the hand of a user 8544, within some enclosed space (not numbered). An emitter, remote, etc. are not individually illustrated for purposes of simplicity; as shown in certain previous examples (e.g., FIG. 59 through FIG. 62) acoustic emitters may be integral with a container at least insofar as to not readily be visible distinct from the container 8532 (and thus also in such instance the container 8532 itself may be considered to be the remote, or at least be integral with the remote). A station 8504 is also shown proximate the user 8544, for example as may be disposed in a back pocket. (However, the position of the station 8504 is an example only, and as described elsewhere a station 8504 may be disposed adjacent the container 8532, elsewhere in the room/space, etc.) In addition, an oversight system 8505 is illustrated in FIG. 85.

As may be seen, the container 8532 is emitting an acoustic emission 8520 therefrom, for example in response to the user 8544 opening the container 8532, etc. The station 8504 is shown with a lightning symbol thereon to denote that the station 8504 is active, e.g., is receiving/has received the acoustic emission 8520. Further, as seen the station 8504 is exchanging outbound and inbound wireless communications 8521A and 8521B with the oversight system 8505. As noted previously not all embodiments necessarily must include an oversight system 8505 as shown. Moreover, as also noted previously an oversight system 8505 may not be a single discrete physical entity as illustrated in FIG. 85, but rather may be a peer-to-peer network (e.g., a group of smart phones), a cloud-based system, etc.

Regardless of the form of the oversight system 8505 (and likewise other elements shown), as may be understood such a system may facilitate functions such as emission, reception, and evaluation of acoustic emissions for purposes such as are already described herein.

With regard to certain functions generally (e.g., not specific to FIG. 85), including but not limited to validation and in particular with regard to intervention via an oversight system, it is noted that certain functions may be carried out in real time, or at least with sufficiently small delay that validation may not be merely data collection "after the fact".

For example, consider a shipment of counterfeit medication that arrives at a given pharmacy. Some early bottles sold thereof may be found to emit invalid acoustic emissions and thus inferred to be at least potentially counterfeit. In such case, as a form of intervention the pharmacy, potential future customers, law enforcement, etc. may be informed while some of that medication remains on the shelf for sale. It may not be necessary to wait medical effects of the counterfeit medication to appear in order to determine that the medication is in fact counterfeit; rather, customers may avoid using counterfeit medication, potential customers may avoid purchasing such counterfeit medication, law enforcement may begin investigating the source of the counterfeit while events are fresh, etc. In more colloquial terms, it may not be necessary to wait until after the damage is done and then merely try to determine what happened when it is too late to change the outcome; instead, timely intervention may allow the distribution of and damage from counterfeit medications to be avoided or at least reduced. Ideally, such intervention may be real-time, e.g., data is passed on to the oversight system and intervention carried out as validation data is collected at the stations. In practice however, intervention need not be perfectly real-time in order to be effective, e.g., minutes, hours, even days of lag time still may enable effective intervention.

At this point it may be illuminating to discuss certain features as may be enabled and/or supported by validation, and/or other actions associated with acoustic emission. For example, an acoustic emission configured for validation, product identification, etc., may be thought of as providing functionality similar on at least some level as to a bar code. Thus in some sense sounds produced, and/or the structures producing those emissions, may be considered as "acoustic bar codes". For example, where a graphical bar code may be configured as a series of printed lines of varying width, an acoustic emission may be configured as a series of clicks of varying pitch (e.g., as strikers of varying length engage with an anvil), or other variable sounds. Acoustic bar codes may be implemented to provide numerous functions, including but not limited to validation (e.g., confirming that a medication or other product is genuine based on the particulars of the acoustic emissions), use tracking (e.g., determining when a medication or other product is used by detecting and recognizing characteristic acoustic emissions as may facilitate recognition that a container has been accessed), first use determination (e.g., distinguishing the initial use of a new container of medication or other product from subsequent uses thereof by detecting acoustic emissions that may be produced only once, such as by a frangible or otherwise self-destructing emitter), product identification (e.g., detecting acoustic emissions as may be specific to one particular medication or other product), product information gathering (e.g., interpreting a lot number, manufacture date, etc. encoded within acoustic emissions), advertising (e.g., producing acoustic emissions such as a "jingle" as may be readily recognizable to a user as being associated with a product, brand, manufacturer, etc.), and various forms of intervention (e.g., tailoring marketing strategies, advising authorities of counterfeit medication, etc.). Regardless of which such function(s) may be implemented in a given embodiment, acoustic bar codes may exhibit a number of notable features, including but not limited to the following.

An acoustic bar code may be considered as being "transparent" to users. As noted herein, acoustic emitters may be disposed in such fashion that producing acoustic emissions may be a consequence of a particular action that the user may already be carrying out. For example, opening a container that includes a striker and anvil arrangement may produce a series of pops as a consequence of that container being opened; no special action or attention may be required of the user to ensure that the acoustic emissions are produced, aside from opening the container. While the user may be aware of the acoustic emissions (e.g., hearing them), and/or may desire that the emissions be produced, the user may not have to "do anything" in order produce them (beyond opening the container itself).

Considered differently, such acoustic emissions may be understood as inherent in the opening of the container. For example, there may be no convenient manner to open the container without producing acoustic emissions from the emitter. Thus it may not be possible for a user to fail to provide acoustic emissions corresponding to an acoustic bar code through forgetfulness (since the acoustic emissions may be produced whether the user remembers or not), through deliberate avoidance (since opening the container produces the acoustic emissions), etc.

An acoustic bar code also may be considered as being in some sense active and/or ambient. That is, for an acoustic bar code a signal may be produced and sent in the form of acoustic emissions. That signal may represent a transmission in itself, and thus may be understood as active. The acoustic bar code also may be ambient, in that sound tends to permeate a volume of space, such that an acoustic bar code may be received from a station within that volume of space. By comparison, a printed bar code typically is simply printing on a surface, rather than being a signal; directing imaging equipment and/or a light at a printed bar code may be required in order for data therein to be obtained. In addition, a printed bar code typically may exist at a specific location in space; the printed bar code must be read from that location. For example, to read a printed bar code a bar code reader may be required to be targeted at the bar code (e.g., putting the bar code reader in close physical proximity of and pointing at the bar code); simply having a bar code reader in the vicinity of a printed bar code may not be sufficient.

In terms of physical implementation, it is noted that an acoustic bar code may be enabled through the use of mechanical components. For example, strikers and anvils in themselves may not require a power source, a processor, electronic components, circuit paths, etc. (Though such elements are not necessarily prohibited; for example, an acoustic emitter could be implemented as a "sound chip" or similar, triggered through the opening or closing of a circuit as a container is opened.) While smart functionality may be enabled through the use of acoustic emitters (and/or as a feature of acoustic bar codes), the emitters themselves may be "dumb" devices, may be purely mechanical in nature, may ad no mechanically moving parts (e.g., a screw cap with strikers may be a moving part with respect to a bottle with an anvil, but such a screw cap may already be required to move in order to function as a cap; the strikers and anvil may be simple solid units, without joints, actuators, or similar), etc.

Thus, an entirely mechanical acoustic emitter may not require certain components and/or materials as may be potentially problematic. For example, batteries may utilize metals such as cadmium and/or caustic chemicals, solder joints may include lead, etc. If present, such substances may be a source of potential contamination to the contents of a container, may pose difficulties in waste disposal, recycling, etc. If a given mechanical acoustic emitter does not require such substances, concerns regarding the use thereof may be avoided (i.e., cadmium leaching from a device may not be possible if no cadmium is present in that device).

Likewise, battery shelf life or power drain, physical fragility, sensitivity to heat or cold, damage from water immersion, etc. electronic interference, as may be associated with certain electronic or other components may be avoided with arrangements that use mechanical acoustic emitters. In colloquial terms, you can't run down a battery that isn't there. Similarly, in avoiding a need for processors, etc. in acoustic emitters, the cost, complexity, power needs, heat generation, etc. associated with such components may be avoided, even while smart functionality is enabled via the use of acoustic barcodes.

Indeed, it is noted that mechanical acoustic emitters may be made of materials similar or identical to materials already in wide use in medication containers, other enclosures, etc. For example, it may be suitable to provide striker-and-anvil arrangements such as those shown herein (though not limited only thereto) of the same or similar polymers to those currently in use to make containers. The use of identical or similar materials may be advantageous in producing acoustic emitters for a variety of reasons. Materials already used in particular containers presumably may be suitably robust for such applications, thus making acoustic emitters for those containers of similar materials may not present issues in regard to fragility. Also, materials already tested and/or approved for use in containers for a particular may be used in the construction of acoustic emitters engaged with those containers; for example, acoustic emitters for cola bottles may be made of materials already found to be suitable for making cola bottles and/or caps therefor (e.g., not imparting off tastes, not degrading from acidic or alkaline soft drinks, etc.), acoustic emitters for eye drop squeeze bottles may be made of materials already medically approved for contact with eye medications, etc.

Similarly, fabrication techniques and/or equipment already in use for producing containers using the materials in question may be readily adaptable to producing acoustic emitters so as to enable the implementation of acoustic bar codes. For example, a 3D printed container may include 3D printed strikers and anvils (or other emitters), an injection-molded container may include injection-molded strikers and anvils, and so forth. In at least certain embodiments the acoustic emitters may be manufactured with the containers in the same operations, e.g., injection molding acoustic emitters as an integral part of a container of the same material in the same injection molding step. In such instance, adding acoustic bar code functionality to an existing container design may be a relatively straightforward matter.

Acoustic bar codes also may be configured so as to be relatively data-rich. For example, while an acoustic bar code in principle could be a brief binary sequence (e.g., a few sounds all at the same pitch) a series of (for example) 24 tones each (e.g., strikers at 15 degree intervals around the perimeter of a cap) exhibiting one of 24 pitches (e.g., two full 12-tone octaves) also may be feasibly implemented in at least certain embodiments. (It is noted that at least certain printed barcodes may be essentially monochromatic, e.g., black lines overlaid onto a white background. By comparison, the pitches of various acoustic emissions—as may correspond in certain cases to color, e.g., frequency—may be variable, either in steps such as may equate to musical notes or continuously.) The length and complexity of acoustic bar codes is not limited, and at least in principle many bits of data may be encompassed therein.

As may be understood, an ability to support large amounts of data may facilitate the transmission of similarly large amounts of data, e.g., the name of a medication, the dosage, the lot number, the manufacturing site, the bottle serial number, a validation sequence, a recognizable auditory "jingle", etc., within the same acoustic bar code. Similarly, a high-data signal may offer opportunities for more robust encryption (and/or similar features) than a low-data signal. In addition, a data rich signal may enable other features. For example, concealing one signal within another may be feasible, e.g., as the data for one digital image file may include a second digital image (or other information). Such steganographic techniques may for example enable validation via a signal that is not immediately apparent to even be present, thus implementing a form of "security through obscurity". In more colloquial terms, in order to counterfeit a signal, the counterfeiter typically must know that the signal is there.

In addition, acoustic barcodes may be directly perceptible by users (e.g., the user can hear the acoustic emissions, and possibly even recognize portions thereof), and/or nevertheless may be resistant to direct inspection by users in at least certain instances. For example, an acoustic emitter that includes strikers enclosed within a double-walled cap may not be readily inspected without opening the container to examine the strikers (e.g., with regard to length, position, material, stiffness, etc.). Thus a potential counterfeiter may find it challenging to determine precisely what acoustic emission a given emitter may produce by inspection "on the shelf", without acquiring, disassembling, test-opening, etc. a given container. (Other arrangements may not reveal particulars even if physically dismantled.) Thus as compared with visible features such as printed barcodes, holograms, distinctive container shape and color, printed labels, etc. acoustic barcodes may exhibit additional practical barriers to counterfeiting. Even so, as noted, acoustic emissions nevertheless may be readily observed by users.

It is noted with regard to counterfeiting and security that acoustic barcodes and/or other acoustic emissions implementations, while at least potentially providing some obstacles to counterfeiting, are not necessarily entirely immune to counterfeiting (nor is immunity to counterfeiting required). In colloquial terms, it is not necessary to make counterfeiting impossible, so long as counterfeiting is more trouble than it's worth. Thus, acoustic emissions employed as a security feature may usefully serve as such even if imperfect. In addition, it is noted that combination of security features based on acoustic emissions with other security features, such as holographic seals, etc., is not prohibited, and may provide enhanced security when so combined for at least certain embodiments.

As another potential feature of acoustic barcodes, as mentioned previously certain embodiments of acoustic emitters may be single-use, in whole or in part. For example, some or all strikers in a striker-and-anvil arrangement may be frangible so as to break after producing one acoustic emission (or otherwise configured so as only to produce sound once). For a container that includes such single-use emitters, acoustic emissions may be produced only the first time the container is opened. Alternately, the acoustic emission produced the first time the container is opened may be distinct from acoustic emissions produced for later openings of that container. (For an arrangement wherein the entire acoustic emitter is single-use, an acoustic emission may be produced only the first time the container is opened; e.g., if all of the strikers have broken away, later openings may produce no acoustic emission.) By contrast, printed bar codes (and certain other systems such as security holograms, etc.) may be essentially fixed; scanning a printed barcode may convey the same data every time. However, the ability of an acoustic barcode to convey when a container is opened the first time, as distinct from later instances, may be useful. For example, it may be of interest in maintaining patient compliance and/or improving medical outcomes to log when the patient starts a new prescription, a new refill, etc.

Also, it is noted that at least certain elements as may be used to implement a system of acoustic barcodes may already be widely available (though this should not be taken to imply that acoustic bar codes themselves are in any way known). For example, a smart phone, smart speaker, desktop computer, tablet, etc. may include the processing power, sensors, and/or other functions necessary so as to serve as a station for acoustic bar codes. Thus, it may not be necessary to develop and/or market dedicated "readers" or other stations for acoustic barcodes (though the use of dedicated stations is not excluded).

With regard not only to acoustic bar codes but also other features referenced herein, it is noted that in at least certain embodiments the vehicle, closure, and/or acoustic emitter as may be present, and/or the vehicle event as may be performed, may be material or "tactile" in nature. That is, the vehicle, closure, acoustic emitter, etc., may be physical objects carrying out physical functions, such as producing acoustic emissions in response to a container being opened. Such arrangements may be distinguished from, for example, an emitter as may operate electrically, or utilizing internal data processing, in order to control the production of an acoustic emission. Likewise, the vehicle event may be a physical action, as may contrast with data processing, etc. In colloquial terms, the container, emitter, etc. may be "hands on" or "manual" elements, and opening the container so as to produce sounds similarly may be a hands on or manual action.

While certain potentially useful and/or noteworthy features regarding acoustic barcodes and/or other acoustic emission features are described herein for explanatory purposes, it is emphasized that such examples are not limiting, and that other arrangements may be suitable.

Figure 86:
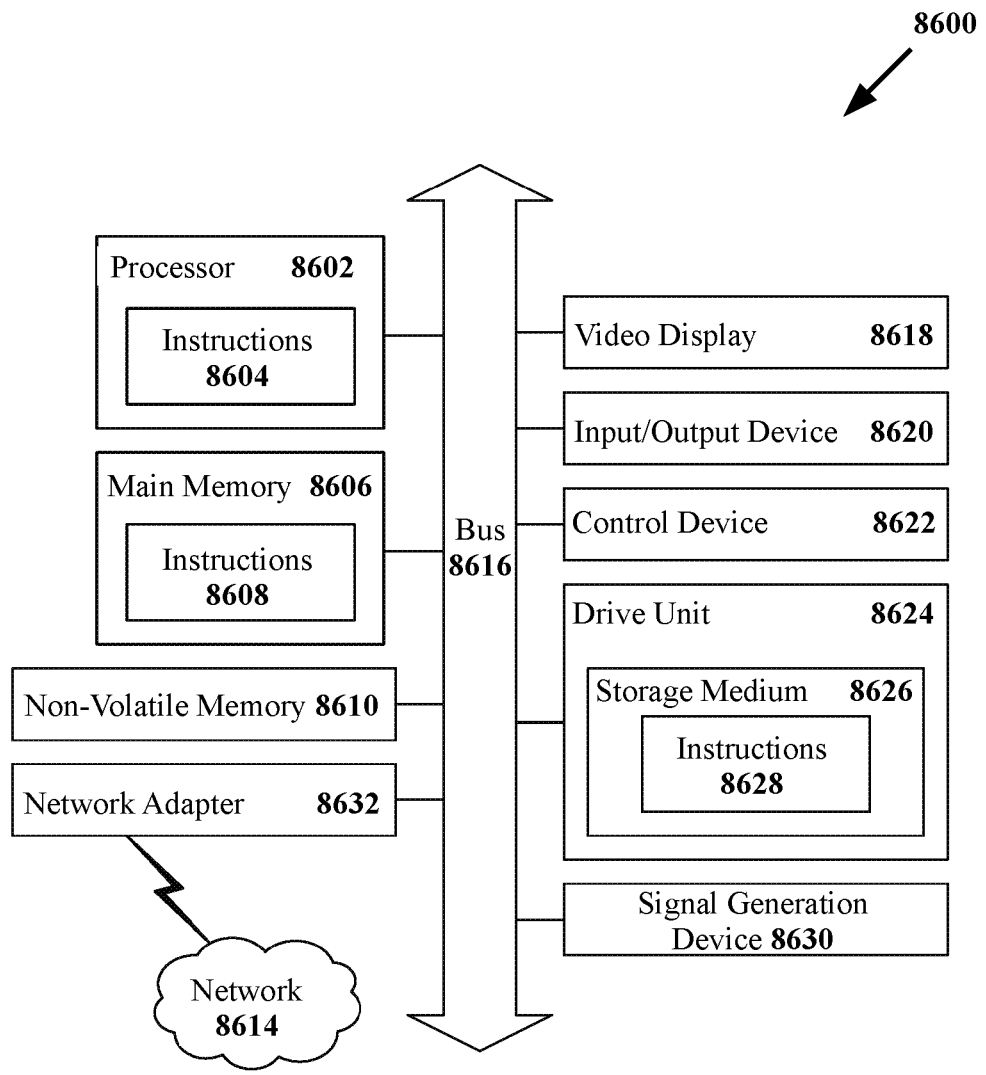
FIG. 86 shows a block diagram illustrating an example of a processing system in which at least some operations described herein can be implemented.

FIG. 86 is a block diagram illustrating an example of a processing system 8600 in which at least some operations described herein can be implemented. The processing system may include one or more central processing units ("processors") 8602, main memory 8606, non-volatile memory 8610, network adapter 8612 (e.g., network interfaces), video display 8618, input/output devices 8620, control device 8622 (e.g., keyboard and pointing devices), drive unit 8624 including a storage medium 8626, and signal generation device 8630 that are communicatively connected to a bus 8616. The bus 8616 is illustrated as an abstraction that represents any one or more separate physical buses, point to point connections, or both connected by appropriate bridges, adapters, or controllers. The bus 8616, therefore, can include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

In various embodiments, the processing system 8600 operates as a standalone device, although the processing system 8600 may be connected (e.g., wired or wirelessly) to other machines. For example, in some embodiments components of the processing system 8600 are housed within a computer device used by a user to access an interface having skin care products or skin care regimens, while in other embodiments components of the processing system 8600 are housed within a network-connected container that holds one or more skin care products. In a networked deployment, the processing system 8600 may operate in the capacity of a server or a client machine in a client-server network environment, or as a peer machine in a peer-to-peer (or distributed) network environment.

The processing system 8600 may be a server, a personal computer (PC), a tablet computer, a laptop computer, a personal digital assistant (PDA), a mobile phone, a processor, a telephone, a web appliance, a network router, switch or bridge, a console, a hand-held console, a (hand-held) gaming device, a music player, any portable, mobile, hand-held device, or any machine capable of executing a set of instructions (sequential or otherwise) that specify actions to be taken by the processing system.

While the main memory 8606, non-volatile memory 8610, and storage medium 8626 (also called a "machine-readable medium) are shown to be a single medium, the term "machine-readable medium" and "storage medium" should be taken to include a single medium or multiple media (e.g., a centralized or distributed database, and/or associated caches and servers) that store one or more sets of instructions 8628. The term "machine-readable medium" and "storage medium" shall also be taken to include any medium that is capable of storing, encoding, or carrying a set of instructions for execution by the processing system and that cause the processing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 8604, 8608, 8628) set at various times in various memory and storage devices in a computer, and that, when read and executed by one or more processing units or processors 8602, cause the processing system 8600 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices 8610, floppy and other removable disks, hard disk drives, optical disks (e.g., Compact Disk Read-Only Memory (CD ROMS), Digital Versatile Disks, (DVDs)), and transmission type media such as digital and analog communication links.

The network adapter 8612 enables the processing system 8600 to mediate data in a network 8614 with an entity that may be external to the computing device 8600, through any known and/or convenient communications protocol supported by the processing system 8600 and the external entity. The network adapter 8612 can include one or more of a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 8612 can include a firewall that can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

As indicated above, the computer-implemented systems introduced here can be implemented by hardware (e.g., programmable circuitry such as microprocessors), software, firmware, or a combination of such forms. For example, some computer-implemented systems may be embodied entirely in special-purpose hardwired (i.e., non-programmable) circuitry. Special-purpose circuitry can be in the form of, for example, application-specific integrated circuits (ASICs), programmable logic devices (PLDs), field-programmable gate arrays (FPGAs), etc.

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

We claim:

1. An apparatus comprising:
a container adapted to contain a product therein and dispense said product therefrom, comprising:
an aperture adapted to pass said product therethrough;
a container thread disposed around said aperture; and
a shoulder disposed around said aperture and said container thread;
a cap adapted to removably engage said container so as to restrict passing said product through said aperture, comprising:
an inner wall;
a cap thread on said inner wall adapted to engage said container thread so as to enable said cap to be removably engaged with said container through rotating said cap relative to said container; and
an outer wall spaced apart from said inner wall so as to define a channel between said inner and outer walls;
an acoustic emitter, comprising:
an anvil disposed on said shoulder of said container and integral with said container;
a plurality of pedestals engaged with said cap between said inner and outer walls and integral with said closure;
a plurality of strikers disposed on said plurality of pedestals and integral therewith, each striker having a striker length;
wherein:
said anvil and strikers are disposed such that rotating said cap engages said strikers sequentially with said anvil so as to produce an acoustic emission from said strikers, without requiring any of a power source, a data processor, and a sensor;
for said strikers, an acoustic emission pitch therefrom corresponds to a striker length thereof, such that said acoustic emission exhibits a sequential nonuniformity of said acoustic emission pitches; and
said striker lengths of said strikers are configured to encode data into said sequential nonuniformity of said acoustic emission pitches.

* * * * *